United States Patent
Provencher et al.

(10) Patent No.: US 11,936,137 B2
(45) Date of Patent: Mar. 19, 2024

(54) SYSTEMS, MONITOR MOUNTS, MONITORS, DOCKS, RACKS, MODULES, BELT MOUNTS, COUPLINGS AND CONNECTORS

(71) Applicant: Drägerwerk AG & Co. KGaA, Lübeck (DE)

(72) Inventors: Andrew T. Provencher, Lowell, MA (US); Juan P. Eslava, Groton, MA (US); John C. Magill, Woburn, MA (US); Noah Hennings, Reading, MA (US); Peter A. Lund, Nashua, NH (US); Thomas Swyst, Arlington, MA (US); Christopher Aiston, Mont Vernon, NH (US); Zachary K. Hennings, Reading, MA (US); Rajesh S. Rane, Andover, MA (US); Daniel Beinart, Narragansett, RI (US)

(73) Assignee: Drägerwerk AG & Co. KGaA

( * ) Notice: Subject to any disclaimer, the term of this patent is extended or adjusted under 35 U.S.C. 154(b) by 228 days.

(21) Appl. No.: 17/419,040

(22) PCT Filed: Dec. 27, 2019

(86) PCT No.: PCT/EP2019/087117
§ 371 (c)(1),
(2) Date: Jun. 28, 2021

(87) PCT Pub. No.: WO2020/136271
PCT Pub. Date: Jul. 2, 2020

(65) Prior Publication Data
US 2022/0077633 A1 Mar. 10, 2022

Related U.S. Application Data
(60) Provisional application No. 62/852,453, filed on May 24, 2019, provisional application No. 62/786,047, filed on Dec. 28, 2018.

(51) Int. Cl.
| | | |
|---|---|---|
| *H01R 13/64* | (2006.01) | |
| *H01R 13/6583* | (2011.01) | |
| *H01R 33/76* | (2006.01) | |
| *A61B 5/00* | (2006.01) | |

(Continued)

(52) U.S. Cl.
CPC ......... *H01R 13/64* (2013.01); *H01R 13/6583* (2013.01); *H01R 33/7657* (2013.01);
(Continued)

(58) Field of Classification Search
CPC ..... H01R 13/64; H01R 13/6583; H01R 24/20
See application file for complete search history.

(56) References Cited

U.S. PATENT DOCUMENTS 4,512,623 A * 4/1985 Tomsa ............... H01R 13/6583
439/607.17
4,577,917 A * 3/1986 Nashimoto ............... B62J 6/01
439/736

(Continued)

FOREIGN PATENT DOCUMENTS

| DE | 102015014492 A1 | 5/2017 |
|---|---|---|
| DE | 202016008631 U1 | 9/2018 |
| IT | 20110329 A1 | 6/2013 |

OTHER PUBLICATIONS

European Patent Office, The International Search Report and The Written Opinion of the International Searching Authority, dated Mar. 23, 2020, for International Application No. PCT/EP2019/087117.

*Primary Examiner* — Neil Abrams
(74) *Attorney, Agent, or Firm* — Design IP

(57) ABSTRACT

A connector system includes a male connecter including a male housing defining a recess and a plurality of pins arranged within the recess; and a female connector including a female housing configured to be insertable into the recess of the male housing. The female housing includes: front and back portions; a pair of longitudinal sides that extend from (Continued)

the front portion to the back portion; a planar side that extends from the front portion to the back portion, the planar side connecting first ends of the pair of longitudinal sides; a rounded side that extends from the front portion to the back portion, the rounded side connecting second ends of the pair of longitudinal sides; a front surface defined at the front portion by the pair of longitudinal sides, the planar side, and the rounded side; and a plurality of sockets formed at the front surface.

20 Claims, 109 Drawing Sheets

(51) Int. Cl.
  *H01R 24/20* (2011.01)
  *H01R 24/28* (2011.01)
  *H01R 107/00* (2006.01)

(52) U.S. Cl.
  CPC .......... *A61B 5/7445* (2013.01); *H01R 24/20* (2013.01); *H01R 24/28* (2013.01); *H01R 33/765* (2013.01); *H01R 2107/00* (2013.01); *H01R 2201/12* (2013.01)

(56) References Cited

U.S. PATENT DOCUMENTS

| | | | | |
|---|---|---|---|---|
| 4,808,126 A * | 2/1989 | Wilson | ............... | H01R 13/6583 439/607.18 |
| 4,869,677 A * | 9/1989 | Johnson | ............... | H01R 12/737 439/108 |
| 4,986,769 A * | 1/1991 | Adams, III | ............. | H01R 13/64 439/368 |
| 5,032,089 A * | 7/1991 | Hansell, III | ......... | H01R 12/775 439/607.17 |
| 5,104,329 A * | 4/1992 | Brown | ................ | H01R 12/724 439/108 |
| 5,975,957 A * | 11/1999 | Noda | ................. | H01R 13/6583 439/607.17 |
| 6,808,428 B1 * | 10/2004 | Korsunsky | ......... | H01R 12/7052 439/680 |
| 6,976,885 B2 * | 12/2005 | Lord | ..................... | G06F 1/1632 439/680 |
| 7,201,612 B1 * | 4/2007 | Hou | ..................... | H01R 13/052 439/678 |
| 7,857,656 B2 * | 12/2010 | Tai | ......................... | H01R 13/50 439/485 |
| D640,206 S * | 6/2011 | Stirling | ........................ | D13/154 |
| 8,323,059 B1 * | 12/2012 | Song | ...................... | H01R 13/64 439/680 |
| 8,460,016 B2 * | 6/2013 | Liu | ........................ | H01R 31/06 439/106 |
| 8,517,756 B2 * | 8/2013 | Song | .................. | H01R 13/6271 439/680 |
| 9,166,339 B2 * | 10/2015 | Sakakura | ............... | H01R 13/64 |
| 2014/0113481 A1 | 4/2014 | Little et al. | | |
| 2018/0083387 A1 | 3/2018 | Preuss et al. | | |
| 2018/0242921 A1 | 8/2018 | Muhsin et al. | | |
| 2022/0077633 A1* | 3/2022 | Provencher | ............ | H01R 24/68 |

* cited by examiner

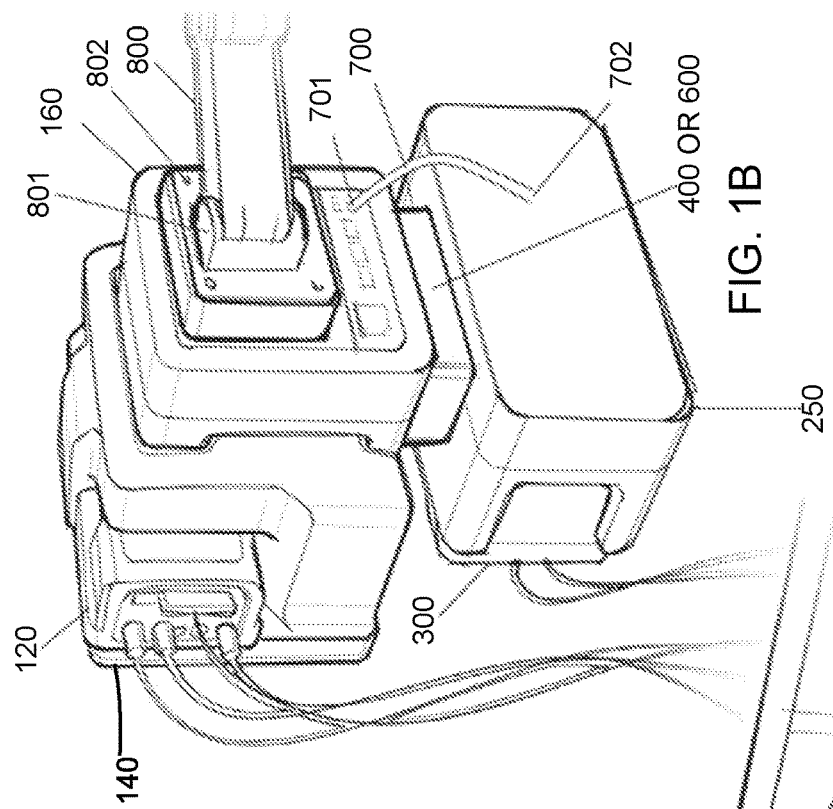
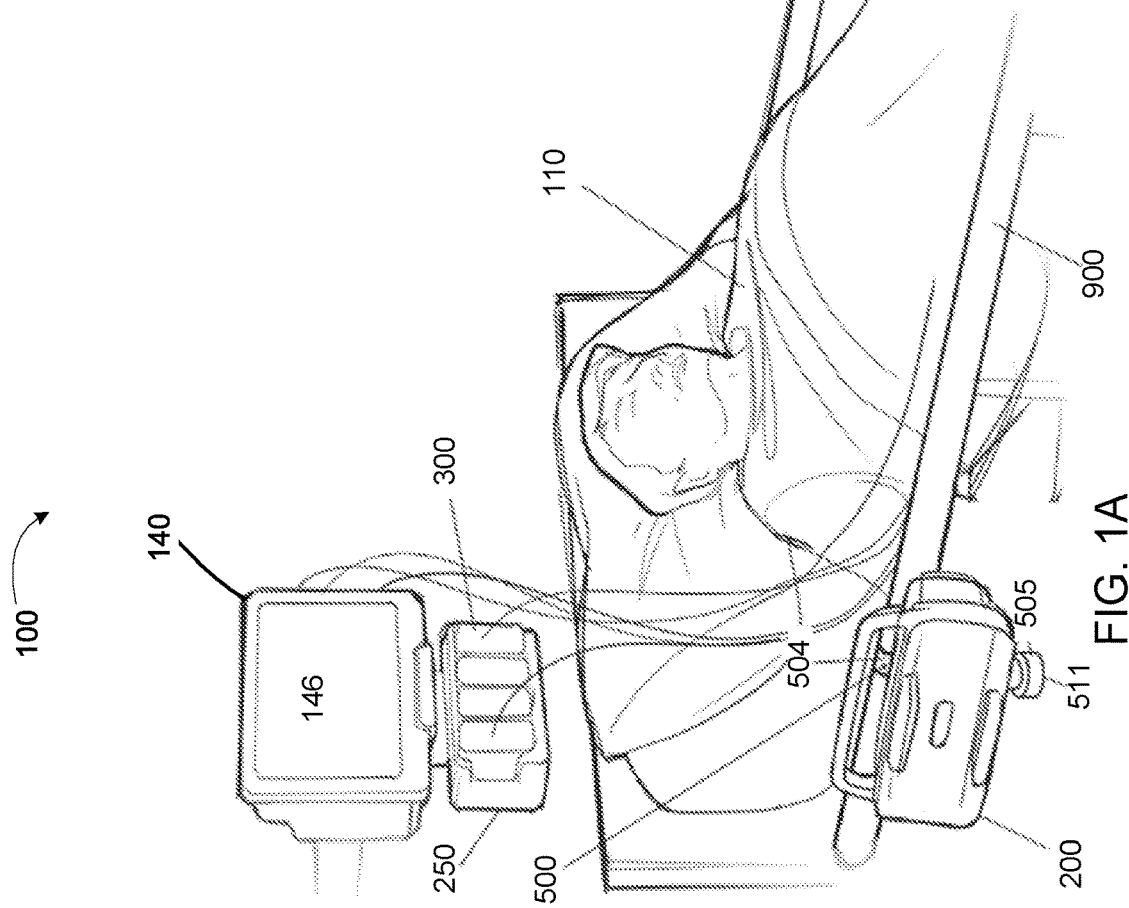

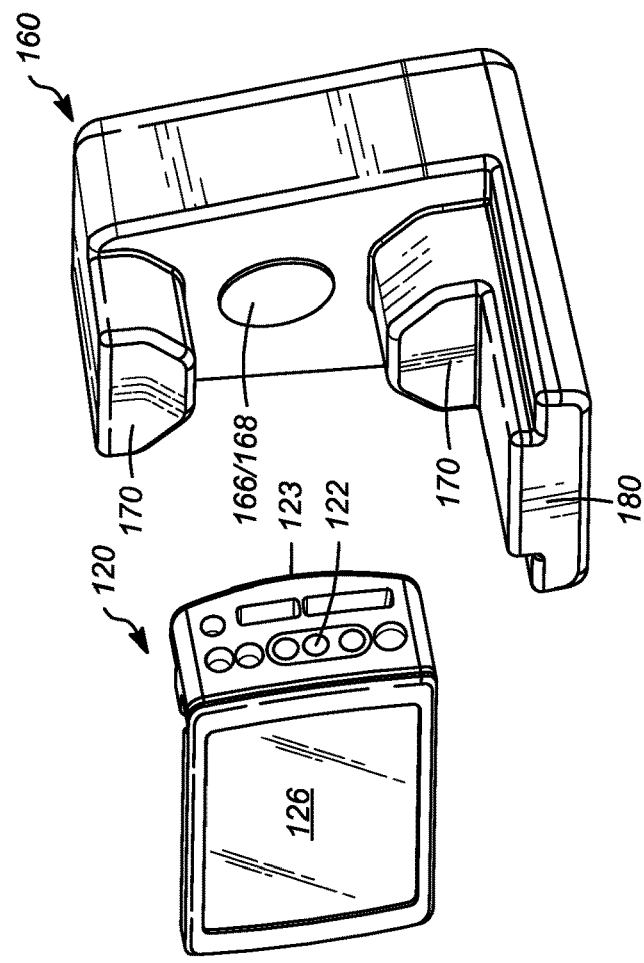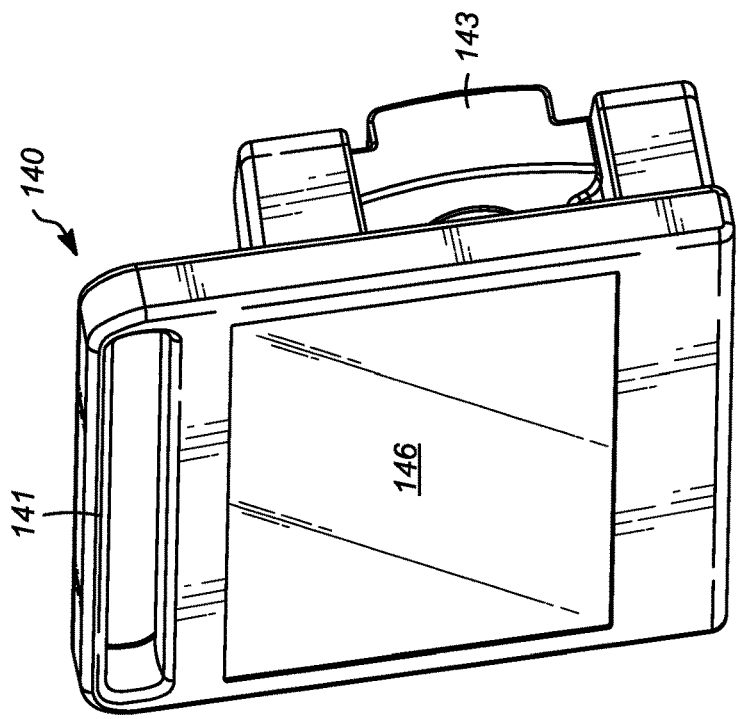
FIG. 4

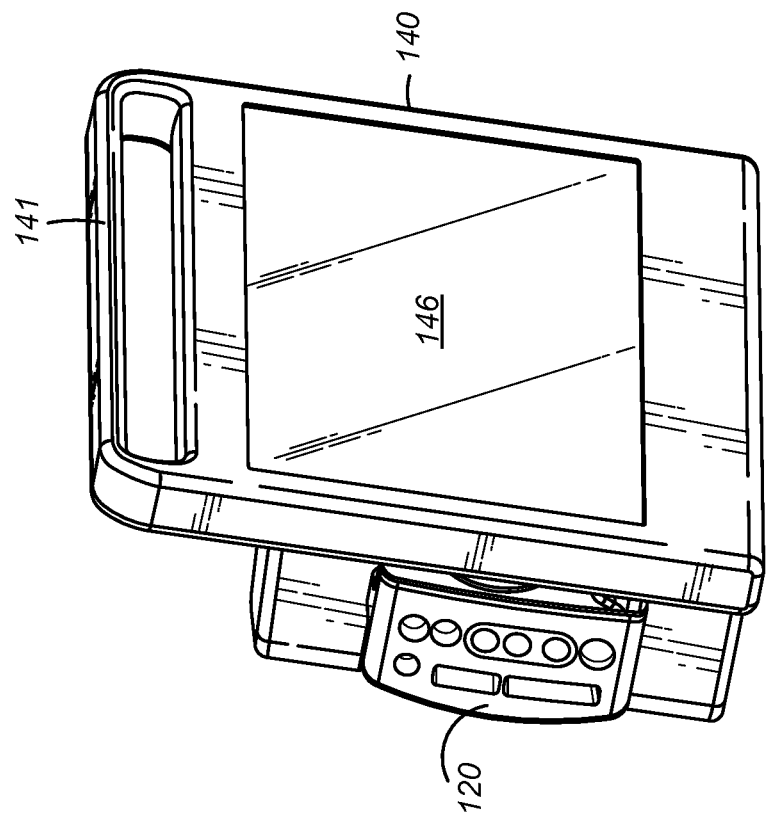
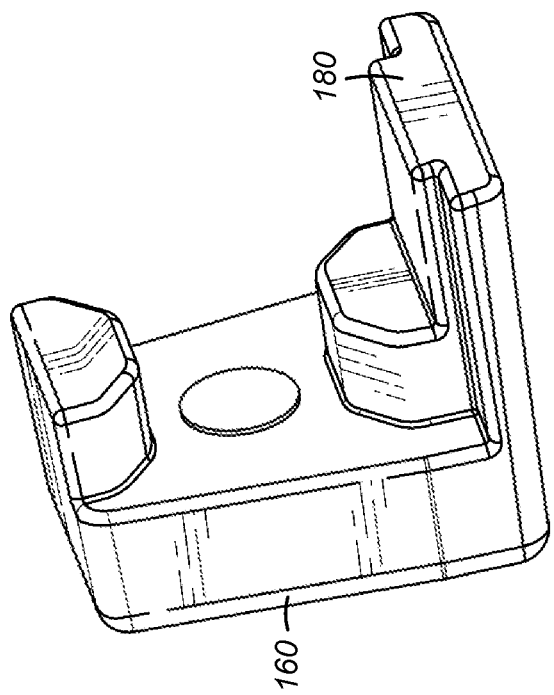
FIG. 13

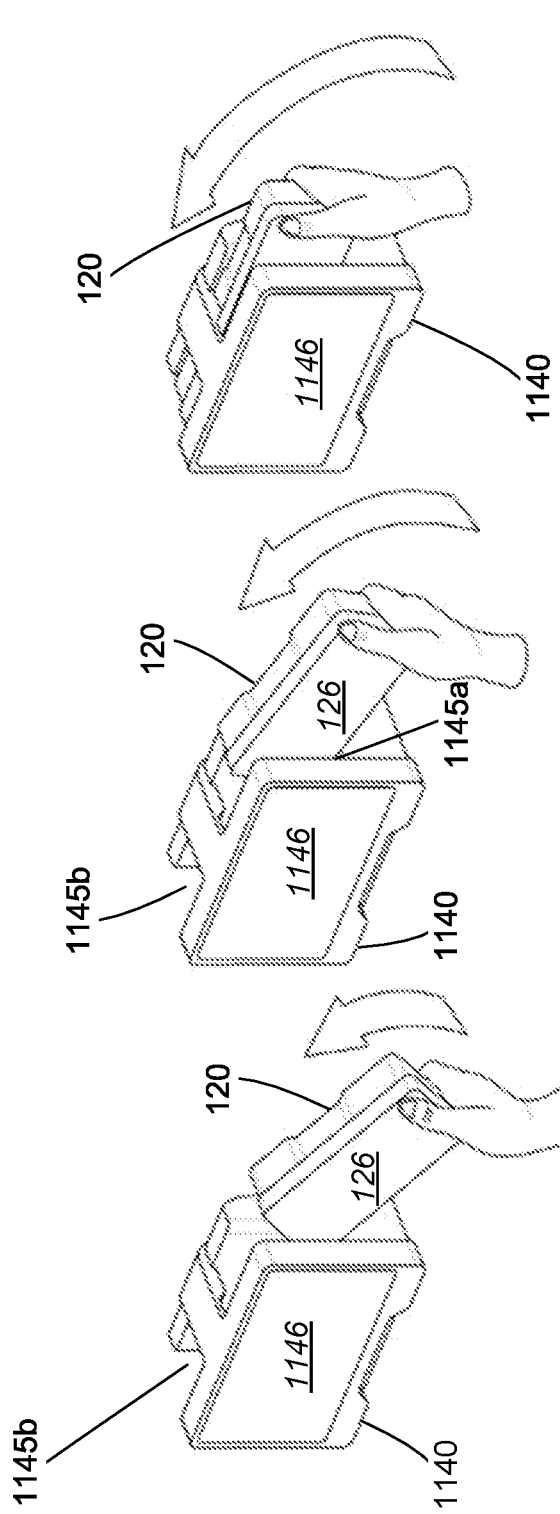

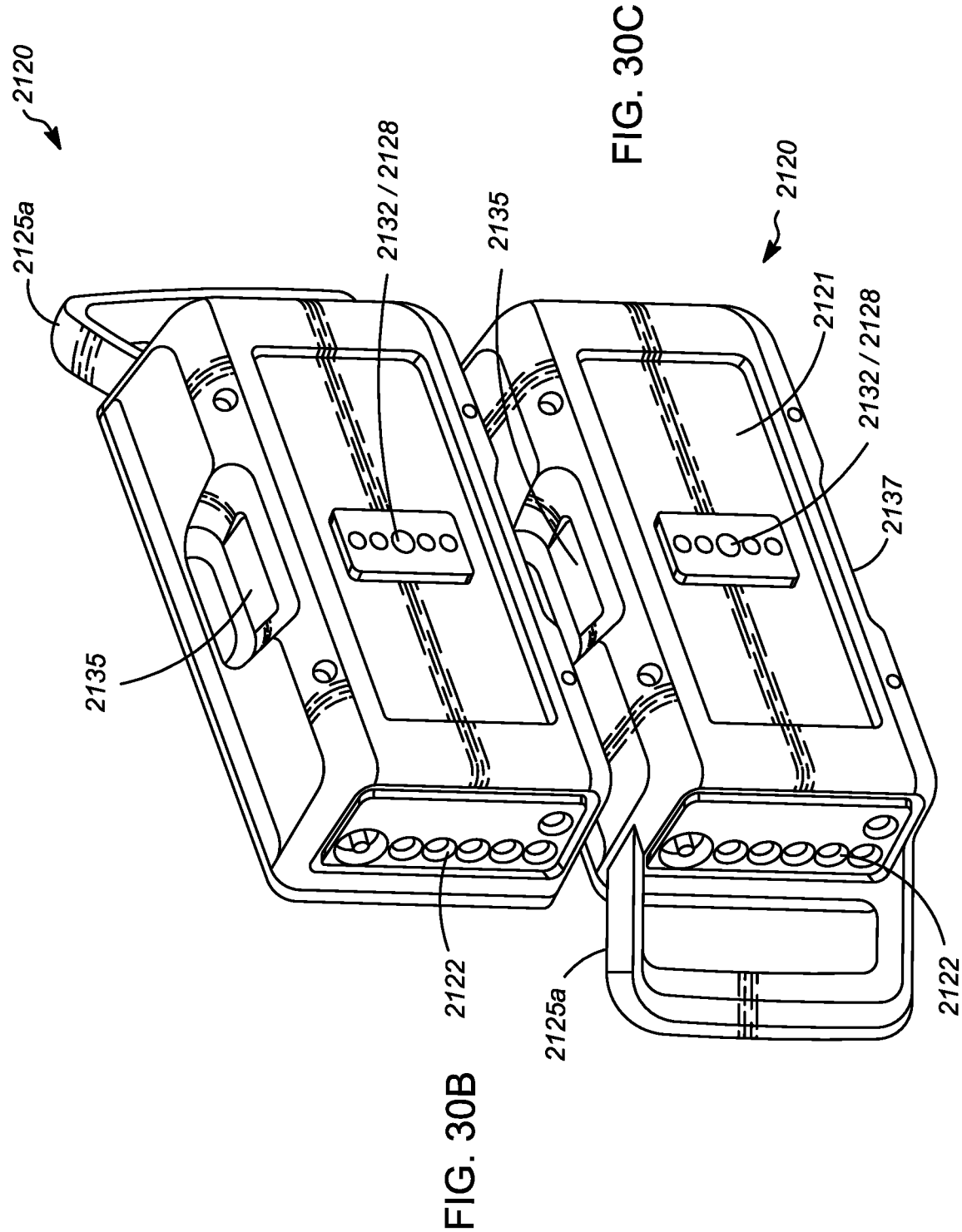

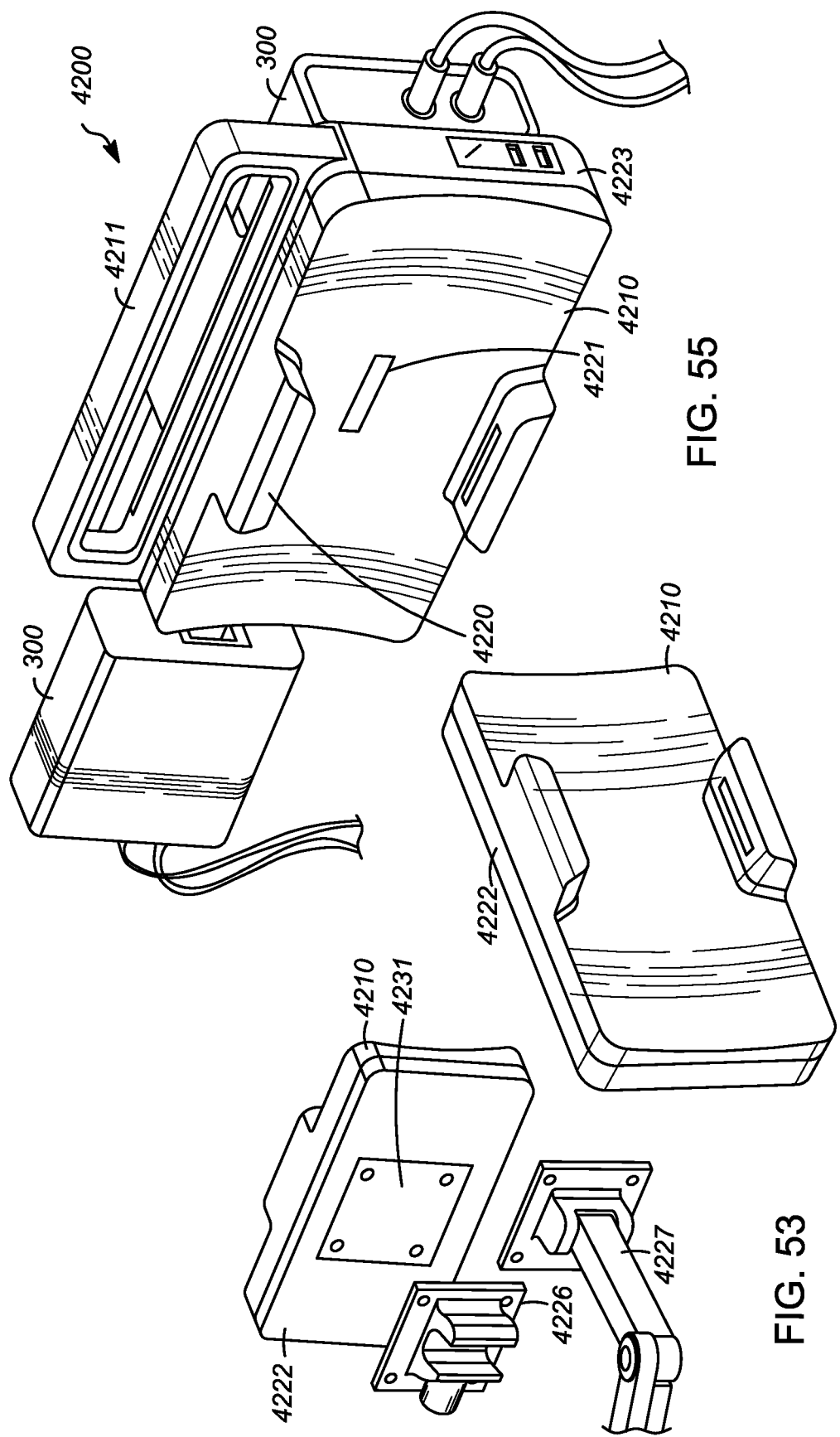

SYSTEMS, MONITOR MOUNTS, MONITORS, DOCKS, RACKS, MODULES, BELT MOUNTS, COUPLINGS AND CONNECTORS

FIELD OF THE DISCLOSURE

The present disclosure generally relates to: a monitor mount that is able to receive differently sized monitors, and more specifically, to a monitor mount that enables data transfer between the monitor mount and the monitors received thereby; a dock that is able to receive a device, and more specifically, to a dock that enables data transfer between the dock and the device received thereby; a first monitor that is able to interface with a second monitor and the monitor mount; a coupling including a rotatable top piece that is able to quickly and easily secure a device to a mount; a belt mount that is able to quickly and rigidly secure a device to a support structure; a coupling including leaves that are able to quickly and easily secure a device to a mount; a rack that is able to secure a module in one of two different positions therein; a connector that is able to electrically connect two devices and provides an electrical connection that can be simply physically or tactually confirmed; and systems comprising any one or more of the above.

BACKGROUND OF THE DISCLOSURE

Monitors that include electronic visual displays are utilized in a large number of applications within a wide variety of industries including, for example, the healthcare industry, the military, and the oil and gas industry. Many of the applications within such industries require such monitors to, at times, be portable, and, at other times, be stationary. For example, in the healthcare industry, when not being used in transport of a patient or when a patient is ambulatory, monitors can be connected to a monitor mount. Such monitor mounts can provide a variety of functions including providing physical support, a power source, and a conduit to one or more computer networks.

One type of monitor is a patient monitor which is used by healthcare facilities to monitor and display information about a patient, such as vital signs, status of connected devices (e.g., physiological sensors, etc.), and the like. Patient monitors can be portable devices that travel with the patient in order to provide continuous monitoring during care. When a patient arrives at a hospital room or other treatment location, the patient monitor is often plugged into or otherwise connected to a patient monitor mount. Patient monitor mounts provide a physical interface for the patient monitor and are generally fixed to the treatment location. Patient monitor mounts can also provide electrical connection to other devices or infrastructure, such as power to recharge patient monitor batteries, network connectivity to other medical devices or hospital computer systems, and the like.

Patient monitors have different sizes and provide different functionalities. With current systems, each type of patient monitor typically requires a dedicated monitor mount, a dedicated controller, and a dedicated user interface. Accordingly, such monitors are not interoperable and the performance advantages of each type of monitor cannot be combined and leveraged.

In addition, there is a growing need in acute care environments to improve clinical workflow, reduce alarm fatigue, and customize medical devices to better suit hospital protocols and use models.

Due to the above problems associated with current systems, there is a need for a modular system providing a universal and scalable platform including a monitor mount capable of mixed use with monitors having different sizes which are interoperable with the same controller and the same user interface, and that can be universally docked to the monitor mount.

As discussed above, during the course of providing healthcare to patients, practitioners typically connect at least one type of sensor to a patient to sense, derive or otherwise monitor at least one type of patient medical parameter. Such patient connected sensors are further connected to a monitor that includes all relevant electronic components that enable conversion, manipulation and processing of the data sensed by the at least one type of sensor in order to generate patient medical parameters. These patient medical parameters may be stored in one or more modules and are usable by healthcare practitioners (e.g., nurses, doctors, physician assistants, or any other person charged with providing a healthcare service to a patient) in monitoring a patient and determining a course of healthcare to be provided to the patient. Additionally or alternatively, the one or more modules may contain data, such as patient treatment data, to be transferred to the dock and/or the monitor.

A monitor may be selectively connected to a patient at any point during which a healthcare professional comes into contact with the patient and may remain connected with the patient as the patient moves through various locations within a particular healthcare enterprise (e.g., hospital) or between different healthcare enterprises (e.g., an ambulance and/or different medical facilities). With conventional systems, the monitor and/or the module can be selectively connected (docked) to a stationary or fixed dock that may serve as a gateway for connecting the monitor and/or the module to a hospital information system (HIS) and/or a central monitoring station and allowing data representing the at least one patient medical parameter to be communicated to other systems within the healthcare enterprise. This data may then be used by different systems in further patient care.

Since such docks have been stationary or fixed (i.e., not mobile or transportable), this can cause gaps in data acquisition. During the course of providing treatment, the patient may be connected to a plurality of different types of monitors that are charged with monitoring the same (or different) patient parameter data. For example, a patient who is travelling between different units in a hospital may be selectively connected to a small portable monitor that may be easily transported around the hospital. However, when the patient returns to their hospital room, the patient may then be connected to a bedside monitor. A drawback associated with this scenario is that each patient monitor needs to be connected to a dedicated cradle or dock which is connected to a central station or HIS enabling transfer of patient data from the respective patient monitor, through the central station or HIS, to a repository of patient data associated with the respective patient. One reason for this is because many conventional portable patient monitors do not have the ability to record and store patient data on a removable storage medium (e.g., memory card). A further drawback with the current state of monitors is, when connecting the patient to a different patient monitor, the newly connected patient monitor must query the repository to acquire the patient parameter data that was recently uploaded by the original patient monitor. The delays associated with the conventional patient parameter data transfer process are not only time consuming and increase the chances of human error associated with manual reconfiguration of patient monitors, but also may result in an interruption in monitoring of the patient.

Therefore, a need exists to provide a mobile or transportable dock for improving the ability to record and store data and transfer data between monitors and/or modules. The dock of the present disclosure addresses deficiencies of transferring data between monitors and/or modules.

Conventional monitors typically have back portions of a standard, generally rectangular shape. Such a rectangular shape makes conventional monitors difficult to grip, difficult to clean, and limits the size and shape of batteries stored therein. Therefore, a need exists to provide a monitor with a back portion having a shape for improving grip, hygiene, and the accommodation of differently sized batteries.

Conventional couplings for a device (e.g., monitor, rack, module, etc.) and a mount require a user to use two hands to fasten and release the device from the mount. Furthermore, the conventional couplings require the device to be fastened to two opposite sides of the mount for stability. In addition, the conventional couplings allow the device to be fastened to the mount in only one orientation, thereby requiring the user to visually confirm the orientation of the device and the mount before fastening, which is time-consuming and burdensome in a hospital setting where rapid treatment and triage are often necessary. The device and the mount are typically bolted together or otherwise rigidly attached and cannot be separated without the use of specialized tools. Therefore, a need exists to provide a quick release coupling which only requires a user to use one hand to fasten and release the device from the mount, only requires the device to be fastened to one side of the mount for stability, allows the device to be fastened to the mount in multiple orientations, and does not require visual confirmation of the orientation of the device and the mount before fastening.

Conventional mounts are difficult to both quickly and rigidly secure to mobile or transportable support structures such as a bed, stretcher, gurney rail, IV pole, ambulance bar, etc. in addition to stationary support structures. Conventional mounts are not adapted to be attached directly to a support structure (e.g., a tubular or rectangular support structure), and generally must be mounted from the ceiling, on a wall, or on a cart. Furthermore, such mounting is time-consuming and burdensome in a hospital setting. Therefore, a need exists to provide a mount that can be both quickly and rigidly secured to mobile or transportable support structures.

Conventional couplings for a device and a mount require a user to visually confirm the orientation of the device and the monitor mount before fastening, which is time-consuming and burdensome in a hospital setting. The device and the mount are typically bolted together or otherwise rigidly attached and cannot be separated without the use of specialized tools. Therefore, a need exists to provide a quick release coupling which does not require specialized tools or visual confirmation of the orientation of the device and the mount before fastening.

Conventional racks for securing modules such as patient parameter modules are only capable of securing the modules in one position. That is, the modules are either fully secured in and electrically connected to the conventional racks or else the modules are electrically disconnected and completely released from the racks. When modules are not secured in the one position in the rack, they usually will fall or drop out of the rack due to gravity. The modules cannot be mechanically retained by the rack while being electrically disconnected from the housing. Also, a user must remove the modules and carry them to another location for transport or storage. However, there are a myriad of scenarios in which it is advantageous to store modules in a rack without an electrical connection therebetween. In this way, inactive modules do not consume power, do not require separate storage, and can be stored in the rack without further effort or possible misplacement. Therefore, a need exists to provide a rack which can store modules in an additional position in which the modules are physically connected to the rack but electrically disconnected from the rack.

Conventional connectors often have inconspicuous keying and are difficult to mate with corresponding interfaces, particularly in low light or dark conditions. Such conventional connectors require painstaking visual confirmation of the orientations of the interfaces in order to ensure a proper connection. Therefore, a need exists to provide a connector that has conspicuous keying and external shapes that are asymmetrical and can be felt in low light conditions, are easy to mate with corresponding interfaces, and provide electrical and mechanical connections that can be simply physically or tactually confirmed.

SUMMARY OF THE DISCLOSURE

In light of the above, the present disclosure is broadly directed to a system comprising a monitor mount, a first monitor and a second monitor. The monitor mount includes a first coupling and a support portion, the first monitor includes a first electronic visual display and a first back portion, and the second monitor includes a second electronic visual display, a second back portion and a second coupling. The first monitor is configured to be detachably secured to the monitor mount by the first coupling. The second monitor is configured to be detachably secured to the monitor mount by the first coupling and the support portion. Each of the first back portion of the first monitor and the second back portion of the second monitor is configured to be detachably secured to the monitor mount by the first coupling. The first monitor is configured to be detachably secured to the second monitor by the second coupling. The second monitor is configured to surround at least a portion of the first electronic visual display of the first monitor when the first monitor is detachably secured to the second monitor. The second monitor can surround only a portion of the first monitor such that ends of the first monitor in a lateral direction of the first monitor are exposed. The monitor mount is able to secure each of the first monitor and the second monitor individually or both of the first monitor and the second monitor concurrently. In other words, the first coupling is configured to accept either the first monitor or the second monitor such that the monitor mount is configured to mount the first monitor alone, the second monitor alone, or a combination of the first monitor and the second monitor.

The monitor mount can also include a first power bus. The first monitor and/or the second monitor can optionally be powered by the first power bus when secured to the monitor mount.

The first monitor and/or the second monitor can also include a second power bus. If only one of the first monitor and the second monitor includes a second power bus, the other of the first monitor or the second monitor can be powered by the second power bus when the first monitor is secured to the second monitor. The first monitor and/or the second monitor, in some variations, is operable solely via the second power bus. In other variations, the first monitor and/or the second monitor is operable via either of the first power bus and the second power bus.

The first monitor and/or the second monitor can include a self-contained power source that allows the first monitor and/or the second monitor to be operated independently of the monitor mount.

The first monitor can include a sensor interface configured to receive data generated by at least one physiological sensor monitoring a physiological parameter of a patient. The at least one physiological sensor can include a wired connection to the sensor interface. The at least one physiological sensor can additionally or alternatively include a wireless connection to the sensor interface.

The second monitor can be a multiparameter monitor for continuously monitoring adult, pediatric and neonatal patients both at a bedside and on transport and can support all patient acuity levels hospital-wide.

Either of the first monitor or the second monitor can capture and display real-time vital signs at the bedside. Either of the first monitor or the second monitor can be used as a standalone monitor or in combination. The system of the present disclosure integrates patient data and provides continuous monitoring at the bedside and on transport.

The second monitor can be configured to be first coupled to the first coupling and the support portion and the first monitor can be configured to be subsequently coupled to the second coupling.

The first monitor can be configured to be coupled to and power the second monitor by the second power bus of the first monitor when neither of the first monitor and the second monitor are secured to the monitor mount.

The second monitor can be configured to be coupled to and power the first monitor by the second power bus of the second monitor when neither of the first monitor and the second monitor are secured to the monitor mount.

Each of the first coupling and the second coupling can take various forms including a mechanical coupling, an electro-mechanical coupling, and/or a magnetic coupling.

The monitor mount can further include a first communications interface coupled to at least one computing network. With this variation, the first monitor and/or the second monitor can include a second communications interface which transmits and receives data over the computing network via the first communications interface when the first monitor and/or the second monitor is secured to the monitor mount.

The monitor mount can also be configured to detachably secure one or more modules for monitoring the physiological parameter of the patient.

The monitor mount can be mounted at the bedside, from the ceiling, on a wall across the room, or even outside the room for isolation purposes.

The first monitor can visualize at least a portion of received data on the first electronic visual display. The second monitor can visualize at least a portion of received data on the second electronic visual display.

The first monitor can be configured to be detachably secured to and removed from a forward face of the monitor mount. In addition or the alternative, the first monitor can be configured to be transversely inserted into and removed from the monitor mount. Furthermore, the first monitor can be configured to be transversely inserted into and removed from the monitor mount from each of a first lateral direction of the monitor mount and a second lateral direction of the monitor mount, wherein the first lateral direction of the monitor mount is opposite to the second lateral direction of the monitor mount. Such transverse insertion and removal can be performed with one hand by a user. In other words, it is not necessary to perform two separate motions to transversely insert or remove the first monitor from the monitor mount.

The first monitor can be configured to be transversely inserted into and removed from the second monitor. Furthermore, the first monitor can be configured to be transversely inserted into and removed from the second monitor from each of a first lateral direction of the second monitor and a second lateral direction of the second monitor, wherein the first lateral direction of the second monitor is opposite to the second lateral direction of the second monitor. Such transverse insertion and removal can be performed with one hand by the user. In other words, it is not necessary to perform two separate motions to transversely insert or remove the first monitor from the second monitor.

The system of the present disclosure enables pick and go transport of a patient from one care area of a hospital to another care area of the hospital without having to disconnect the patient from a patient monitor. For example, the system of the present disclosure streamlines workflows by being able to go from bedside to transport in the push of a button. Cables and modules can remain attached to the patient and parameters and alarms can continue to be monitored in real time, while recording data during travel. The system of the present disclosure can also provide seamless wired-to-wireless networking, so surveillance can be continuous. No disconnection or reconnection of leads is required and there are no gaps in monitoring or data acquisition. As a result, all parameters that are monitored at the bedside can continue to be monitored on transport.

The system of the present disclosure therefore allows monitors to be mixed and matched across different care areas and geographies such that workflow is optimized. The system of the present disclosure also requires fewer mounting points than current systems, thereby reducing installation and maintenance costs. Since the monitor mount and one or more monitors are integrated and consolidated, the space required for the system of the present disclosure is minimized. The system of the present disclosure can be used in dry and wet zones and contributes to an enhanced level of hygiene. According to caregiver preference, the system of the present disclosure can be scaled to the patient's needs—from basic monitoring to using the full range of all of the monitors. To support individual workflow, multiple monitors can be used, for example, to support anesthesiologists, perfusionists, and surgeons if a surgical display controller is used.

The system of the present disclosure provides a high acuity care system that improves aesthetics and ergonomics by allowing different caregivers to view the information they need at the same place. The system of the present disclosure can be used as part of a healthcare enterprise solution and can bring comprehensive information to the point of care, while continuously monitoring the patient. For example, the system of the present disclosure can provide access to images, lab results and other clinical data, while displaying real-time vital signs data at the point of care. Furthermore, the performance advantages of differently sized monitors can be combined and leveraged. For example, the portability of a smaller monitor and the increased functionality of a larger monitor can be independently or concurrently capitalized upon.

The subject matter described herein provides many technical advantages. For example, the current subject matter enables the mounting of two monitors having different sizes, shapes, and functionality on a single monitor mount.

The details of one or more variations of the subject matter described herein are set forth in the accompanying drawings and the description below. Other features and advantages of the subject matter described herein will be apparent from the description and drawings, and from the claims.

A dock for a device (e.g., monitor, module, etc.) is disclosed. The dock may include a housing portion that selectively supports the module. At least one coupling is positioned on the housing portion for receiving a module therein.

The dock enables optimized transport and transitions to and from transport easily. Clinicians often put the monitor and the module on the patient bed during transport which requires multiple steps for transitions to and from transport. In some variations, the dock can include a lower power consumption display to be used on transport. A monitor and a module can be electrically interconnected and mounted in the dock and be ready for transport. In some variations, the dock itself may serve as a mount.

The dock may be used for stick and stay monitoring (i.e., monitoring in a non-transport setting such as an operating room (OR) or intensive care unit (ICU)). In the ICU, the dock can be detachably secured to a mount, a traditional bedside monitor, or an acute care system with an arm or a cart. In the OR, the dock can be detachably secured to a rolling stand, a pole, an arm or a mount. The dock may also be used for monitoring in a transport setting.

In one embodiment, the dock can include a basic mechanical dock design comprising a coupling operable to receive a small, portable monitor and one or more modules. The dock can include a handle and/or a bottom support, facing frontward. In some variations, the dock can receive the monitor on a front face and the one or more physiological parameter modules on a back face or a side face. The dock can include a housing portion to receive the one or more modules or the one or more modules can be detachably secured directly to the dock in a modular, scalable manner, such as in a piggyback configuration to enable a user to configure the dock as needed for a particular scenario. The module may be detachably secured by being inserted, either partially or fully, within the housing portion.

In another embodiment, the dock can include mechanical and electrical functionalities similar to a monitor mount. Accordingly, the equipment can be ready to go on transport without moving or disconnecting the monitor or the one or more modules. The monitor and the one or more module can be already electrically interconnected and mounted in the dock, which can be mounted in a monitor mount. The dock can be detached from the monitor mount while the monitor and one or more modules remain with the dock.

In another embodiment, the dock can include mechanical and electrical functionalities similar to a larger monitor.

BRIEF DESCRIPTION OF THE DRAWINGS

The following detailed description references the drawings, wherein:

FIGS. 1A and 1B are front and rear perspective views of an example environment for an example system including a small monitor, a large monitor, a monitor mount, a dock, a rack, a module, a coupling or a coupling, a belt mount, a cable, a male connector, and a female connector;

FIG. 4 is an exploded perspective view of the example system including the small monitor, a first exemplary implementation of the large monitor, and the first exemplary implementation of the monitor mount;

FIG. 13 is an exploded perspective view of the example system including a third exemplary implementation of the monitor mount, the small monitor and the first exemplary implementation of the large monitor;

FIGS. 18D-18F are side perspective views of a second exemplary sequence of the small monitor being detachably secured in the second exemplary implementation of the large monitor;

FIG. 30B is a rear perspective view of the third exemplary implementation of the small monitor with a cover thereof in a first orientation;

FIG. 30C is a rear perspective view of the third exemplary implementation of the small monitor with the cover thereof in a second orientation;

FIG. 53 is an exploded perspective view of an example system including the fifth exemplary implementation of the dock including a case and an adapter to be detachably secured to an attachment mechanism, and a support structure;

FIG. 54 is a front perspective view of an example system including a case and an adapter;

FIG. 55 is a side perspective view of an example system including the fifth exemplary implementation of the dock including a case, a handle, a power accessory, a module accessory, and two modules;

FIG. 99H is a perspective view of the male connector shown in FIG. 99G with a modified shield groove;

FIG. 100 is an exploded perspective view of an exemplary implementation of the male connector;

FIG. 101 is an exploded perspective view of an exemplary implementation of the female connector;

FIG. 102 is a front perspective view of a first exemplary implementation of a cable holder;

FIG. 103 is a front perspective view of the first exemplary implementation of the cable holder detachably securing a cable;

FIG. 104 is a front perspective view of a second exemplary implementation of a cable holder;

FIG. 105 is a bottom perspective view of the second exemplary implementation of the cable holder; and FIG. 106 is a front perspective view of the second exemplary implementation of the cable holder detachably securing a cable.

DETAILED DESCRIPTION

Figure 2:
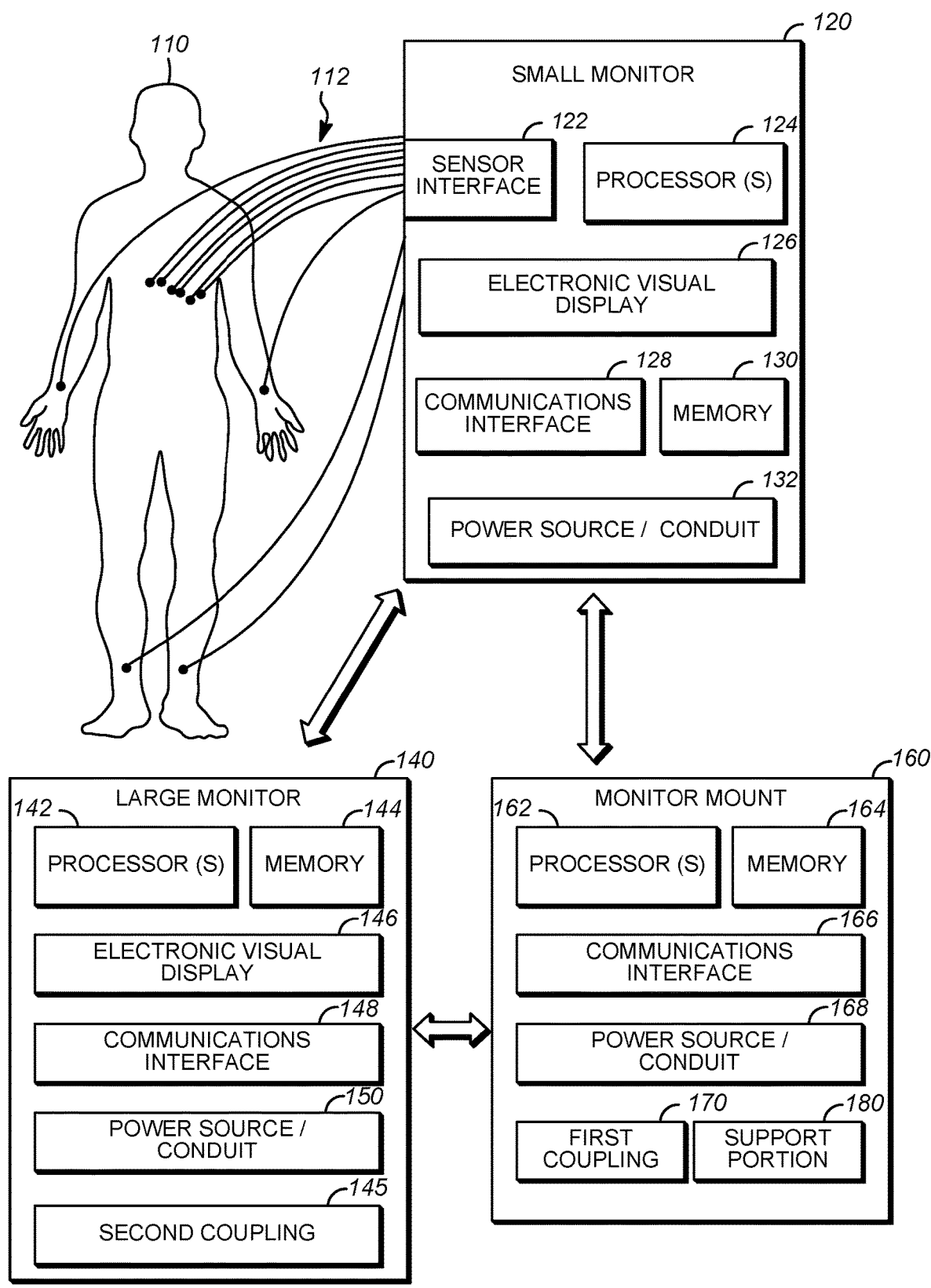
FIG. 2 is a logical diagram illustrating the example system including a small monitor, a large monitor, and a monitor mount.

The following description is made with reference to the accompanying drawings and is provided to assist in a comprehensive understanding of various example embodiments of the present disclosure. The following description includes various details to assist in that understanding, but these are to be regarded as merely examples. Accordingly, those of ordinary skill in the art will recognize that various changes and modifications of the examples described herein can be made without departing from the spirit and scope of the present disclosure. In addition, descriptions of well-known functions and constructions may be omitted for clarity and conciseness.

The terms and words used in the following description and claims are not limited to the bibliographical meanings, but are merely used to enable a clear and consistent understanding of the present disclosure. Accordingly, it should be apparent to those skilled in the art that the following description of the present disclosure is provided for illustration purposes only, and not for the purpose of limiting the present disclosure as defined by the appended claims and their equivalents.

It is to be understood that the singular forms "a", "an", and "the", include plural referents unless the context clearly dictates otherwise. Thus, for example, reference to "a processor" or "a memory" includes reference to one or more of such processors or memories.

The expressions such as "include" and "may include" which may be used in the present disclosure denote the presence of the disclosed functions, operations, and constituent elements, and do not limit the presence of one or more additional functions, operations, and constituent elements. In the present disclosure, terms such as "include" and/or "have", may be construed to denote a certain characteristic, number, operation, constituent element, component or a combination thereof, but should not be construed to exclude the existence of or a possibility of the addition of one or more other characteristics, numbers, operations, constituent elements, components or combinations thereof.

In the present disclosure, the expression "and/or" includes any and all combinations of the associated listed words. For example, the expression "A and/or B" may include A, may include B, or may include both A and B.

In the present disclosure, expressions including ordinal numbers, such as "first", "second", and/or the like, may modify various elements. However, such elements are not limited by the above expressions. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

Unless otherwise defined, all terms including technical and/or scientific terms used herein have the same meaning as commonly understood by one of ordinary skill in the art to which the present disclosure pertains. In addition, unless otherwise defined, all terms defined in generally used dictionaries may not be overly interpreted.

The subject matter described herein is directed to systems and apparatuses directed to monitors (e.g., display monitors having visual electronic displays) and monitor mounts providing physical support and, in some cases, power and access to a communications/computer network. Use of such systems and apparatuses can, for example, occur in a medical environment such as the scene of a medical event, an ambulance, a hospital or a doctor's office. When a patient undergoes initial patient monitoring in such an environment, a minimum set of sensors can be connected to a patient to collect various types of patient information as described in detail herein. As a patient is moved from one area of care within the medical environment to another area of care, the patient monitor can travel with the patient. In some situations, the patient monitor can be mounted to a monitor mount to provide for stationary observation of the patient information on a visual electronic display. During the course of patient monitoring, the number of sensors can also increase due to increased testing and/or monitoring of the patient. In such a scenario, a patient monitor initially monitoring the patient can be docked into monitor mount having a second, larger monitor in order to expand the number of sensors available for patient monitoring and/or increase the number of patient parameters on a single visual electronic display by docking the smaller patient monitor within a larger patient monitor. The initial patient monitor can either remain within the larger patient monitor or be removed from the larger patient monitor.

FIGS. 1A and 1B are front and rear perspective views of an example environment for an example system including a small monitor 120, a large monitor 140, a monitor mount 160, a dock 200, a rack 250, a module 300, a coupling 400 or a coupling 600, a belt mount 500, a cable 700, a male connector 701, and a female connector 702. In the embodiments shown in FIGS. 2-18F, the monitor mount 160, 1160 can detachably secure (or otherwise physically interface with) the small monitor 120 and/or the large monitor 140, 1140, and the large monitor 140 can detachably secure (or otherwise physically interface with) the small monitor 120. FIGS. 19-36 show various embodiments of a small monitor 1120, 2120, a large monitor 2140, 3140, 4140, and a monitor mount 2160, 3160.

Figure 63:
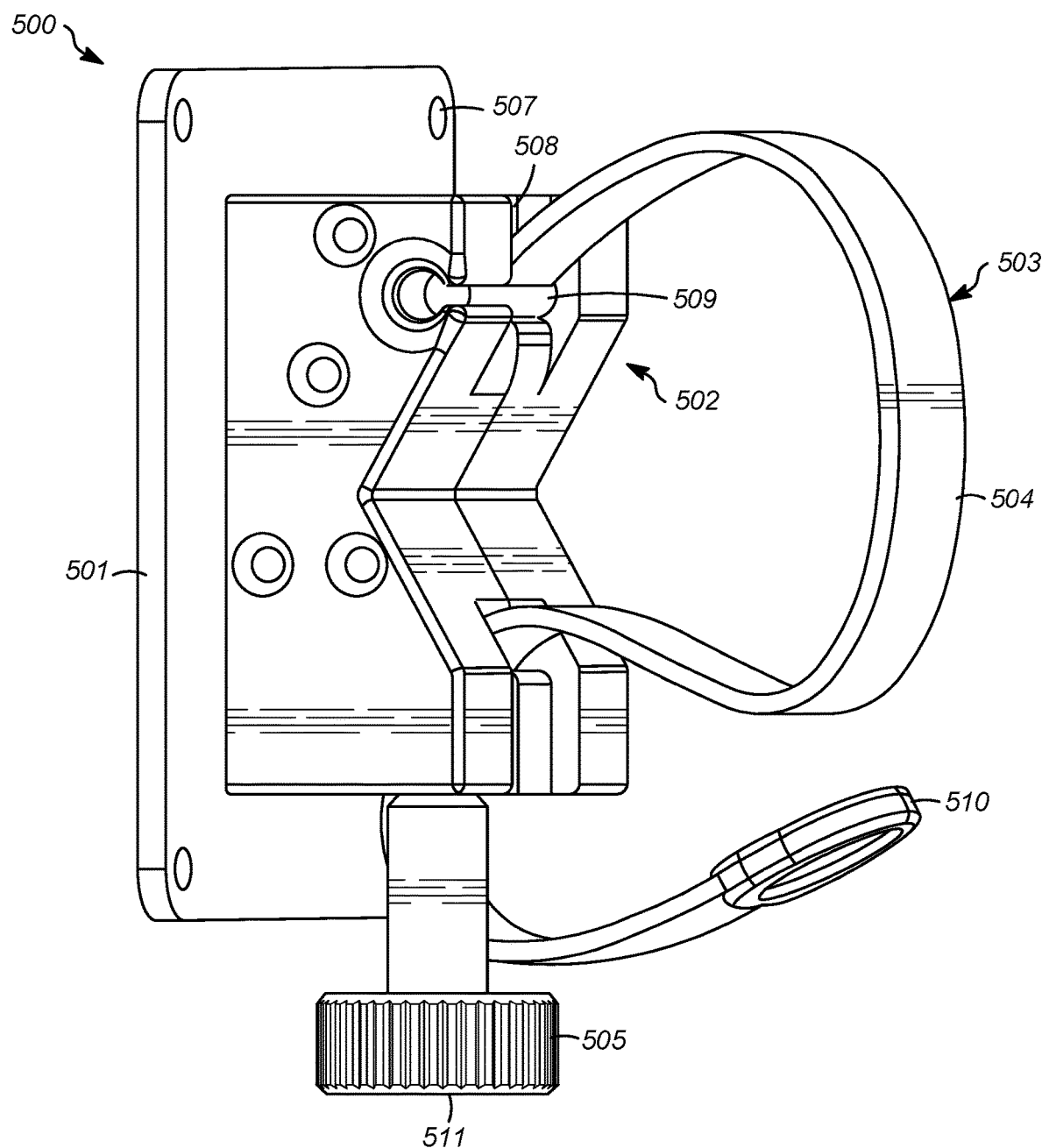
FIG. 63 is a back perspective view of a belt mount including a support plate, a base, a first fastener, and a second fastener.
Figure 65:
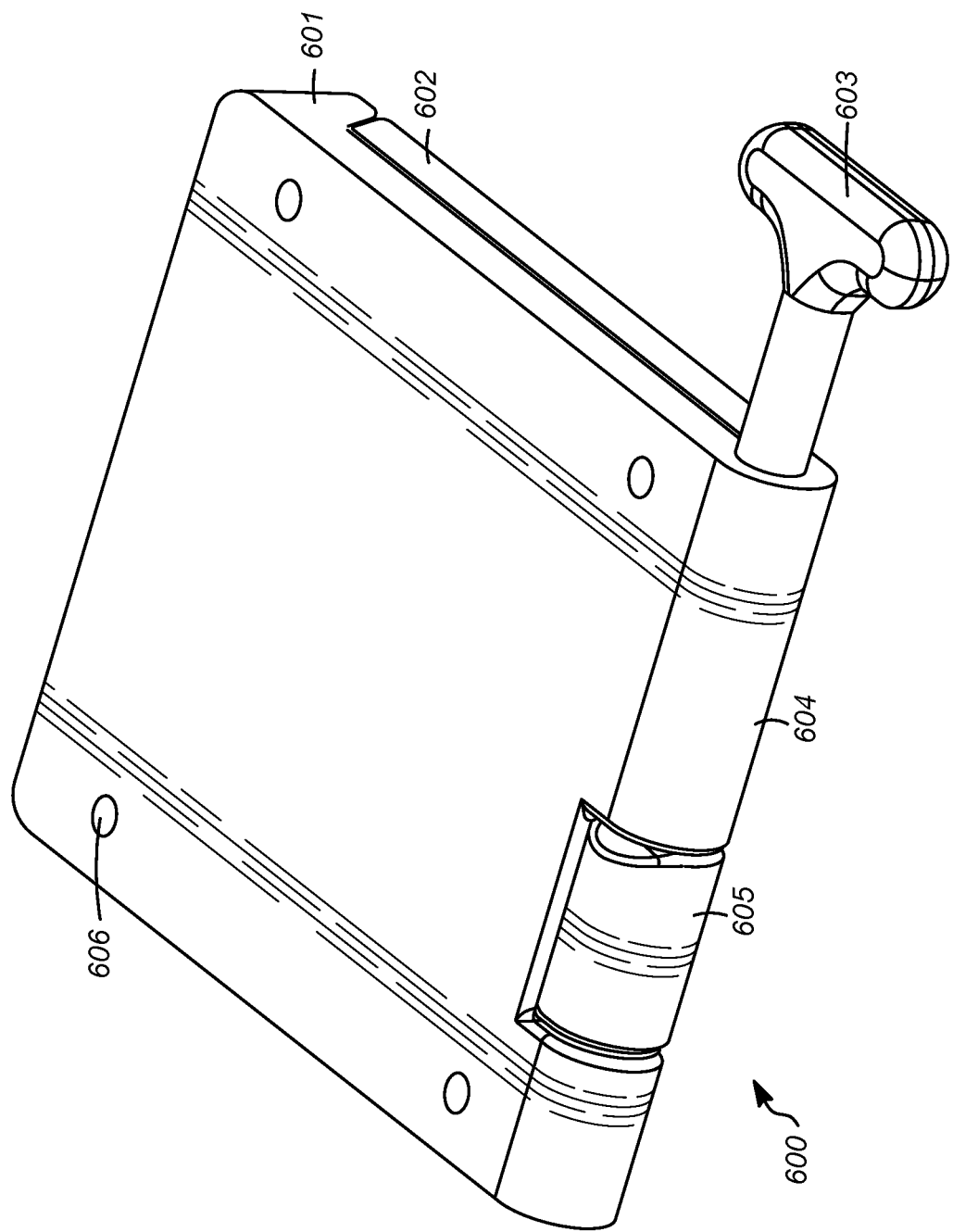
FIG. 65 is a top perspective view of a coupling including a first leaf, a second leaf, a pin, and a handle.
Figure 66:
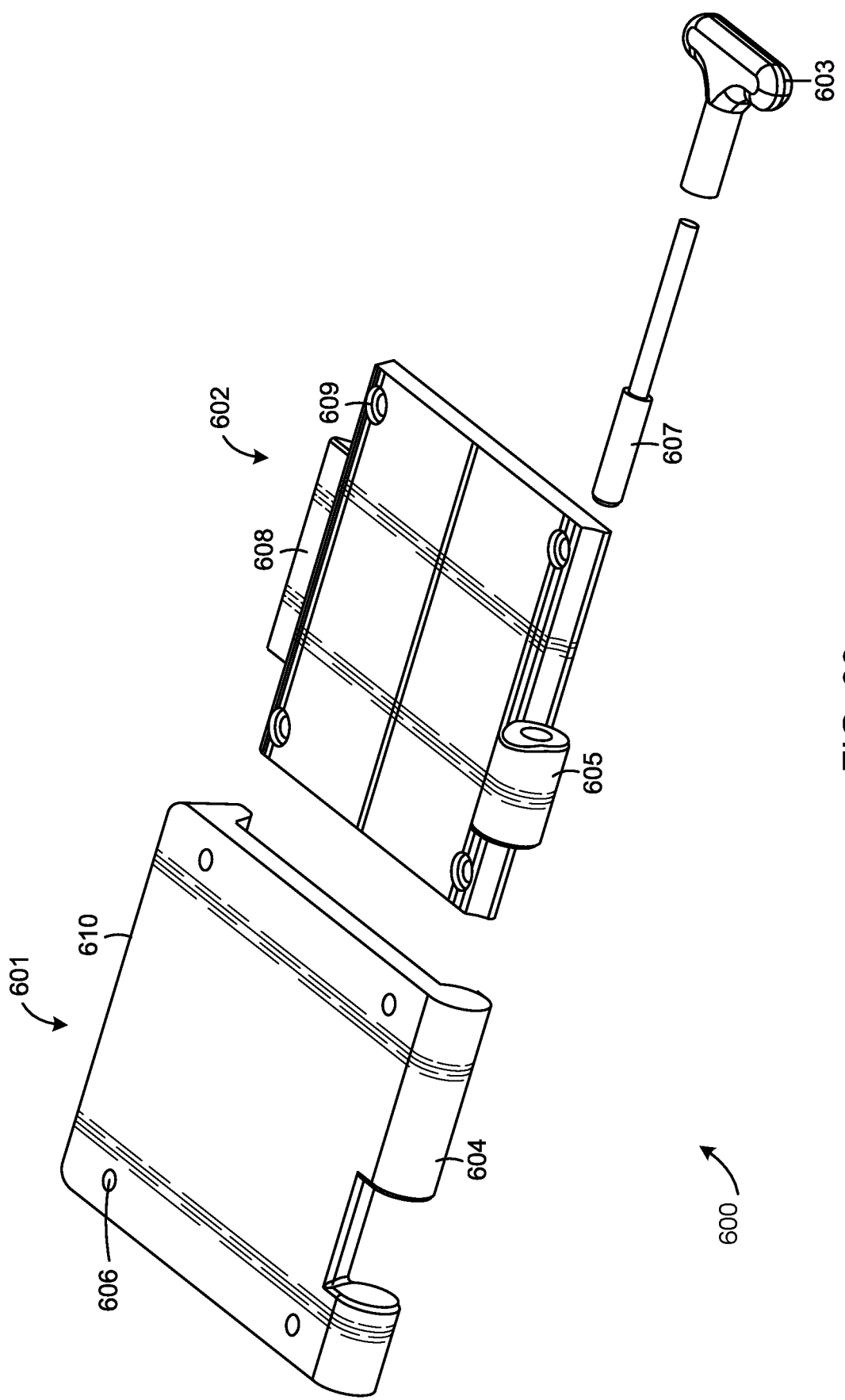
FIG. 66 is an exploded top perspective view of the coupling including the first leaf 601, the second leaf, the pin, and the handle.
Figure 67:
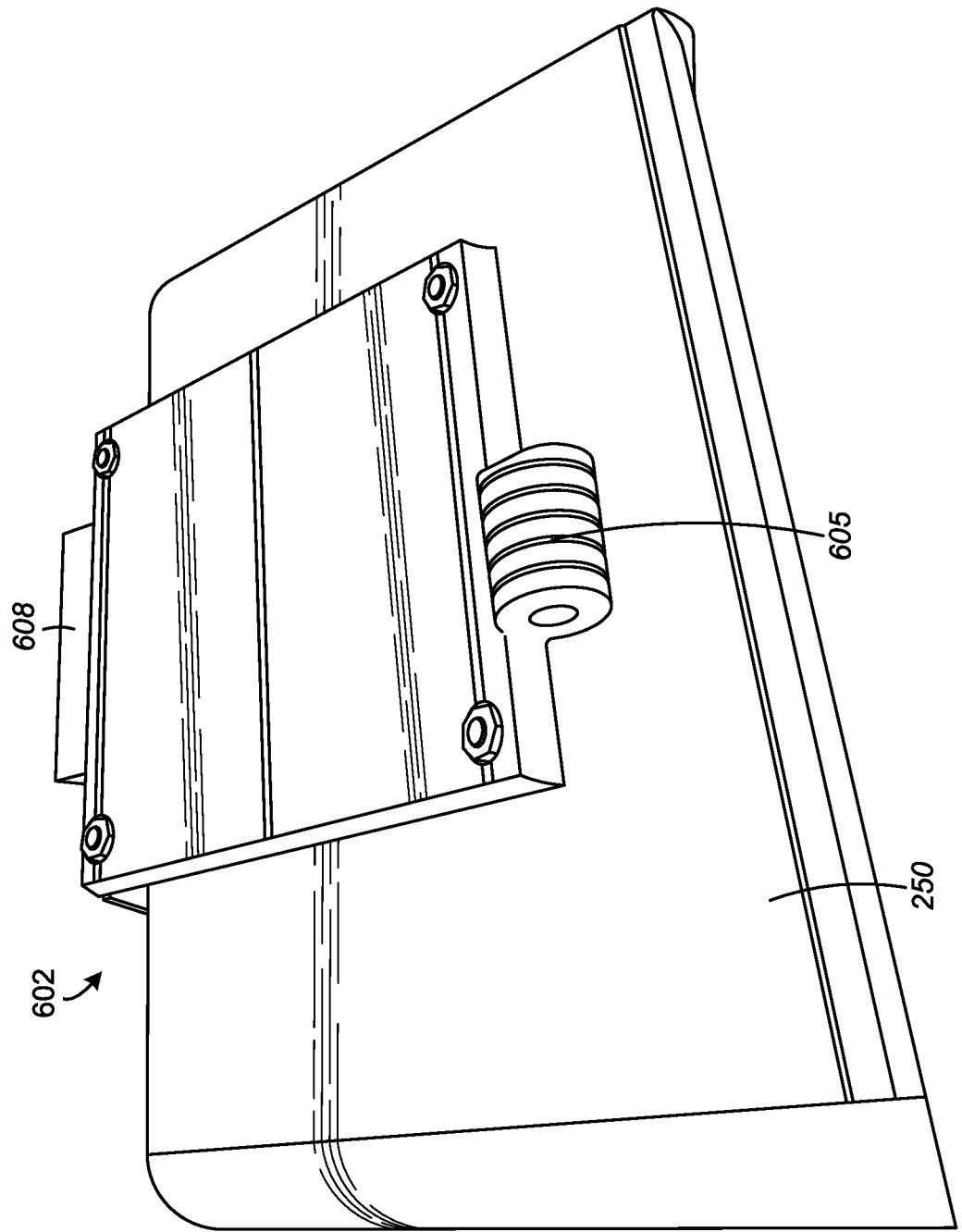
FIG. 67 is a bottom perspective view of the second leaf detachably secured to a rack.
Figure 68:
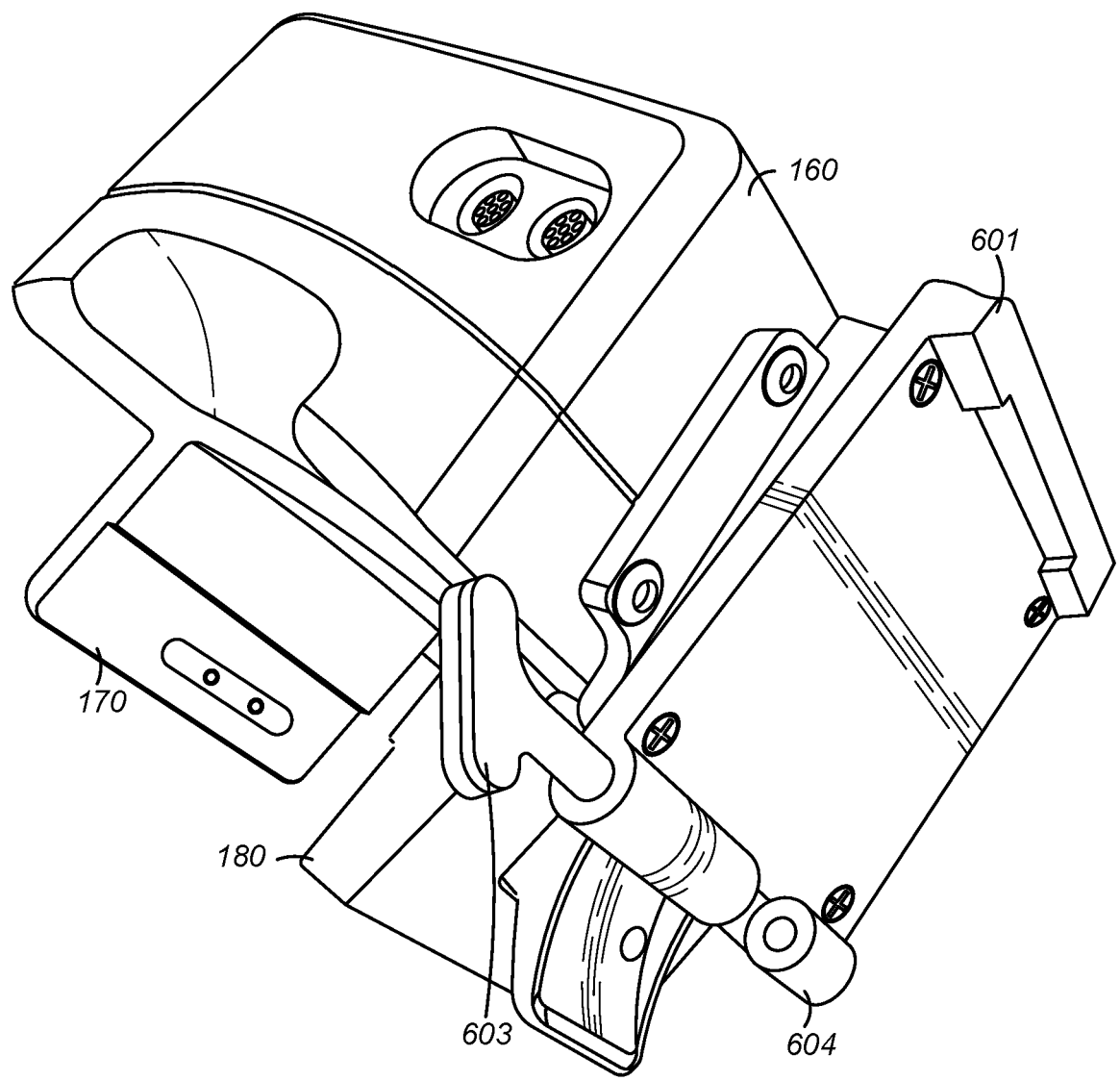
FIG. 68 is a bottom perspective view of the first leaf and the handle detachably secured to a monitor mount.
Figure 69:
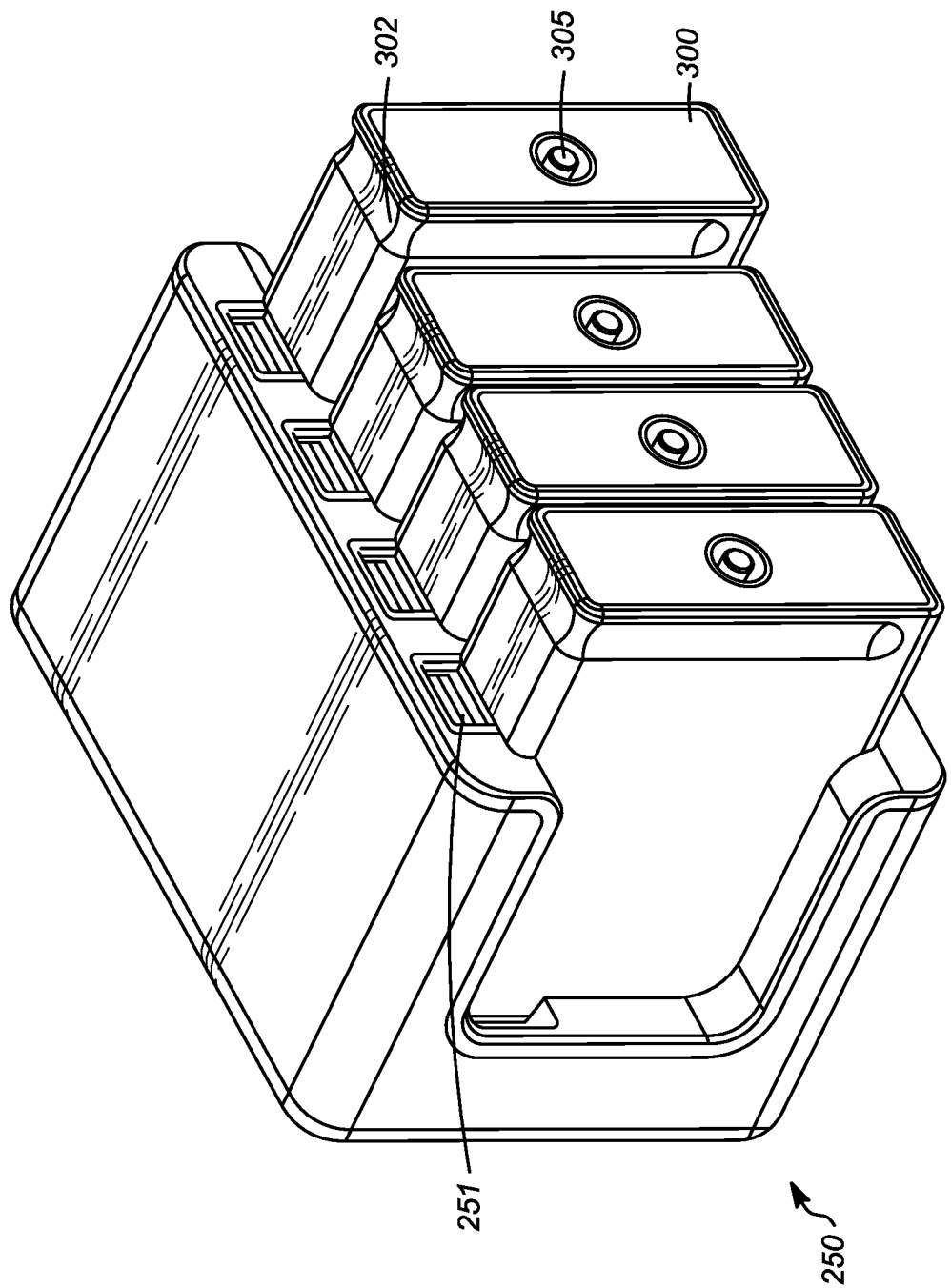
FIG. 69 is a front perspective view of a first exemplary implementation of a rack detachably securing first exemplary implementations of a module.
Figure 70:
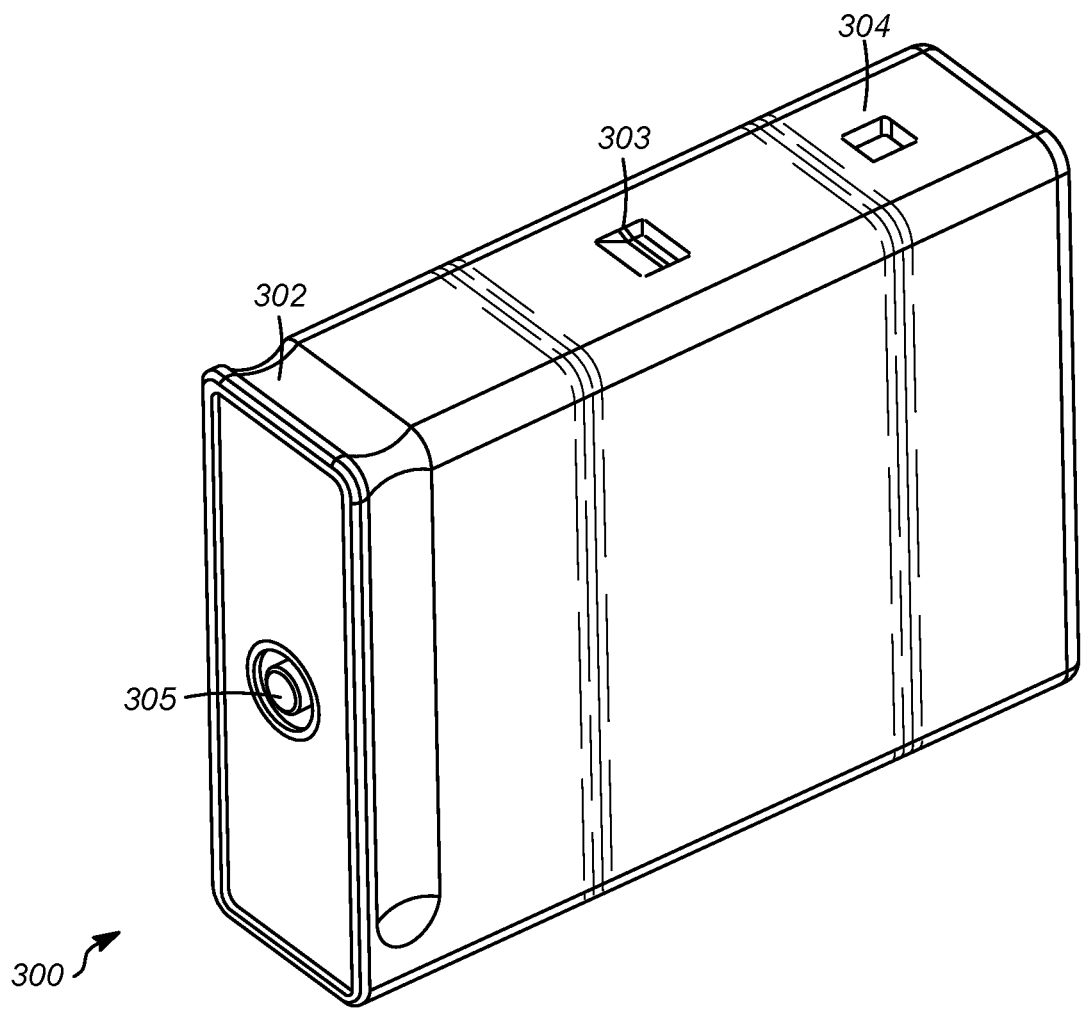
FIG. 70 is a side perspective view of the first exemplary implementation of the module.
Figure 71:
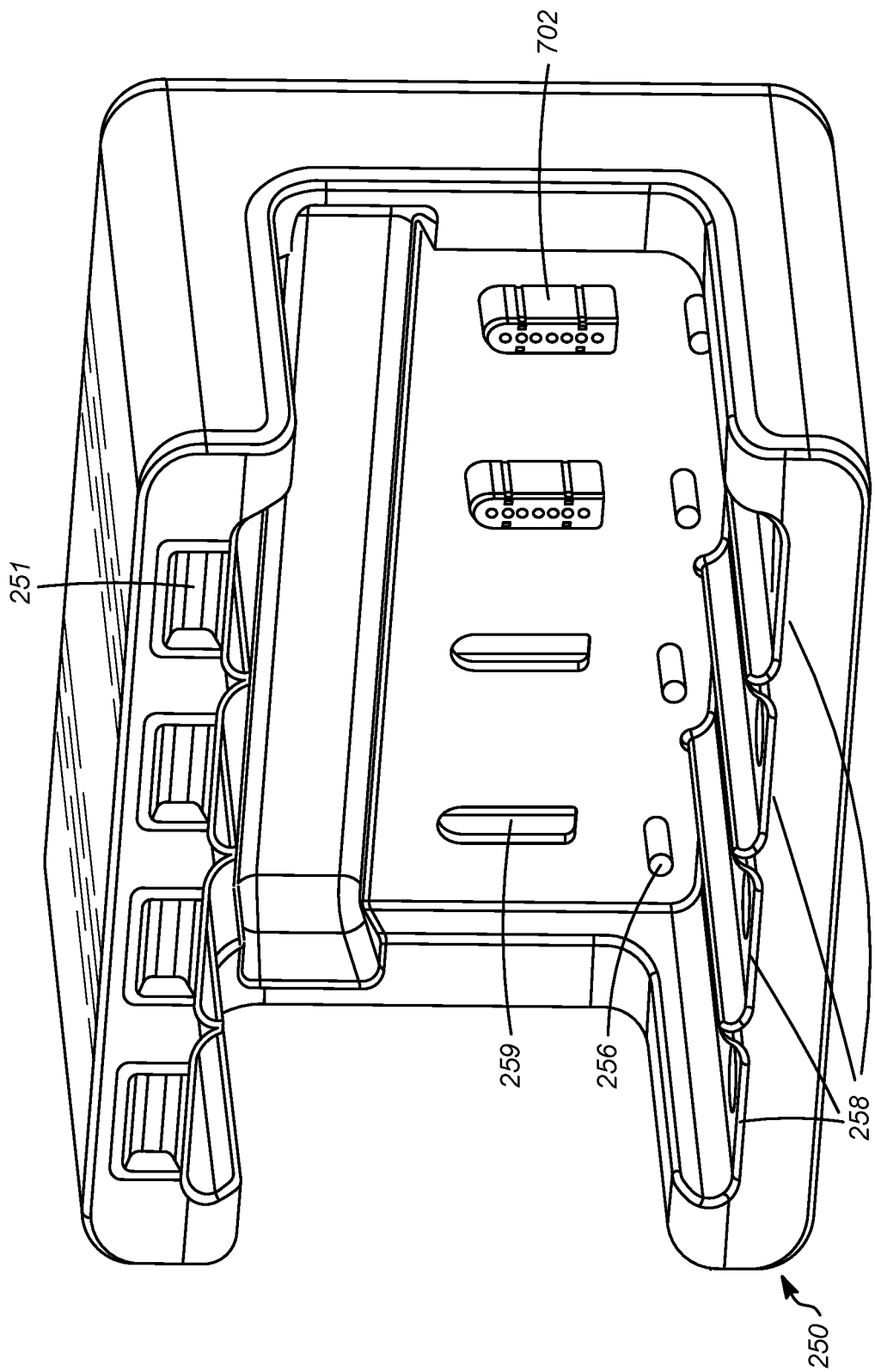
FIG. 71 is a front perspective view of the first exemplary implementation of the rack.
Figure 72:
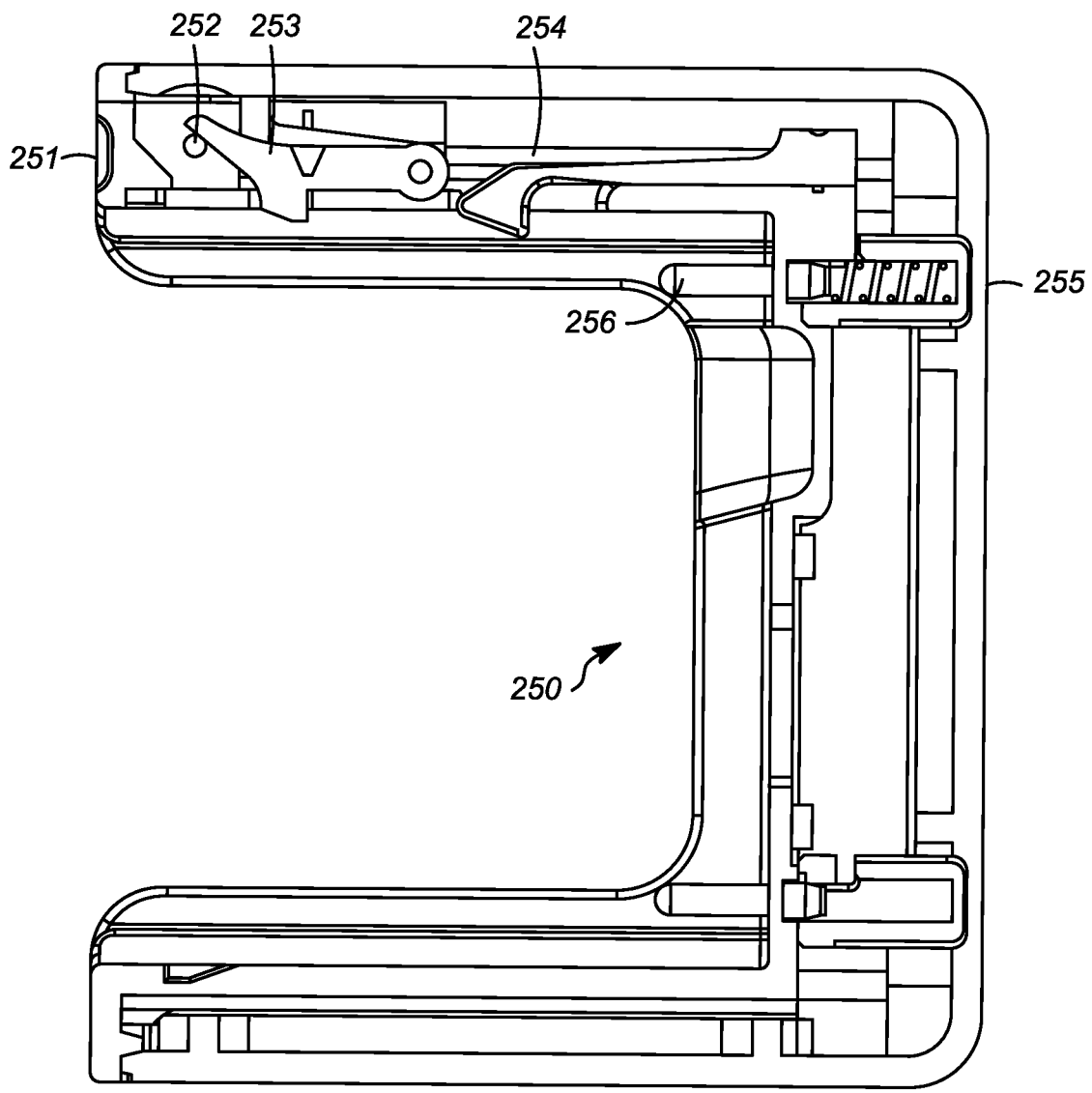
FIG. 72 is a cross-sectional view of the first exemplary implementation of the rack.
Figure 73:
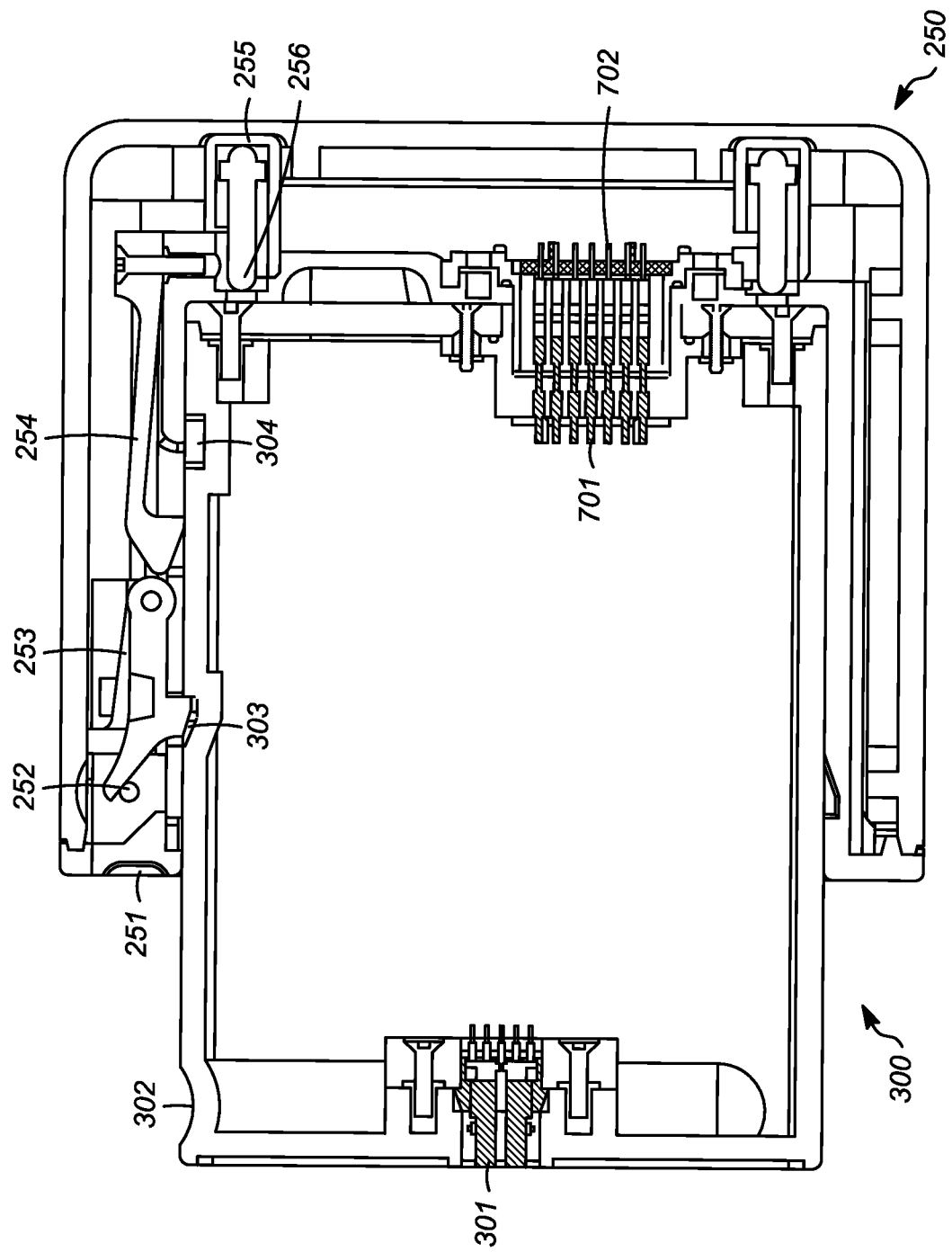
FIG. 73 is a cross-sectional view of the first exemplary implementation of the rack detachably securing the first exemplary implementation of the module.
Figure 74:
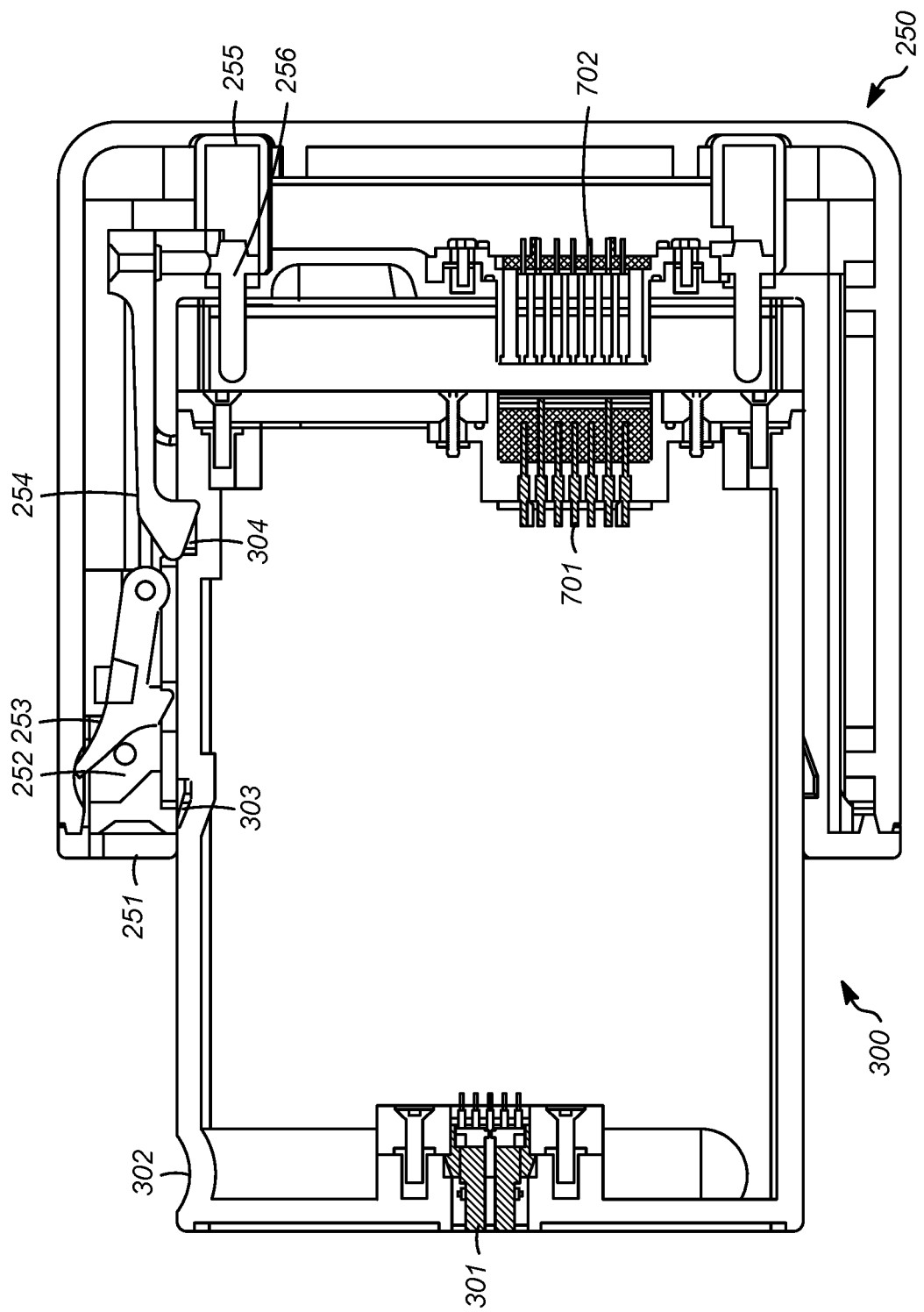
FIG. 74 is another cross-sectional view of the first exemplary implementation of the rack detachably securing the first exemplary implementation of the module.
Figure 75:
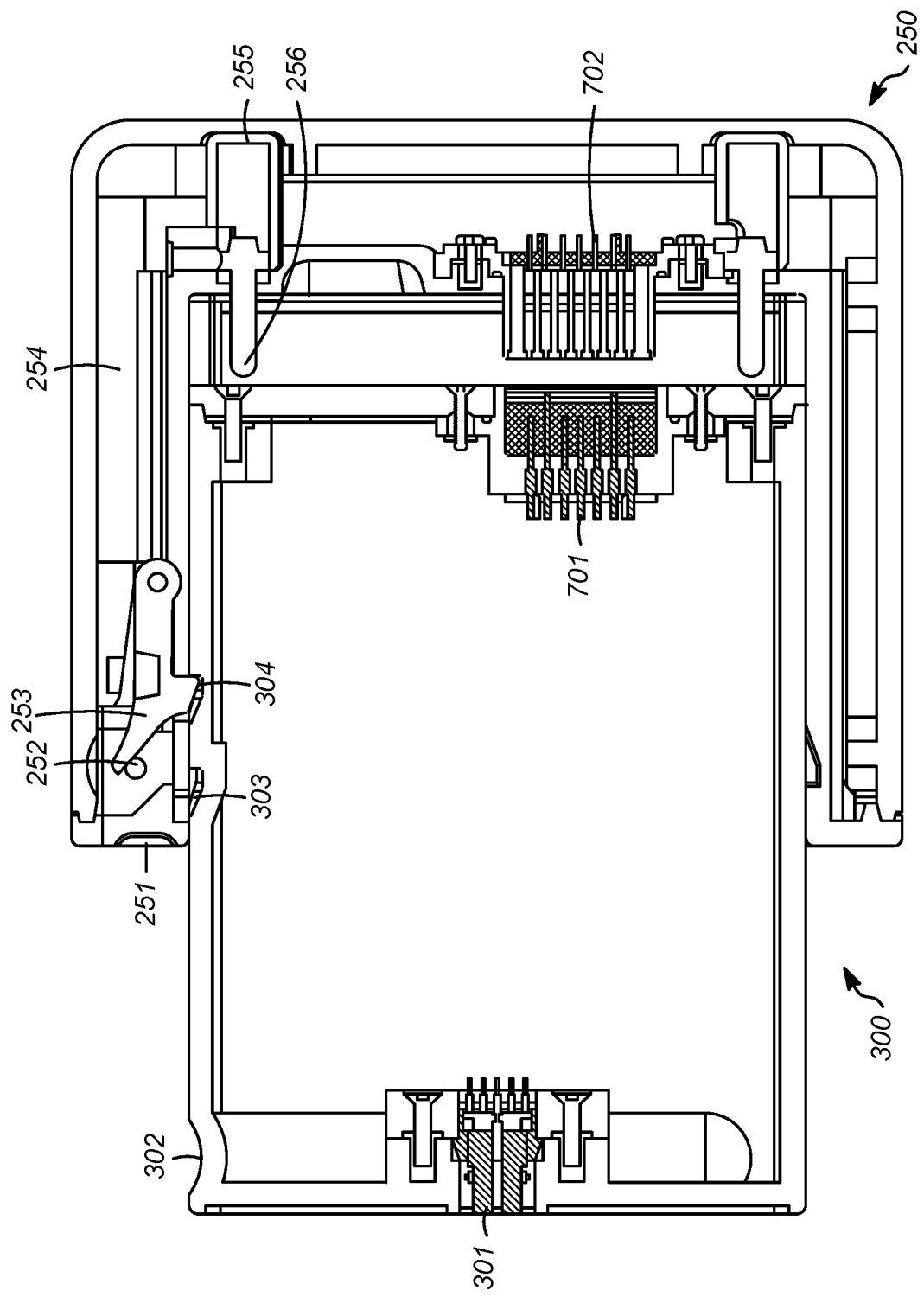
FIG. 75 is further cross-sectional view of the first exemplary implementation of the rack detachably securing the first exemplary implementation of the module.
Figure 76:
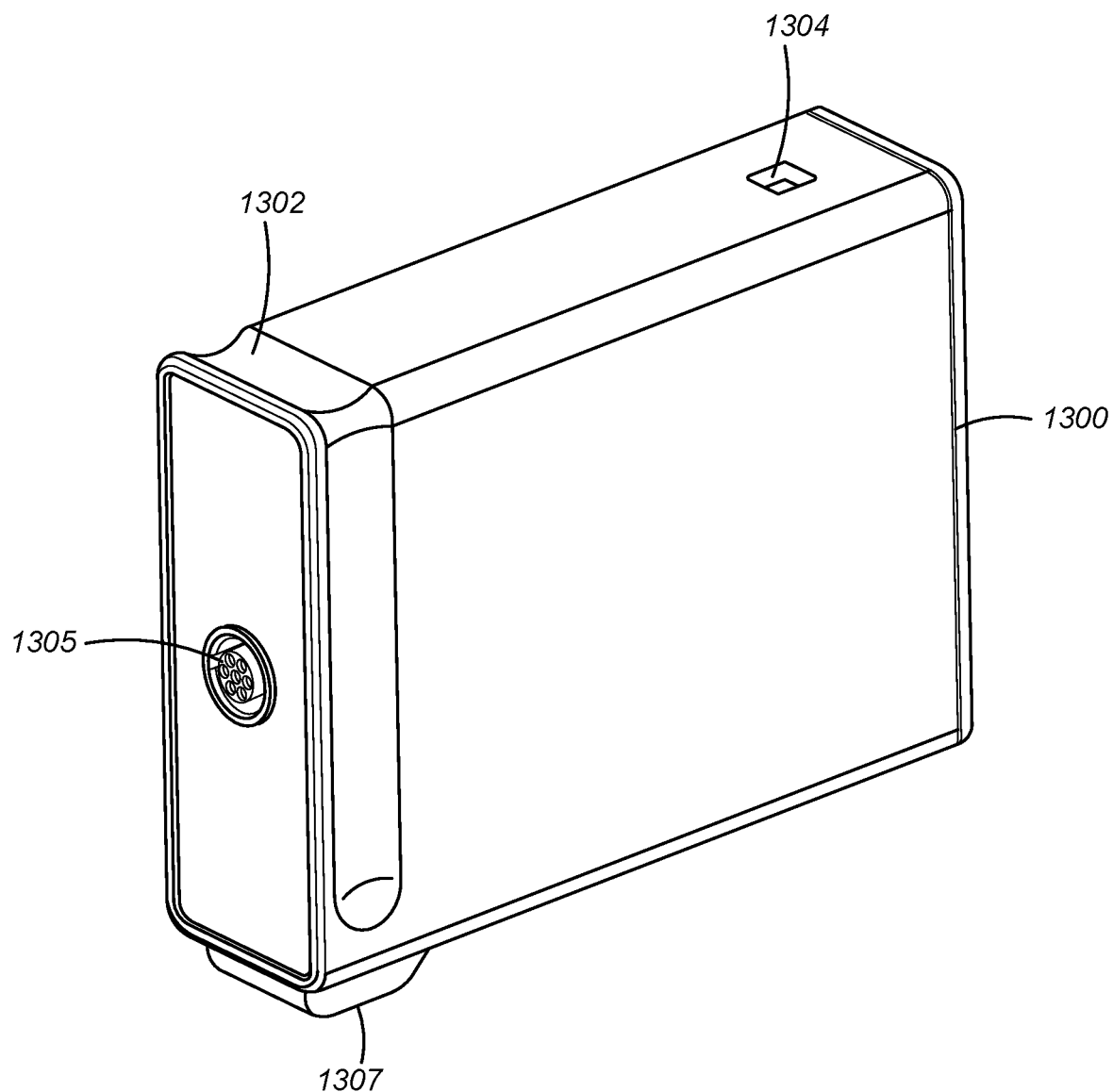
FIG. 76 is a side perspective view of the second exemplary implementation of the module.
Figure 77:
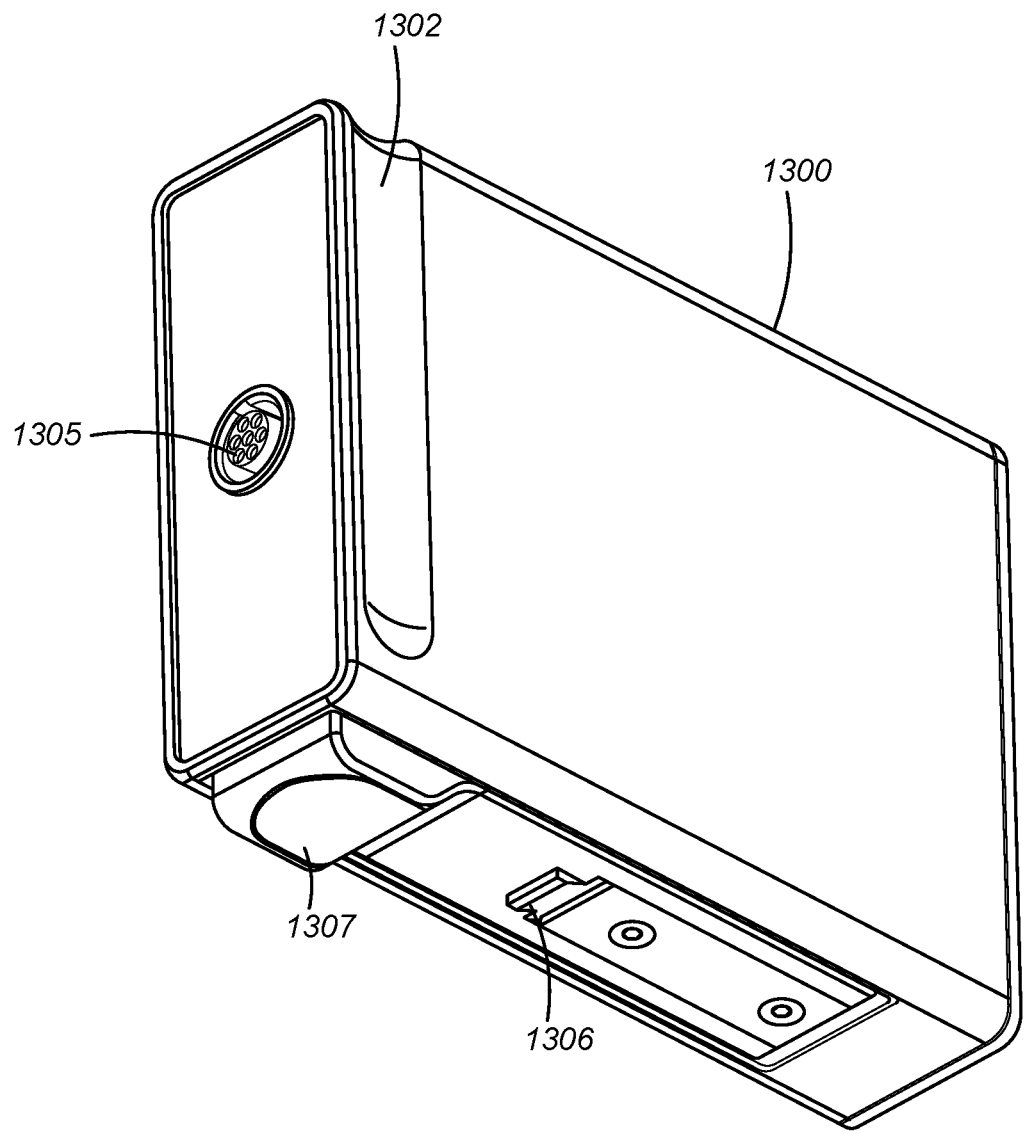
FIG. 77 is another side perspective view of the second exemplary implementation of the module.
Figure 78:
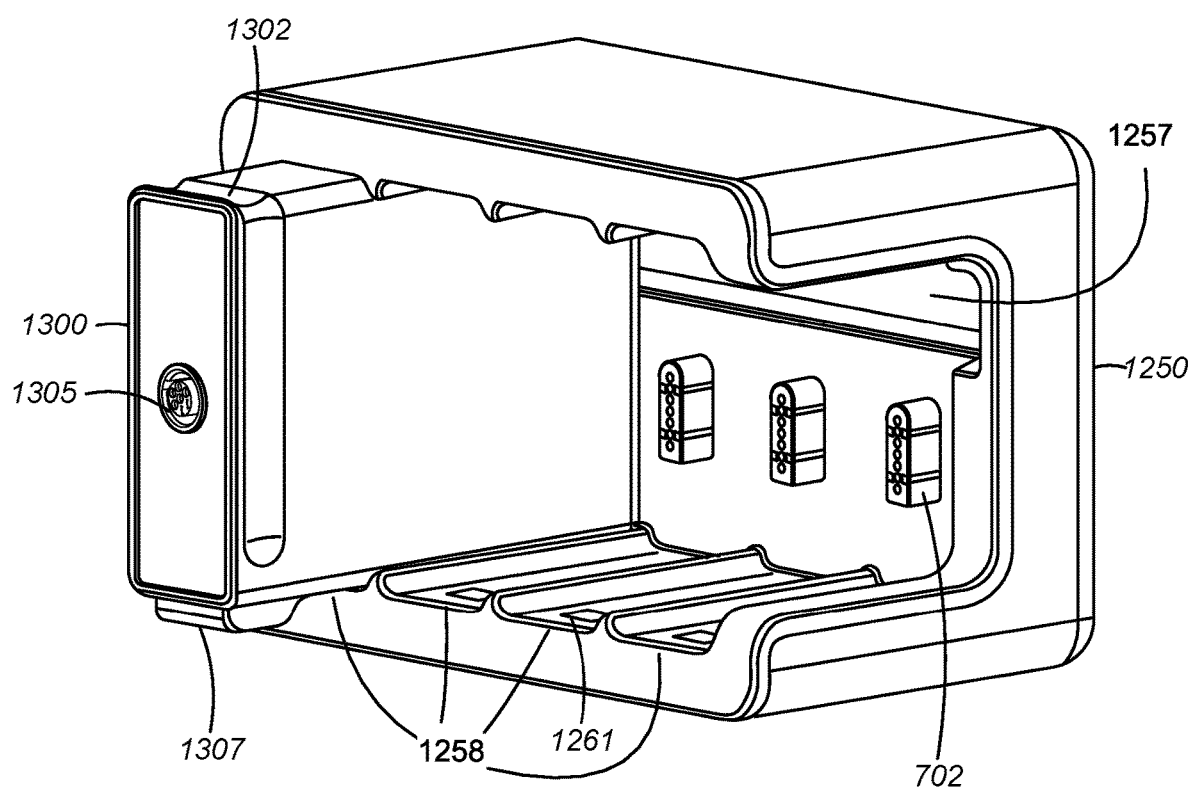
FIG. 78 is a front perspective view of a second exemplary implementation of the rack detachably securing a second exemplary implementation of the module.
Figure 79:
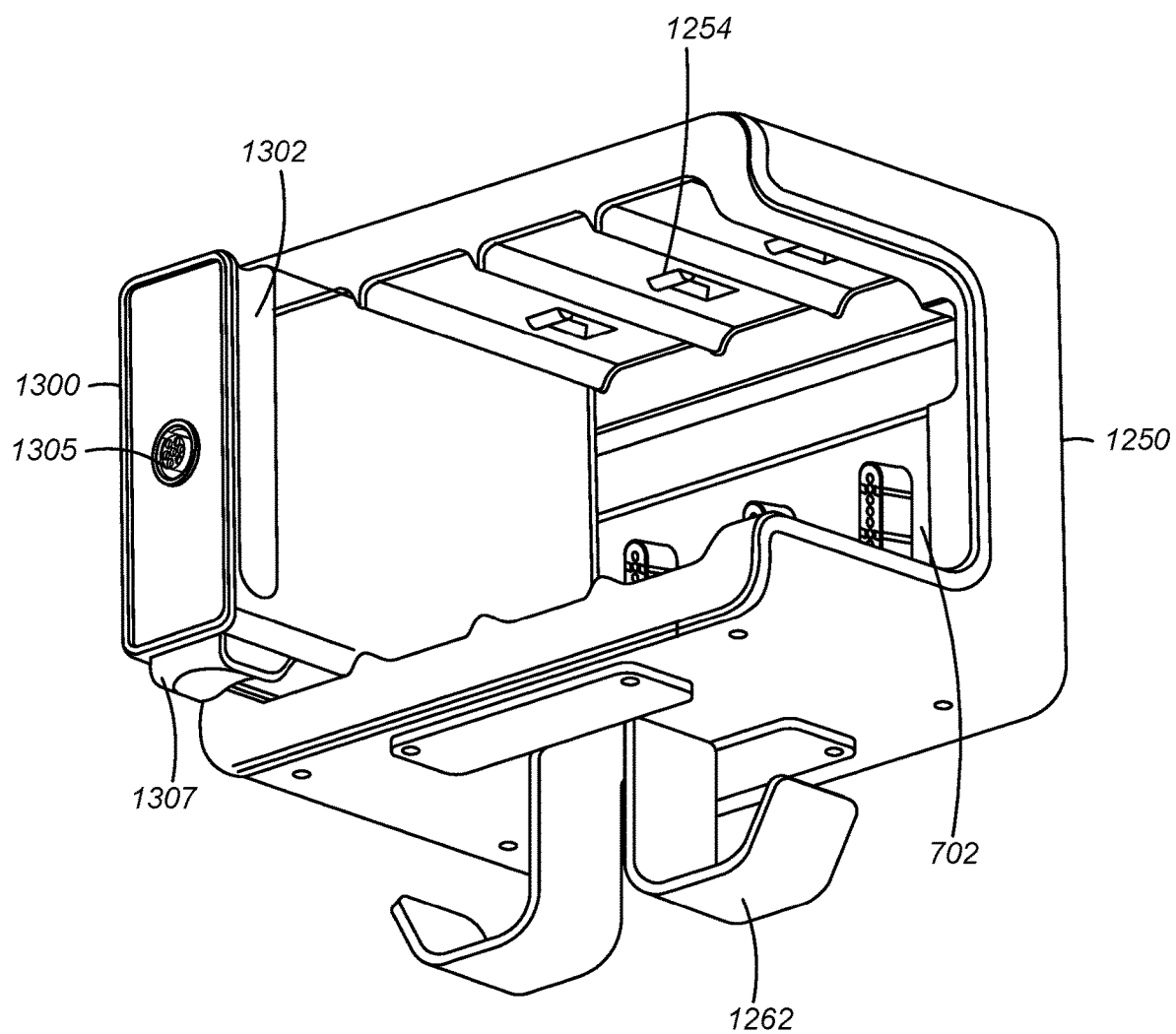
FIG. 79 is a front perspective view of the second exemplary implementation of the rack detachably securing the second exemplary implementation of the module and further including at least one cable management feature.
Figure 80:
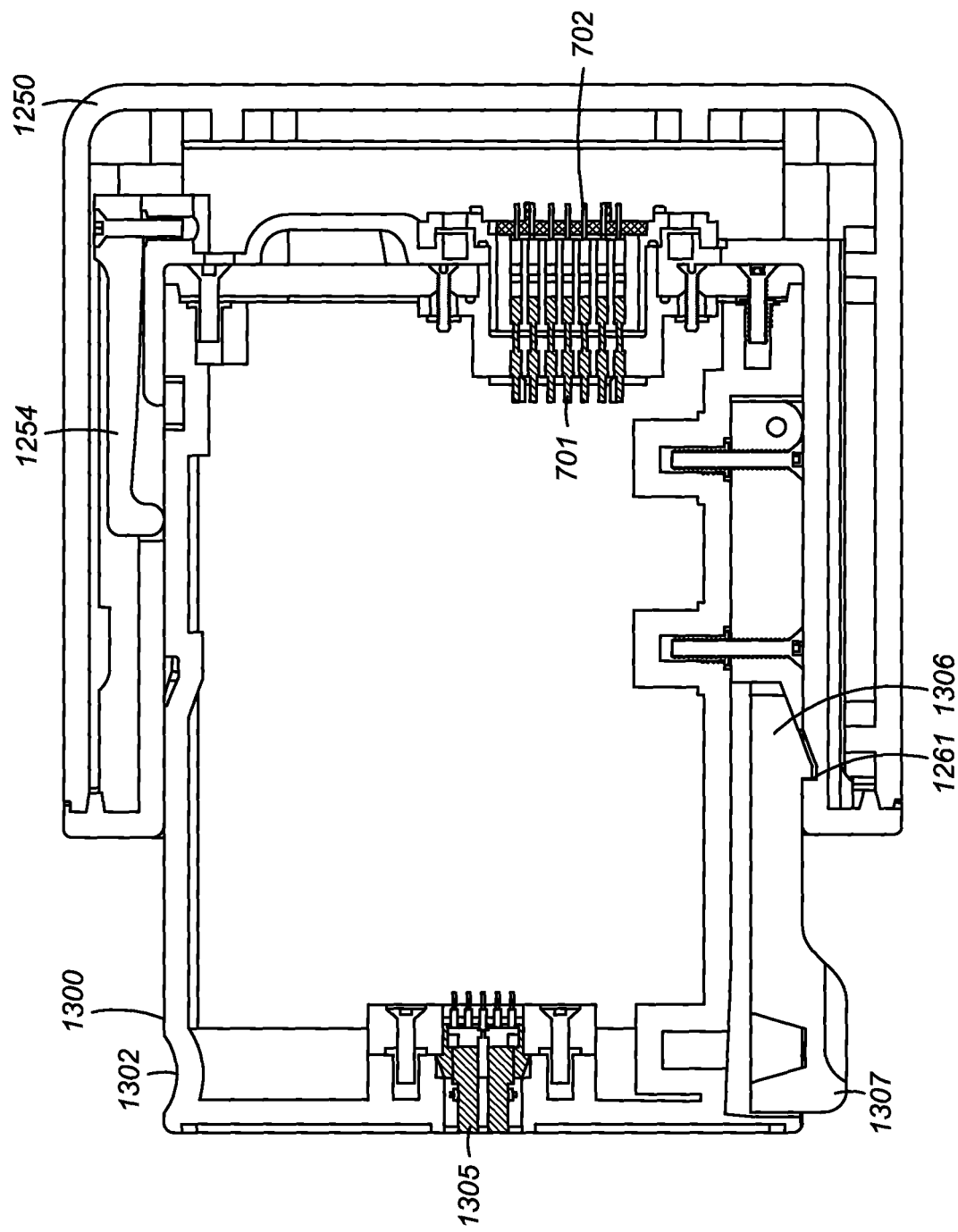
FIG. 80 is a cross-sectional view of the second exemplary implementation of the rack detachably securing the second exemplary implementation of the module.
Figure 81:
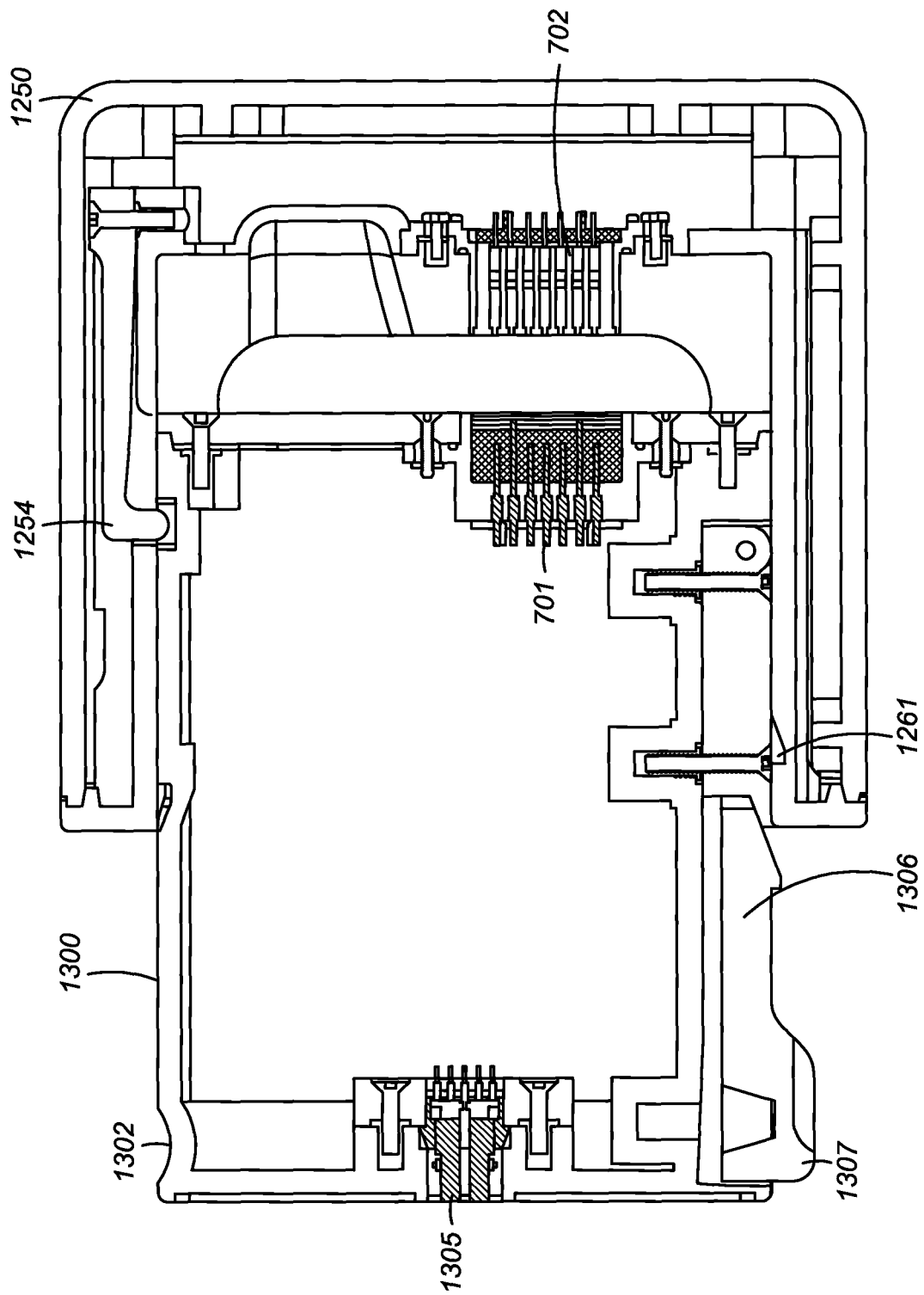
FIG. 81 is another cross-sectional view of the second exemplary implementation of the rack detachably securing the second exemplary implementation of the module.
Figure 82:
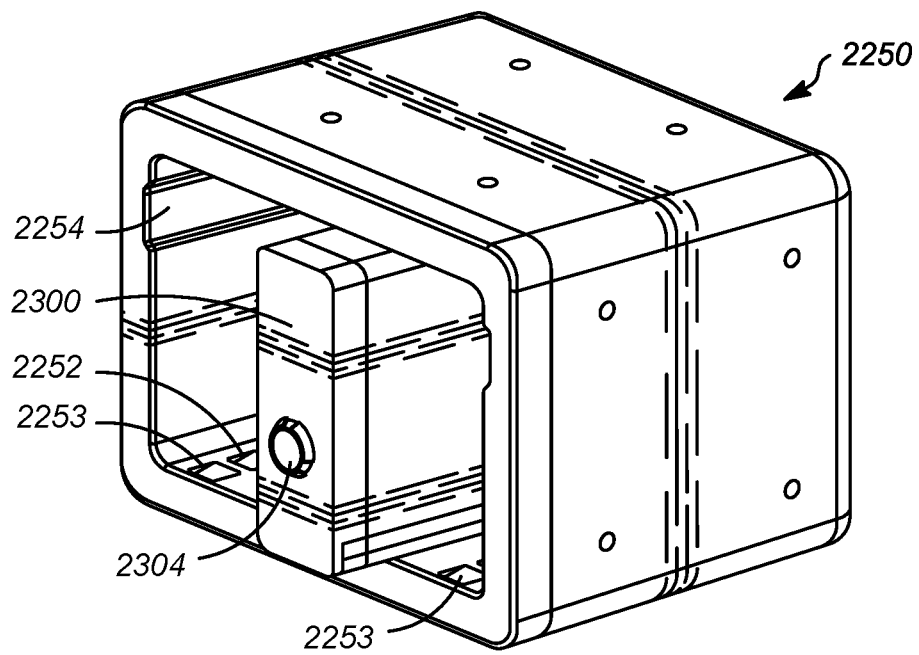
FIG. 82 is a front perspective view of a third exemplary implementation of a rack detachably securing a third exemplary implementation of a module.
Figure 83:
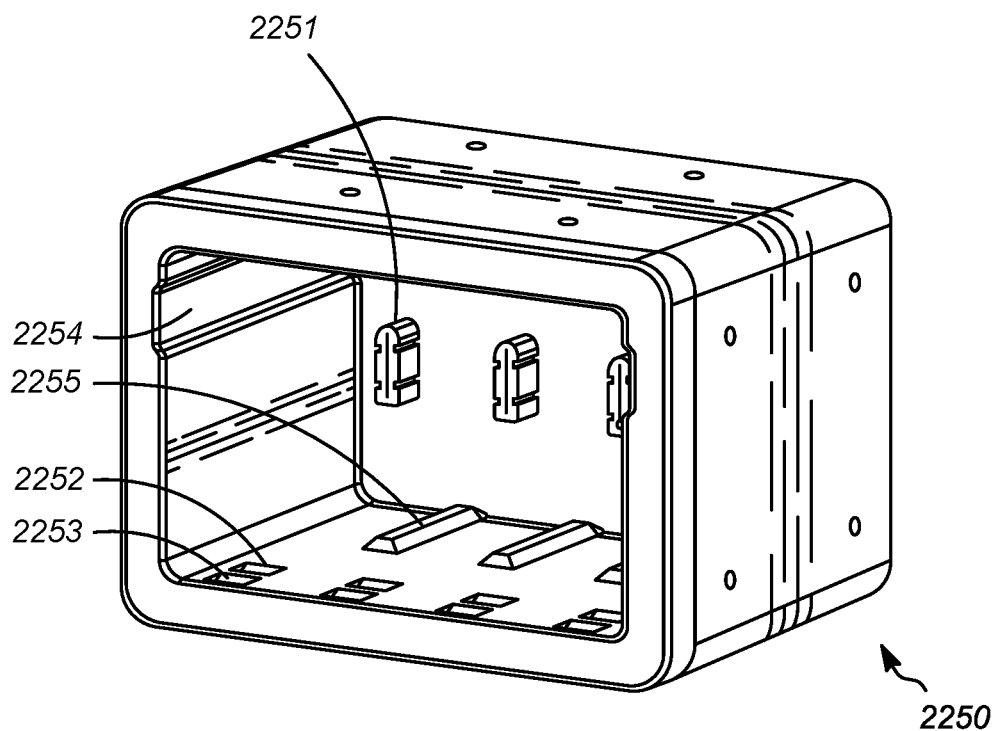
FIG. 83 is a front perspective view of the third exemplary implementation of the rack.

In the embodiments shown in FIGS. 37-58, the dock 200 can detachably secure (or otherwise physically interface with) the small monitor 120 and/or one or more of a module 300. A coupling 400 (as shown in FIG. 59) may be used to detachably secure a device (e.g., monitor, rack, module, etc.) to a mount (e.g., monitor mount, workstation, stand, etc.). A belt mount 500 (as shown in FIG. 63) may be used to detachably secure a device (e.g., monitor, rack, module, etc.) to a support structure 900 (e.g., bed, stretcher, gurney rail, IV pole, ambulance bar, monitor mount, workstation, stand, etc.). A coupling 600 (as shown in FIG. 65) may be used to detachably secure a device (e.g., monitor, rack, module, etc.) to a mount (e.g., monitor mount, workstation, stand, etc.).

In the embodiments shown in FIGS. 69-87, a rack 250, 1250, 2250 can detachably secure (or otherwise physically interface with) one or more of modules 300, 1300, 2300. In the embodiments shown in FIGS. 88-101, male and female portions or connectors 701*a*-701*c*, 702*a*-702*e* can be used to electrically connect any two or more devices (e.g., a monitor mount 160, a rack 250, and/or a module 300).

In an exemplary implementation, as shown in FIGS. 1A and 1B, the monitor mount 160 may be detachably secured to a support structure 800 (e.g., a wall-mounted arm) via any attachment mechanism 801 such as a Video Electronics Standards Association (VESA) mounting interface 802 adapted to an attachment mechanism 801 in a hospital room in which a patient 110 is being monitored and/or treated via one or more of module 300, for example one or more physiological sensors and/or medical devices. The monitor mount 160 may detachably secure the large monitor 140, and the large monitor 140 can detachably secure (or otherwise physically interface with) the small monitor 120. The rack 250 may be coupled to the monitor mount 160 via a coupling, for example, the coupling 400 or the coupling 600. The rack 250 may detachably secure one or more of the module 300. The dock 200 may be detachably secured to a support structure 900 (e.g., a bed rail) to await use on transport for detachably securing the small monitor 120 and/or the one or more of module 300, for example. Alternatively, the dock 200 may serve as a stationary monitor mount. In addition to the dock 200 or in lieu of the dock 200, a coupling such as the belt mount 500 may be detachably secured to the support structure 900 (e.g., a bed rail) to await use on transport for detachably securing the small monitor 120, for example. Alternatively, the belt mount 500 may serve as a stationary monitor mount. In the embodiment shown in FIGS. 1A and 1B, a cable 700 including a male connector 701 and a female connector 702 may be used to electrically connect the monitor mount 160, the rack 250, and/or the one or more of module 300.

Therefore, the example system provides an interconnected, versatile, and comprehensive patient care solution with a high degree of configurability. The example system acquires data at the bedside and on transport, without having to disconnect a patient as he or she is moved from care area to care area. The example system can be scaled depending on the patient's changing acuity level and medical devices can be customized to better suit hospital protocols and use models. Accordingly, the example system thereby improves clinical workflow.

Figure 9:
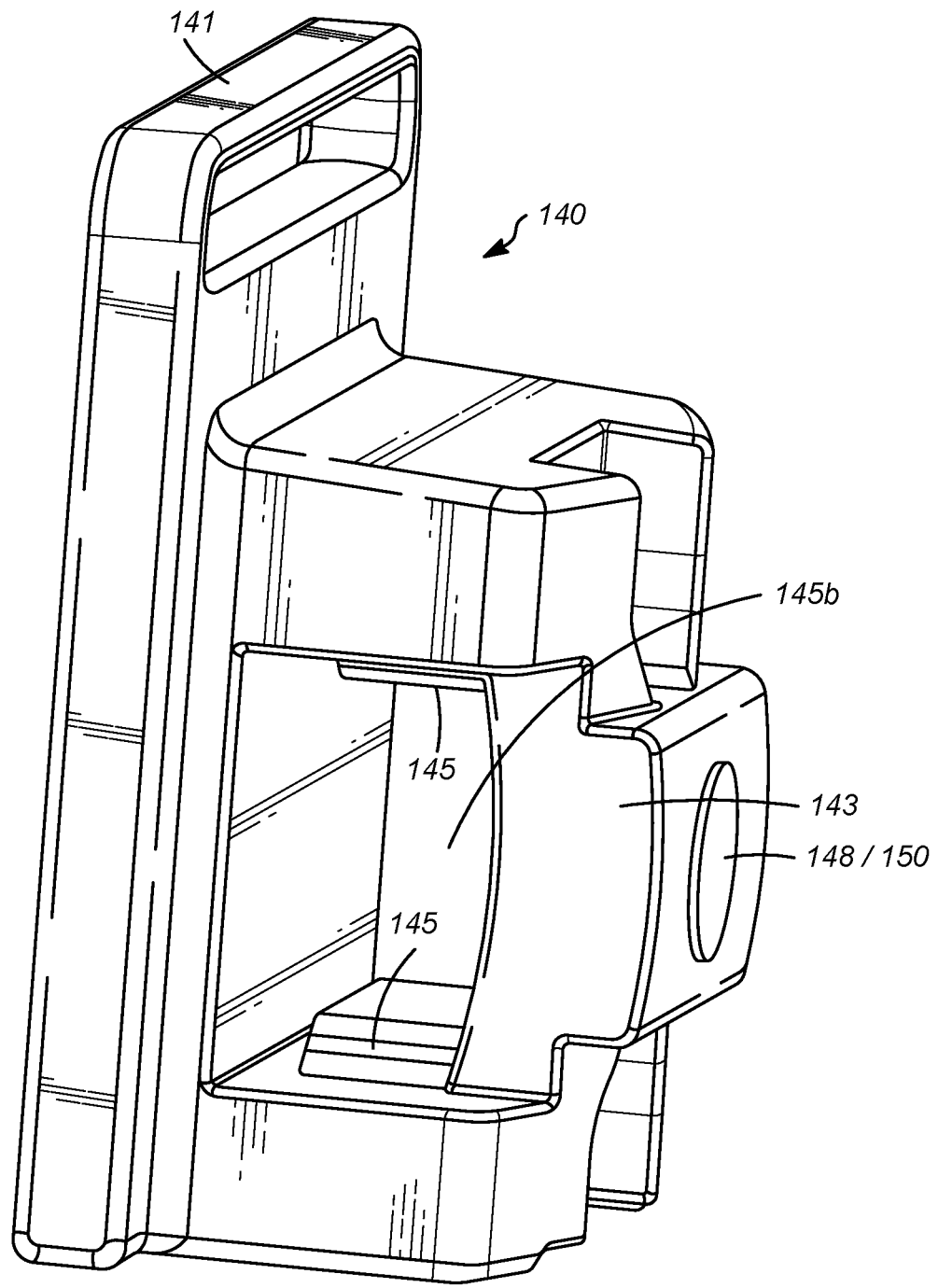
FIG. 9 is a side perspective view of a first exemplary implementation of the large monitor 140.
Figure 10:
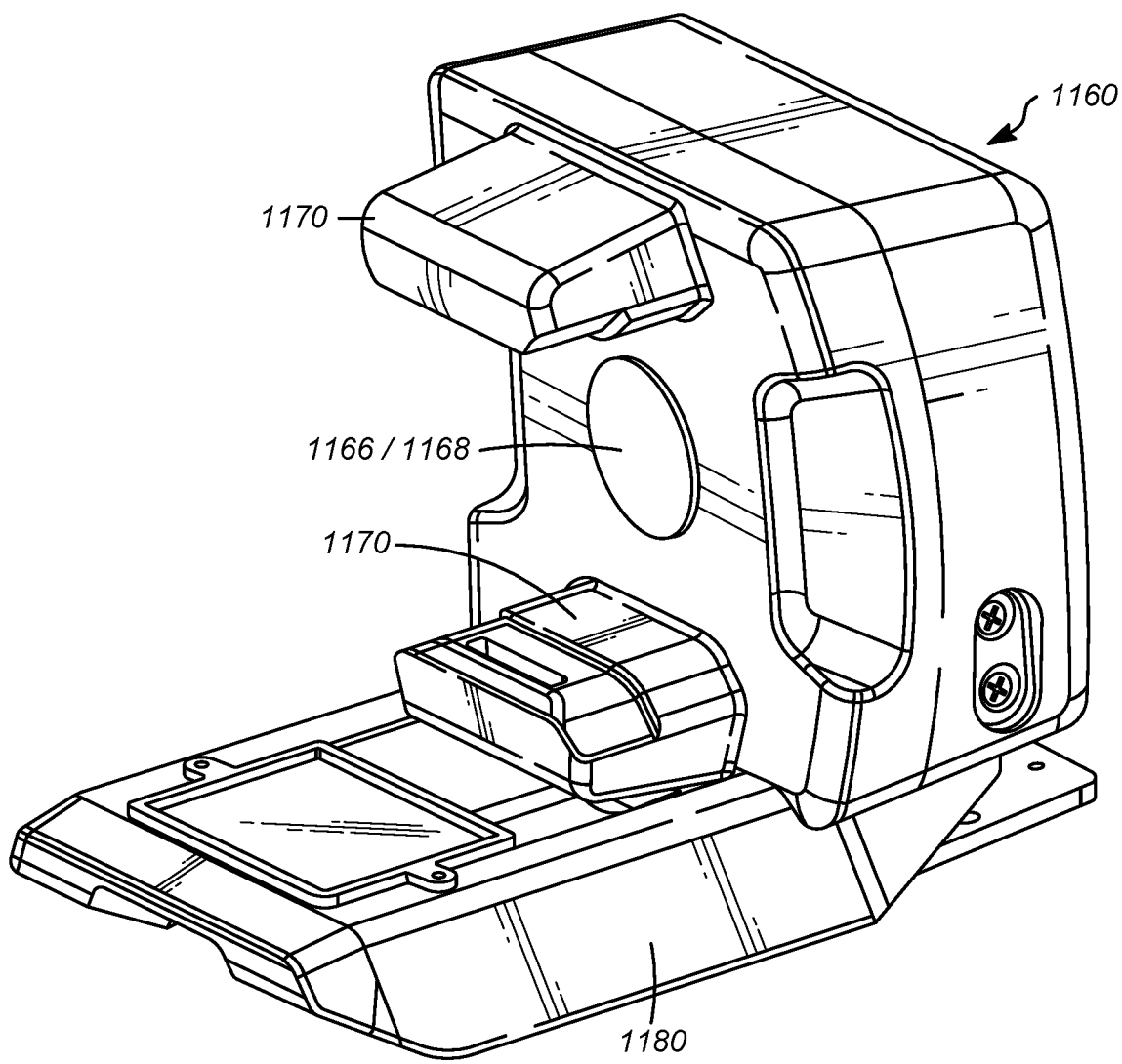
FIG. 10 is a perspective view of a second exemplary implementation of the monitor mount 160.
Figure 11:
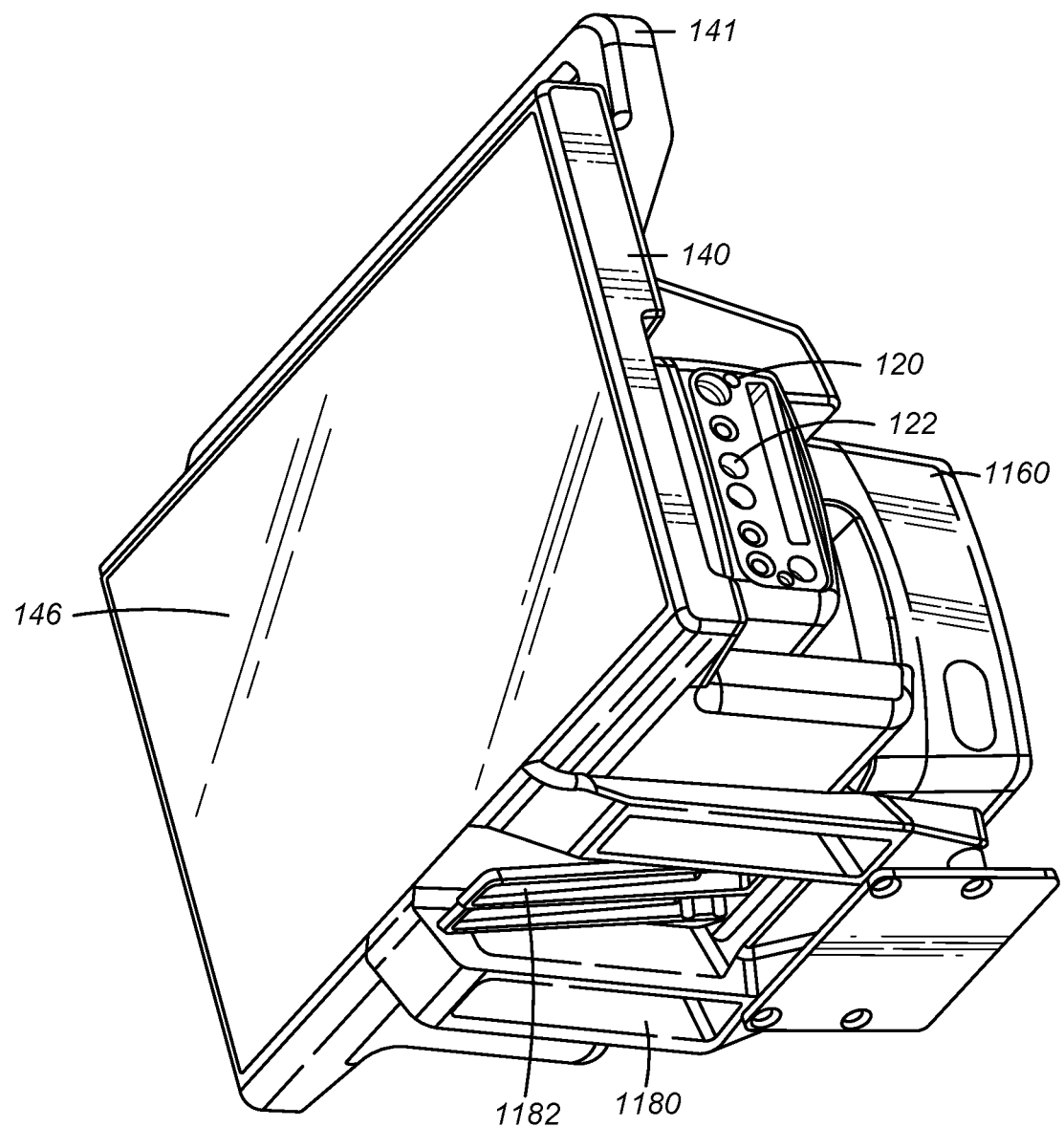
FIG. 11 is a bottom perspective view of the example system including the second exemplary implementation of the monitor mount detachably securing both of the small monitor 120 and the first exemplary implementation of the large monitor.
Figure 12:
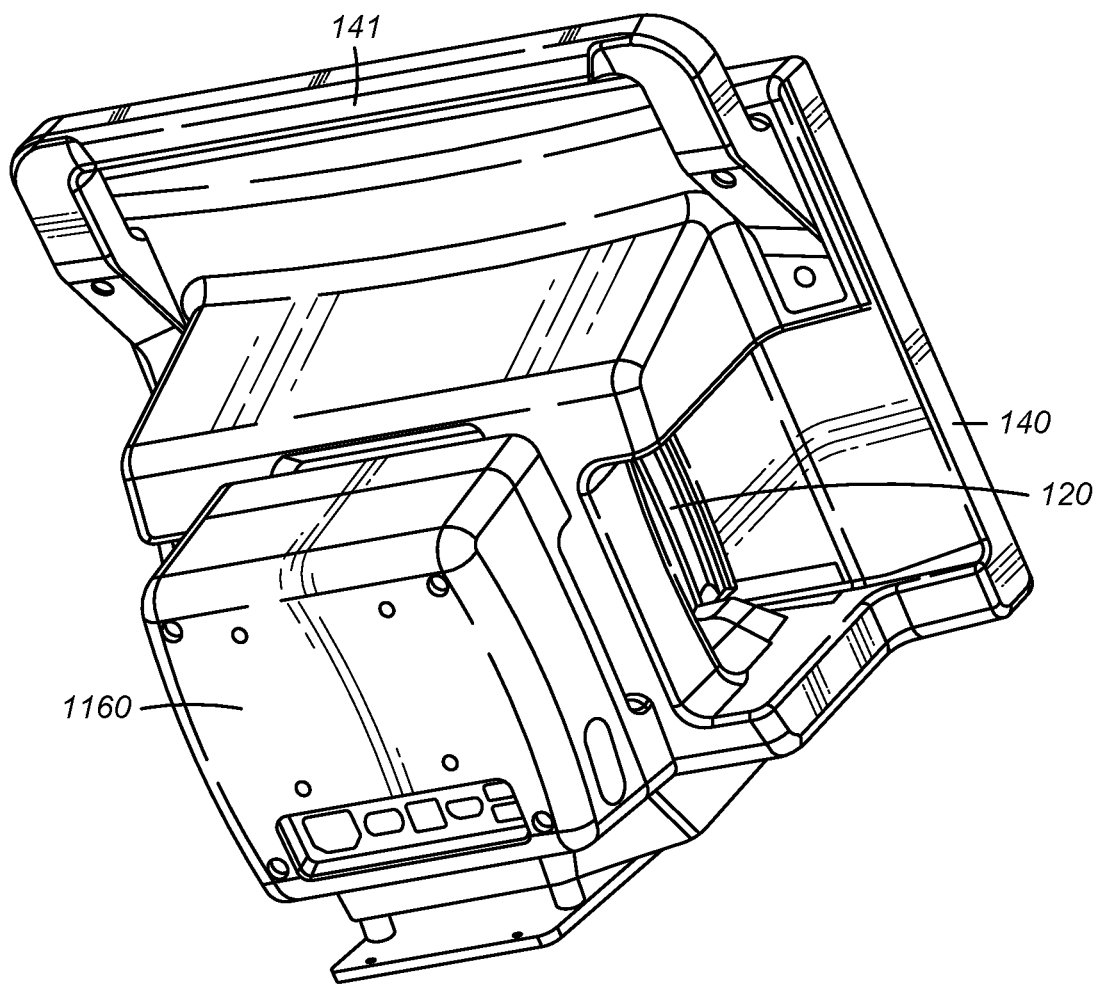
FIG. 12 is a back perspective view of the example system including the second exemplary implementation of the monitor mount detachably securing both of the small monitor 120 and the first exemplary implementation of the large monitor.
Figure 14:
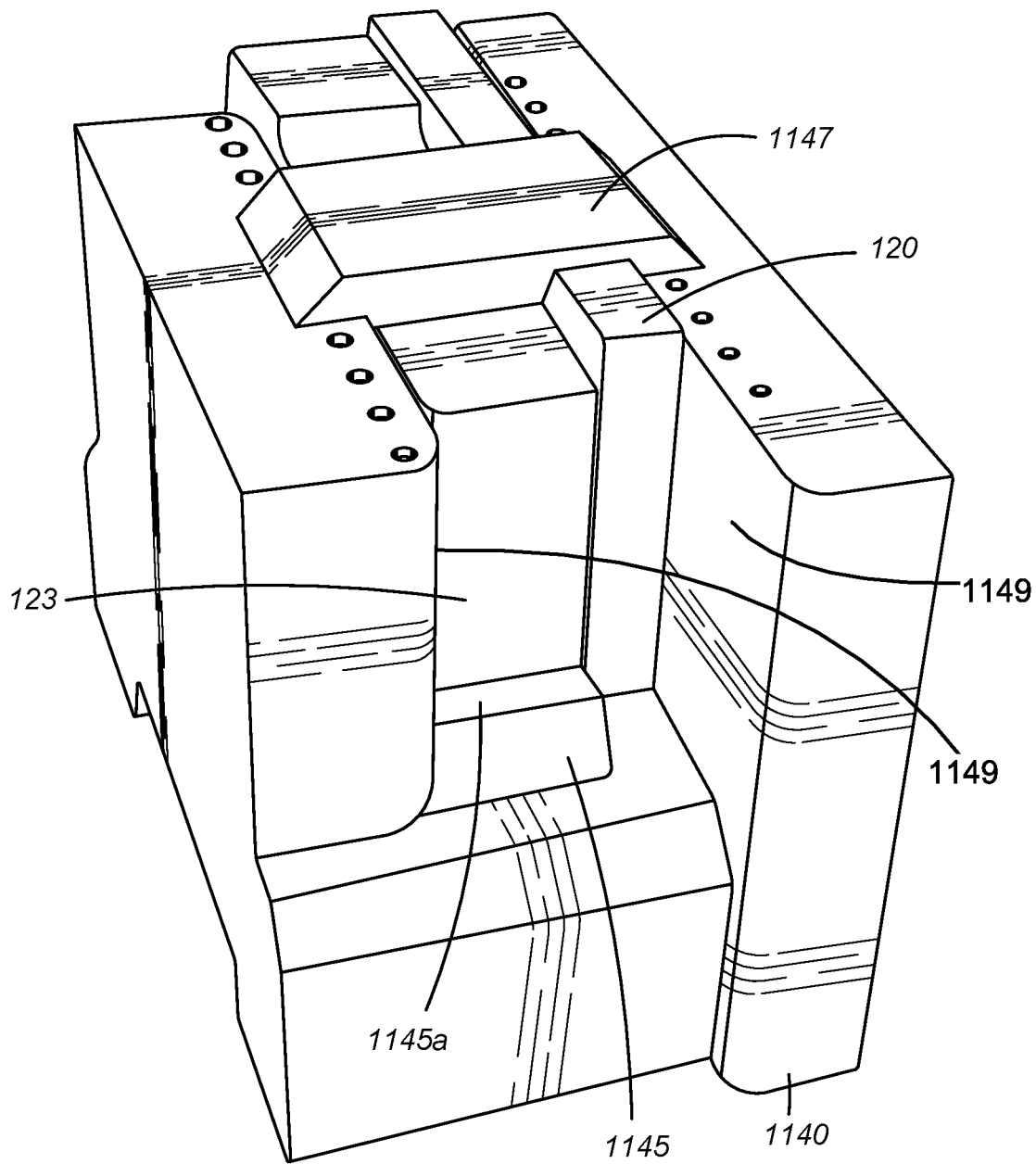
FIG. 14 is a side perspective view of a second exemplary implementation of the large monitor 1140 detachably securing the small monitor.
Figure 15:
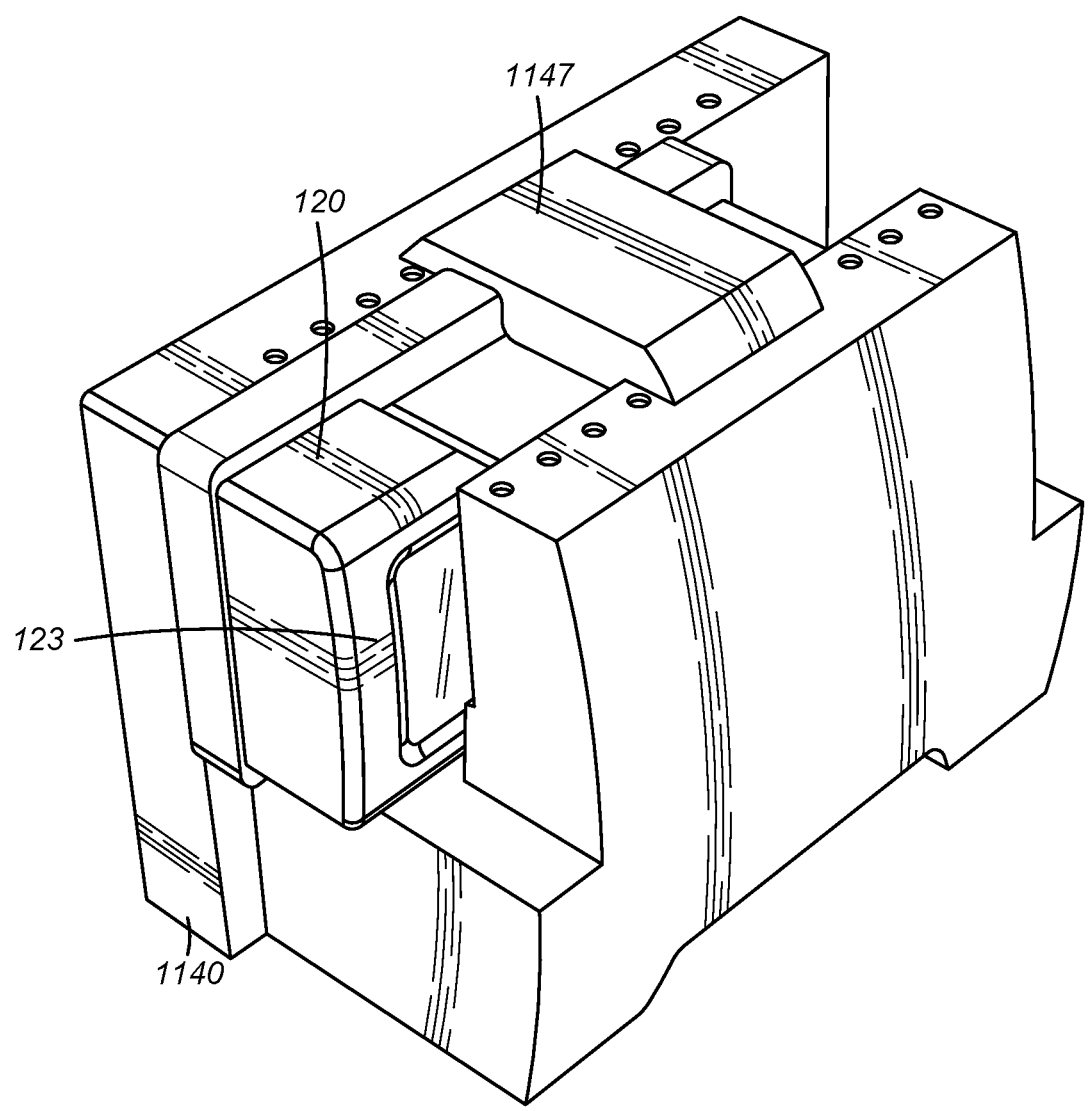
FIG. 15 is a back perspective view of the second exemplary implementation of the large monitor 1140 detachably securing the small monitor.
Figure 16:
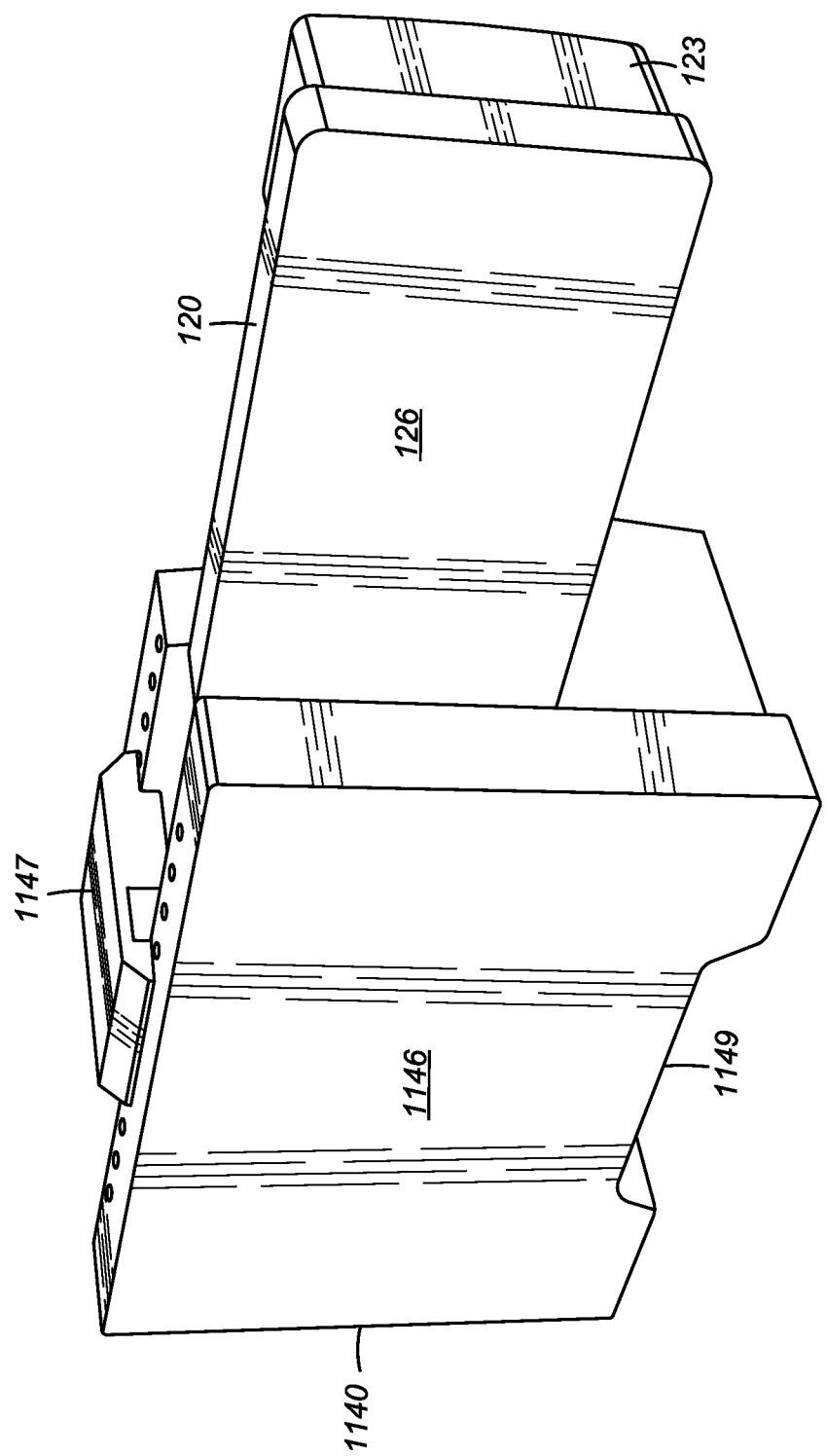
FIG. 16 is a front perspective view of the second exemplary implementation of the large monitor 1140 partially receiving the small monitor.
Figure 17:
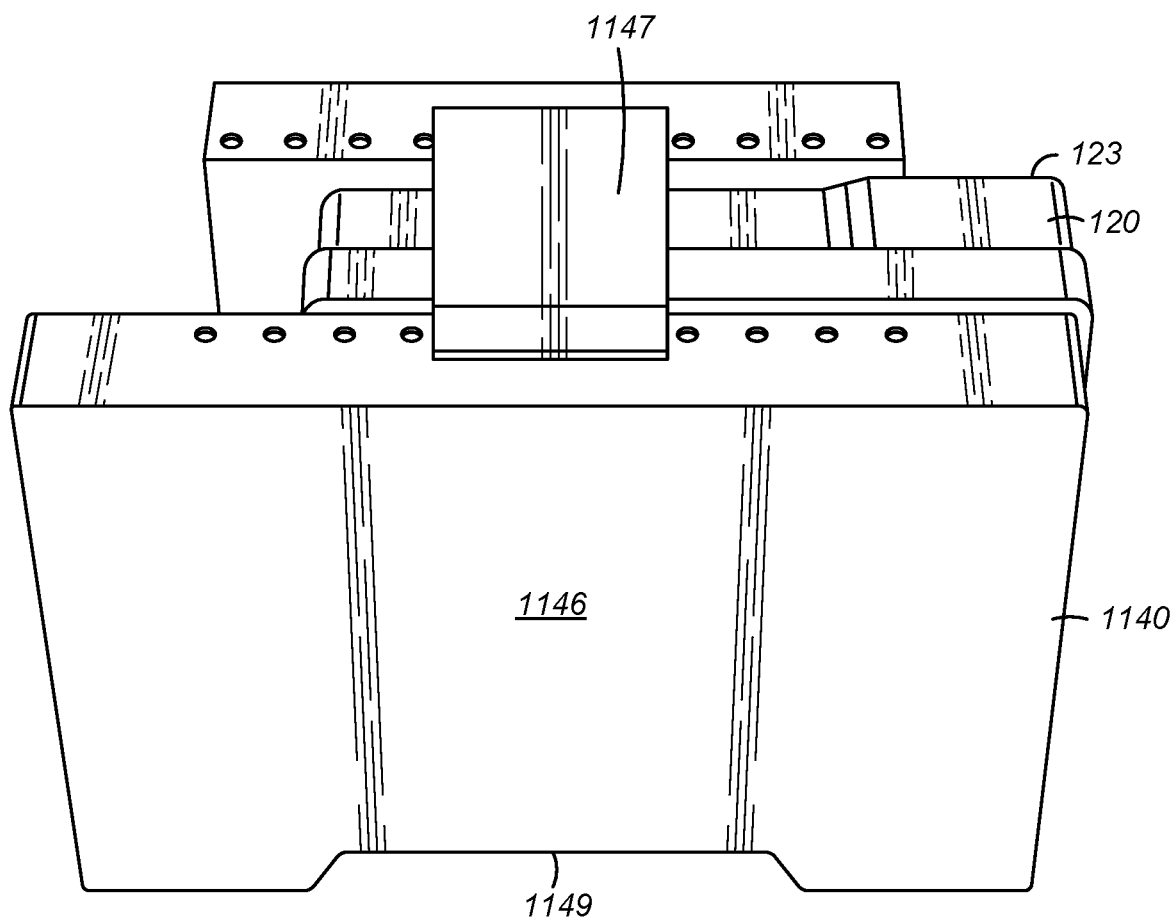
FIG. 17 is a front view of the second exemplary implementation of the large monitor 1140 detachably securing the small monitor.

FIG. 2 is a logical diagram of a small monitor 120, a large monitor 140, and a monitor mount 160 which can detachably secure (or otherwise physically interface with) both of the small monitor 120 and the large monitor 140. FIGS. 3-9 illustrate an example system including the small monitor 120, a first exemplary implementation of the large monitor 140, and a first exemplary implementation of the monitor mount 160. FIGS. 10-12 illustrate the example system including the small monitor 120, the first exemplary implementation of the large monitor 140, and a second exemplary implementation of the monitor mount 1160. FIG. 13 illustrates the example system including the small monitor 120, the large monitor 140, and an alternative implementation of the monitor mount 160. FIGS. 14-18F illustrate an example system including the small monitor 120 and another exemplary embodiment of the large monitor 1140.

As will be described in further detail below, the small monitor 120 has a shape and size which differs from that of the large monitor 140. Nonetheless, both of the small monitor 120 and the large monitor 140 are able to be concurrently secured to the monitor mount 160. In addition, while certain configurations are illustrated with regard to the monitor mount 160 and the small monitor 120 and the large monitor 140, it will be appreciated that these illustrations in FIGS. 1-18F are examples and not limiting in nature (unless otherwise specified).

The small monitor 120 can, for example, be a patient monitor that is used to monitor various physiological parameters for a patient 110. With such a variation, the small monitor 120 can include a sensor interface 122 that can be used to connect via wired and/or wireless interfaces to one or more physiological sensors and/or medical devices 112 (e.g., ECG electrodes, $SPO_2$ sensor, blood pressure cuffs, apnea detection sensors, respirators, etc.) associated with the patient 110. The small monitor 120 can include one or more processors 124 (e.g., programmable data processors, etc.) which can execute various instructions stored in memory 130 of the small monitor 120. Various data and graphical user interfaces can be conveyed to a user via an electronic visual display 126 included in the small monitor 120. This information can, for example, relate to the measured physiological parameters of the patient 110 and the like (e.g., blood pressure, heart related information, pulse oximetry, respiration information, etc.). Other types of information can also be conveyed by the electronic visual display 126. In some variations, the electronic visual display 126 includes a touch screen interface that allows a user of the small monitor 120 to input data and/or modify the operation of the small monitor 120.

The small monitor 120 can additionally include a communications interface 128 which allows the small monitor 120 to directly or indirectly (via, for example, the monitor mount 160) access one or more computing networks. The communications interface 128 can include, various network cards/interfaces to enable wired and wireless communications with such computing networks. The communications interface 128 can also enable direct (i.e., device-to-device, etc.) communications (i.e., messaging, signal exchange, etc.) such as from the monitor mount 160 to the small monitor 120.

The small monitor 120 can optionally also include a power source and/or conduit 132 that can be used to power the various components of the small monitor 120 (and optionally various components of the large monitor 140 and/or the monitor mount 160). The power source/conduit 132 can include a self-contained power source such as a battery pack and/or the power source/conduit 132 can include an interface to be powered through an electrical outlet (either directly or by way of the large monitor 140 and/or the monitor mount 160). In some variations, the small monitor 120 can only be powered and render information when secured or otherwise connected to one or more of the large monitor 140 and the monitor mount 160.

Figure 6:
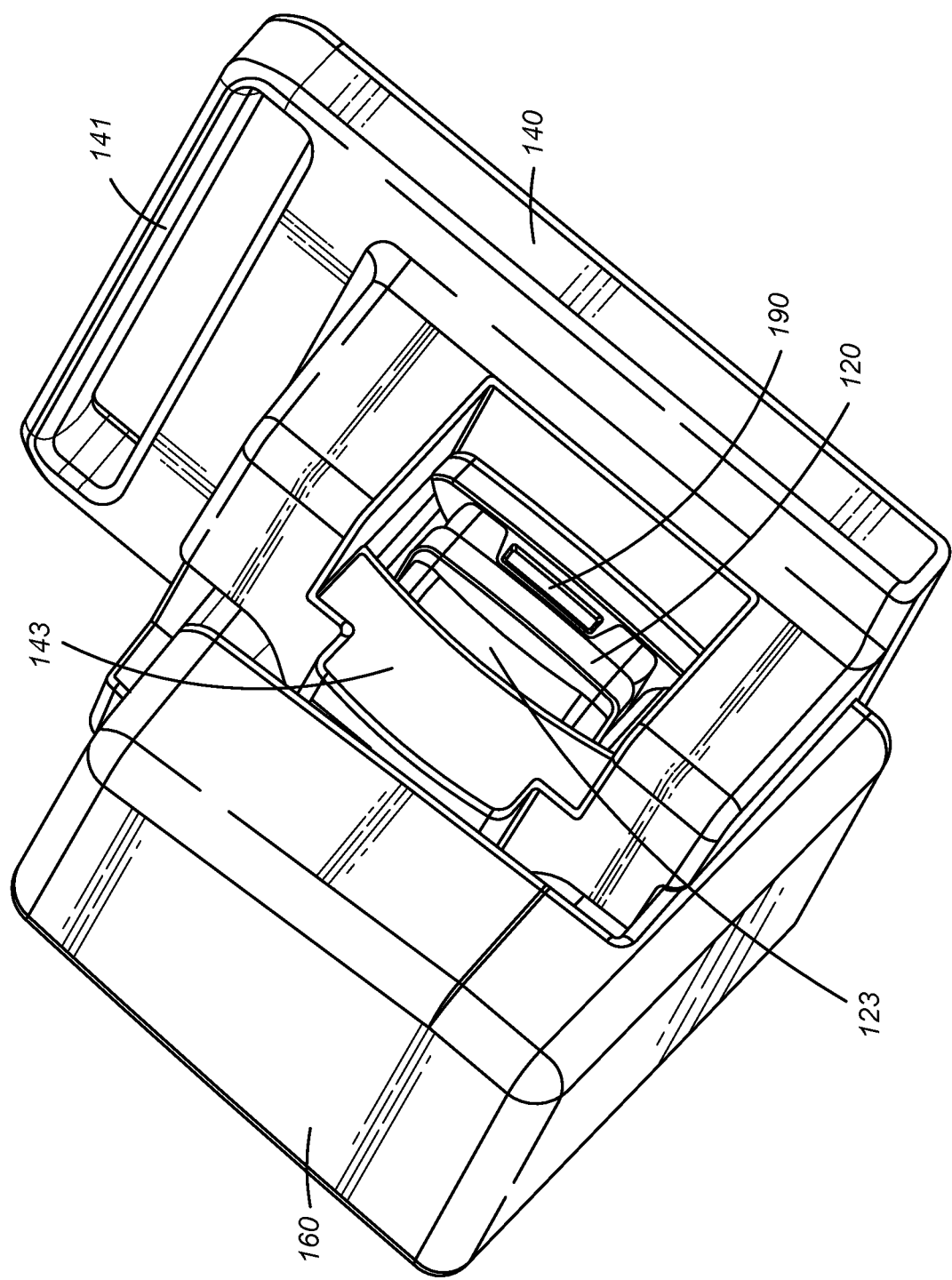
FIG. 6 is a side perspective view of the example system including the first exemplary implementation of the monitor mount detachably securing both of the small monitor and the first exemplary implementation of the large monitor.

The small monitor 120 can include a first electrical connector 190 (as shown in FIG. 6) configured to connect with a second electrical connector (not shown) of the large monitor 140 via a direct connection. When the small monitor 120 is secured with the large monitor 140, a connection is made by the first electrical connector 190 with the second electrical connector (not shown). In some variations, the small monitor 120 may not include the first electrical connector 190. Instead, the data communication between the small monitor 120 and the large monitor 140 may be wireless (e.g., optical), occurring across the communications interface 128 of the small monitor 120.

The large monitor 140 can include one or more processors 142 (e.g., programmable data processors, etc.) which can execute various instructions stored in memory 144 of the large monitor 140. Various data and graphical user interfaces can be conveyed to the user via an electronic visual display 146 included in the large monitor 140. This information can, for example, relate to the measured physiological parameters of the patient 110 and the like (e.g., blood pressure, heart related information, pulse oximetry, respiration information, thermoregulation, neonatal information, ventilator information, anesthesia information, incubation information, etc.) as received from the small monitor 120. Other types of information can also be conveyed by the electronic visual display 146. In some variations, the electronic visual display 146 includes a touch screen interface that allows a user of the large monitor 140 to input data and/or modify the operation of the large monitor 140.

The large monitor 140 can additionally include a communications interface 148 which allows the large monitor 140 to directly or indirectly (via, for example, the small monitor 120 and/or the monitor mount 160) access one or more computing networks. The communications interface 148 can include various network cards/interfaces to enable wired and wireless communications with such computing networks. The communications interface 148 can also enable direct (i.e., device-to-device, etc.) communications (i.e., messaging, signal exchange, etc.) such as from the monitor mount 160 to the large monitor 140 and the small monitor 120 to the large monitor 140.

The large monitor 140 can optionally also include a power source and/or conduit 150 that can be used to power the various components of the large monitor 140 (and optionally various components of the small monitor 120). The power source/conduit 150 can include a self-contained power source such as a battery pack and/or the power source/conduit 150 can include an interface to be powered through an electrical outlet (either directly or by way of the small monitor 120 and/or the monitor mount 160). In some variations, the large monitor 140 can only be powered and render information when secured or otherwise connected to one or more of the small monitor 120 and the monitor mount 160.

The large monitor 140 can include a second coupling 145 which is configured to detachably secure the small monitor 120. In some variations, the second coupling 145 may be positioned in a receptacle 145b (as shown in FIG. 9) of the large monitor 140. The receptacle 145b may be defined in a lateral direction of the large monitor 140 and have open side portions for receiving the small monitor 120. For example, the user can visually confirm the location of the second coupling 145 and transversely insert the small monitor 120 into the large monitor 140. In some variations, the receptacle 145b may have an open top portion instead of open side portions such that the small monitor 120 can be dropped into the large monitor 140 from above; and removed from the large monitor 140 from above.

The monitor mount 160 can include one or more processors 162 (e.g., programmable data processors, etc.) which can execute various instructions stored in memory 164 of the monitor mount 160. The monitor mount 160 can additionally include a communications interface 166 which allows the monitor mount 160 to directly or indirectly access one or more computing networks. The communications interface 166 can include various network cards/interfaces to enable wired and wireless communications with such computing networks. The communications interface 166 can also enable direct (i.e., device-to-device, etc.) communications (i.e., messaging, signal exchange, etc.) such as with the small monitor 120 and/or the large monitor 140.

The monitor mount 160 can optionally also include a power source and/or conduit 168 that can be used to power the various components of the monitor mount 160 and/or the small monitor 120 and/or the large monitor 140 when secured to the monitor mount 160. The power source/conduit 168 can include a self-contained power source such as a battery pack and/or the power source/conduit 168 can include an interface to be powered through an electrical outlet.

Any of the processors 124, 142, 162 may acquire data from any of the monitor mount 160 and one or more of the small and large monitors 120, 140 and store the acquired data in a memory and, upon connection of the monitor mount 160 and one or more of the small and large monitors 120, 140, transfer the data stored in the memory to the monitor mount 160 or one or more of the small and large monitors 120, 140. The data may include any of patient identification data including information identifying a patient; patient parameter data representing at least one type of patient parameter being monitored; and device configuration data including information associated with configuration settings for the monitor mount 160 and/or the one or more small and large monitors 120, 140.

The monitor mount 160 can optionally also include any mounting interface, such as a VESA mounting interface (e.g., a 75 mm or 100 mm square pattern) for mounting the monitor mount at the bedside, from the ceiling, on a wall of the room, or even outside the room for isolation purposes.

The monitor mount 160 can optionally also include an interface configured to receive a connector of a cable or wired connection for connecting a module, a monitor, other external unit or the like.

The monitor mount 160 can optionally also include one or more recesses for facilitating removal of the small monitor 120 and/or the large monitor 140.

In some variations, the one or more processors 162 and the memory 164 are omitted such that the monitor mount 160 provides only physical support and optionally a power source.

The monitor mount 160 has a shape and size which allows the monitor mount 160 to detachably secure both of the small monitor 120 and the large monitor 140 such that the respective small and large monitors 120 and 140 can be removed by the user when desired.

Figure 3:
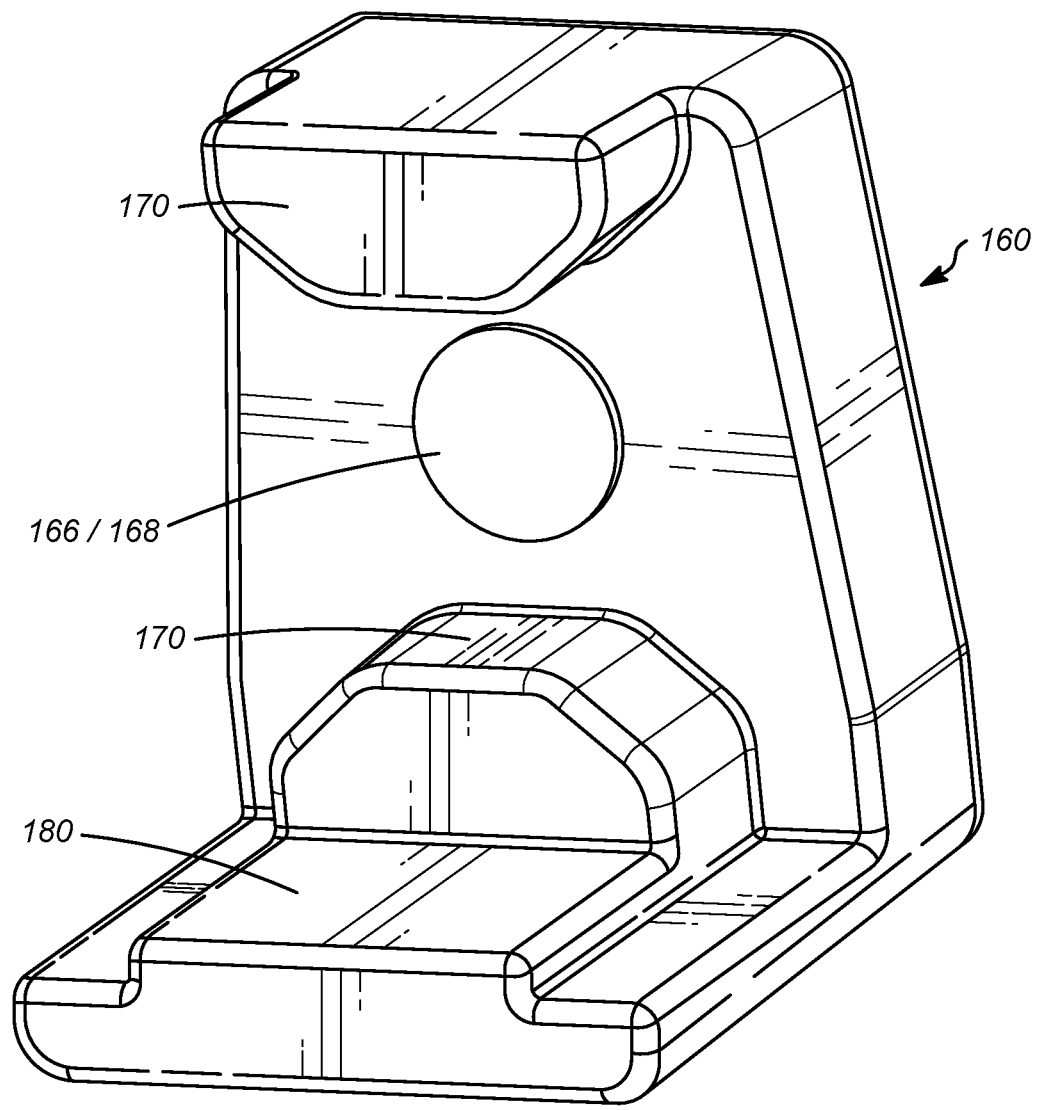
FIG. 3 is a front perspective view of a first exemplary implementation of the monitor mount.

The monitor mount 160 can include a first coupling 170 to allow the small monitor 120 and/or large monitor 140 to be secured to the monitor mount 160. The monitor mount 160 is able to secure each of the small monitor 120 and the large monitor 140 individually or both of the small monitor 120 and the large monitor 140 concurrently. In other words, the first coupling 170 is configured to accept either the small monitor 120 or the large monitor 140 such that the monitor mount 160 is configured to mount the small monitor 120 alone, the large monitor 140 alone, or a combination of the small monitor 120 and the large monitor 140. The first coupling 170 can include any mechanical attachment means such as a ledge, a rail, a rib, an abutment, and the like, or any combination thereof. The first coupling 170 can additionally or alternatively include different securing mechanisms including magnetic and/or electromagnetic locking mechanisms which cause the small monitor 120 to selectively be secured to the monitor mount 160. In some cases, the small monitor 120 can slide into and out of the first coupling 170 from one or more lateral directions (i.e., from one or more sides of the monitor mount 160) while in other variations, the small monitor 120 can be mounted to and removed from the front face of the monitor mount 160. In some implementations, the small monitor 120 can both slide into and out of the first coupling 170 from one or more lateral directions and be mounted to and removed from the front face of the monitor mount 160. Reference is made to FIG. 3 which shows the first coupling 170 in which the small monitor 120 can be inserted.

The positioning of the small monitor 120 when secured to the monitor mount 160 can be such that the communications interface 128 on the small monitor 120 aligns with the communications interface 166 of the monitor mount 160 to allow, for example, a direct connection (e.g., electrical connection). In other variations, the communications interface 128 of the small monitor 120 exchanges data with the communications interface 166 of the monitor mount 160 wirelessly (via, for example, optical communication by way of respective optical windows on the small monitor 120 and the monitor mount 160). The communications interface 128 of the small monitor 120 may be located on the first back portion 123 of the small monitor 120.

The positioning of the small monitor 120 when secured to the monitor mount 160 can also align the power source/ conduit 132 of the small monitor 120 to be coupled to the power source/conduit 168 of the monitor mount 160 which causes the monitor mount 160 to power the small monitor 120.

The monitor mount 160 can include a support portion 180 to allow the large monitor 140 to be secured to the monitor mount 160. The support portion 180 may be positioned at a top of the monitor mount 160 or a bottom of the monitor mount 160. The support portion 180 can include any mechanical attachment means such as a ledge, a rail, a rib, an abutment, and the like, or any combination thereof. The positioning of the large monitor 140 when secured to the monitor mount 160 can be such that the communications interface 148 on the large monitor 140 aligns with the communications interface 166 of the monitor mount 160 to allow, for example, a direct connection (e.g., electrical connection). In other variations, the communications interface 148 of the large monitor 140 exchanges data with the communications interface 166 of the monitor mount 160 wirelessly (via, for example, optical communication by way of respective optical windows on the large monitor 140 and the monitor mount 160). The communications interface 148 of the large monitor 140 may be located on the second back portion 143 of the large monitor 140.

The support portion 180 can enable front-to-back docking of the large monitor 140 within monitor mount 160 by providing a shelf or similar feature extending outwardly. This feature of the support portion 180 can support and/or disperse the weight of the large monitor 140 during positioning of the large monitor 140. For example, a user attempting to position the large monitor 140 within the monitor mount 160 can rest the large monitor 140 on the support portion 180 during the positioning while attaching the second back portion 143 of the large monitor 140 to the first coupling 170. The support portion 180 can support a bottom face of the large monitor 140.

Alternatively or additionally, as shown in FIG. 13, the support portion 180 can enable hanging or suspension of a handle 141 of the large monitor 140 from the monitor mount 160 by providing any mechanical attachment means such as a ledge, a rail, a rib, an abutment, and the like, or any combination thereof extending laterally from the top portion of monitor mount 160. This feature of the support portion 180 can support and/or disperse the weight of the large monitor 140 during positioning of the large monitor 140. For example, a user attempting to position the large monitor 140 within the monitor mount 160 can hang or suspend the handle 141 of the large monitor 140 from the support portion 180 during the positioning while attaching the second back portion 143 of the large monitor 140 to the first coupling 170.

The positioning of the large monitor 140 when secured to the monitor mount 160 can also align the power source/conduit 150 of the large monitor 140 to be coupled to the power source/conduit 168 of the monitor mount 160 which causes the monitor mount 160 to power the large monitor 140 or vice-versa. In some variations, the positioning of the large monitor 140 when secured to the monitor mount 160 and/or when the small monitor 120 is also secured to the monitor mount 160 can also align the power source/conduit 150 of the large monitor 140 to be coupled to the power source/conduit 132 of the small monitor 120 (which in turn is connected to the power source/conduit 168 of the monitor mount 160) which causes the small monitor 120 to power the large monitor 140.

FIG. 3 is a front perspective view that shows a first exemplary implementation of the monitor mount 160. As illustrated in FIG. 3, the monitor mount 160 includes the first coupling 170 and the support portion 180. The communications interface 166 and the power source/conduit 168 can be positioned intermediate of the first coupling 170 so that the small monitor 120 or the large monitor 140 may interface therewith. Similarly, the communications interface 166 and the power source/conduit 168 can alternatively be included as part of the support portion 180 so that the large monitor 140 may interface therewith at that location. In some variations, communications interface 166 can be a wireless (e.g., optical) interface providing wireless (e.g., optical) communications between the monitor mount 160 and the small monitor 120, between the monitor mount 160 and the large monitor 140, and/or between the small monitor 120 and the large monitor 140 coupled together. FIG. 3 also shows various aspects of the monitor mount 160 including details about how the small monitor 120 can be transversely inserted into the monitor mount 160 (i.e., the small monitor 120 can slide into the monitor mount 160) between the two portions of the first coupling 170.

FIG. 4 is an exploded perspective view that shows the relationship among the small monitor 120, the large monitor 140, and the first exemplary implementation of the monitor mount 160. The first back portion 123 of the small monitor 120 or the second back portion 143 of the large monitor 140 can be detachably secured to the first coupling 170. The small monitor 120 can also be detachably secured to the second coupling 145 of the large monitor 140.

Figure 5:
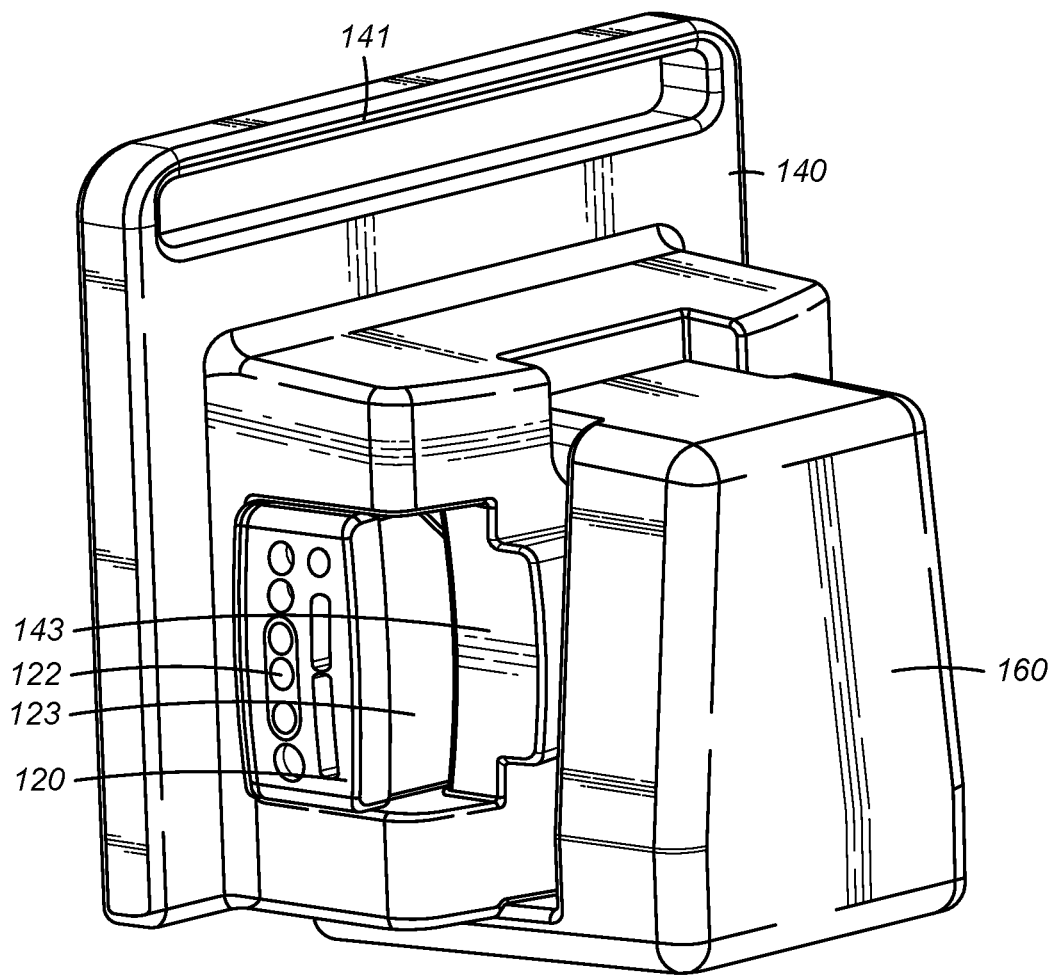
FIG. 5 is a side perspective view of the example system including the first exemplary implementation of the monitor mount detachably securing both of the small monitor and the first exemplary implementation of the large monitor.

FIG. 5 is a side perspective view showing the relationship among the small monitor 120, the large monitor 140, and the first exemplary implementation of the monitor mount 160 when all the units are connected. As illustrated in FIG. 5, the second back portion 143 of the large monitor 140 is detachably secured to the first coupling 170 of the monitor mount 160 and the small monitor 120 is detachably secured to the second coupling 145 of the large monitor 140. In some variations, as is illustrated in FIG. 5, a portion such as a back portion of the large monitor 140 can surround/obscure at least a portion of the small monitor 120; such portion of the small monitor 120 may include some or all of the electronic visual display 126 of the small monitor 120. The small monitor 120 can be removed from the monitor mount 160 independently of the large monitor 140 (for example, with reference to FIG. 5, by being removed transversely from the monitor mount 160). In addition, the monitor mount 160 can be arranged to allow left side and/or right side transverse removal of the small monitor 120 from the monitor mount 160. The large monitor 140 can be arranged to allow left side and/or right side transverse removal of the small monitor 120 from the large monitor 140. In still other variations, the large monitor 140 with the small monitor 120 disposed therein can be removed from the monitor mount 160. Stated differently, the combination of the small monitor 120 and the large monitor 140 can together be detached from the monitor mount 160. In some variations, the large monitor 140 can have a shape and size to completely envelop and secure the small monitor 120 within the receptacle 145b. The small monitor 120 can be secured and interface within the second coupling 145 in the receptacle 145b of the large monitor 140. In some variations, when the small monitor 120 is mounted within the receptacle 145b of the large monitor 140, the communications interface 148 (e.g., optical communications interface), and optionally the power source/conduit 150, on the large monitor 140 provide data communications with, and optionally power to, the small monitor 120 via the communications interface 128 (e.g., optical communications interface), and optionally the power source/conduit 132, on the small monitor 120 within the receptacle 145b.

For example, with such an arrangement, data that otherwise would have been displayed by the electronic visual display 126 of the small monitor 120 can be displayed by the electronic visual display 146 of the large monitor 140.

Therefore, the monitor mount 160 of the present disclosure is capable of mixed use with small and large monitors 120, 140 having different sizes which are interoperable with the same controller and the same user interface, and which can be universally docked to the monitor mount 160.

FIG. 6 is another side perspective view showing the relationship among the small monitor 120, the large monitor 140, and the first exemplary implementation of the monitor mount 160. As illustrated in FIG. 6, the second back portion 143 of the large monitor 140 is detachably secured to the first coupling 170 and the small monitor 120 is detachably secured to the second coupling 145. The small monitor 120 may include the first electrical connector 190.

Figure 7:
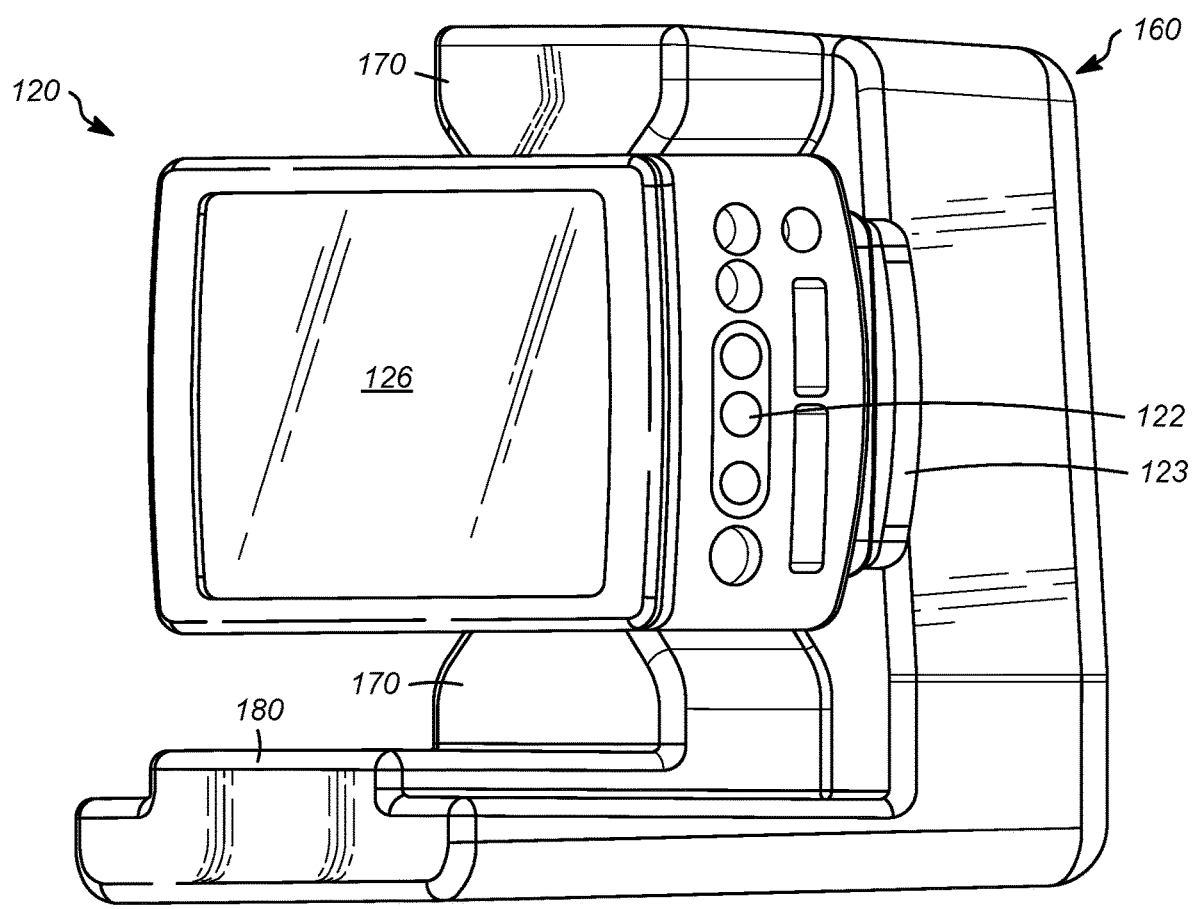
FIG. 7 is a front perspective view of the first exemplary implementation of the monitor mount 160 detachably securing the small monitor.

FIG. 7 is a front perspective view showing the relationship between the small monitor 120, and the first exemplary implementation of the monitor mount 160 without the large monitor 140 being present. In FIG. 7, the first back portion 123 of the small monitor 120 is detachably secured to the first coupling 170.

Figure 8:
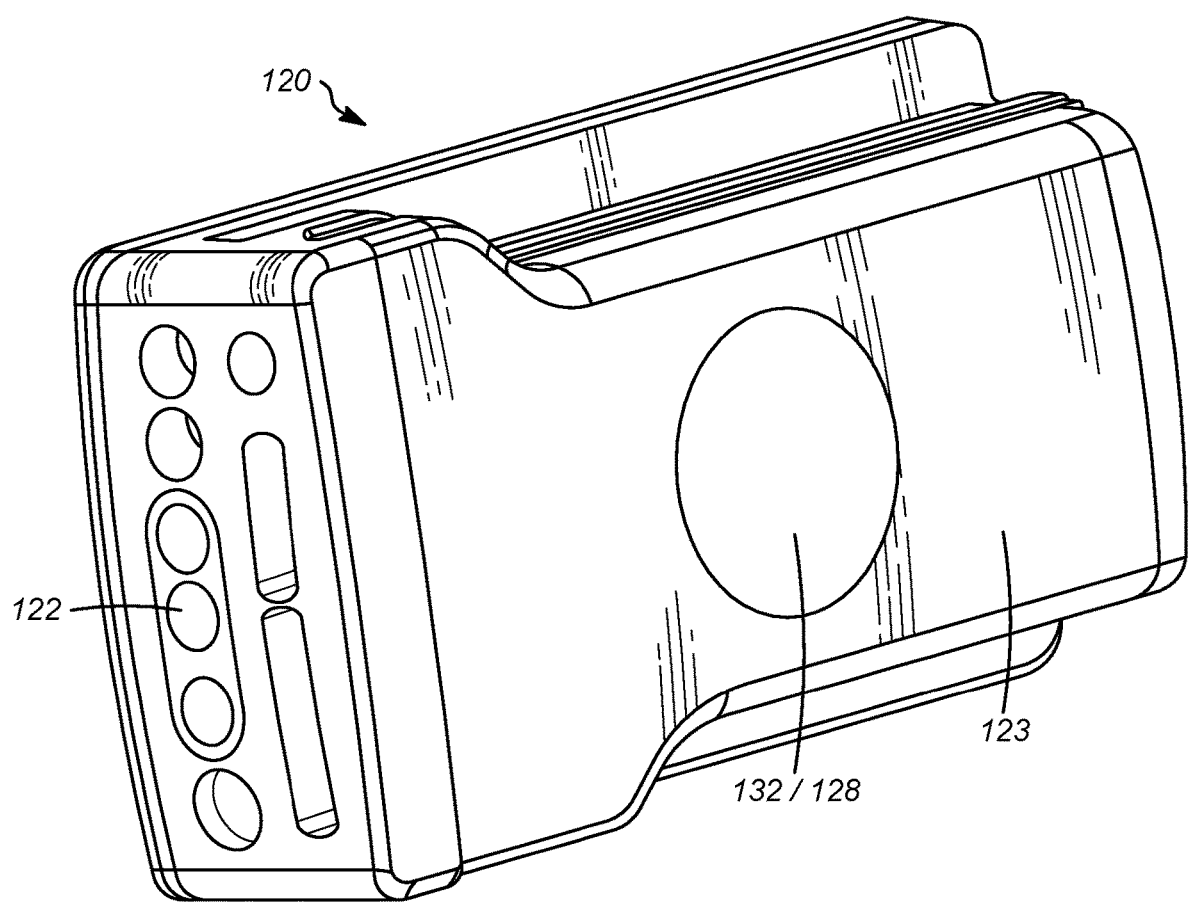
FIG. 8 is a back perspective view of an exemplary implementation of the small monitor 120.

FIG. 8 is a back perspective view of the small monitor 120. As illustrated in FIG. 8, the small monitor 120 has the sensor interface 122, the first back portion 123, the power source and/or conduit 132, and the communications interface 128. The small monitor 120 may include one or more of a groove, a slit, an aperture, a rib, a wall portion, a ridge, an abutment, or the like for facilitating the transverse insertion and/or removal of the small monitor 120 into the receptacle 145b of the large monitor 140 and/or into the first coupling 170 of the monitor mount 160.

FIG. 9 is a side perspective view of the large monitor 140. As illustrated in FIG. 9, the large monitor 140 has the handle 141, the second back portion 143, the second coupling 145, the communications interface 148, and the power source and/or conduit 150. The handle 141 can facilitate the detachable securing of the large monitor 140 to the support portion 180 (as shown in FIG. 13) and/or the first coupling 170. The second coupling 145 can have one or more guiding surfaces 145a for facilitating the transverse insertion and/or removal of the small monitor 120 into the receptacle 145b of the large monitor 140.

FIG. 10 is a front perspective view that shows a second exemplary implementation of the monitor mount 1160. As illustrated in FIG. 10, the monitor mount 1160 includes the first coupling 1170 and the support portion 1180. The communications interface 1166 and the power/source conduit 1168 can be positioned intermediate the first coupling 1170 so that the small monitor 120 may interface therewith. Similarly, the communications interface 1166 and the power/source conduit 1168 can alternatively be included as part of the support portion 1180 so that the large monitor 140 may interface therewith. Further, the monitor mount 1160 includes recesses on either side of the first coupling 1170 that can facilitate coupling/uncoupling of the small monitor 120 and/or the large monitor 140 to and from the monitor mount 1160.

FIG. 11 is a bottom perspective view that shows the relationship among the small monitor 120, the large monitor 140, and the second exemplary implementation of the monitor mount 1160. As illustrated in FIG. 11, the support portion 1180 of the monitor mount 1160 can additionally include a release mechanism 1182 which causes the large monitor 140 to selectively be released from the monitor mount 1160.

FIG. 12 is a back perspective view that shows the relationship among the small monitor 120, the large monitor 140, and the second exemplary implementation of the monitor mount 1160.

FIG. 13 is an exploded perspective view showing an alternative relationship between the first exemplary implementation of the monitor mount 160 and the large monitor 140 detachably securing the small monitor 120, where the monitor mount 160 is inverted prior to securing to the large monitor 140 and the small monitor 120.

Figure 18A:
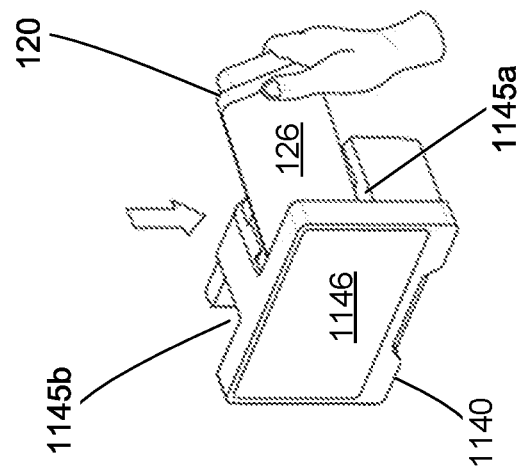
FIGS. 18A-18C are side perspective views of a first exemplary sequence of the small monitor being detachably secured in the second exemplary implementation of the large monitor.
Figure 18B:
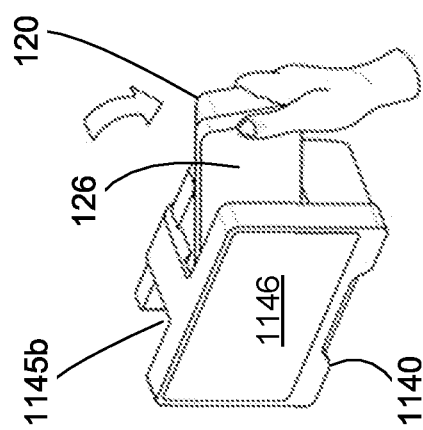
Figure 18C:
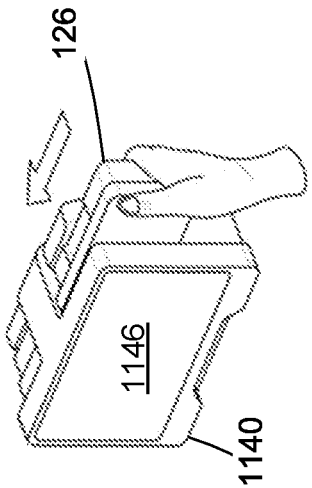

FIGS. 14-18F show the second exemplary implementation of the large monitor 1140 detachably securing the small monitor 120. The large monitor 1140 may include a second electronic visual display 1146 and a receptacle 1145b including the second coupling 1145, a bridge portion 1147 and two parallel surfaces 1149. The bridge portion 1147 may connect the two parallel surfaces 1149 and extend over the small monitor 120 when the small monitor 120 is secured in the large monitor 1140. A width of the bridge portion 1147 in a lateral direction of the large monitor 1140 may be less than a width of the large monitor 1140 in the lateral direction of the large monitor 1140. Furthermore, a width of the bridge portion 1147 in the lateral direction of the large monitor 1140 may be less than a width of the small monitor 120 in a lateral direction of the small monitor 120. In other words, the width of the receptacle 1145b in these variations can be less than the width of the receptacle 1145b in other variations. Such decreased receptacle width facilitates self-location of the small monitor 120 by the user. For example, the user can hold the small monitor 120 overhead, and without visually confirming the location of the second coupling 1145, insert the small monitor 120 such that the small monitor 120 contacts at least one guiding surface 1145a of the second coupling 1145 and slides into a position in which the small monitor 120 is detachably secured in the large monitor 1140. Stated differently, the at least one guiding surface 1145a of the second coupling 1145 is configured to initially receive the small monitor 120 and guide the small monitor 120 to a secured position within the large monitor 1140. As a first example, as shown in FIGS. 18A-18O, the small monitor 120 can be inserted downwardly from above into the receptacle 1145b of the large monitor 1140 by first holding the small monitor 120 at a downward angle against a floor (i.e., the at least one guiding surface 1145a) of the receptacle 1145b, and thereafter the small monitor 120 can be rotated downwardly and into the large monitor 1140. As a second example, as shown in FIGS. 18D-18F, the small monitor 120 can be inserted upwardly from below into the receptacle 1145b of the large monitor 1140 by first holding the small monitor 120 at an upward angle against the floor (i.e., the at least one guiding surface 1145a) of the receptacle 1145b, and thereafter the small monitor 120 can be rotated upwardly and into the large monitor 1140. This provides an advantage over a full-width receptacle because it is difficult to align a small monitor 120 with a full-width receptacle if the full-width receptacle is overhead. Such insertion and removal can be performed with one hand by the user. In other words, it is not necessary to perform two separate motions to insert or remove the small monitor 120 from the large monitor 1140. In some variations not shown, the receptacle may have an open top portion instead of open side portions such that the small monitor 120 can be dropped into the large monitor 1140 from above; and removed from the large monitor 1140 from above. The small monitor 120 may be received in the receptacle 1145b of the large monitor 1140 such that the small monitor 120 is adjacent to the bridge portion 1147, the two parallel surfaces 1149, and the second coupling 1145. A floor of the receptacle 1145b may include the second coupling 1145. Furthermore, the second coupling 1145 may include at least one guiding surface 1145a configured to initially receive the small monitor 120 at an angle such that the small monitor 120 is rotated and thereafter guide the small monitor 120 to a secured position within the large monitor 1140. The bridge portion 1147 may include a lateral slot and a top portion of the small monitor 120 may be transversely inserted into the lateral slot. The large monitor 1140 may also include a handle and the bridge portion 1147 and the handle may be formed as a single unit. In some variations, a top portion of the large monitor 1140 may include holes for repositioning the bridge portion 1147.

Figure 19:
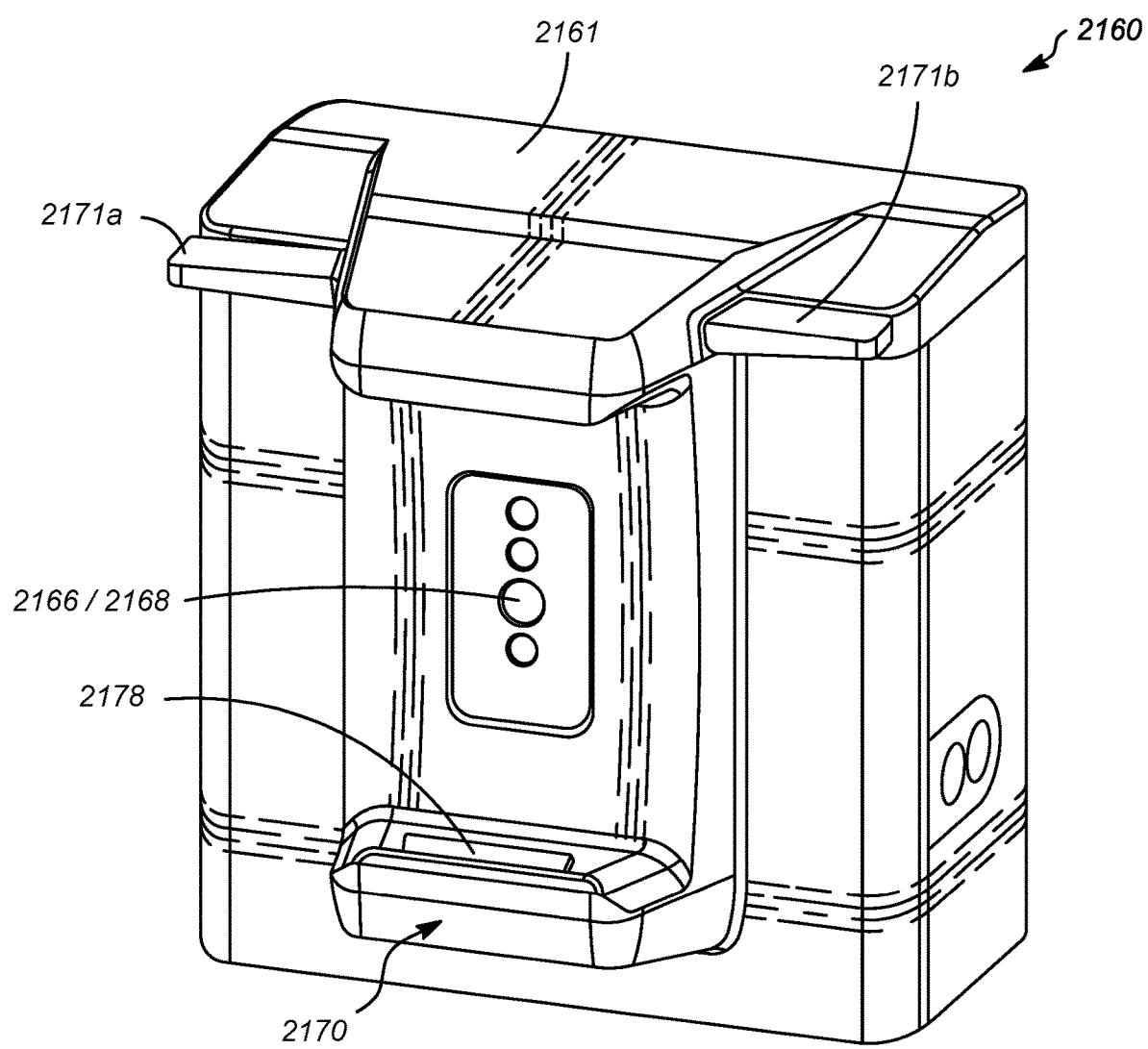
FIG. 19 is a front perspective view of a third exemplary implementation of the monitor mount with a first exemplary implementation of a top portion.

FIG. 19 is a front perspective view that shows the third exemplary implementation of the monitor mount 2160 with a first exemplary implementation of the top portion 2161. The communications interface 2166 and the power source/conduit 2168 can be positioned intermediate of the first coupling 2170 so that the small monitor 120 or the large monitor 140 may interface therewith. In some variations, communications interface 2166 can be a wireless (e.g., optical) interface providing wireless (e.g., optical) communications between the monitor mount 2160 and the small monitor 120, between the monitor mount 2160 and the large monitor 140, and/or between the small monitor 120 and the large monitor 140 coupled together.

Figure 20:
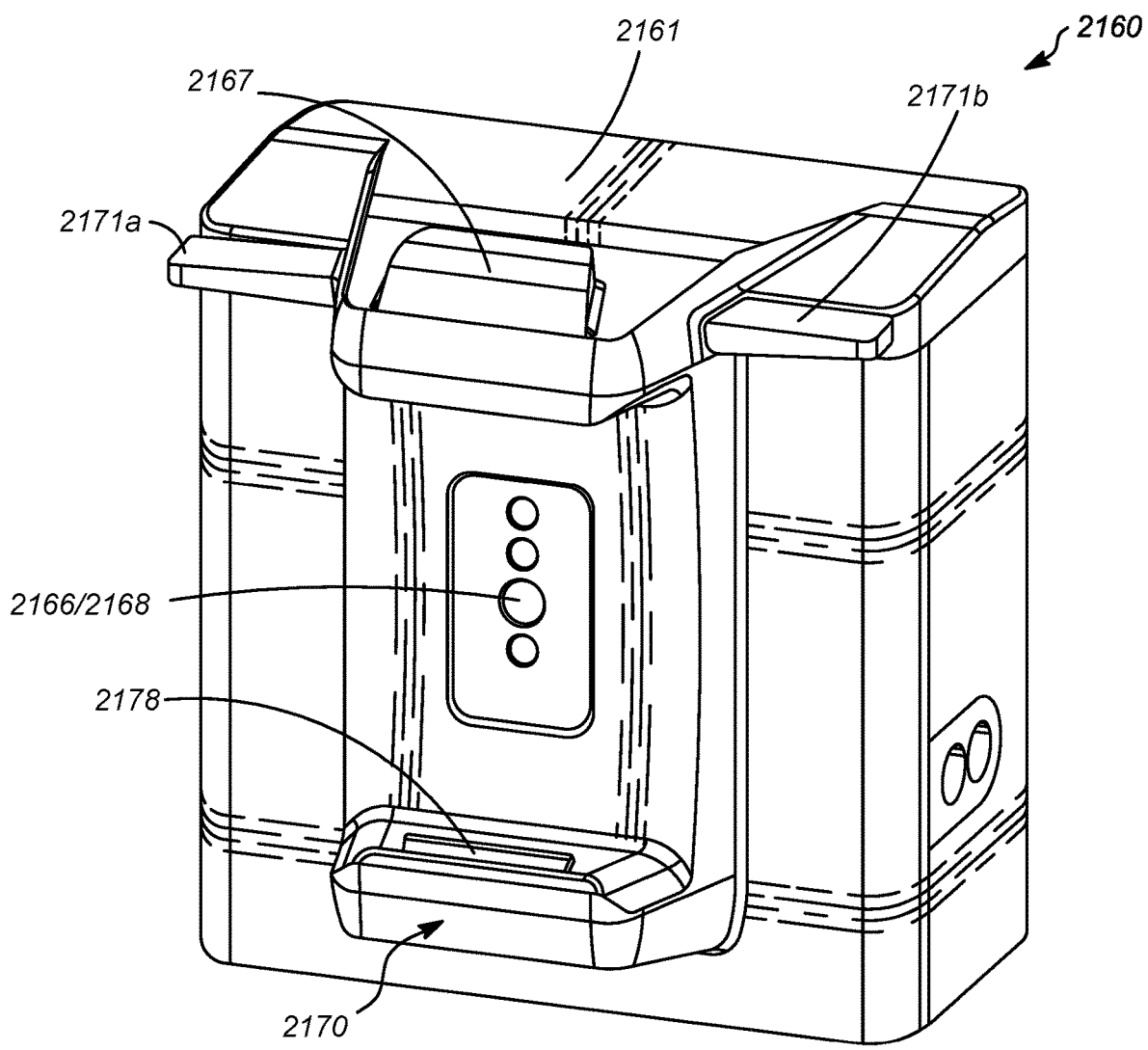
FIG. 20 is a front perspective view of the third exemplary implementation of the monitor mount with a second exemplary implementation of the top portion.

FIG. 20 is a front perspective view that shows the third exemplary implementation of the monitor mount 2160 with a second exemplary implementation of the top portion 2161. As illustrated in FIG. 20, the monitor mount 2160 includes the first coupling 2170 and the support portion 2167.

Figure 21:
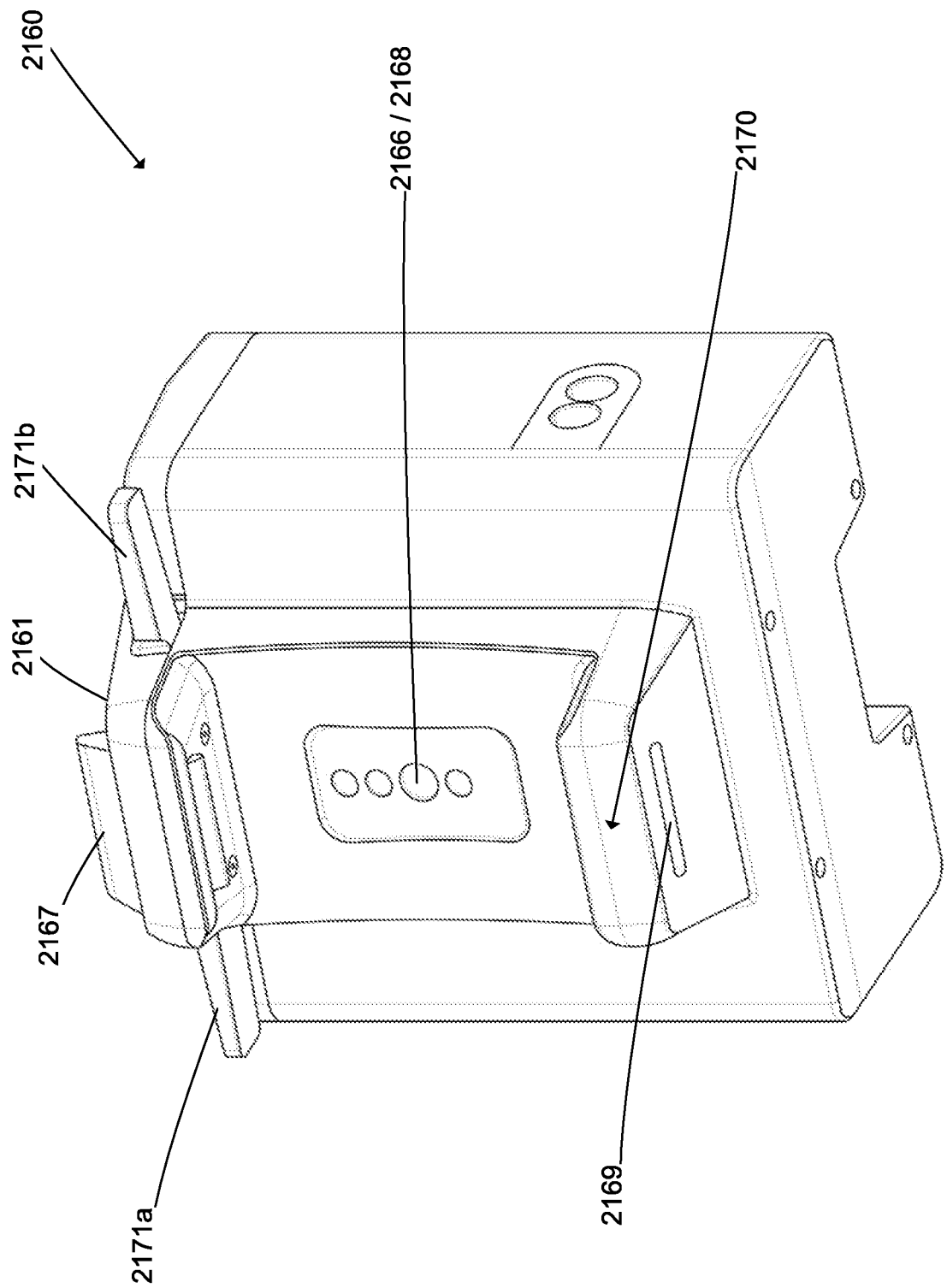
FIG. 21 is a bottom perspective view of the third exemplary implementation of the monitor mount with the second exemplary implementation of the top portion.

FIG. 21 is a bottom perspective view that shows the third exemplary implementation of the monitor mount 2160 with the second exemplary implementation of the top portion 2161. As illustrated in FIG. 21, the monitor mount 2160 includes the first coupling 2170 and the support portion 2167. In the embodiment shown in FIG. 21, a slot 2169 is defined in an underside of the first coupling 2170.

Figure 22:
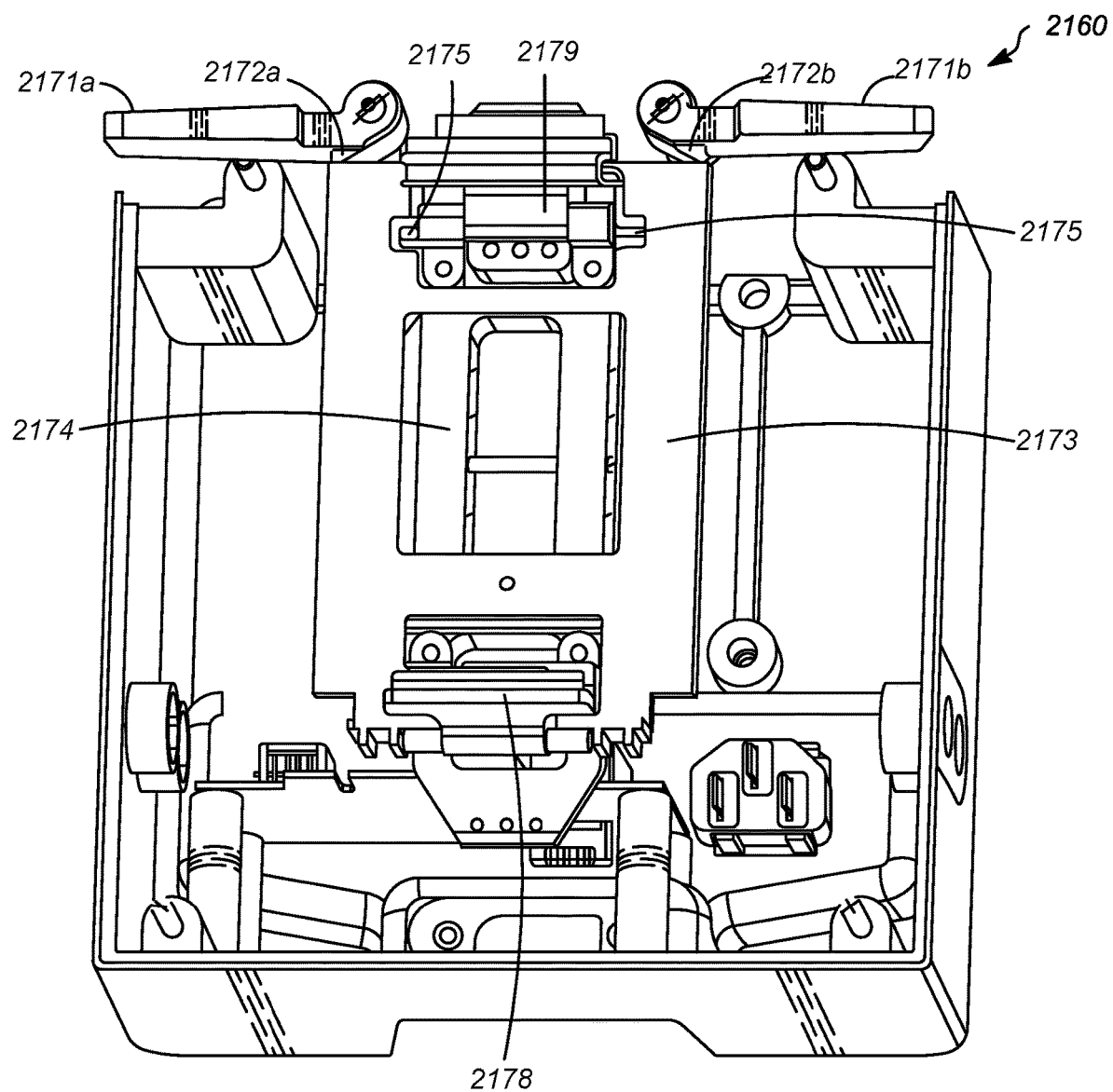
FIG. 22 is a front perspective view of the third exemplary implementation of the monitor mount 2160 with a front face thereof removed.

FIG. 22 is a front perspective view of the third exemplary implementation of the monitor mount 2160 with a front face thereof removed.

Figure 23:
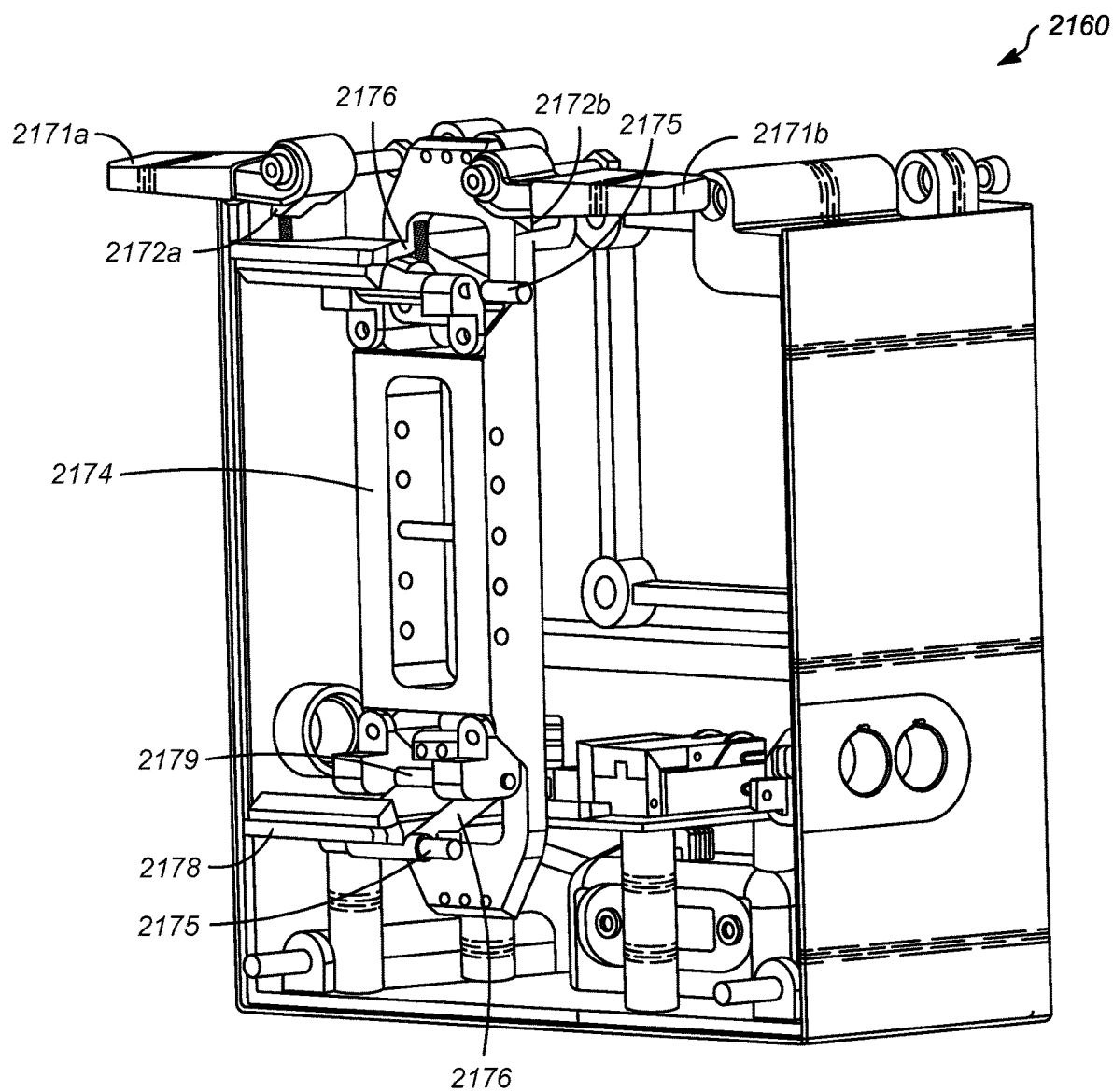
FIG. 23 is a side perspective view of the third exemplary implementation of the monitor mount 2160 with a front face and a slider thereof removed.

FIG. 23 is a side perspective view of the third exemplary implementation of the monitor mount 2160 with a front face and a slider 2173 thereof removed.

As shown in FIGS. 19-23, the third exemplary implementation of the monitor mount 2160 may comprise the first coupling 2170 configured to detachably secure a small monitor 120 and/or large monitor 140 to the monitor mount 2160, and a release mechanism configured to disengage the first coupling 2170 so as to release the small monitor 120 and/or large monitor 140 from the monitor mount 2160. The release mechanism may include at least one actuator (see first and second actuators 2171a, 2171b), at least one cam (see first and second cams 2172a, 2172b), and a slider 2173. The at least one cam may be positioned on an underside of the at least one actuator. In some variations, the at least one cam and the at least one actuator may be formed as a single unit. The at least one cam may be attached to the at least one actuator, configured to be rotated by the at least one actuator, and configured to cause the slider 2173 to slide. The slider 2173 may be linked to the first coupling 2170, and configured to disengage the first coupling 2170 upon sliding. In the embodiments shown in FIGS. 19-23, the first and second actuators 2171a, 2171b are levers. In the embodiments shown in FIGS. 19-23, the first and second actuators 2171a, 2171b are provided on respective left and right sides of the monitor mount 2160 and the first and second cams 2172a, 2172b are positioned on respective undersides of the first and second actuators 2171a, 2171b. The slider 2173 may be configured to slide based on activation of one or both of the first and second actuators 2171a, 2171b. In other words, the slider 2173 may be configured to slide based on activation of either of the first and second actuators 2171a, 2171b such that the slider 2173 is configured to slide based on activation of one of the first and second actuators 2171a, 2171b individually or activation of both the first and second actuators 2171a, 2171b simultaneously.

In some variations, the first coupling 2170 includes at least one arm (see arms 2176), at least one latch (see latches 2178) extending from the at least one arm, at least one pin (see pins 2175) extending from the at least one arm, and at least one hinge 2179. The latches 2178 may extend from, for example, a top portion of the arms 2176. The pins 2175 may extend from, for example, a side portion of the arms 2176. In the implementation shown in FIGS. 22 & 23, the first coupling 2170 includes two arms 2176 (i.e., a first arm and a second arm) provided on respective top and bottom sides of the monitor mount 2160. The release mechanism may also include a chassis 2174 for supporting the first coupling 2170 and the slider 2173.

In the implementations shown in FIGS. 19-23, the monitor mount 2160 may additionally include a top portion 2161 for supporting the first and second actuators 2171a, 2171b and the first and second cams 2172a, 2172b. For example, each of the first and second actuators 2171a, 2171b may be attached to the top portion 2161 via a shaft such that the first and second actuators 2171a, 2171b are rotatable with respect to the top portion 2161.

Furthermore, the chassis 2174 may extend behind and alongside a front face of the monitor mount 2160. Each of the arms 2176 may be attached the chassis 2174 via a hinge 2179 such that the arm 2176 is rotatable with respect to the chassis 2174. The slider 2173 may be configured to disengage the latches 2178 upon sliding. In the embodiment shown in FIGS. 22 & 23, the slider 2173 may be attached to the pins 2175 of the arms 2176 such that, upon sliding of the slider 2173, the pins 2175 are displaced so as to rotate the arms 2176 outwardly such that the latches 2178 are disengaged and the small and large monitors 120, 140 can be released from the monitor mount 2160. The latches 2178 may be biased by springs (not shown). In the embodiment shown in FIGS. 22 & 23, the pins 2175 of the arms 2176 may be positioned inwardly of the latches 2178. Such a configuration causes the latches 2178 to grip more tightly to prevent accidental release of the small monitor 120 and/or large monitor 140. In the embodiment shown in FIGS. 22 & 23, the pins 2175 of one of the arms 2176 may be closer to the chassis 2174 than the pins of the other of the arms 2176. Such a configuration allows the arms 2176 to move equal amounts upon sliding of the slider 2173 and results in different pivot lengths of the arms 2176 so as to enable opposite movement of the arms 2176. By configuring the monitor mount 2160 as described above, a low profile can be obtained and a space between the small monitor 120 and/or large monitor 140 and the monitor mount 2160 can be minimized when the small monitor 120 and/or large monitor 140 is detachably secured to the monitor mount 2160.

The monitor mount 2160 may be configured to receive interchangeable top portions for accommodating monitors of different types. The monitors of different types may include monitors of different sizes such as small and large monitors 120, 140. In other words, a top portion 2161 as shown in FIG. 19 may be implemented such that the monitor mount 2160 is able to accommodate a small monitor 120. As shown in FIGS. 20 & 21, a top portion 2161 may be implemented such that the monitor mount 2160 is able to accommodate a large monitor 140 or a combination of a small monitor 120 and a large monitor 140. Any of the top portions may be contoured so as to facilitate thermal mitigation.

Figure 24:
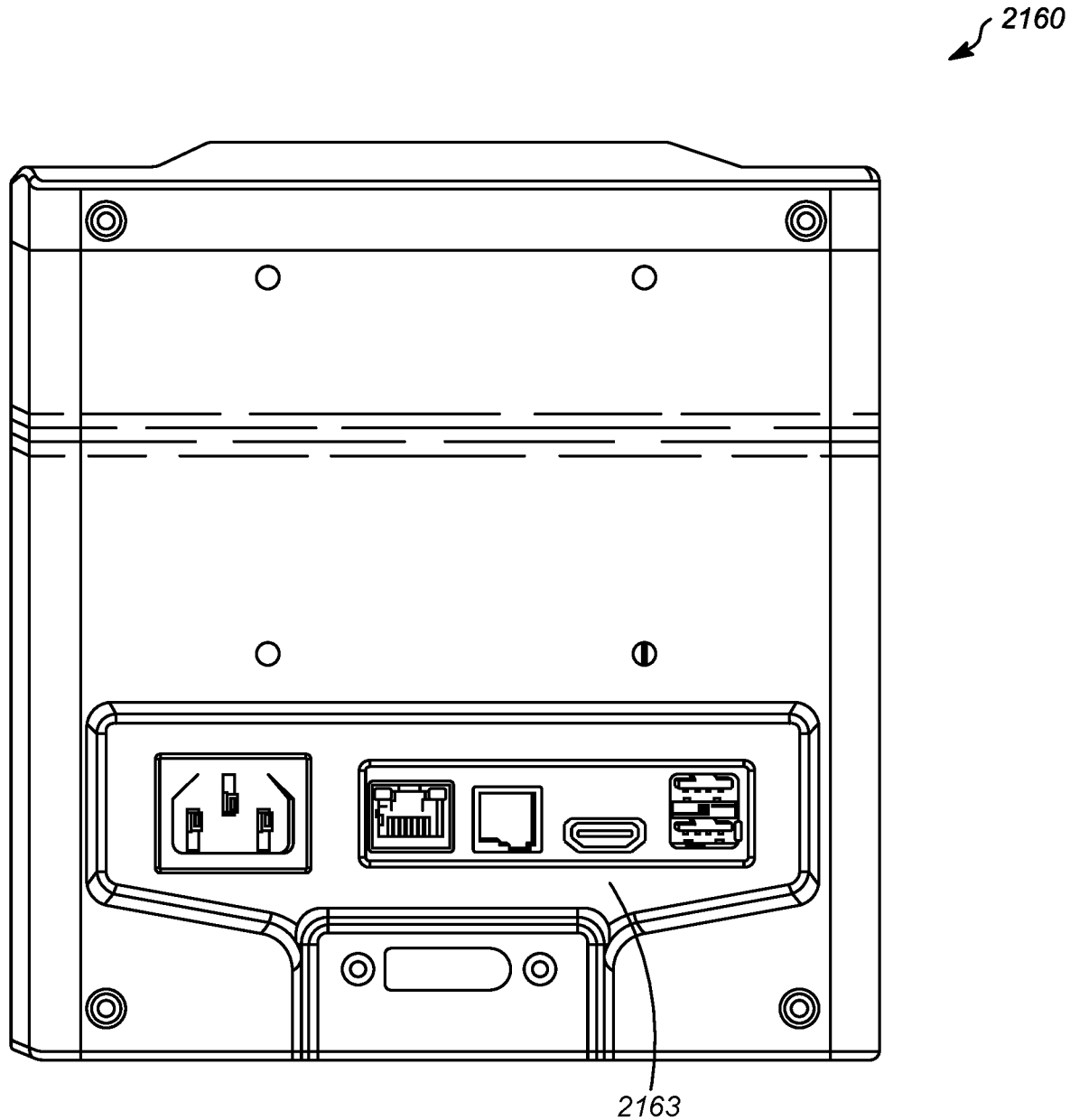
FIG. 24 is a rear view of the third exemplary implementation of the monitor mount.

FIG. 24 is a rear perspective view that shows the third exemplary implementation of the monitor mount 2160. The monitor mount 2160 may include a cutout 2163 on a back surface thereof for permitting a flow of fluid. In this way, the fluid is directed away from electrical connections of the monitor mount 2160 and damage thereto is prevented.

Figure 25:
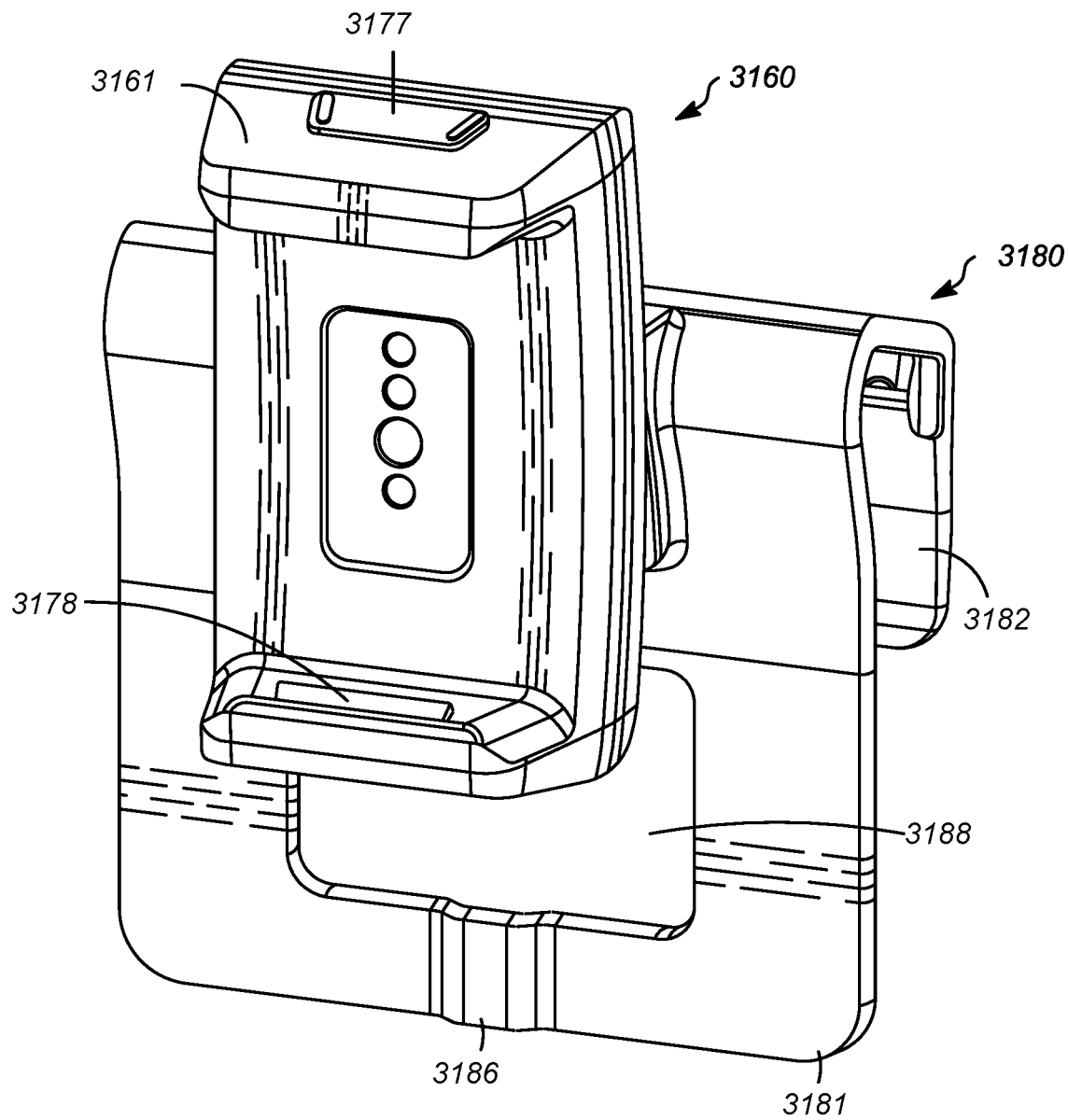
FIG. 25 is a front perspective view of a fourth exemplary implementation of the monitor mount with a clip.
Figure 26:
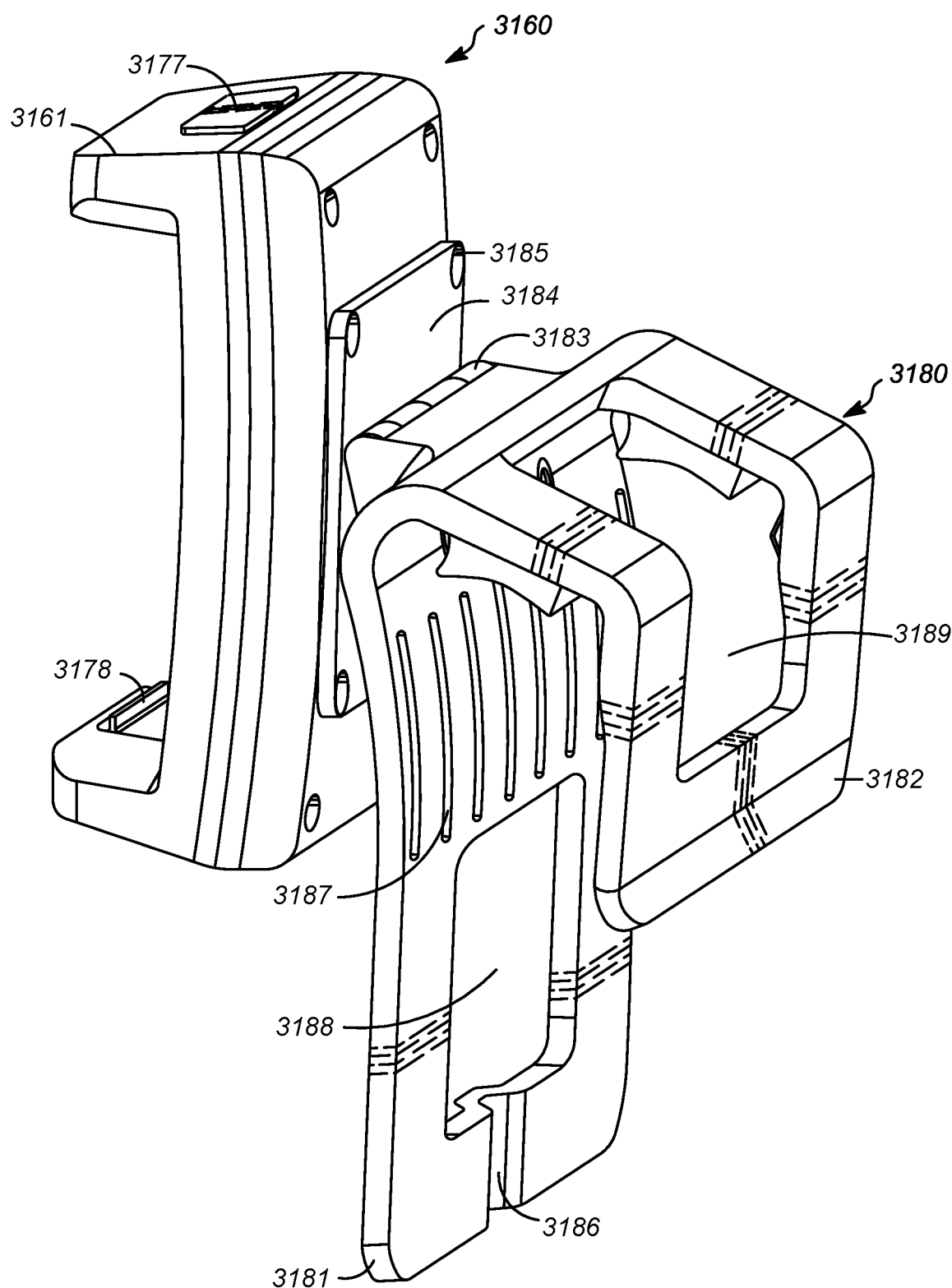
FIG. 26 is a side perspective view of the fourth exemplary implementation of the monitor mount with the clip.

FIGS. 25 & 26 show a fourth exemplary implementation of the monitor mount 3160 for detachably securing a device (e.g., monitor, rack, module, etc.) to a support structure (e.g., bed, stretcher, gurney rail, IV pole, ambulance bar, monitor mount, workstation, stand, etc.). In the implementation shown in FIGS. 25 & 26, the actuator 3177 is a push button located on the top portion 3161 (as an alternative to the lever shown in FIGS. 19-23). Pressure applied to the push button causes the slider (not shown) to slide and disengage the latches 3178 as explained above.

The fourth exemplary implementation of the monitor mount 3160 may include a mounting plate 3184 attached to a back surface of the monitor mount 3160 and a clip 3180 configured to detachably secure the monitor mount 3160 to the support structure. The clip 3180 is important for clinical workflow challenges with transport and moving the patient between care areas (e.g., from an Emergency Department to Radiology or from a CT scan to the OR). The small monitor 120 and/or large monitor 140 can be attached to an IV pole, bed rail, etc., using the clip 3180 so that the small monitor 120 and/or large monitor 140 does not fall or get wrapped in bedsheets on transport. The clip 3180 may be portable and can be used with various types of connectors to patient monitoring devices, portable structures, or stationary structures.

The clip 3180 may allow for long-term or short-term attachment of a monitor to another structure. A short-term attachment fitting allows a user to mount the clip 3180 to a difficult location on a structure and then interchange the monitor as needed. Conversely, a long-term attachment fitting allows for a robust connection, in which the clip position can be changed as needed without excessive concern from the user about the stability of the location of the monitor. The clip 3180 can allow the small monitor 120 and/or large monitor 140 to rotate with respect to the clip 3180 affixed to a rail, pole, or other structure. Though this rotation is described below in discrete increments of 90°, this rotation can include increments of less than 90°, greater than 90°, or an arbitrary rotation. One of the advantages of the ability to rotate the small monitor 120 and/or large monitor 140 relative to the clip 3180 is that cable and cord routing from the small monitor 120 and/or large monitor 140 to the patient can be simplified. Another advantage of this ability to rotate the small monitor 120 and/or large monitor 140 relative to the clip 3180 is that the assembly can adapt to more locations around a patient's bed.

Accordingly, the clip 3180 can attach to a bed rail, a shelf or ledge near a patient's bed, or onto a rack or pole used for other equipment that is near a patient, and the small monitor 120 and/or large monitor 140 can be turned to a convenient orientation about the clip 3180 because of this ability to rotate. Accordingly, the small monitor 120 and/or large monitor 140 can be accommodated to each patient's environment. In other words, the clip 3180 may be attached to the mounting plate 3184 by a hinge 3183 such that the mounting plate 3184 is rotatable with respect to the clip 3180. For example, the mounting plate 3184 is rotatable across 270° with respect to the clip 3180 such that the mounting plate 3184 can be positioned in a vertical orientation and a horizontal orientation. The mounting plate 3184 can include any mounting interface such as a VESA mounting interface 3185.

The clip 3180 may define a hook including a base plate 3181 on a first side of the clip 3180 and a back plate 3182 on a second side of the clip 3180. In some variations, a length of the base plate 3181 may be greater than a length of the back plate 3182. The back plate 3182 may be flexible so as to facilitate mounting of the monitor mount 3160 on the support structure. The base plate 3181 and back plate 3182 have ergonomic features that can allow a user to better utilize the clip 3180. For example, the base plate 3181 may further include a grip portion 3187 for gripping a vertical member (not shown) of the support structure. For example, the grip portion 3187 may be comprised of an elastomeric material. The base plate 3181 may also include a notch 3186 for receiving the vertical member of the support structure. The notch 3186 prevents rotation of the monitor mount 3160 around the vertical member of the support structure. Furthermore, a bottom edge of the base plate 3181 may be configured to be supported on a horizontal member (not shown) of the support structure. Such a configuration allows for a robust connection between the monitor mount 3160 and the support structure. In some variations, the base plate 3181 may include an opening 3188 defined therein and/or the back plate 3182 may include an opening 3189 defined therein. The openings 3188, 3189 may serve to reduce the overall mass of the clip 3180, thereby improving the portability of the clip 3180. In some variations, at least one of the openings 3188, 3189 may be square. In other variations, the openings 3188, 3189 may be arcuate. In the embodiment shown in FIGS. 25 & 26, electrical connections may be omitted such that the monitor mount 3160 provides only physical support. Therefore, the second exemplary implementation of the monitor mount 3160 enables a user to quickly and easily secure and remove a monitor from a support structure.

Figure 27:
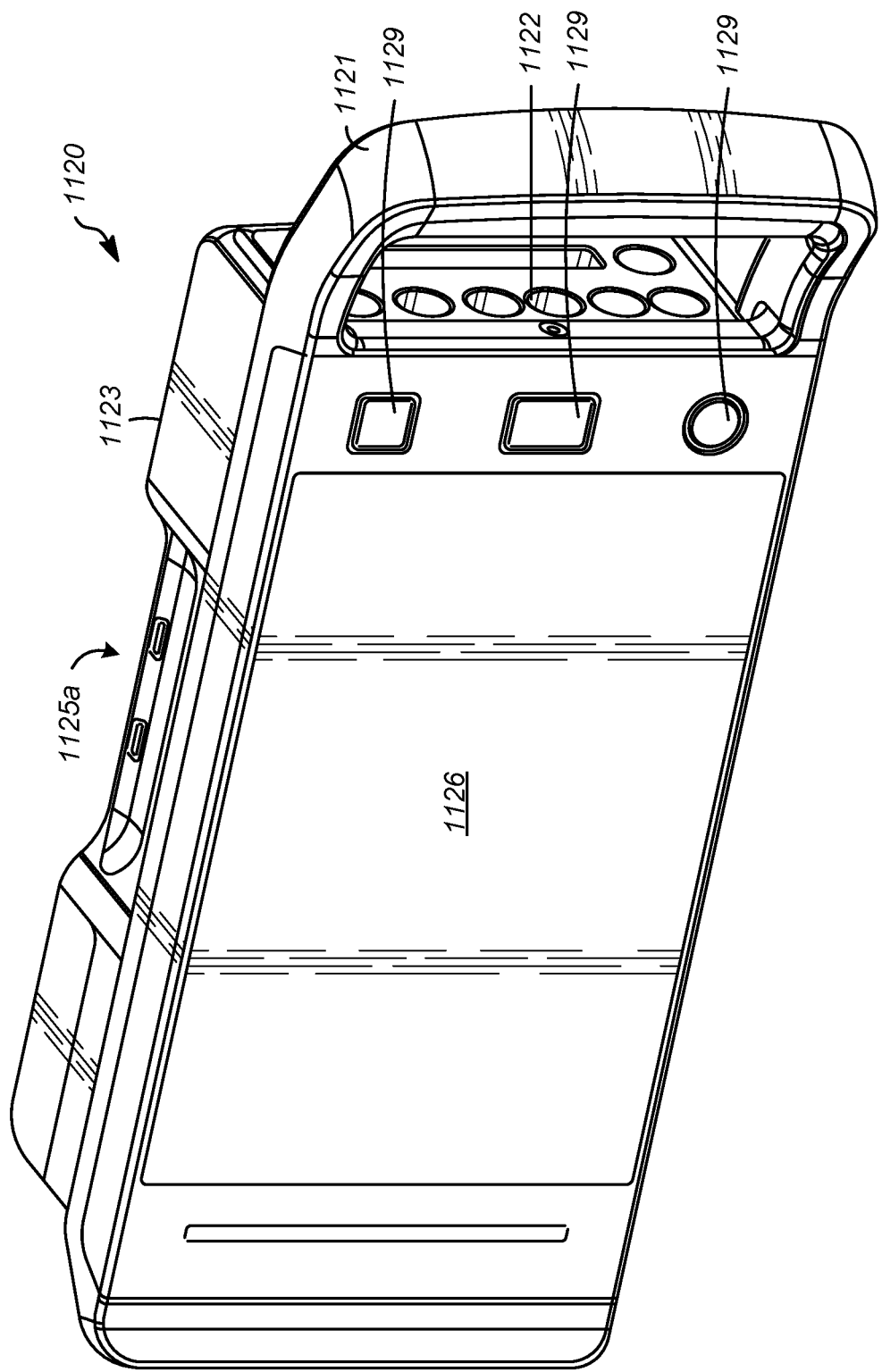
FIG. 27 is a front perspective view of a second exemplary implementation of the small monitor.
Figure 28:
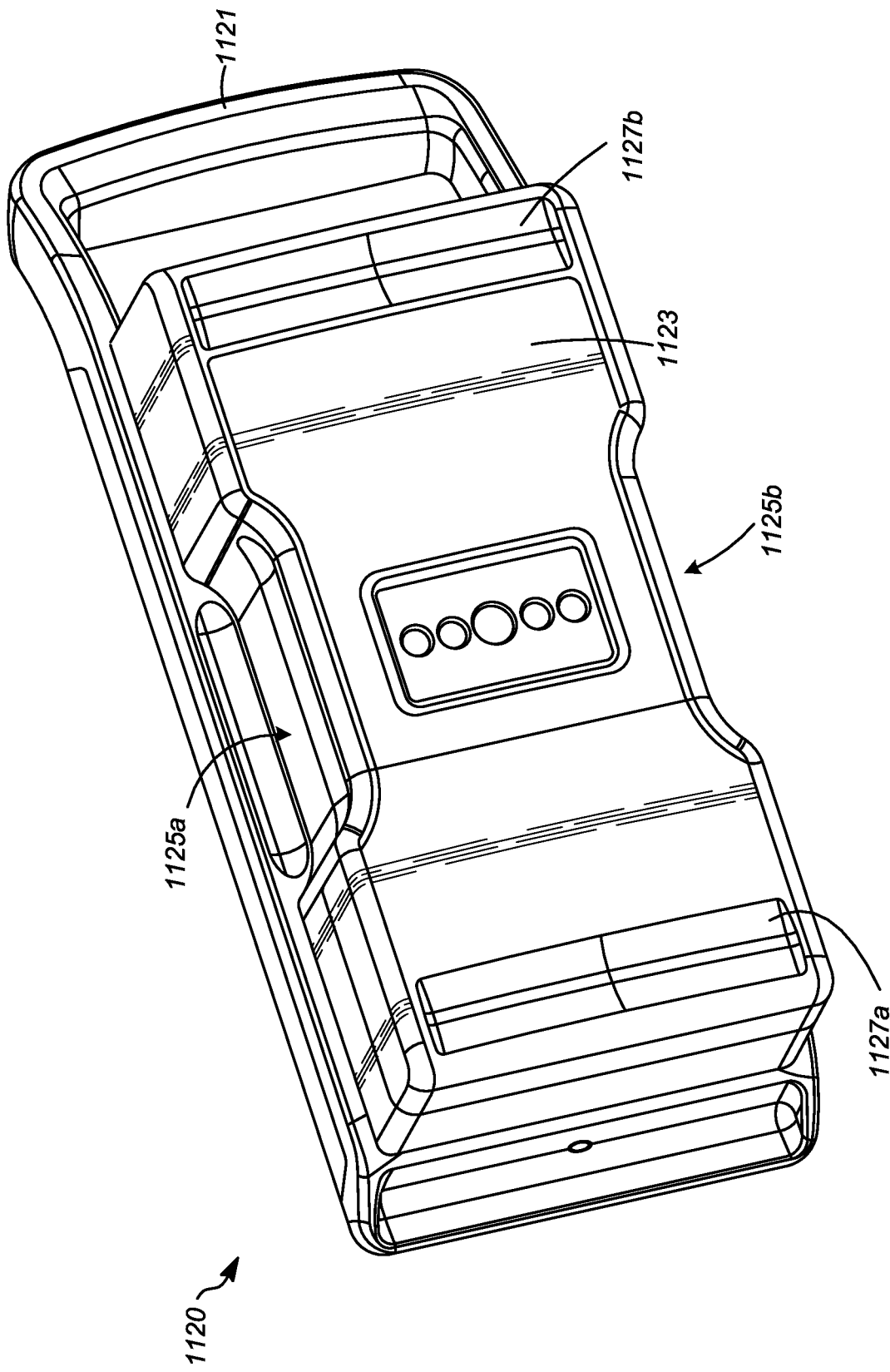
FIG. 28 is a back perspective view of the second exemplary implementation of the small monitor.

FIGS. 27 and 28 show a second exemplary implementation of the small monitor 1120. The small monitor 1120 may have an electronic visual display 1126, a back portion 1123 including a first concave surface 1125a and a second concave surface 1125b, and a handle 1121. The first concave surface 1125a may be defined in a first longitudinal side of the back portion 1123 at a central part of the back portion 1123. The second concave surface 1125b may be defined in a second, opposite longitudinal side of the back portion 1123 at the central part of the back portion 1123. The back portion 1123 may thus have a dog bone-shape such that a distance between the first concave surface 1125a and the second concave surface 1125b at the central part of the back portion 1123 is less than a distance between the first longitudinal side of the back portion 1123 and the second longitudinal side of the back portion 1123 at any part of the back portion 1123 other than the central part of the back portion 1123. Such a dog bone-shape facilitates gripping for the user by increasing the grip back volume, facilitates a mechanical interface with a universal mount, and enables the storage of larger batteries.

In addition, the first back portion 123 may include a first recess 1127a and a second recess 1127b together defining a grip portion for holding the small monitor 1120. A user's fingers can be inserted into any of the first concave surface 1125*a*, the second concave surface 1125*b*, the first recess 1127*a* or the second recess 1127*b*. Each of the first recess 1127*a* and the second recess 1127*b* may extend in a direction parallel to the first concave surface 1125*a* or the second concave surface 1125*b*. The first concave surface 1125*a* and the second concave surface 1125*b* also assist with thermal mitigation by facilitating air flow. The back portion 1123 may also include a battery door which can have a texture or pattern for increasing grip. The handle 1121 may be modular such that it can be reversibly secured to the electronic visual display 1126 in multiple different orientations of the electronic visual display 1126. Such orientations may be opposite to one another. A sensor interface 1122 may be located on either lateral side of the small monitor 1120. A front side of the small monitor 1120 may have a maximum surface area of the sides of the small monitor 1120, may provide any one or more of a user interface, an alarm bar, a speaker opening, buttons 1129 and/or cover glass. The buttons 1129 may be flush with the front side of the small monitor 1120 so as to prevent accidental actuation. The handle 1121 may be in line with a perimeter of the small monitor 1120 surrounding the electronic visual display 1126. Alternatively, the handle 1121 may be at an oblique angle with respect to the perimeter of the small monitor 1120 surrounding the electronic visual display 1126. The handle 1121 may be curved or arcuate. In some variations, no handle 1121 may be included or more than one of the handle 1121 may be included. The handle 1121 may extend across a full width of the small monitor 1120 in a lateral direction. The small monitor 1120 is versatile, contributes to a high level of hygiene, is easily cleanable, is compact in size, reduces costs, features easy assembly, and is quickly reparable. The small monitor 1120 is also resistant to shocks or drops and water ingress.

Figure 29:
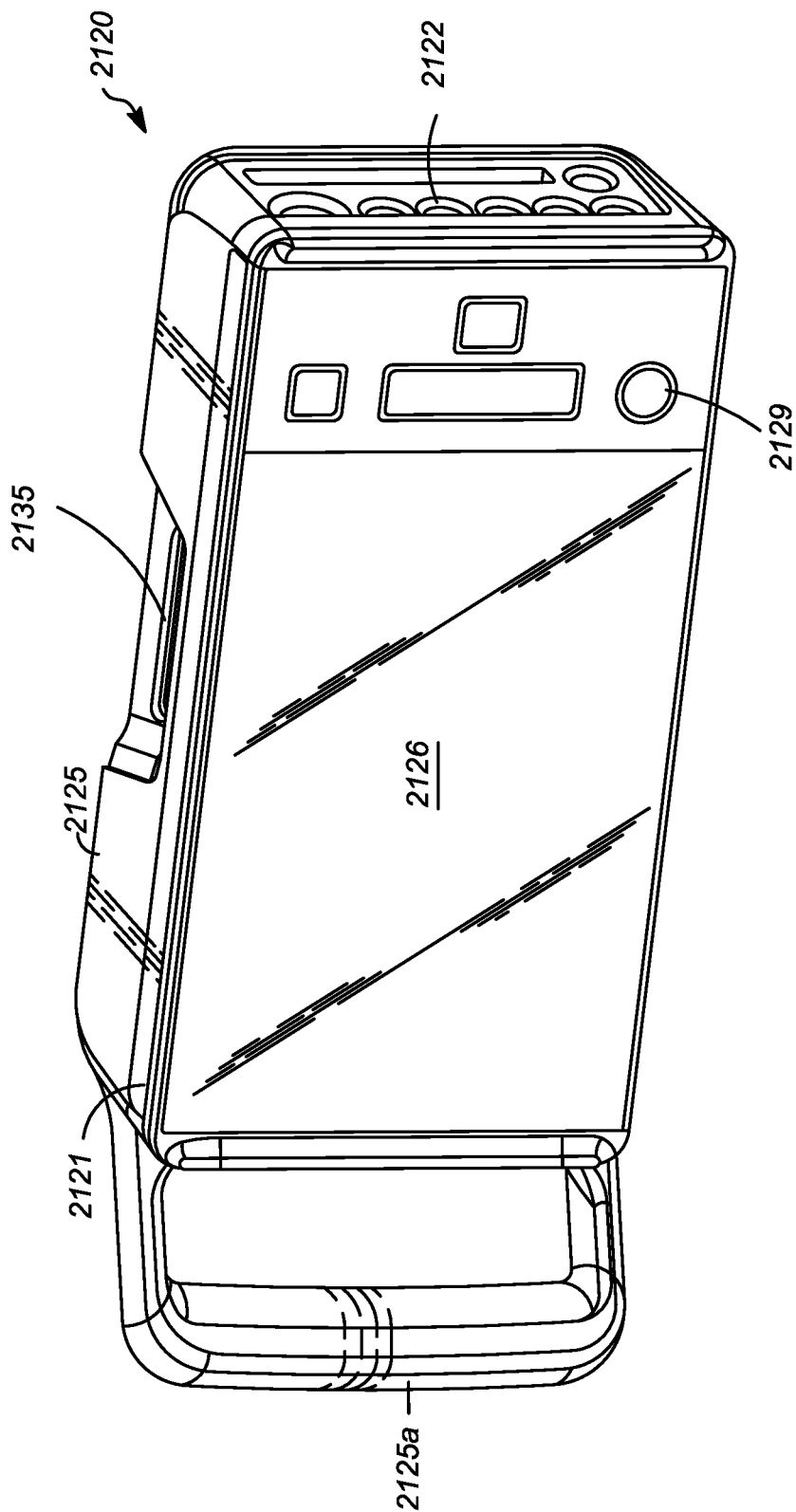
FIG. 29 is a front perspective view of a third exemplary implementation of the small monitor.
Figure 30A:
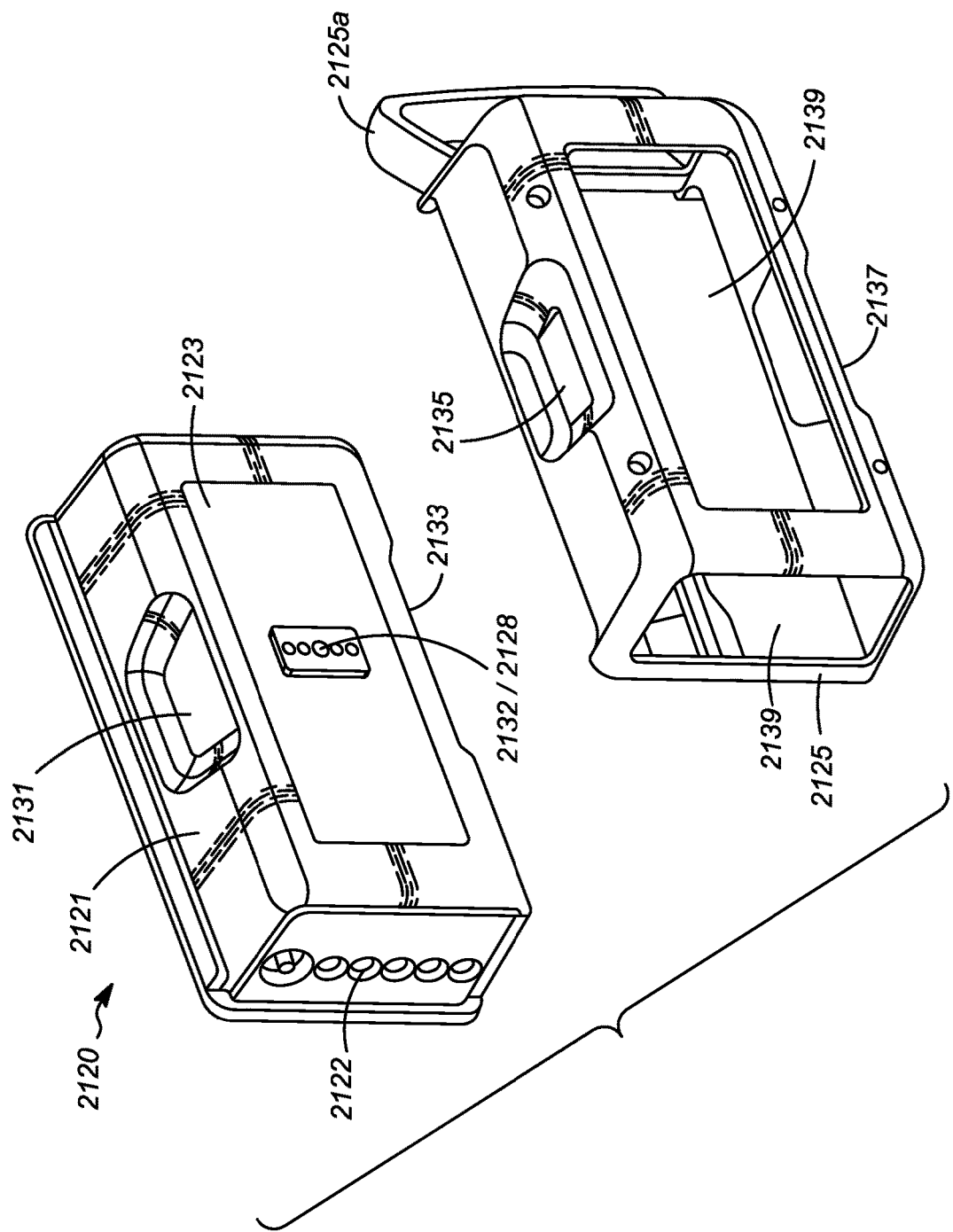
FIG. 30A is an exploded rear perspective view of the third exemplary implementation of the small monitor.

FIGS. 29-30C show a third exemplary implementation of the small monitor 2120. As illustrated in FIGS. 30A-30C, the small monitor 2120 has a case 2121, the sensor interface 2122, the first back portion 2123, a cover 2125, the communications interface 2128, and the power source and/or conduit 2132. The case 2121 may be configured to hold an electronic visual display 2126, and the cover 2125 may be configured to be detachably secured to the case 2121. For example, the cover 2125 may be configured to be detachably secured to a back portion of the case 2121 and may also surround the back portion of the case 2121. In some variations, the cover 2125 may be detachably secured to the case 2121 via at least one fastener (not shown). For example, the at least one fastener may be a screw. The cover 2125 may extend across a full width of the small monitor 2120 in a lateral direction. The cover 2125 may be modular such that it can be reversibly secured to the case 2121 in multiple different orientations of the case 2121. Such orientations may be opposite to one another.

As shown in FIGS. 30A-30C, the cover 2125 may be symmetrical with respect to a longitudinal center axis of the small monitor 2120. In addition, an interface between the cover 2125 and the case 2121 may be symmetrical with respect to a longitudinal center axis (e.g., X-axis) of the small monitor 2120 and a lateral center axis (e.g., Y-axis) of the small monitor 2120. The symmetrical design thereby enables the provision of, for example, both left-hand and right-hand configurations using a single cover 2125. As shown in FIG. 30A, the cover 2125 may include an opening 2139 defined in at least one of a side portion of the cover 2125 or a back portion of the cover 2125. The opening 2139 provides access for connectors and user interface areas regardless of the orientation in which the cover 2125 is positioned. The opening 2139 can also expose a product label on the first back portion 2123 of the case 2121.

In some variations, the cover 2125 may include a handle 2125*a* extending from, for example, a side portion of the cover 2125. The cover 2125 and the handle 2125*a* may be formed as a single unit. The handle 2125*a* may be in line with a perimeter of the cover 2125. Alternatively, the handle 2125*a* may be at an oblique angle with respect to the perimeter of the cover 2125. Such an oblique angle may optimize the center of gravity of the small monitor 2120 and provide a clearance for connectors for a sensor interface 2122 which may be located on either lateral side of the small monitor 2120 such that interference of associated cables for the connectors is avoided. The handle 2125*a* may be curved or arcuate. In some variations, no handle 2125*a* may be included or more than one handle of the 2125*a* may be included on respective sides of the cover 2125. In other variations, the handle 2125*a* may be included; for example, on a side of the cover 2125 corresponding to a side of the small monitor 2120 in which a battery (not shown) is located.

In addition, the case 2121 may include a first recess 2131 and a second recess 2133 together defining either a grip portion for a user's fingers and/or a mount portion for mounting the cover 2125 to the case 2121. For example, the first recess 2131 may be defined in a top portion of the case 2121 and the second recess 2133 may be defined in a bottom portion of the case 2121. Similarly, the cover 2125 may include a first recess 2135 and a second recess 2137 together defining a mount portion configured to physically interface with the first coupling 170. For example, the first recess 2135 may be defined in a top portion of the cover 2125 and the second recess 2137 may be defined in a bottom portion of the cover 2125.

A front side of the small monitor 2120 may have a maximum surface area of the sides of the small monitor 2120, may provide any one or more of a user interface, an alarm bar, a speaker opening, buttons 2129 and/or cover glass. The buttons 2129 may be flush with the front side of the small monitor 2120 so as to prevent accidental actuation. In some variations, the case 2121 and/or the cover 2125 may be comprised of plastic. The small monitor 2120 can be adapted for ambulance, air medical services, shock-susceptible, vibration-susceptible, and/or military specification applications where a more robust monitor configuration is appropriate. The small monitor 2120 is versatile, contributes to a high level of hygiene, is easily cleanable, is compact in size, reduces costs, features easy assembly, and is quickly reparable. The small monitor 2120 is also resistant to shocks or drops and water ingress.

Figure 31:
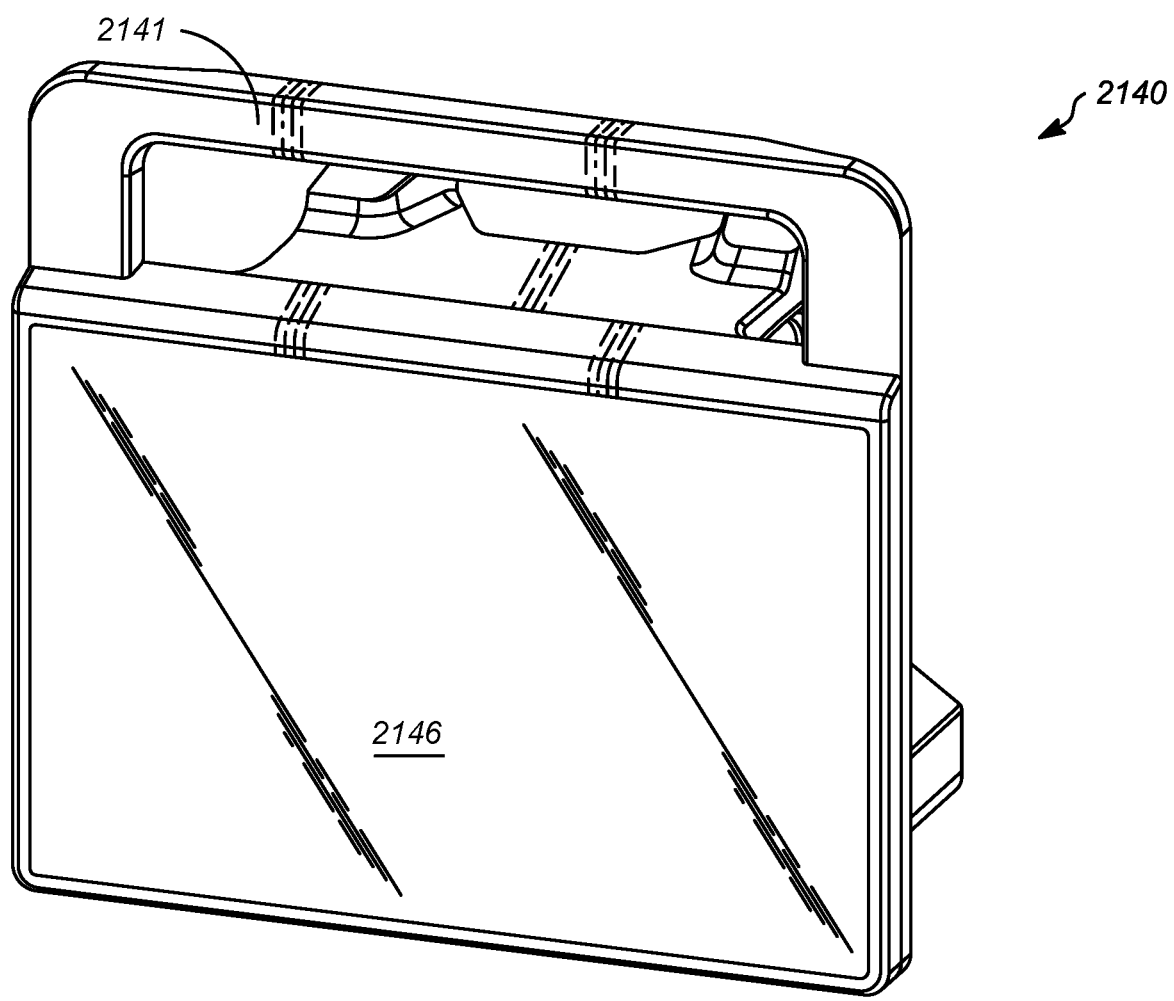
FIG. 31 is a front perspective view of a third exemplary implementation of the large monitor.

FIG. 31 is a front perspective view of a third exemplary implementation of the large monitor 2140. As illustrated in FIG. 31, the large monitor 2140 has a handle 2141, and an electronic visual display 2146.

Figure 32:
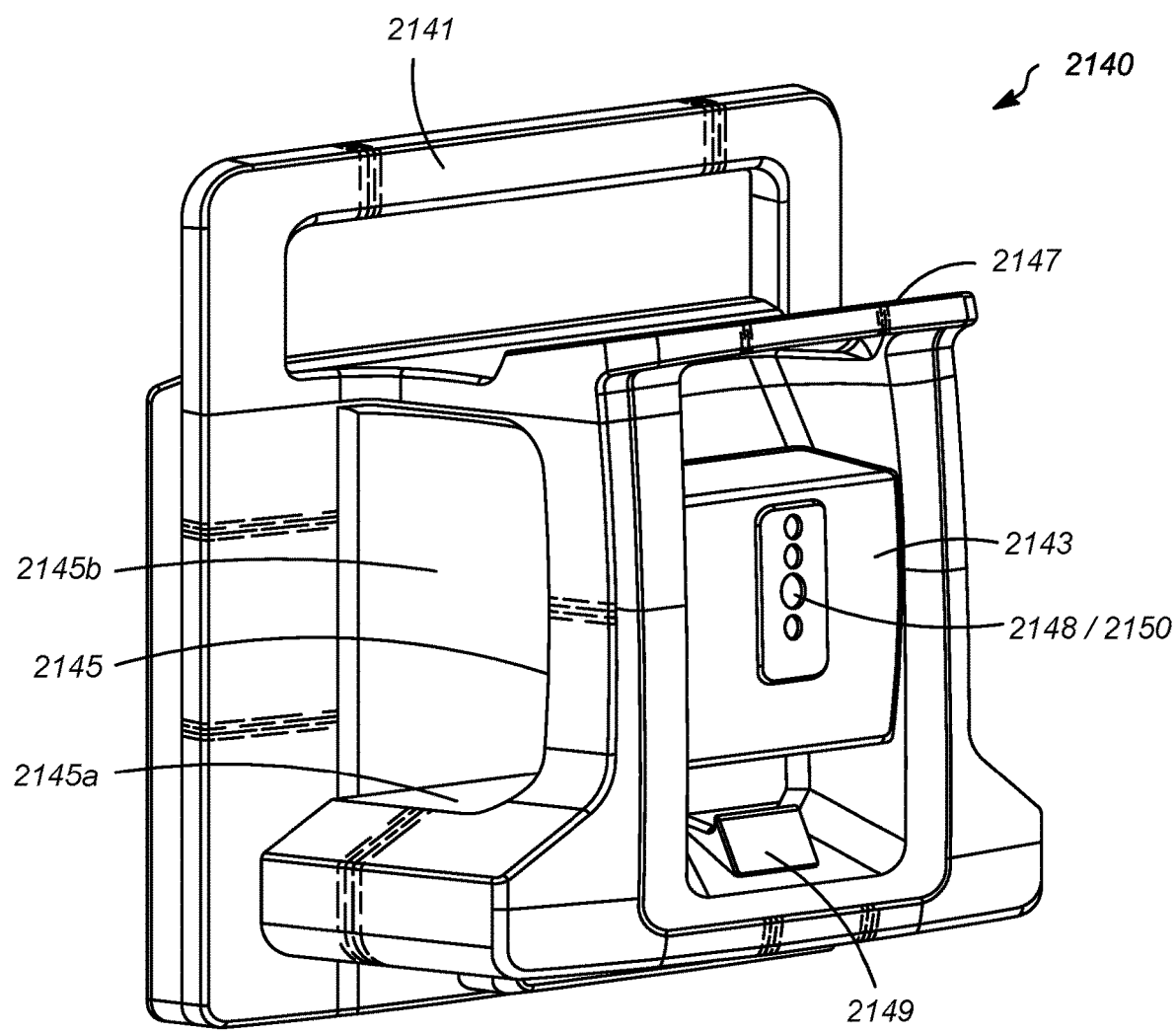
FIG. 32 is a rear perspective view of the third exemplary implementation of the large monitor.

FIG. 32 is a rear perspective view of the third exemplary implementation of the large monitor 2140. As illustrated in FIG. 32, the large monitor 2140 has a handle 2141, a back portion 2143, a coupling 2145, a hook portion 2147, a communications interface 2148, and a power source and/or conduit 2150. The hook portion 2147 can facilitate the detachable securing of the large monitor 2140 to the support portion 2167 (as shown in FIGS. 20 and 21) and/or the first coupling 2170. The coupling 2145 can have one or more guiding surfaces 2145*a* for facilitating the transverse insertion and/or removal of the small monitor 120 into the receptacle 2145*b* of the large monitor 2140. The first exemplary implementation of the large monitor 2140 may further include a latch 2149. In some variations, the latch 2149 can facilitate the detachable securing of the large monitor 2140 to the first coupling 2170 by fitting into a slot 2169 defined in an underside of the first coupling 2170 (as shown in FIG. 21). The latch 2149 may be spring-loaded such that the latch 2149 is biased into the slot 2169 (shown in FIG. 21) when the large monitor 2140 is being detachably secured to the monitor mount 2160. For example, the hook portion 2147 may be located on a top side of the back portion 2143 and the latch 2149 may be located on a bottom side of the back portion 2143.

Figure 33:
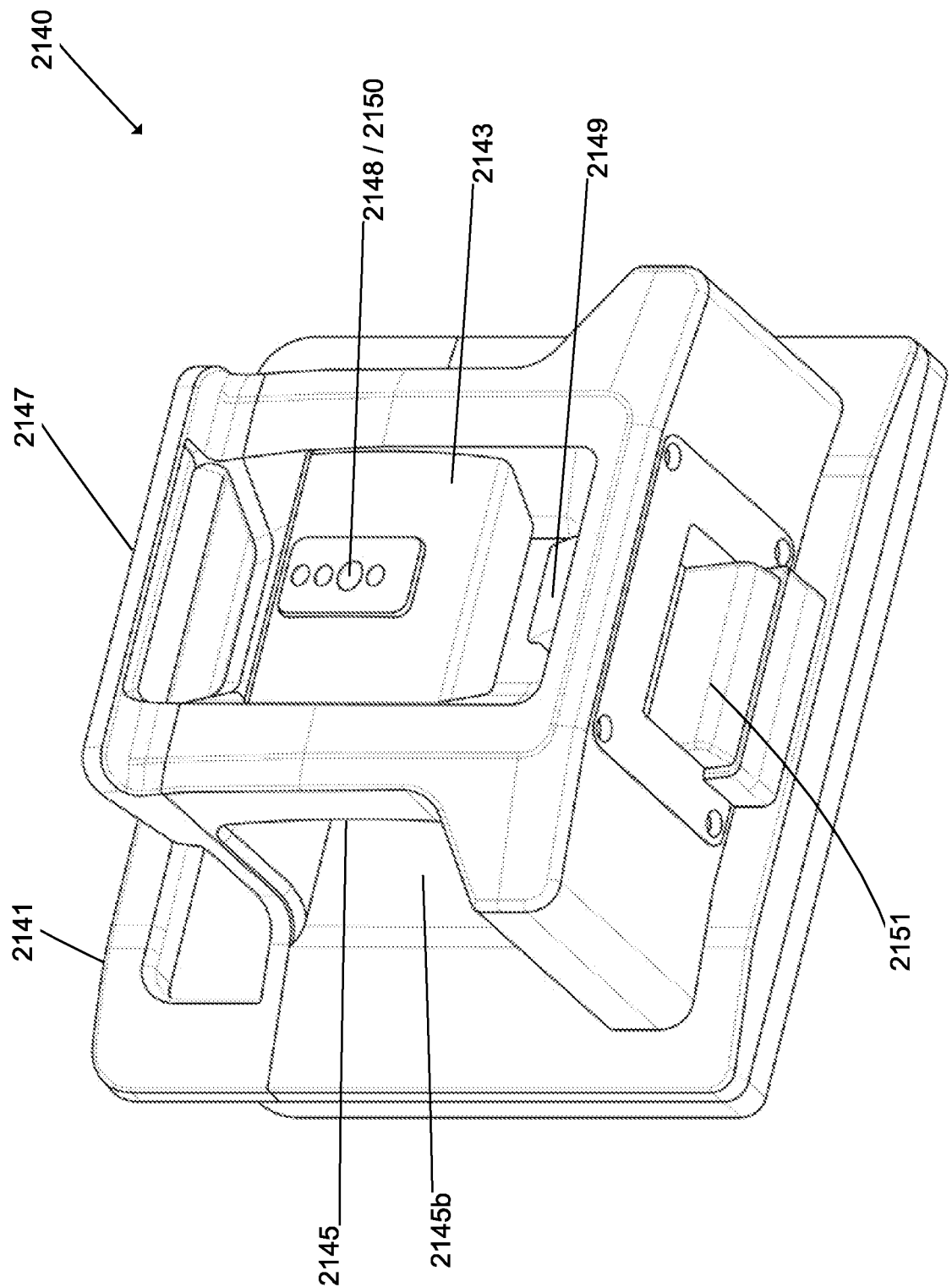
FIG. 33 is a bottom perspective view of the third exemplary implementation of the large monitor.

FIG. 33 is a rear perspective view of the first exemplary implementation of the large monitor 2140. As illustrated in FIG. 33, the large monitor 2140 has another handle 2151 linked to the latch 2149. In some variations, the large monitor 2140 may be removed from the monitor mount 160 by pressing the handle 2151 so as to disengage the latch 2149 from the slot 2169 defined in the first coupling 170 of the monitor mount 2160. For example, the handle 2151 may be located underneath the latch 2149 on an underside of the large monitor 2140 and a user may grip the underside of the large monitor 2140 so as to operate the handle 2151.

Figure 34:
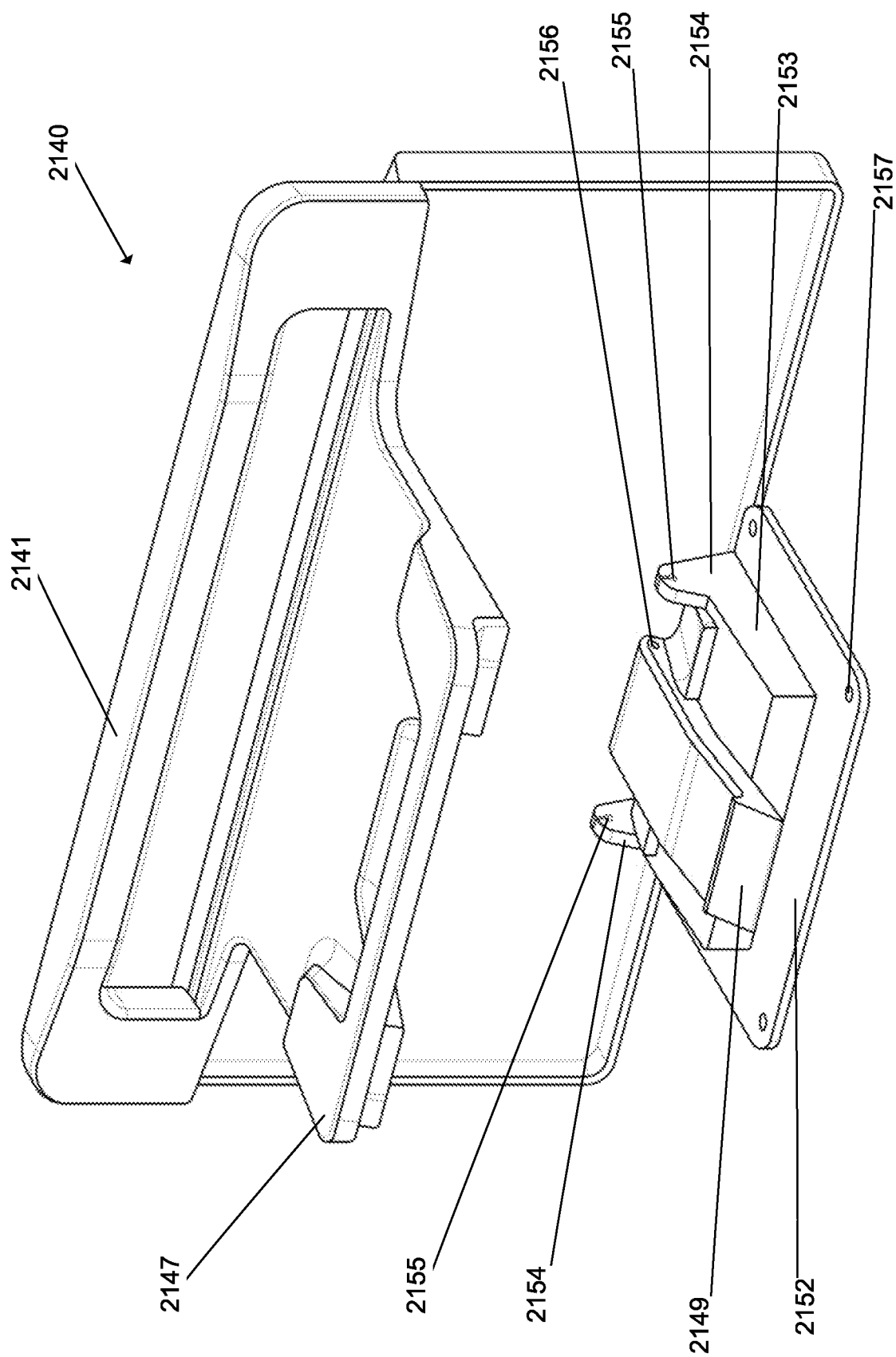
FIG. 34 is a rear perspective view of the third exemplary implementation of the large monitor with a rear housing thereof removed.

FIG. 34 is a rear perspective view of the third exemplary implementation of the large monitor 2140 with a rear housing thereof removed. As illustrated in FIG. 34, the large monitor 2140 includes a base plate 2152 and a latch cover 2153 fixed to the base plate 2152. In some variations, the latch 2149 is configured to pivot relative to the latch cover 2153. The latch cover 2153 may include at least one protrusion 2154 extending away from the base plate 2152, and an aperture 2155 defined in the at least one protrusion 2154. An aperture 2156 may also be defined in the latch 2149. In some variations, the aperture 2155 may be defined adjacent to a distal end of the at least one protrusion 2154 and the aperture 2156 may be defined adjacent to a proximal end of the latch 2149. Each of the apertures 2155, 2156 may be configured to receive an axle rod (not shown) around which the latch 2149 is pivotable and which extends through the latch 2149 and the latch cover 2153. For example, the axle rod may be cylindrical and may extend along a longitudinal direction of the large monitor 2140. As described above, the latch 2149 may be spring-loaded such that the latch 2149 is biased into the slot 2169 (shown in FIG. 21) when the large monitor 2140 is being detachably secured to the monitor mount 160. For example, the large monitor 2140 may include at least one spring (not shown) between the latch 2149 and the latch cover 2153 for biasing the latch 2149 into the slot 2169. The large monitor 2140 may further include any mounting interface 2157 such as a VESA mounting interface.

Figure 35:
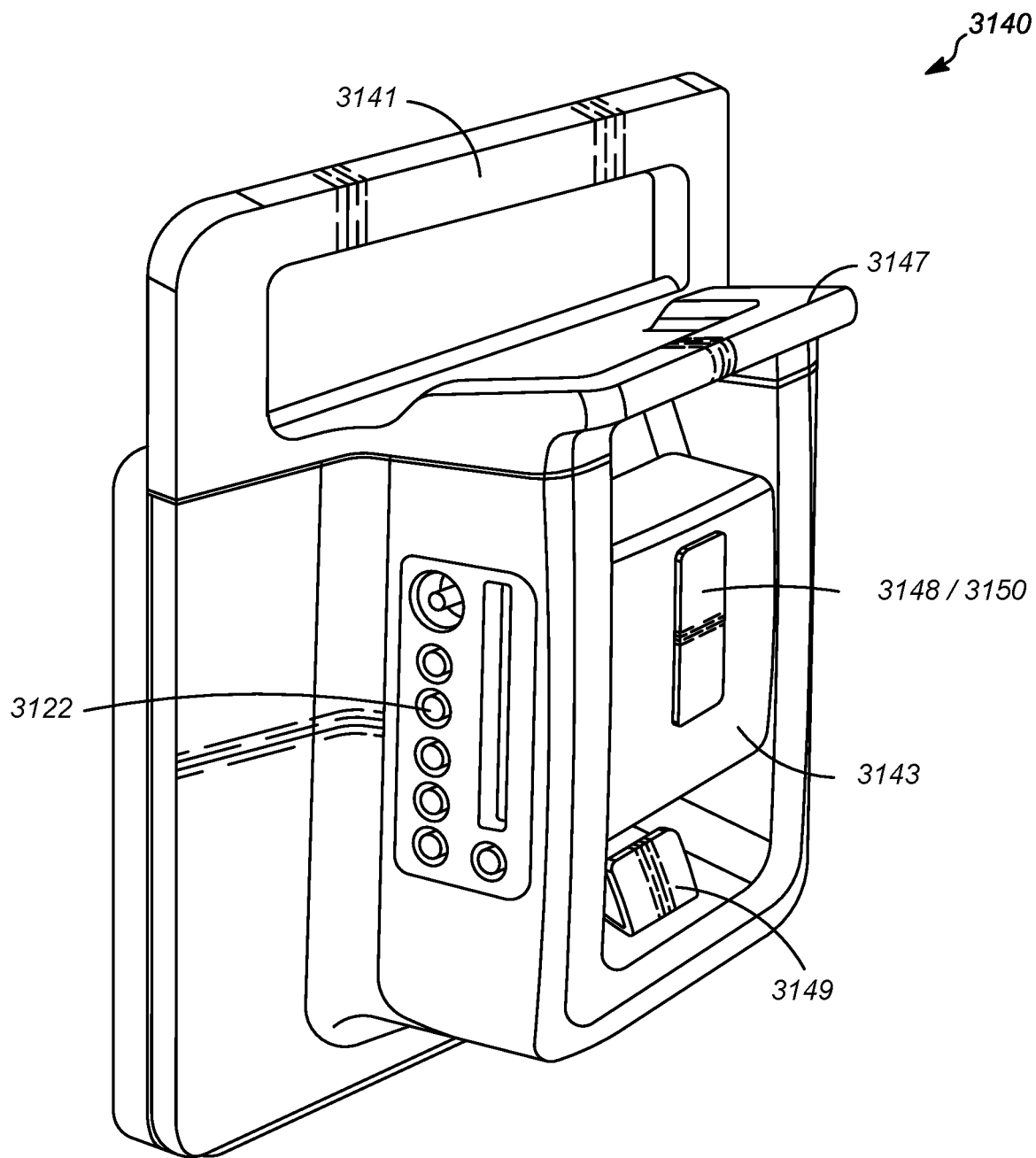
FIG. 35 is a rear perspective view of a fourth exemplary implementation of the large monitor.

FIG. 35 is a rear perspective view of a fourth exemplary implementation of the large monitor 3140. For example, a smaller monitor (e.g., small monitor 120) is used to monitor various physiological parameters for a patient 110, and a larger monitor (e.g., large monitor 3140) is used to expand the number of sensors available for patient monitoring and/or increasing the number of patient parameters on a single visual electronic display. In other words, the smaller monitor can generally include a sensor interface configured to receive data generated by at least one physiological sensor monitoring a physiological parameter of a patient. The larger monitor can be a multiparameter monitor for continuously monitoring adult, pediatric and neonatal patients both at a bedside and on transport and can support all patient acuity levels hospital-wide.

In some variations, only one of the small monitor 120 and the large monitor 140 is provided. In some variations, both the small monitor 120 and the large monitor 140 are provided and the small monitor 120 is docked in the large monitor 140. As illustrated in FIG. 35, the large monitor 3140 integrates the functionalities of a smaller monitor and a larger monitor into one single unit and includes the sensor interface 3122. In the embodiment shown in FIG. 35, the large monitor 3140 further includes a handle 3141, a hook portion 3147, a communications interface 3148, a latch 3149, and a power source and/or conduit 3150. In the embodiment shown in FIG. 35, the large monitor 3140 does not include a second coupling 145. The back portion 3143 of the large monitor 3140 shown in FIG. 35 can be reduced in thickness compared to the back portion 2143 of the large monitor 2140 shown in FIG. 32 and therefore has a slimmer overall volume.

Figure 36:
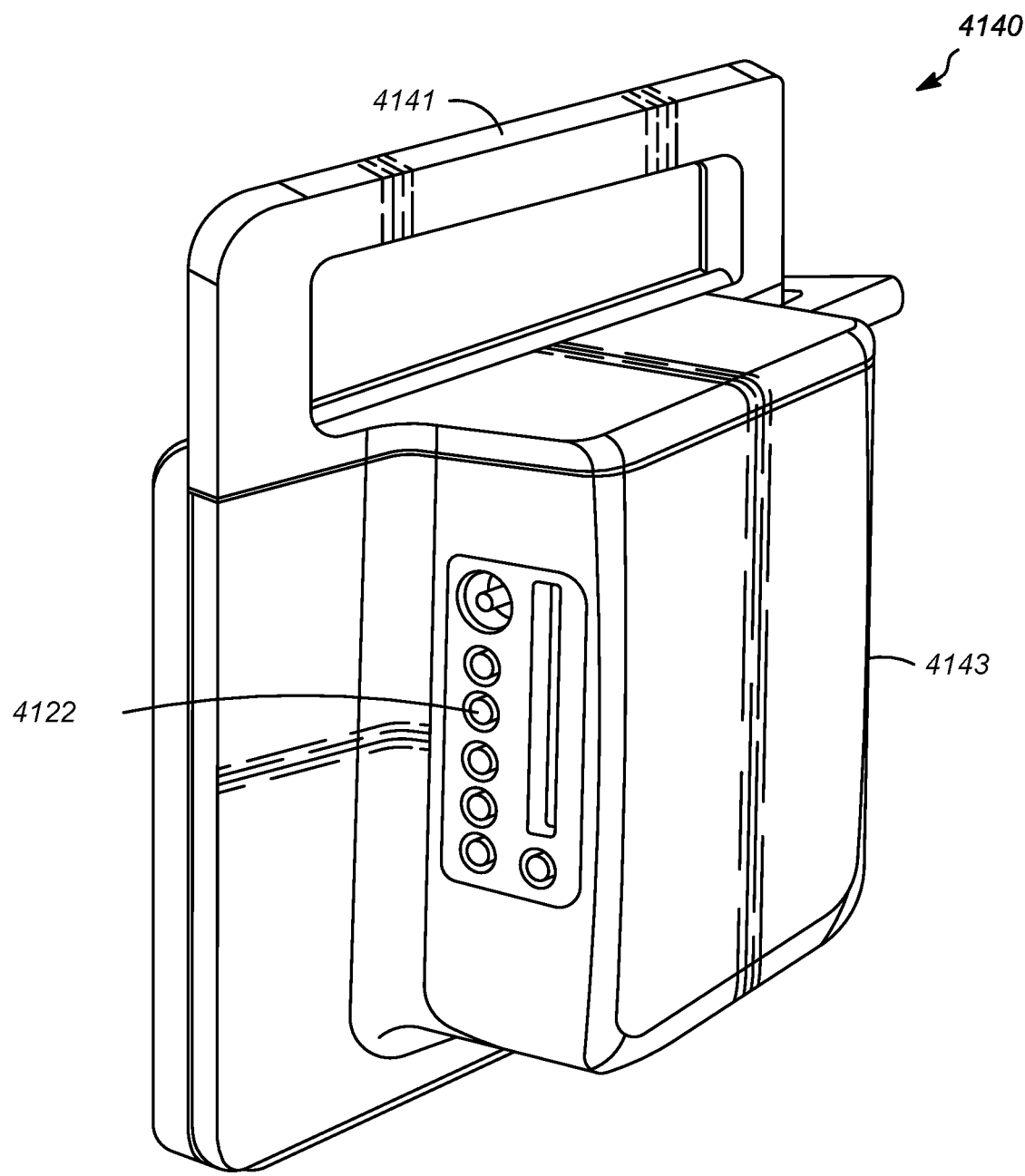
FIG. 36 is a rear perspective view of a fifth exemplary implementation of the large monitor.

FIG. 36 is a rear perspective view of a fifth exemplary implementation of the large monitor 4140. As illustrated in FIG. 36, the large monitor 4140 integrates the functionalities of a smaller monitor and a larger monitor into one single unit and includes the sensor interface 4122. In the embodiment shown in FIG. 36, the large monitor 4140 has a handle 4141 and a simplified back portion 4143. That is, a back surface of the back portion 4143 is continuous and the back surface does not include couplings or electrical connections. In other words, in the embodiment shown in FIG. 36, the large monitor does not include a second coupling, a hook portion, a communications interface, a latch, or a power source and/or conduit. The back portion 4143 of the large monitor 4140 shown in FIG. 36 can be reduced in thickness compared to the back portion 2143 of the large monitor 2140 shown in FIG. 32 and therefore has a slimmer overall volume.

Figure 37:
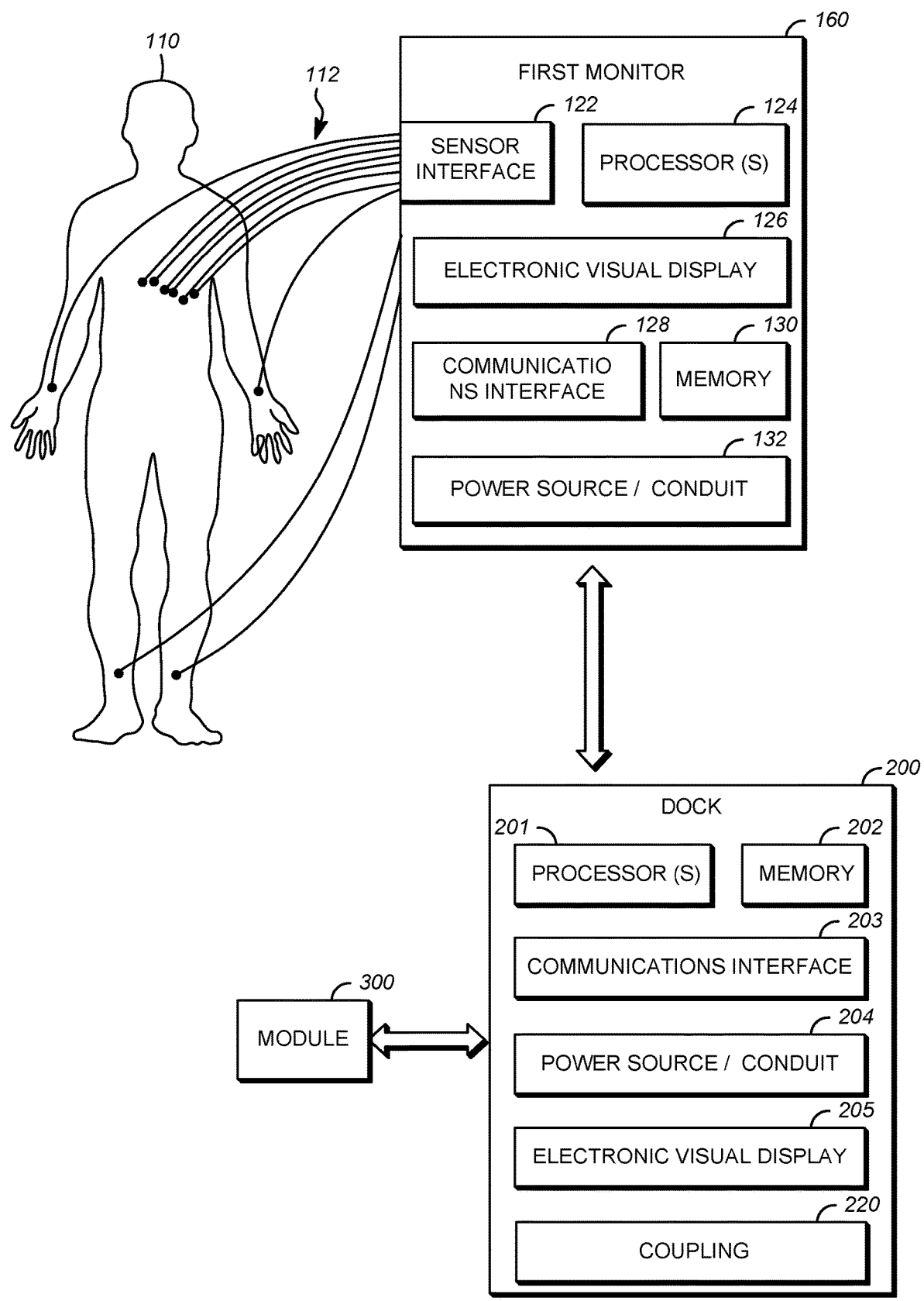
FIG. 37 is a logical diagram illustrating an example system including a small monitor, a dock and a module.
Figure 38:
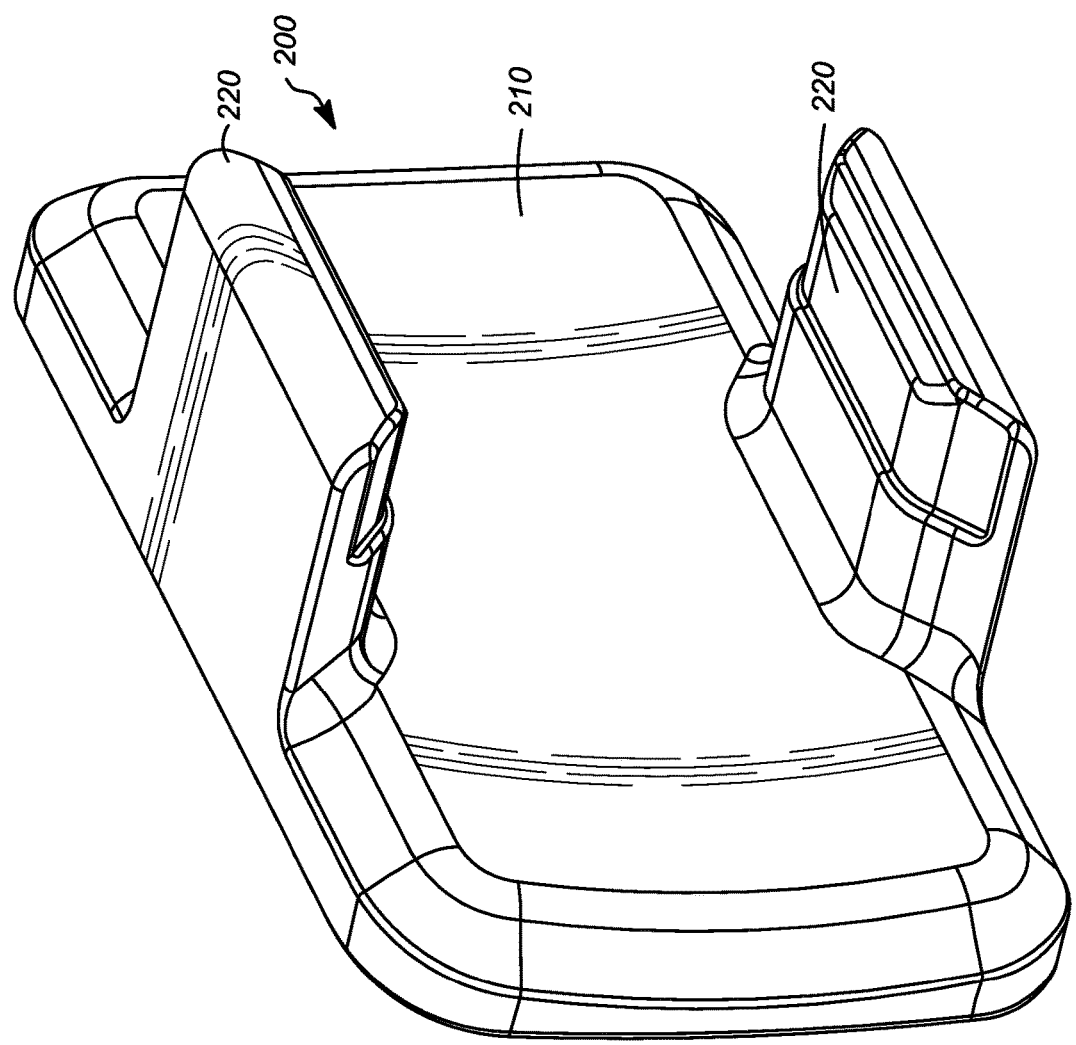
FIG. 38 is a front perspective view of a first exemplary implementation of the dock.
Figure 39:
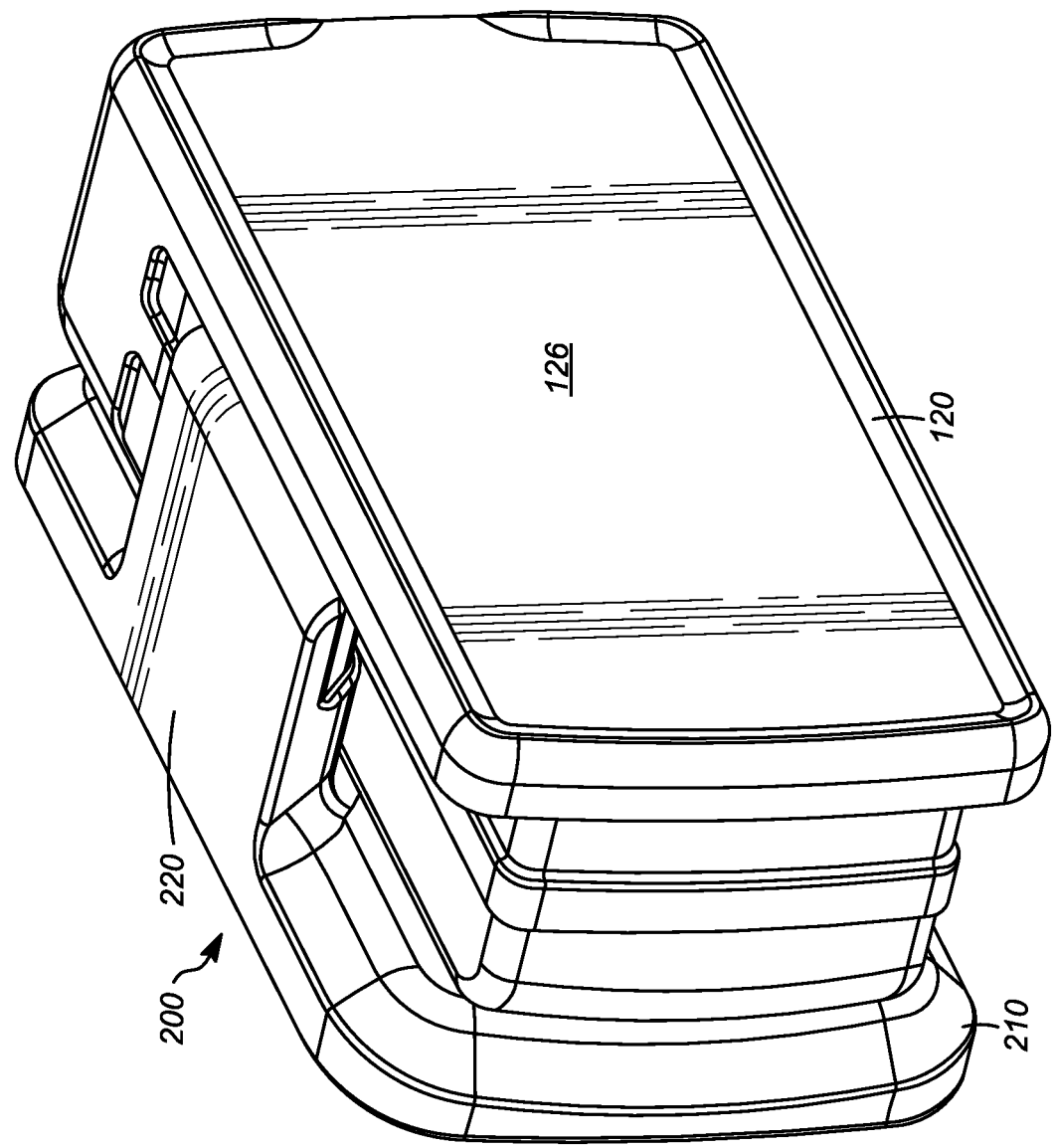
FIG. 39 is a front perspective view of an example system including the first exemplary implementation of the dock detachably securing a small monitor.
Figure 40:
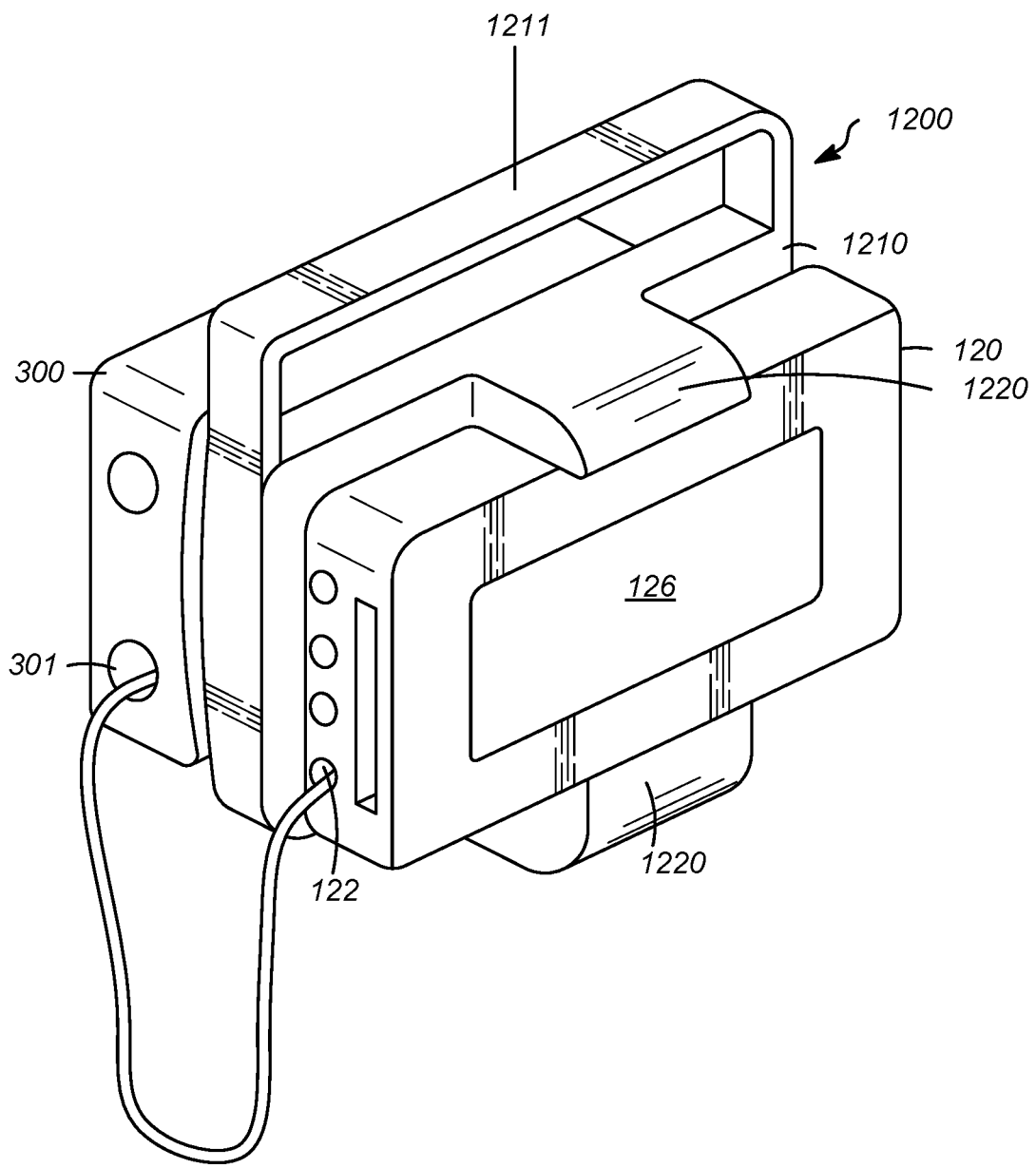
FIG. 40 is a front perspective view of an example system including a second exemplary implementation of the dock detachably securing a small monitor and a module.
Figure 41:
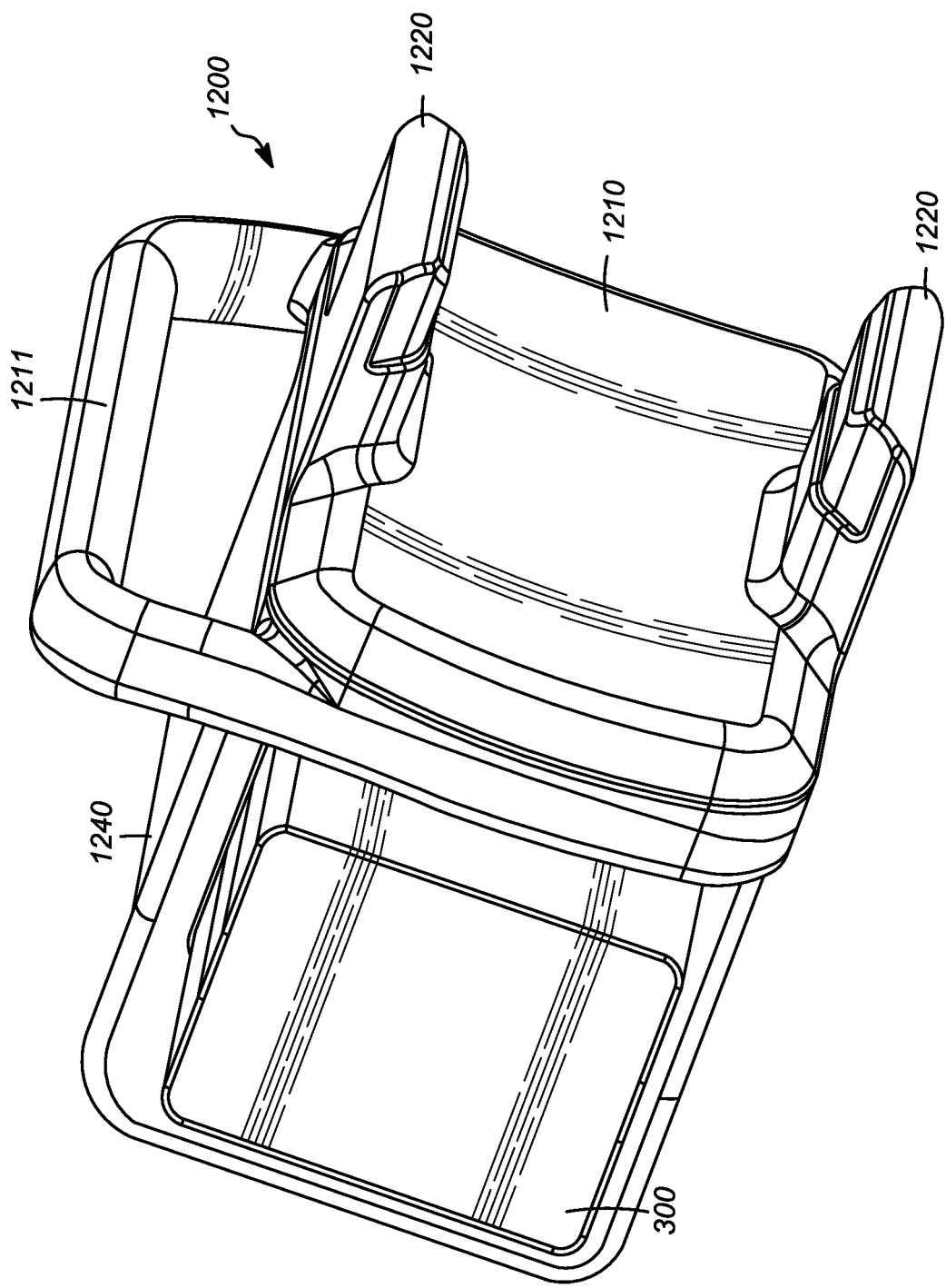
FIG. 41 is a front perspective view of an example system including the second exemplary implementation of the dock detachably securing a module.

FIG. 37 is a logical diagram of a small monitor 120, a module 300 and a dock 200 which can detachably secure (or otherwise physically interface with) at least one of the small monitor 120 and the module 300. FIGS. 38 and 39 illustrate a first exemplary implementation of the dock 200. FIGS. 40 and 41 illustrate a second exemplary implementation of the dock 1200. FIGS. 42-45 illustrate a third exemplary implementation of the dock 2200. FIGS. 46-50 illustrate a fourth exemplary implementation of the dock 3200. FIGS. 34-40 illustrate a fifth exemplary implementation of the dock 4200. While certain configurations are illustrated with regard to the dock 200 and its alternative implementations, the small monitor 120, and/or the module 300, it will be appreciated that these illustrations in FIGS. 19-40 are examples and not limiting in nature (unless otherwise specified).

The dock 200 can have a basic mechanical design to transport a portable small monitor 120 and one or more of module 300. That is, the dock 200 can have a shape and size which allows the dock 200 to detachably secure one or both of the small monitor 120 and the module 300 such that the small monitor 120 and/or the module 300 can be attached and removed by the user when desired.

The dock 200 can include a first coupling 220 to allow the small monitor 120 to be secured to the dock 200. The first coupling 220 can include any mechanical attachment means such as a ledge, a rail, a rib, an abutment, and the like, or any combination thereof. The first coupling 220 can additionally or alternatively include different securing mechanisms including magnetic and/or electromagnetic locking mechanisms which cause the small monitor 120 to selectively be secured to the dock 200. In some cases, the small monitor 120 can slide into and out of the first coupling 220 from one or more lateral directions (i.e., from one or more sides of the dock 200) while in other variations, the small monitor 120 can be mounted to and removed from the front face of the dock 200. In some implementations, the small monitor 120 can both slide into and out of the first coupling 220 from one or more lateral directions and be mounted to and removed from the front face of the dock 200. Reference is made to FIG. 21 which shows a portion of the first coupling 220 in which the small monitor 120 can be inserted. The first coupling 220 may be configured to detachably secure opposite sides of a center of a perimeter of the small monitor 120 therebetween such that end portions of the perimeter of the small monitor 120 extend beyond opposite ends of the first coupling 220 in a direction along a lateral direction of the case when the small monitor 120 is secured to the dock 200. The dock 200 can include a case 210 and the first coupling 220 may extend from a side of the case 210.

The positioning of the small monitor 120 when secured to the dock 200 can be such that the communications interface 128 on the small monitor 120 aligns with the communications interface 203 of the dock 200 to allow, for example, a direct connection (e.g., electrical connection). In other variations, the communications interface 128 of the small monitor 120 exchanges data with the communications interface 203 of the dock 200 optically (via, for example, respective optical windows on the small monitor 120 and the dock 200).

The positioning of the small monitor 120 when secured to the dock 200 can also align the power source/conduit 132 of the small monitor 120 to be coupled to the power source/conduit 204 of the dock 200 which causes the dock 200 to power the small monitor 120.

The dock 200 can optionally include one or more processors 201 (e.g., programmable data processors, etc.) which can execute various instructions stored in memory 202 of the dock 200. As noted above, the dock 200 can optionally include the communications interface 203 which allows the dock 200 to directly or indirectly access one or more computing networks. The communications interface 203 can include various network cards/interfaces to enable wired and wireless communications with such computing networks. The communications interface 203 can also enable direct (i.e., device-to-device, etc.) communications (i.e., messaging, signal exchange, etc.) such as with the small monitor 120 and/or the module 300. Various data and graphical user interfaces can be conveyed to a user via an electronic visual display 205 optionally included in or connected to the dock 200. The electronic visual display can configured to be detachably secured in the case 210 such that an electrical connector (not shown) of the electronic visual display 205 is connected to an electrical connector (not shown) of the dock 200. In some variations, the electronic visual display 205 includes any of a touch screen interface, an electronic ink display, or an electronic paper display. The electronic visual display 205 of the dock 200 can be configured to operate with less power than the electronic visual display 146 of the small monitor 120; for example, an electronic ink or paper display can consume relatively less power.

The dock 200 can optionally also include a power source and/or conduit 204 that can be used to power the various components of the small monitor 120 (and optionally various components of the module 300). The power source/conduit 204 can include a self-contained power source such as a battery pack and/or the power source/conduit 204 can include an interface to be powered through an electrical outlet (either directly or by way of the small monitor 120).

In some variations, the small monitor 120 can only be powered and render information when secured or otherwise connected to the dock 200.

The dock 200 optionally includes features to enable additional functionality similar to a monitor mount or a traditional sized monitor, such as a CPU, a radio, a battery, electronic circuitry, a relay module/board (e.g., PCB3), a multimedia device communications panel, additional communication ports such as for additional physiological measurement modules, an enclosure with a handle, an optical interface, LED indicators, etc. The dock 200 may be detachably secured to a support structure such as a bed or stretcher or gurney rail, IV pole, etc. via any attachment mechanism such as a VESA mounting interface adapted to an attachment mechanism. The attachment mechanism may detachably secure the dock to a support structure, including a support structure that is tubular or rectangular.

In some variations, the one or more processors 201 and the memory 202 are omitted such that the dock 200 provides only physical support and optionally a power source. In other words, the dock 200 may not include electrical connections such that the dock 200 may be configured to provide only physical support for the small monitor 120. The dock 200 therefore provides flexibility in mounting and cable management.

The dock 200 may be used in conjunction with a workstation with monitoring, anesthesia and information technology functionalities. The dock 200 may be used or mounted outside of a sterile field within the OR.

Possible specifications for the dock 200 include a lightweight package under 2.0 lbs. or 0.9 kg., capability to support one or more additional modules (e.g., for $CO_2$ monitoring), battery run time of over 3.5 hours, built-in wireless communications, and defibrillator synchronization.

The module 300 can provide one or more different functions used in delivering healthcare to a patient. The module 300 can acquire patient data including the monitored parameters allocated to a given patient from a network and collate the information for storage in a database. The module 300 can be any of a patient monitoring module for acquiring and processing data generated by at least one physiological sensor monitoring a physiological parameter of a patient (e.g., gas measurement, end-tidal carbon dioxide ($etCO_2$), SCIO, patient gas, thermoregulation, blood pressure, heart related measurement, pulse oximetry, respiration, neonatal measurement, ventilation, anesthesia information, incubation information, etc.), a patient treatment module for delivering treatment to the patient (e.g., monitoring fluids administered to the patient and supplying anesthesia to the patient, respectively), a control module, a charging module, a compartment module, a converter module, a transmitter module, a relay module, a battery module, a camera module, a purge module, a robot module, an internal and/or external communication module, a power supply module, a global positioning system (GPS) module, a mobile and/or stationary data transfer module, an output board, a facility module, a Trace Work Area (TWA) control module, an output board, a dock module, an adapter module, a passive treatment module, an active treatment module, etc. A processor can process signals derived from the module. In the embodiment depicted in FIG. 37, a processor 124 in a small monitor 120 and/or a processor 201 in a dock 200 can process signals derived from the module 300. In other embodiments, such as the embodiment depicted in FIG. 2, a processor 162 in a monitor mount 160 and/or a processor 142 in another (second) monitor 140 can similarly process signals derived from the module 300. The monitor mount 160, the small and large monitors 120, 140 and the dock 200 communication interface provides bidirectional communication between the corresponding processor and the module via a network.

FIG. 38 is a front perspective view of a first exemplary implementation of the dock 200. The dock 200 may include a case 210 and a first coupling 220. The first coupling 220 may extend from a side of the case 210. The first coupling 220 may be configured to detachably secure a small monitor 120 including an electronic visual display 126. The first coupling 220 may be adapted to have the small monitor 120 transversely inserted into and removed therefrom from each of a first lateral direction of the case 210 and a second lateral direction of the case 210. In this regard, the first lateral direction of the case 210 may be opposite to the second lateral direction of the case 210.

FIG. 39 is a front perspective view of an example system including the first exemplary implementation of the dock 200 detachably securing a small monitor 120. The first coupling 220 may be configured to detachably secure opposite sides of a center of a perimeter of the small monitor 120 therebetween such that end portions of the perimeter of the small monitor 120 extend beyond opposite ends of the first coupling 220 in a direction along a lateral direction of the case 210 when the monitor is secured to the dock 200.

FIG. 40 is a front perspective view of an example system including a second exemplary implementation of the dock 1200 detachably securing a small monitor 120 and a module 300. The dock 1200 may include a handle 1211 by which the dock 1200 is carried or transported. The dock 1200 may enable power sharing and data transfer between the small monitor 120 and the module 300. The dock 1200 may be used in a stick and stay configuration in an OR. The small monitor 120 may be detachably secured to a first side of the case 1210 and the module 300 may be detachably secured to a second side of the case 1210. As shown in FIG. 40, the first side of the case 1210 may be a front face of the dock 1200 and the second side of the case 1210 may be a back face of the dock 1200. The module 300 may include an interface 301 that can be used to connect via wired and/or wireless interfaces to the sensor interface 122 of the small monitor 120.

FIG. 41 is a front perspective view of an example system including the second exemplary implementation of the dock 1200 detachably securing a small monitor 120 and a module 300. The dock 1200 includes a first coupling 1220 and may include a housing portion 1240. In the embodiment depicted in FIG. 41, for example, the housing portion 1240 is fixed to the dock 1200. In other embodiments, for example, the embodiment shown in FIG. 30, the housing portion 1240 is modular and is detachably secured to the dock 1200. The small monitor 120 may be detachably secured to a first side of the case 1210 and the module 300 may be detachably secured to a second side of the case 1210 via the housing portion 1240. As shown in FIG. 40, the first side of the case 1210 may be a front face of the dock 1200 and the second side of the case 1210 may be a side at which the housing portion 1240 is located. The module 300 may be detachably secured by being inserted, either partially or fully, within housing portion 1240.

Figure 42:
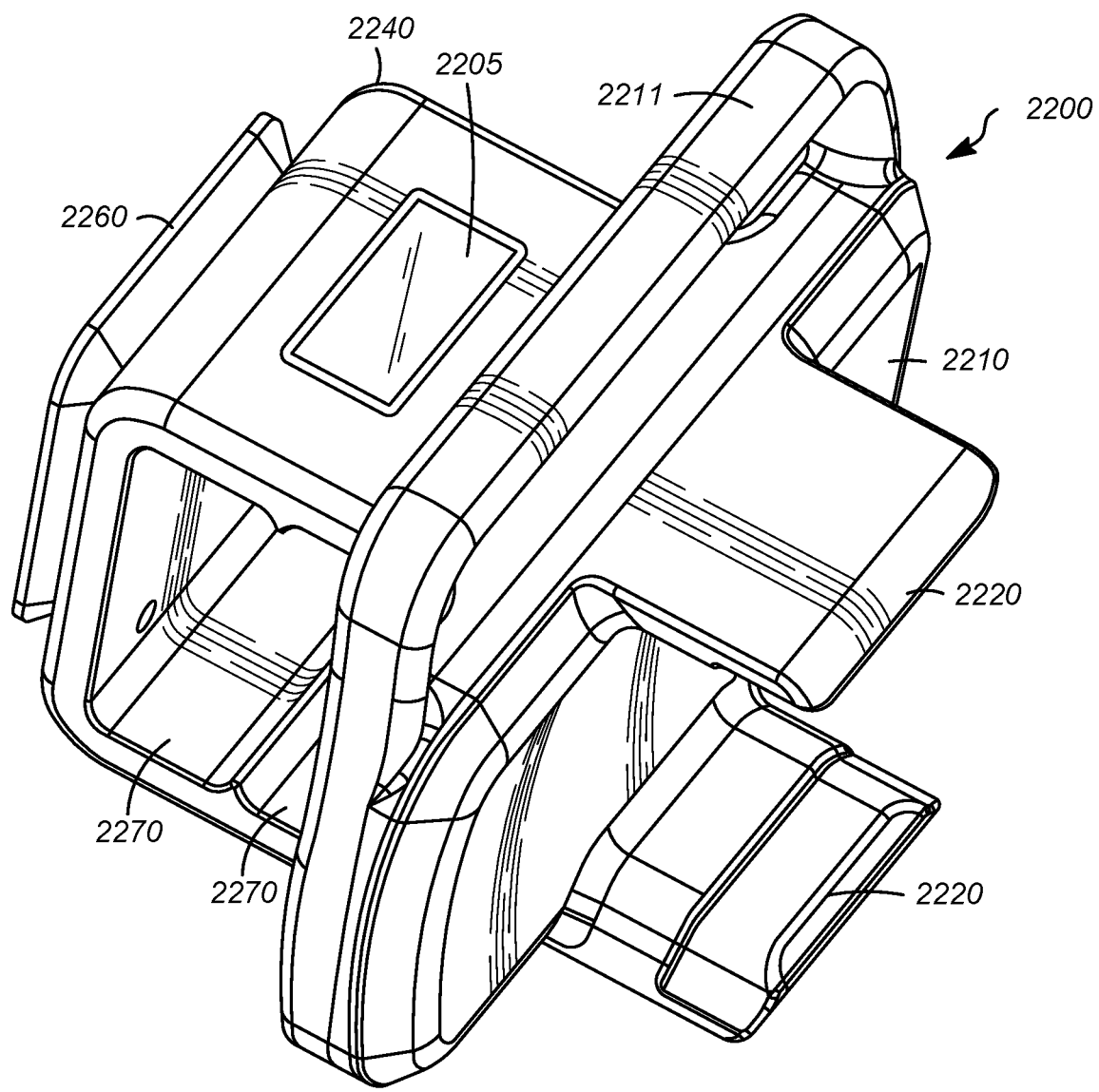
FIG. 42 is a top perspective view of a third exemplary implementation of the dock including a housing portion.

FIG. 42 is a top perspective view of a third exemplary implementation of the dock 2200. The dock 2200 may have a case 2210 including at least one of the processor 201, the memory 202, the communications interface 203, and the power source and/or conduit 204. The dock 2200 may have a housing portion 2240 including the electronic visual display 2205. The dock 2200 can be hooked to a large monitor 140. In this variation, the dock 2200 does not have fragile parts that are exposed. The electronic visual display 2205 may be a low power display (i.e., a display that requires less power to operate than a small monitor 120 or a large monitor 140) such as an electronic ink or other electrophoretic or electronic paper display technology for display of important physiological patient parameters during transport. Certain parameters such as blood pressure, heart related information, pulse oximetry, and respiration information are important to monitor during transport, and a low power display can provide such parameters without significant power requirements. An electronic paper display also provides the advantage of better visibility in outdoor locations, e.g., while boarding or disembarking an ambulance or aircraft. The electronic ink display may visualize a non-continuous parameter. Furthermore, the housing portion 2240 may include one or more second couplings 2270, each of the second couplings 2270 being configured to detachably secure a module 300. In addition, the dock 2200 may optionally also include any attachment means such as a VESA mounting interface 2260 for mounting the dock 2200 at the bedside, from the ceiling, on a wall of the room, or even outside the room for isolation purposes.

Figure 43:
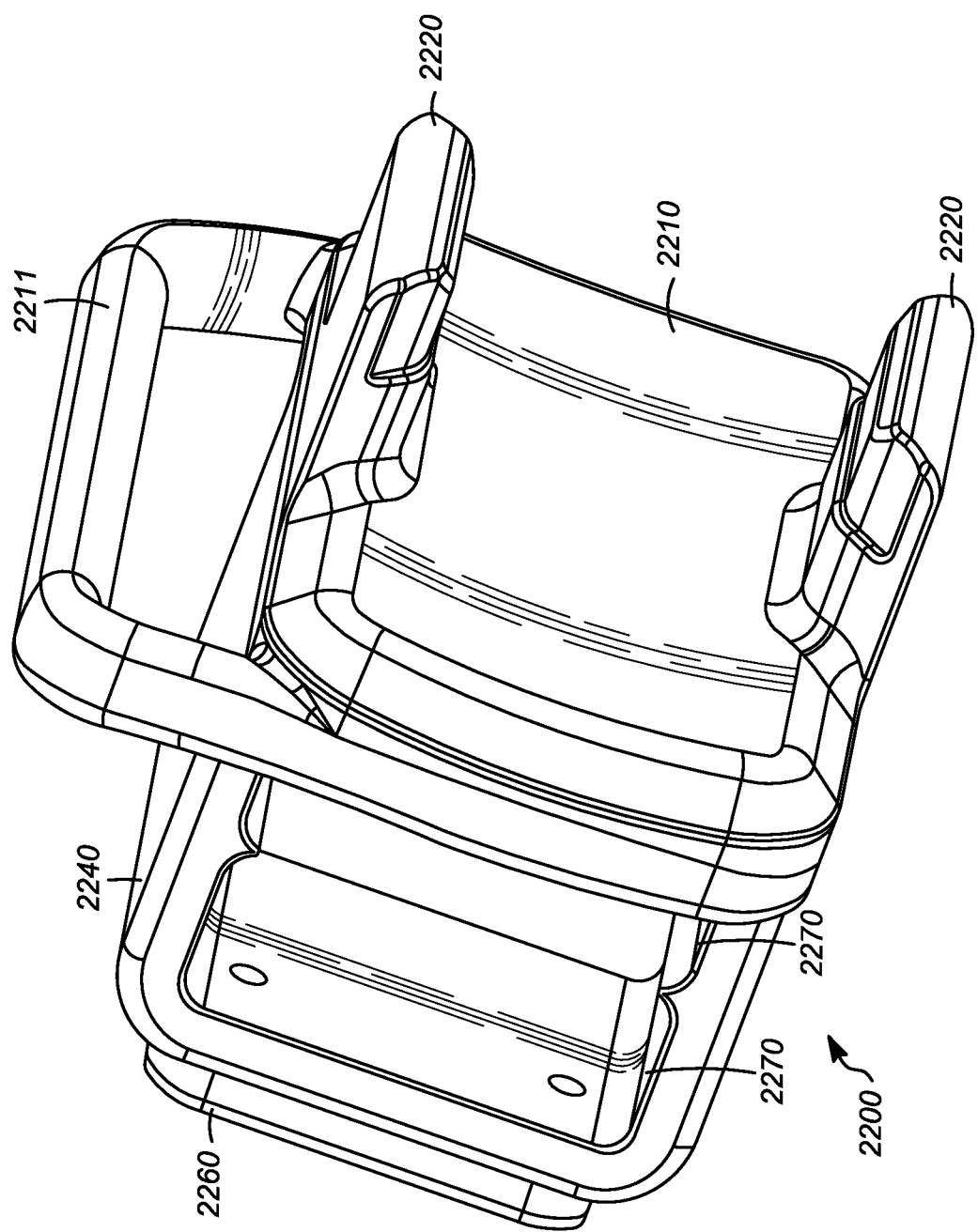
FIG. 43 is a side perspective view of the third exemplary implementation of the dock including a housing portion.

FIG. 43 is a side perspective view of the third exemplary implementation of the dock 2200 including a housing portion 2240.

Figure 44:
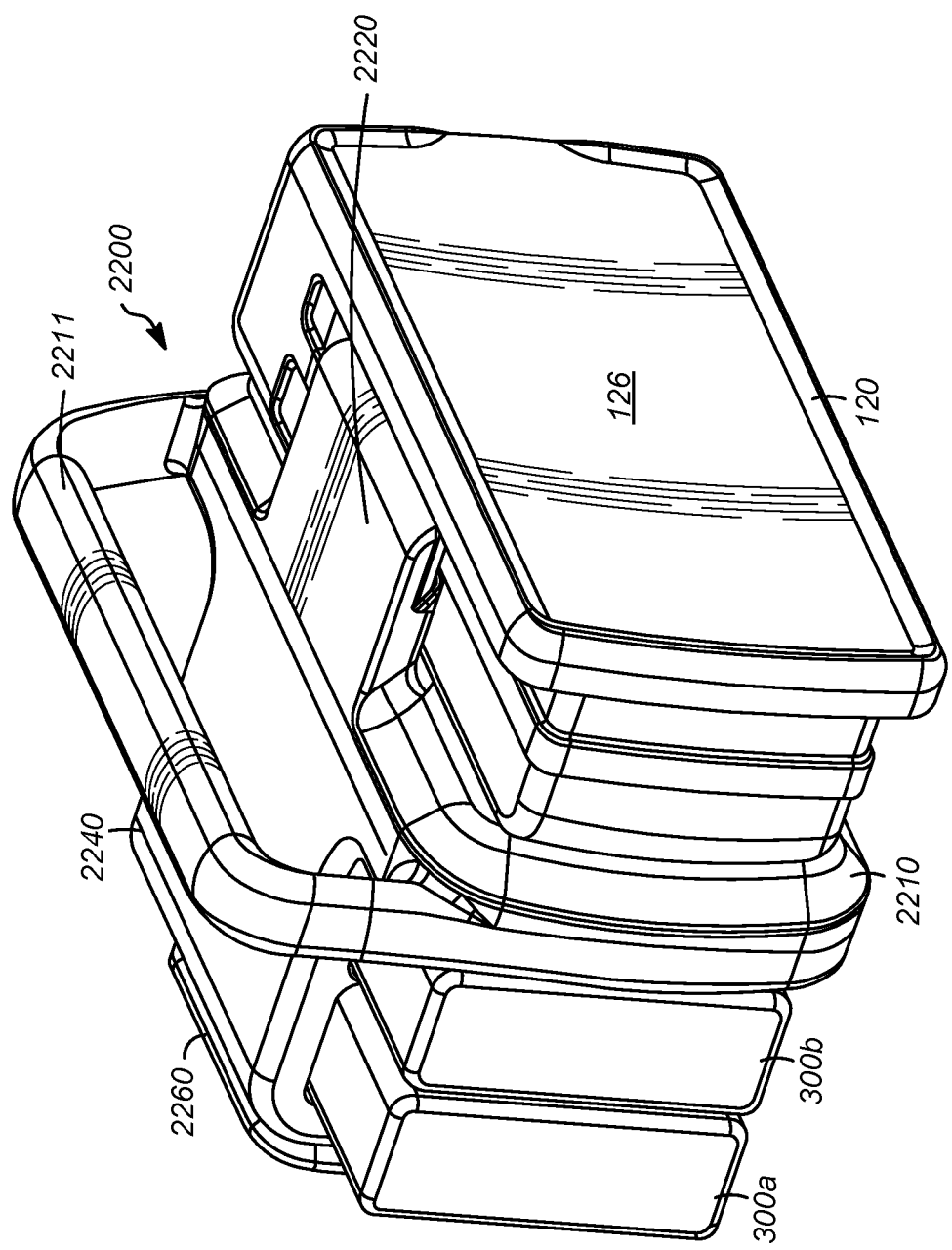
FIG. 44 is a side perspective view of the third exemplary implementation of the dock including a housing portion, the dock detachably securing a small monitor and a module in the housing portion.

FIG. 44 is a side perspective view of the third exemplary implementation of the dock 200 including a housing portion 2240, the dock 2200 detachably securing a small monitor 120 via the first coupling 2220 and two modules 300*a*, 300*b* via the housing portion 2240.

Figure 45:
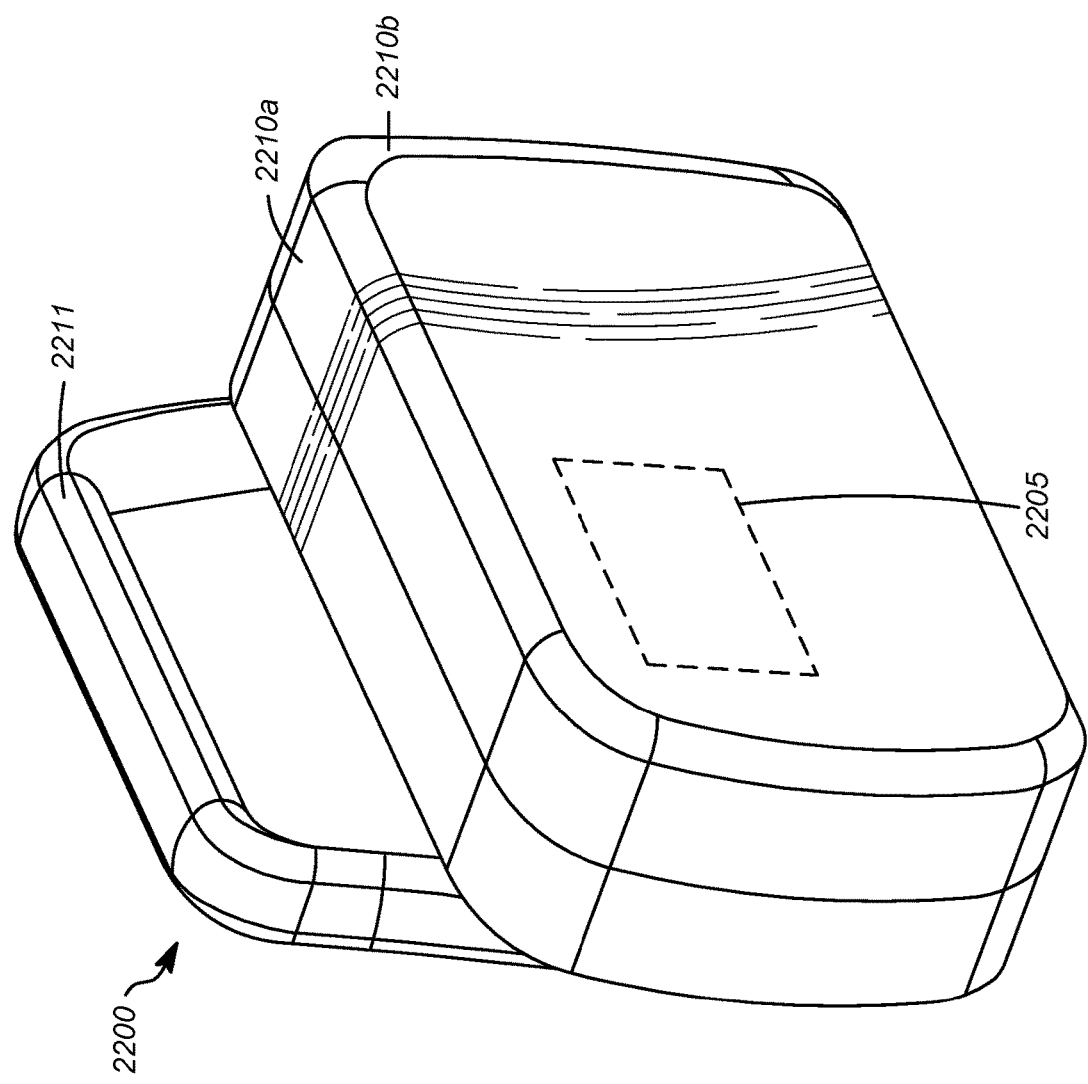
FIG. 45 is a side perspective view of a modification of the third exemplary implementation of the dock.

FIG. 45 is a side perspective view of a modification of the third exemplary implementation of the dock 2200. The dock 2200 may include a first case 2210*a*, a second case 2210*b* including a first electrical connector, a handle 2211, a processor 201, a communications interface (not shown) configured to transmit and receive data over a computing network, and an electronic visual display 2205 configured to visualize at least a portion of received data and provide a user interface, the electronic visual display 2205 including a second electrical connector. The electronic visual display 2205 may be configured to be detachably secured in the second case 2210*b* such that the first electrical connector is connected to the second electrical connector. The handle 2211 may extend from a side of the first case 2210*a* or a side of the second case 2210*b*.

Figure 46:
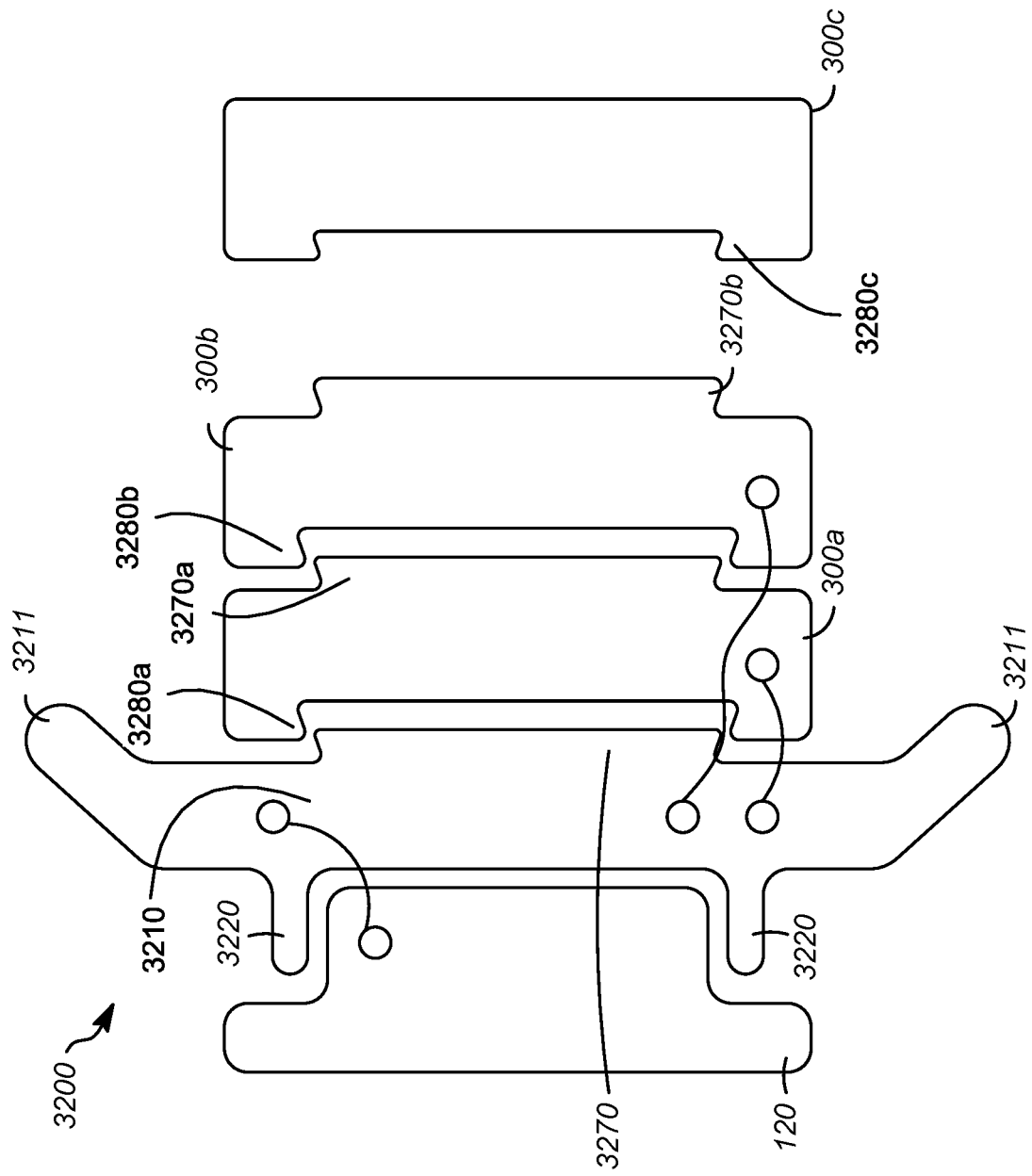
FIG. 46 is a side view of an example system including a fourth exemplary implementation of the dock 3200 detachably securing a small monitor and three of the module.

FIG. 46 is a side view of an example system including a fourth exemplary implementation of the dock 3200 detachably securing a small monitor 120 and three modules 300*a*-300*c*. The modules 300*a*-300*c* can be detachably secured directly to the dock 3200 in a modular, scalable manner, such as in a piggyback configuration. The dock 3200 may include a first coupling 3220 extending from a first side of the case 3210 and a second coupling 3270 extending directly from a second side of the case 3210. The second coupling 3270 may be configured to detachably secure one or more of the modules 300*a*-300*c*. The second coupling 3270 may include any attachment means such as one of a notch and a groove and each of the modules 300*a*-300*c* may include a third coupling (see third couplings 3280*a*-3280*c*) including another of the notch and the groove which is configured to be detachably secured to the one of the notch and the groove in the second coupling 3270. In addition, the modules 300*a*, 300*b* may also include a second coupling (see second couplings 3270*a*, 3270*b*) that is configured to be detachably secured to the third coupling (i.e., third coupling 3280*a* or third coupling 3280*b*) of an adjacent module (i.e., module 300*b* or module 300*c*. Accordingly, the dock 3200 and the one or more modules 300a-300c may be attached in a piggyback configuration such that the notch and groove of each combination of a second coupling 3270, 3270a, 3270b and a third coupling 3280a, 3280b, 3280c provide a dovetail joint in one exemplary implementation. Any kind of attachment between the modules 300a-300c can be used instead of the dovetail joint or in addition to the dovetail joint. For example, the attachment be any form of latching mechanism. These coupling features are helpful for seamlessly transporting multiple modules at the same time with the small monitor 120, particularly for high acuity patients that need higher parameter sets for monitoring on transport. One of the modules 300a-300c (for example, the module 300c) may be an auxiliary battery pack that may be added to the dock 3200 so as to provide power to the modules 300a, 300b and the small monitor 120. The dock 3200 may also include one or more handles, for example, dual handles 3211 as shown.

Figure 47:
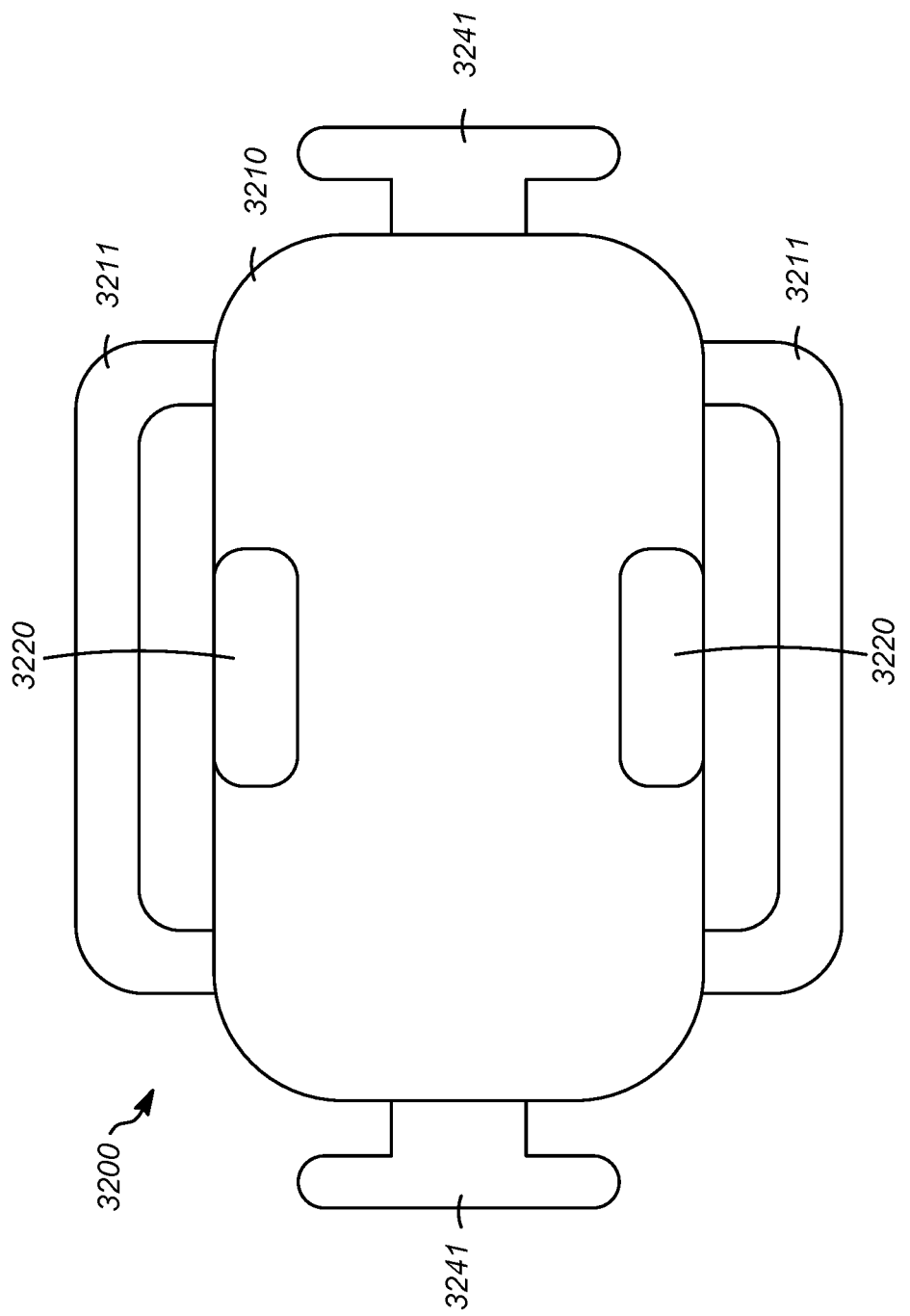
FIG. 47 is a front view of the fourth exemplary implementation of the dock.

FIG. 47 is a front view of the fourth exemplary implementation of the dock 3200. The dock 3200 can include the dual handles 3211 extending from the top and bottom of the case 3210. As shown in FIG. 47, the dock 3200 may include at least one cable management feature 3241 on a lateral side of the dock 3200 for managing one or more cables connecting the module 300 to the dock 3200. Cables can be easily wrapped around the cable management feature rather than dangling and causing inconvenience on transport. Such cable management is helpful with respect to seamless workflow.

Figure 48:
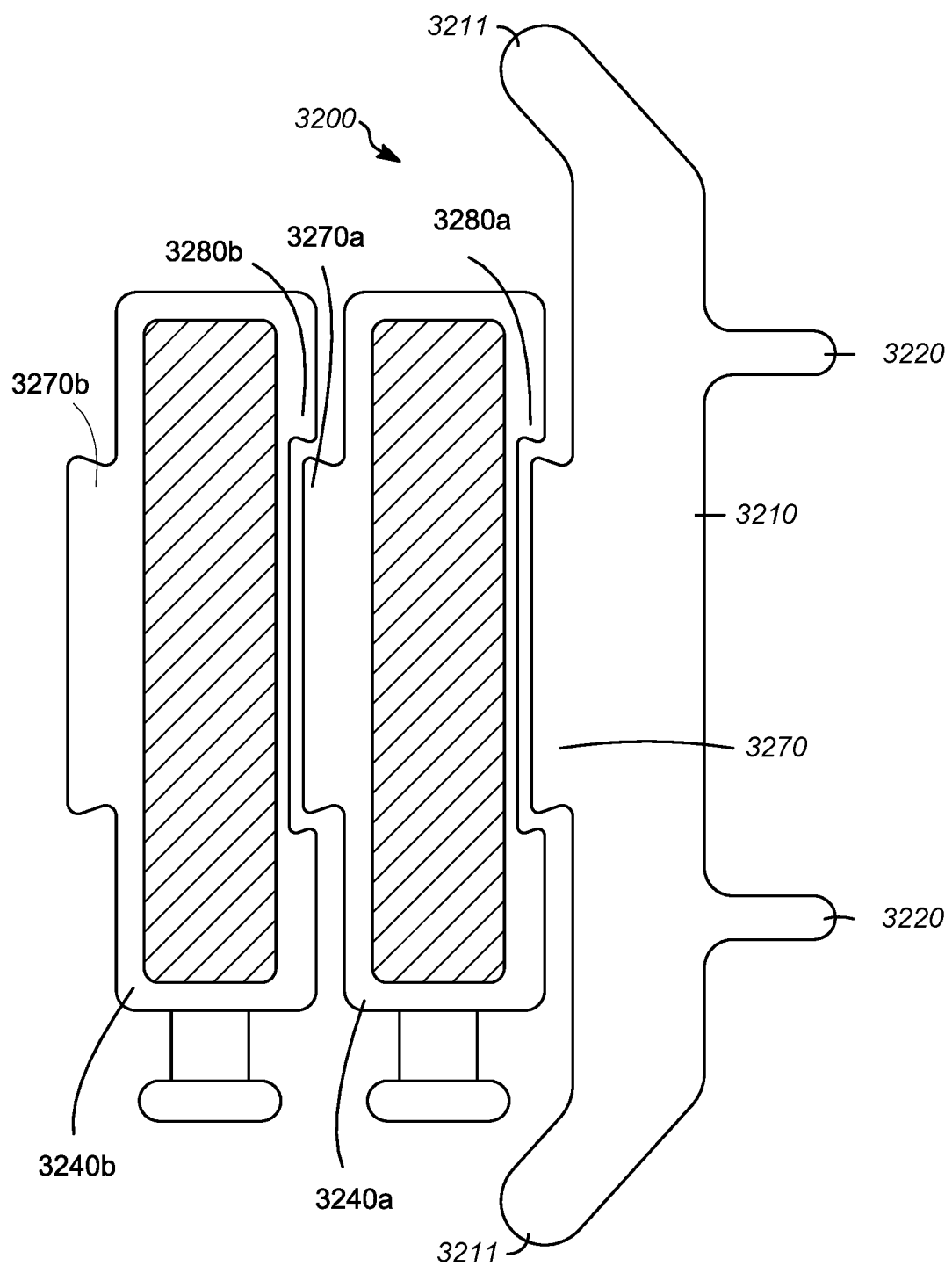
FIG. 48 is a side view of an example system including a fourth exemplary implementation of the dock including housing portions.

FIG. 48 is a side view of an example system including a fourth exemplary implementation of the dock 3200 including housing portions 3240a, 3240b. The housing portions 3240a, 3240b may include second couplings 3270a, 3270b and third couplings 3280a, 3280b configured to be detachably secured to the second coupling 3270 of the dock 3200 or the second couplings 3270a, 3270b of another one of the housing portions 3240a, 3240b. In some embodiments, a housing portion 3240b can be detachably secured to another housing portion 3240a in a modular, scalable manner, such as in a piggyback configuration.

Figure 49:
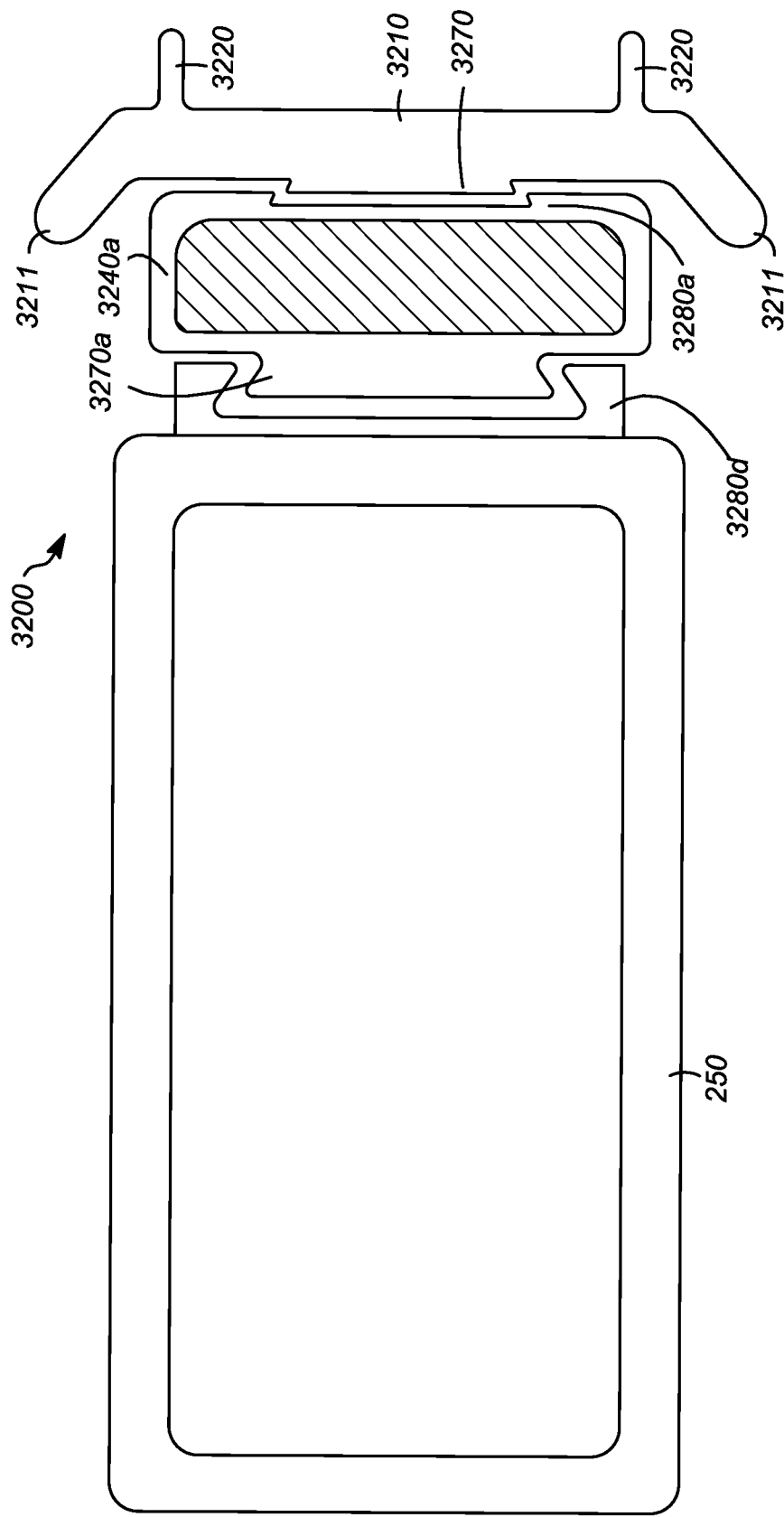
FIG. 49 is a side view of an example system including the fourth exemplary implementation of the dock including a housing portion and a rack.

FIG. 49 is a side view of an example system including the fourth exemplary implementation of the dock 3200 including a housing portion 3240a and a rack 250. The housing portion 3240a may include a second coupling 3270a and a third coupling 3280a and the rack 250 may include also include a third coupling 3280d, which can be detachably secured to the second coupling 3270a of the housing portion 3240a or the second coupling 3270 of the dock 3200. The third coupling receiver 3280d of the rack 250 may extend from a lateral side of the rack 250 such that the rack 250 can be mounted transversely with respect to the housing portion 3240. Each of the housing portion 3240a and the rack 250 may be configured to detachably secure one or more modules 300.

Figure 50:
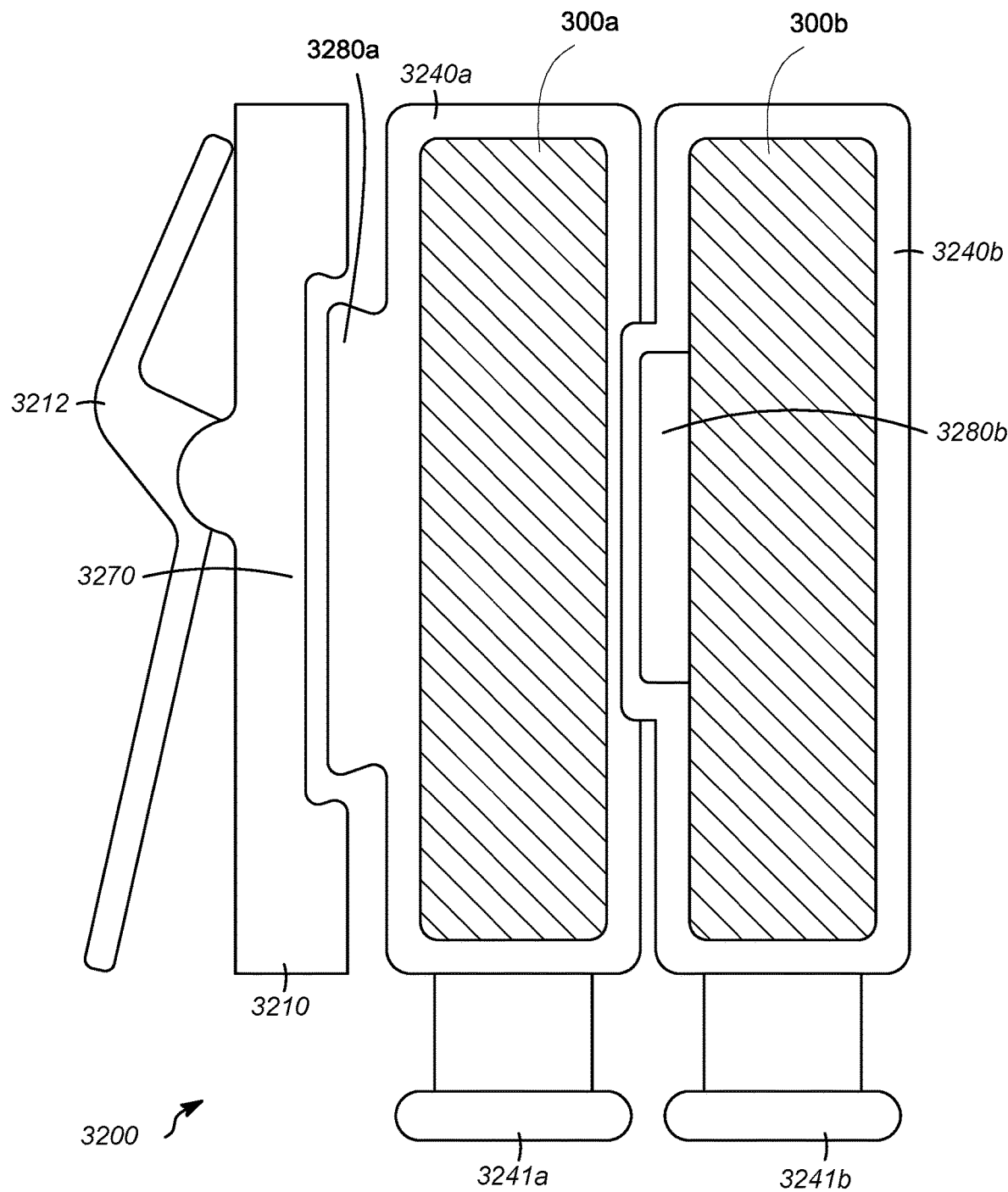
FIG. 50 is a side view of an example system including the fourth exemplary implementation of the dock including housing portions, and a clip.

FIG. 50 is a side view of an example system including the fourth exemplary implementation of the dock 3200 including housing portions 3240a, 3240b and a portable clip 3212 (see U.S. Pat. No. 9,657,893, incorporated herein by reference in its entirety) for attaching the dock 3200 to a support structure. The clip 3212 is important for clinical workflow challenges with transport and moving the patient between care areas (e.g., from an Emergency Department to Radiology or from a CT scan to the OR). The modules 300a, 300b can be attached to an IV pole, bed rail, etc., using the clip 3212 so that the modules 300 do not fall or get wrapped in bedsheets on transport. The housing portions 3240a, 3240b may include at least one cable management feature (see cable management features 3241a, 3241b) for managing one or more cables to be connected to the module 300. The clip 3212 may be portable and can be used with various types of connectors to docks, patient monitoring devices, portable structures, or stationary structures. The clip 3212 may allow for long-term or short-term attachment of a dock or patient monitoring device to another structure. A short-term attachment fitting allows a user to mount the clip 3212 to a difficult location on a structure and then interchange the dock or patient monitoring device as needed. Conversely, a long-term attachment fitting allows for a robust connection, in which the clip position can be changed as needed without excessive concern from the user about the stability of the location of the dock or patient monitoring device. The clip 3212 can allow the dock 3200 to rotate with respect to the clip 3212 affixed to a rail, pole, or other structure. Though this rotation is described in discrete increments of 90°, this rotation can include increments of less than 90°, greater than 90°, or an arbitrary rotation. One of the advantages of the ability to rotate the dock 3200 relative to the clip 3212 is that cable and cord routing from the dock 3200 to the patient and/or monitoring device can be simplified. Another advantage of this ability to rotate the dock 3200 relative to the clip 3212 is that the assembly can adapt to more locations around a patient's bed. Accordingly, the clip 3212 can attach to a bed rail, a shelf or ledge near a patient's bed, or onto a rack or pole used for other equipment that is near a patient, and the dock 3200 can be turned to a convenient orientation about the clip 3212 because of this ability to rotate. The clip 3212 may have a design (not shown) that includes a base plate with an interface portion on one side and a clamp attached to a lever arm on the opposed side. The base plate and lever arm have ergonomic features that can allow a user to better utilize the clip 3212. Accordingly, the dock 3200 can be accommodated to each patient's environment.

Figure 51:
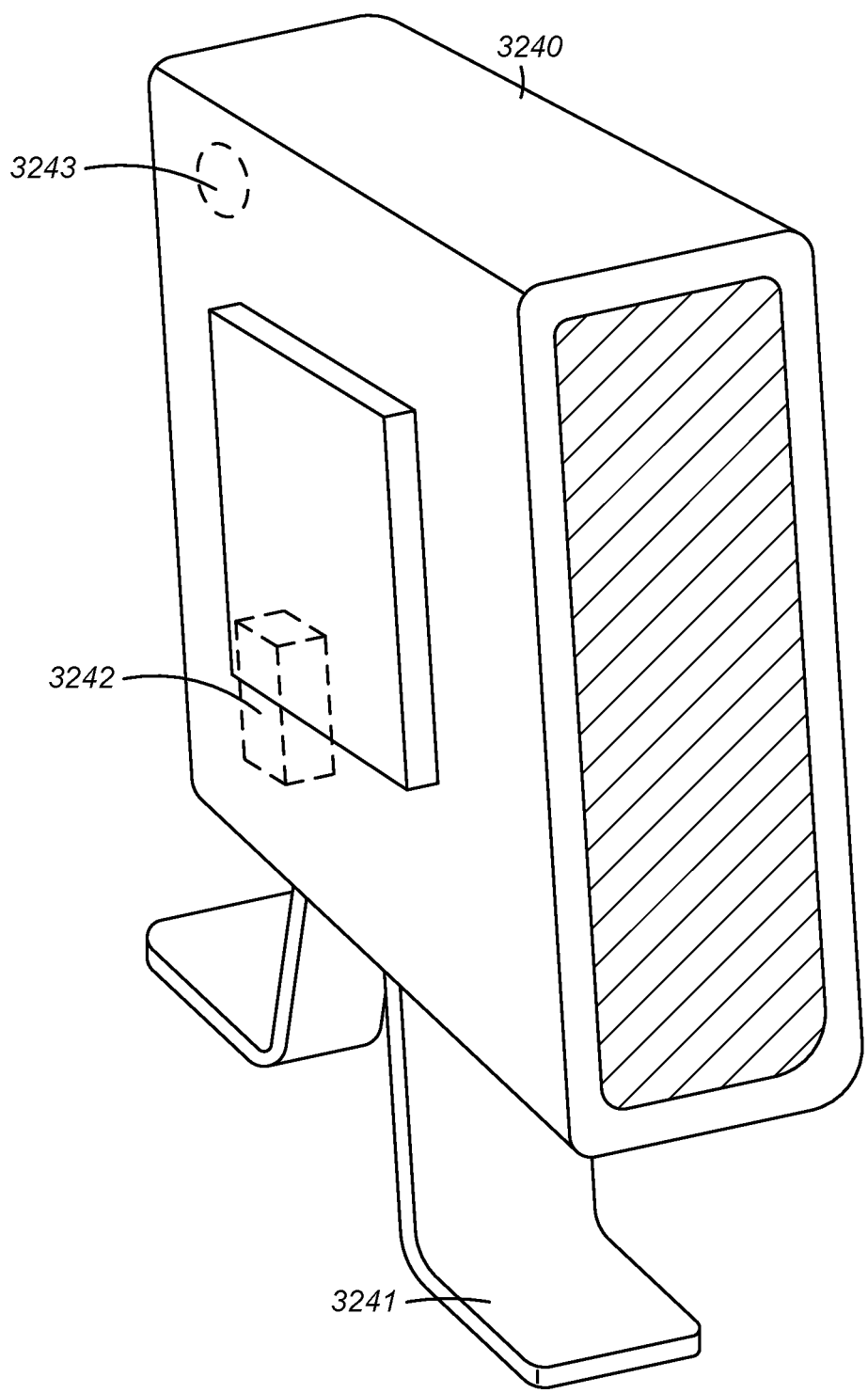
FIG. 51 is a front perspective view of a housing portion.

FIG. 51 is a front perspective view of a housing portion 3240. The housing portion 3240 may include may include at least one cable management feature 3241 for managing one or more cables to be connected to the module 300. The housing portion 3240 may further include at least one connector 3242 and/or a circular connector 3243 for connecting to a module.

Figure 52:
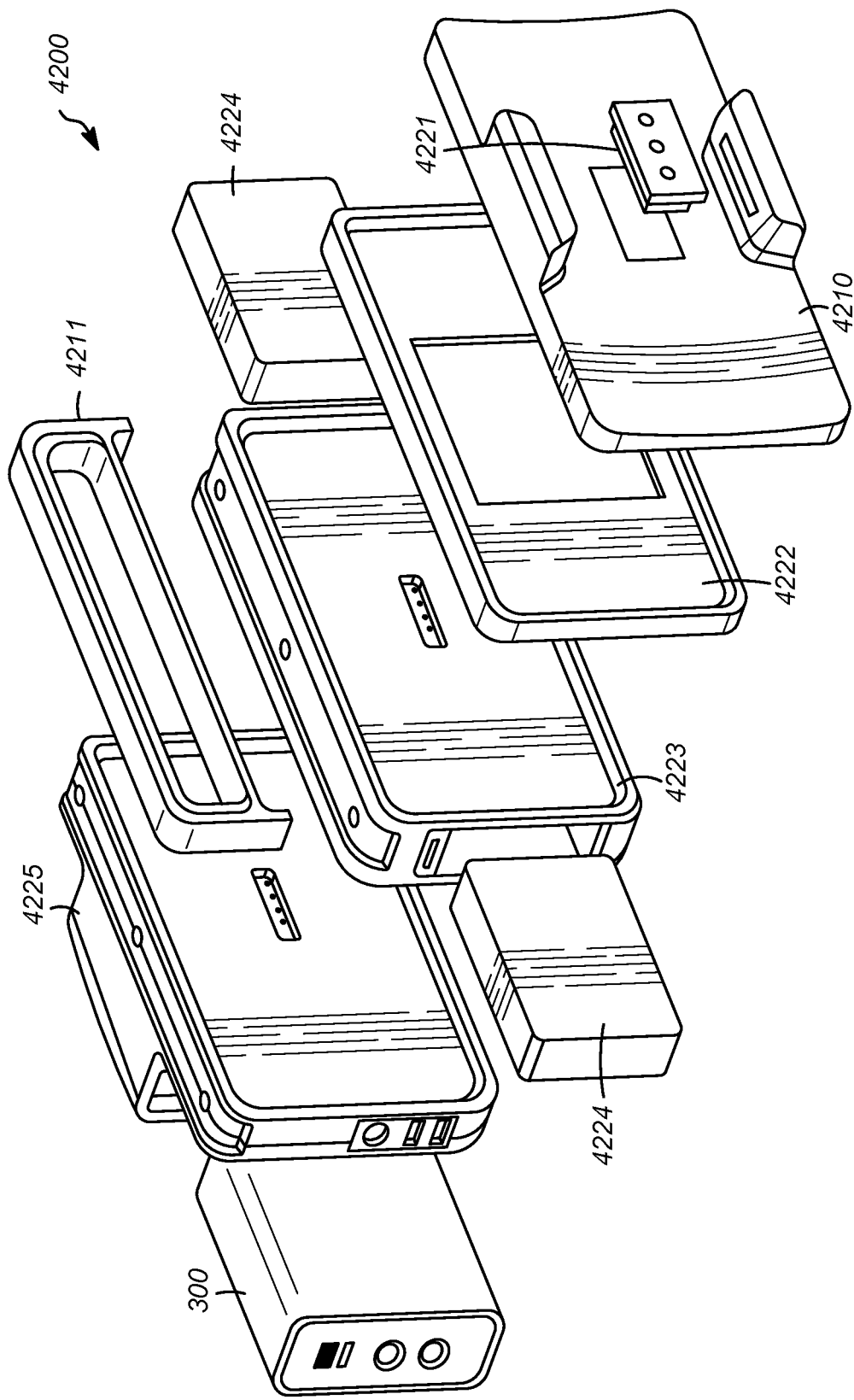
FIG. 52 is an exploded perspective view of an example system including a fifth exemplary implementation of the dock including a case, a handle, an adapter, a power accessory, battery modules, a module accessory, and a module.

FIG. 52 is an exploded perspective view of an example system including a fifth exemplary implementation of the dock 4200 including a case 4210, a handle 4211, a first coupling 4220, an adapter 4222, a power accessory 4223, battery module 4224, a module accessory 4225, a connector 4221 and a module 300. This example system may be modular. The case 4210 may be configured to be detachably secured to the adapter 4222. The adapter 4222 may be configured to be detachably secured to the power accessory 4223. The handle 4211 may also be configured to be detachably secured to the power accessory 4223 or the module accessory 4225. The battery modules 4224 may additionally be configured to be coupled to the power accessory 4223. The power accessory 4223 may be configured to be detachably secured to the module accessory 4225. The module accessory 4225 may be configured as a housing portion that may be configured to surround at least a portion of the module 300 when the module 300 is secured in the dock 4200. The connector 4221 may be configured to be electrically connected to the power source and/or conduit 132 of the small monitor 120 and/or the communications interface 128 of the small monitor 120. In some variations, any of the components can be omitted without preventing the remaining components from being combined. For example, the module accessory 4225 can be omitted and the module 300 can be directly attached to the case 4210. When the case 4210 is used by itself, an intervening element may be used to secure the case 4210 to a support structure (e.g., bedrail, IV pole, etc.). Such intervening element can be an adapter 4222 with any mounting interface such as a VESA mounting interface. The adapter 4222 can provide mechanical connectivity across different interfaces. In the embodiment shown in FIG. 52, the adapter 4222 facilitates attachment of the case 4210 to the power accessory 4223.

FIG. 53 is an exploded perspective view of an example system including the fifth exemplary implementation of the dock 4200 including a case 4210 and an adapter 4222 to be detachably secured to an attachment mechanism 4226, and a support structure 4227. The dock 4200 may be detachably secured to a structure such as a bed or stretcher or gurney rail, IV pole, etc. via any mechanical interface such as a VESA mounting interface 4231 adapted to an attachment mechanism 4226. The attachment mechanism 4226 may detachably secure the dock 4200 to a tubular or rectangular support structure 4227. In the embodiment shown in FIG. 53, the adapter 4222 facilitates attachment of the case 4210 to the attachment mechanism 4226.

FIG. 54 is a front perspective view of an example system including a case 4210 and an adapter 4222.

FIG. 55 is a side perspective view of an example system including the fifth exemplary implementation of the dock 4200 including a case 4210, a power accessory 4223, a module accessory 4225, and two modules 300.

Figure 56:
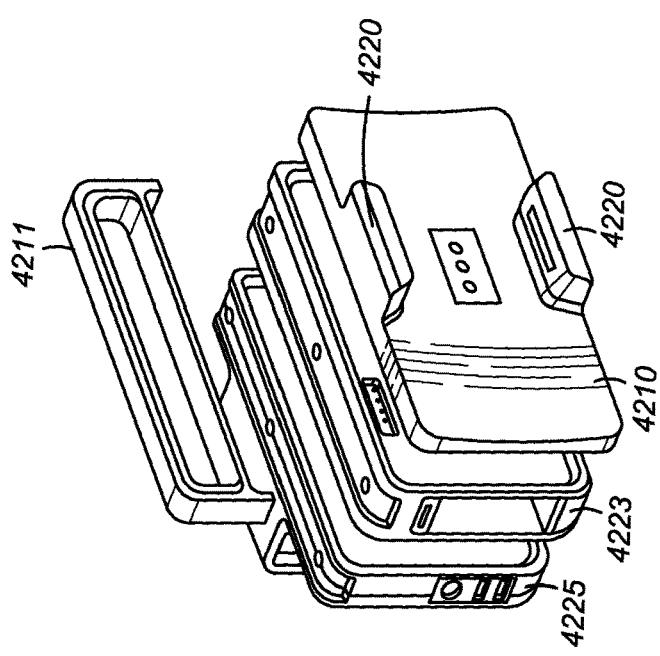
FIG. 56 is an exploded perspective view of an example system including the fifth exemplary implementation of the dock including a case, a handle, a power accessory, and a module accessory.

FIG. 56 is an exploded perspective view of an example system including the fifth exemplary implementation of the dock 4200 including a case 4210, a power accessory 4223, and a module accessory 4225.

Figure 57:
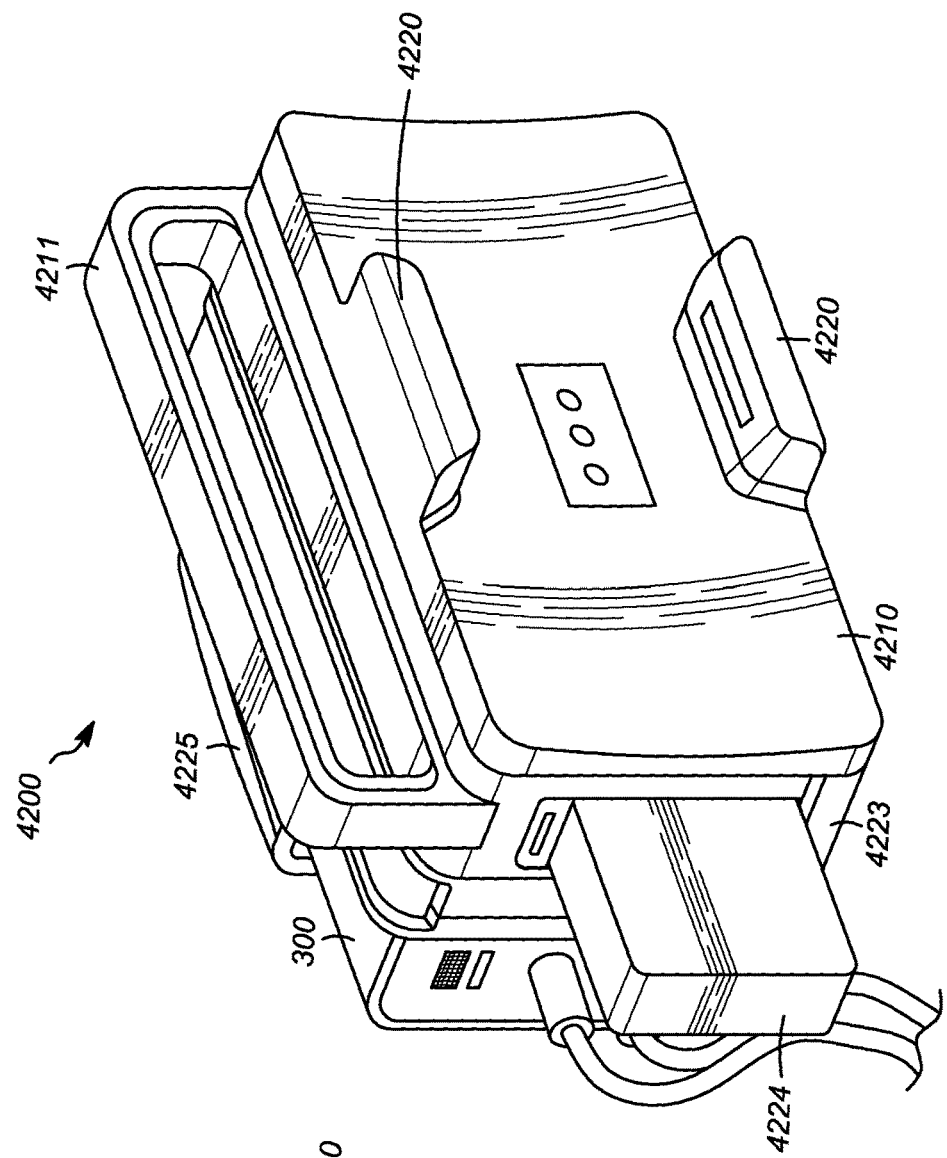
FIG. 57 is a side perspective view of an example system including the fifth exemplary implementation of the dock including a case, a handle, a power accessory, a battery module, a module accessory, and a module.

FIG. 57 is a side perspective view of an example system including the fifth exemplary implementation of the dock 4200 including a case 4210, a power accessory 4223, a battery module 4224, a module accessory 4225, and a module 300.

Figure 58:
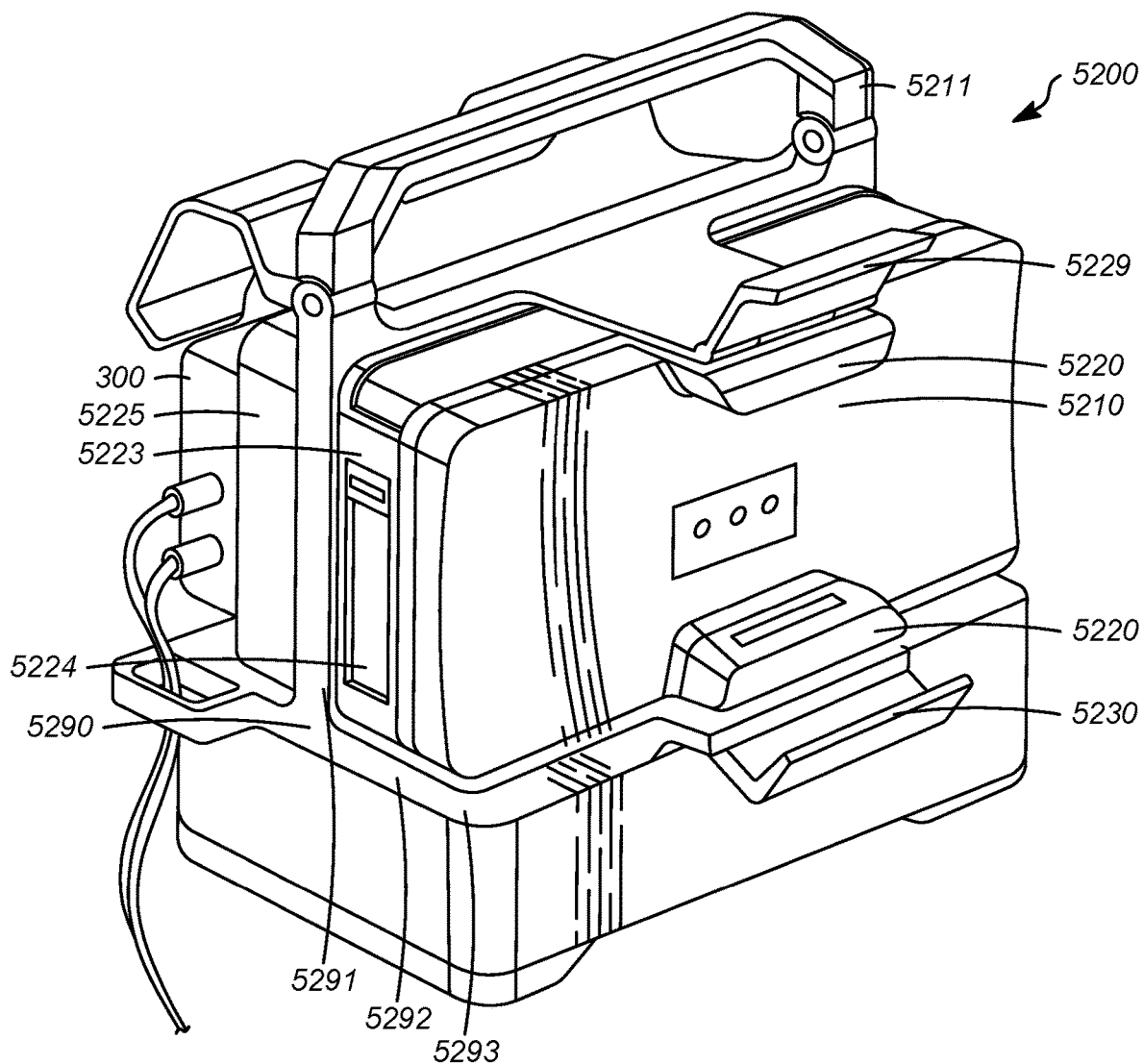
FIG. 58 is a side perspective view of an example system including a sixth exemplary implementation of the dock including a case, a handle, a power accessory, a battery module, a module accessory, a module, a frame (including a wall portion and a base), a module, a first clamp, and a second clamp.
Figure 59:
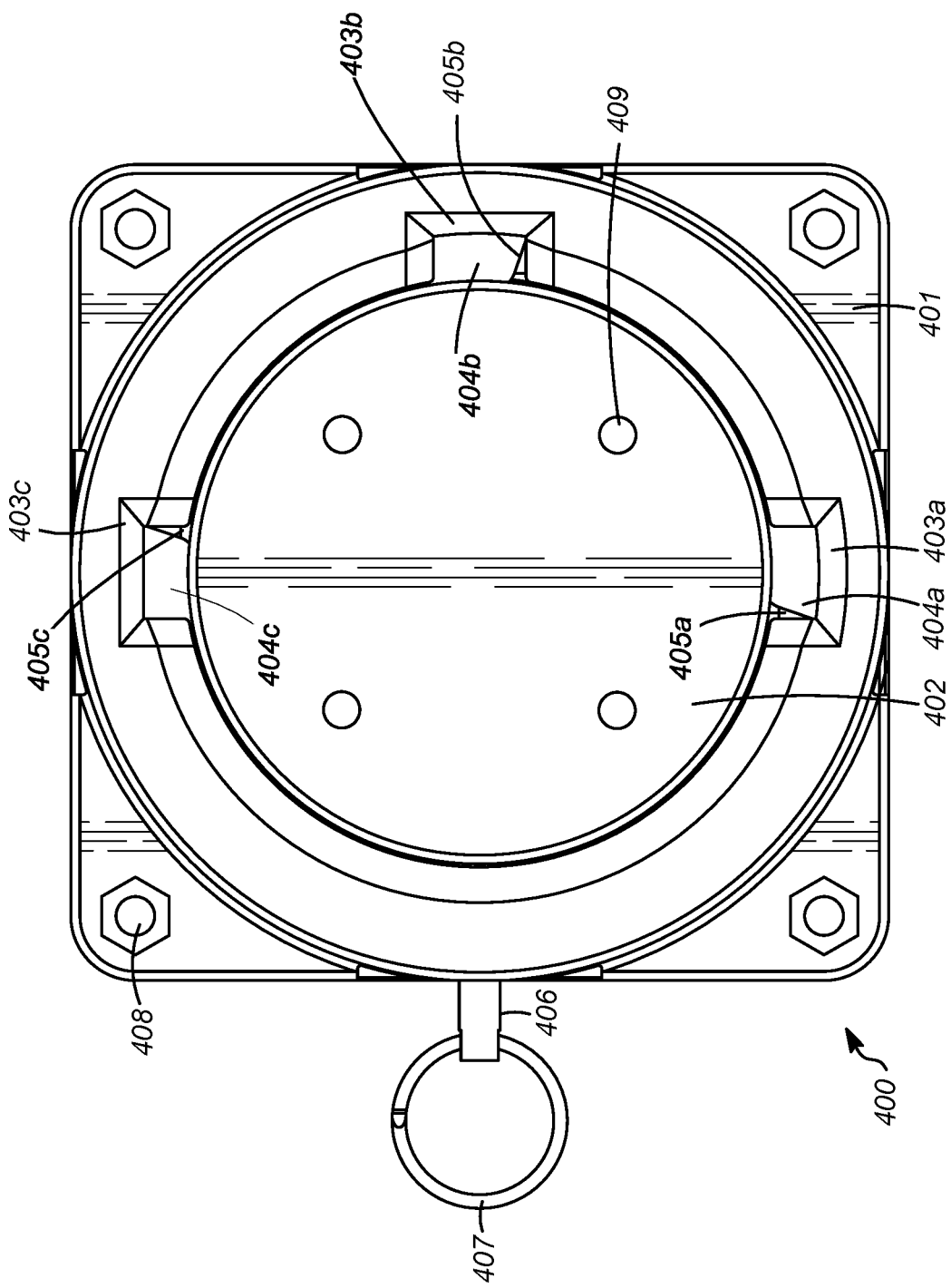
FIG. 59 is a top view of a coupling including a base plate, a top piece, and a locking mechanism.
Figure 60:
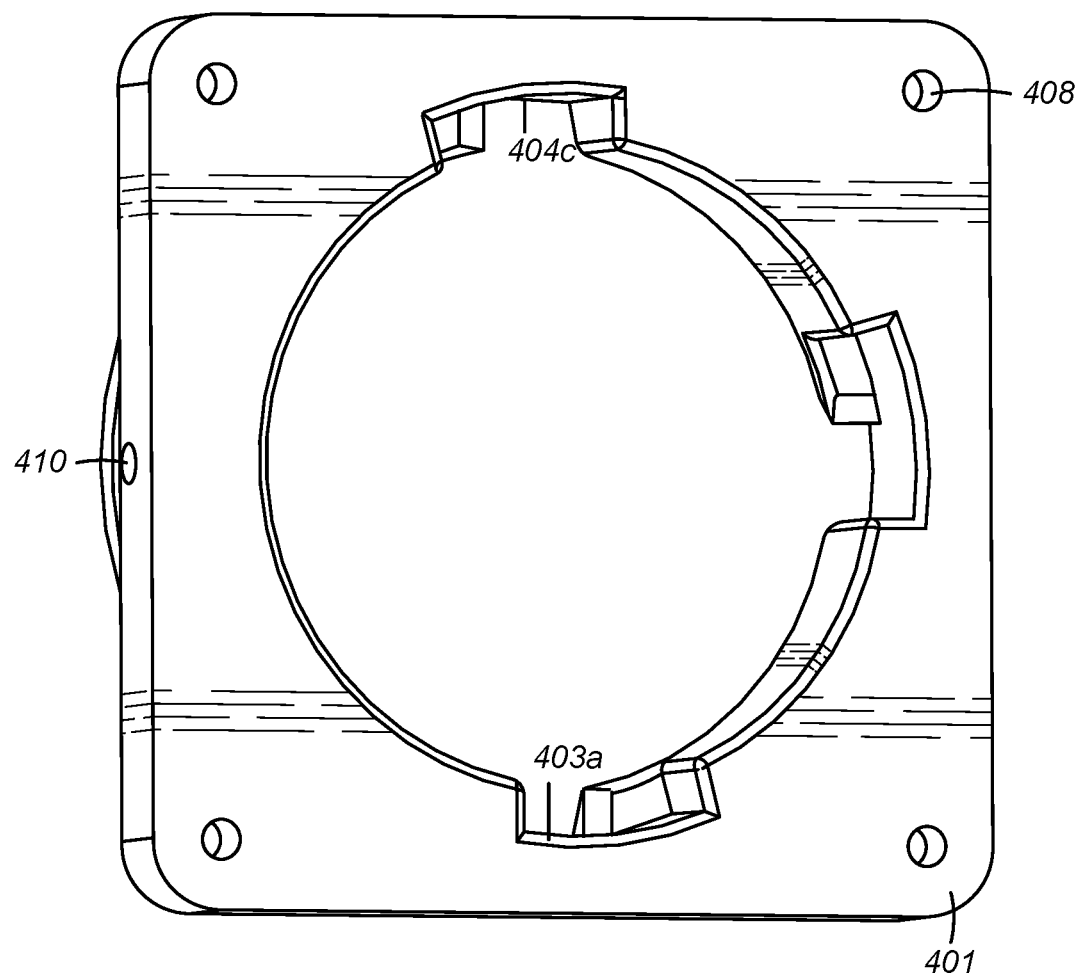
FIG. 60 is a bottom view of the base plate.

FIG. 58 is a side perspective view of an example system including a sixth exemplary implementation of the dock 5200 including a case 5210, a handle 5211, a coupling 5220, a power accessory 5223, a battery module 5224, a module accessory 5225, a connector (not shown), a module 300, a frame 5290 (including a wall portion 5291 and a base 5292), a module 5293, a first clamp 5229, and a second clamp 5230. The system can be adapted for ambulance, air medical services, shock-susceptible, vibration-susceptible, and/or military specification applications where a more robust dock configuration is appropriate. For example, the system can satisfy any and all of the following specifications: MIL-STD-1791 for design in fixed wing aircraft applications, MIL-STD-810G for vibration testing applications, and EN 1789 for ambulatory applications. The system is not limited to the above-noted specifications and can satisfy other specifications as desired. The first clamp 5229 can be configured to lock the module 300 to the frame 5290; and the second clamp 5230 can be configured to lock the small monitor 120 to the frame 5290. The system may also include an AC/DC converter (not shown). The wall portion 5291 and the base 5292 may be formed as a single unit. The handle 5211 may be rotatable with respect to the frame 5290. The frame 5290 may be configured to detachably secure another module 5293 to a bottom face thereof. For example, the module 5293 may be an optional backup battery compartment and/or a transport ventilator.

FIGS. 59-62 show a coupling 400 for detachably securing a device (e.g., monitor, rack, module, etc.) to a mount (e.g., monitor mount, workstation, stand, etc.). The coupling 400 includes a base plate 401, a top piece 402, and a locking mechanism 406. The base plate 401 can include an opening and an inner surface around the opening. The inner surface can include at least one indentation (see indentations 403a-403c). The top piece 402 can include an outer surface including at least one projection (see projections 405a-405c). In some variations, three indentations 403a-403c and three projections 405a-405c can be provided. Spacing between the indentations 403a-403c generally corresponds to spacing between the projections 405a-405c. In the depicted embodiment, the indentations 403a-403c are asymmetrically spaced around the base plate 401. In other embodiments (not shown) the spacing between the indentations 403a-403c can be different than the spacing that is shown in the depicted embodiment. In other words, a first circumferential distance between a first adjacent pair of the indentations 403a-403c can be greater than a second circumferential distance between a second adjacent pair of the indentations 403a-403c. Similarly, intervals between the projections 405a-405c can be different such that the projections 405a-405c are asymmetrically spaced around the top piece 402. In some variations, the indentations 403a-403c can be positioned at 0°, 90° and 180° on the base plate 401 and the projections 405a-405c can be positioned at 0°, 90° and 180° on the top piece 402. The top piece 402 may be mounted in the base plate 401 such that the top piece 402 is rotatable in the opening of the base plate 401 if the locking mechanism 406 is disengaged. In some variations, an indentation can define a slot (see slots 404a-404c) and an abutment (not shown). The projections 405a-405c can be initially received in the slots 404a-404c, the top piece 402 can be rotated, and thereafter the projections 405a-405c can be secured to the abutments (not shown). If the top piece 402 has three projections 405a-405c, this configuration allows for only 10° of rotation of the top piece 402 in one direction to lock a device in place.

The locking mechanism 406 can be located in an aperture 410 of the base plate 401 and can be operable to be inserted into the top piece 402. In a locked position, a part of the locking mechanism 406 is engaged with the top piece 402 such that the top piece 402 is not rotatable in the opening of the base plate 401. In an unlocked position, the locking mechanism 406 is disengaged from the top piece 402 such that the top piece 402 is rotatable. The top piece 402 can be inserted into and released from the base plate 401 when the locking mechanism 406 is in the unlocked position and the top piece 402 is in a position at which the projections 405a-405c and the indentations 403a-403c are in alignment. The top piece 402 can be secured to the base plate 401 when the locking mechanism 406 is in the locked position and/or the top piece 402 is in any position at which the projections 405a-405c and the indentations 403a-403c are out of alignment. The locking mechanism 406 may include a spring (not shown) and a plunger whereby an end of the plunger is inserted into an aperture 412 of the top piece 402 in the locked position of the locking mechanism 406. In the unlocked position of the locking mechanism 406, the plunger is retracted or withdrawn from the aperture 412 of the top piece 402. The top piece 402 may include a track 411 which guides and depresses the plunger upon rotation of the top piece 402. In other words, the plunger may slide on the track 411 during rotation of the top piece 402. The aperture 412 of the top piece 402 can be defined at an end of the track 411. Accordingly, the track 411 on the top piece 402 allows for a device to be automatically locked without any extra steps. A tab 407 may also be attached to an external end of the locking mechanism 406. The tab 407 may be pulled to unlock the locking mechanism 406 from the locked position such that the device can be removed from the mount. Otherwise, the spring may impart a force to the plunger so as to bias the locking mechanism 406 to the locked position such that the device is secured to the mount. The tab 407 may be in the form of a ring. Instead of having to bolt the device directly to the mount, which takes time and can require specialized personnel, users can use the coupling 400 to easily remove and install a device in any desired configuration. The coupling 400 is quick and easy to use by anyone and can lock automatically with an audible click to provide confirmation of secure retention. Furthermore, the base plate 401 can include any mounting interface such as a VESA mounting interface 408. The top piece 402 can also include holes 409 for receiving fasteners for attaching the top piece 402 to a device. Therefore, the coupling 400 enables a user to quickly and easily secure and remove a device from a mount.

Figure 64:
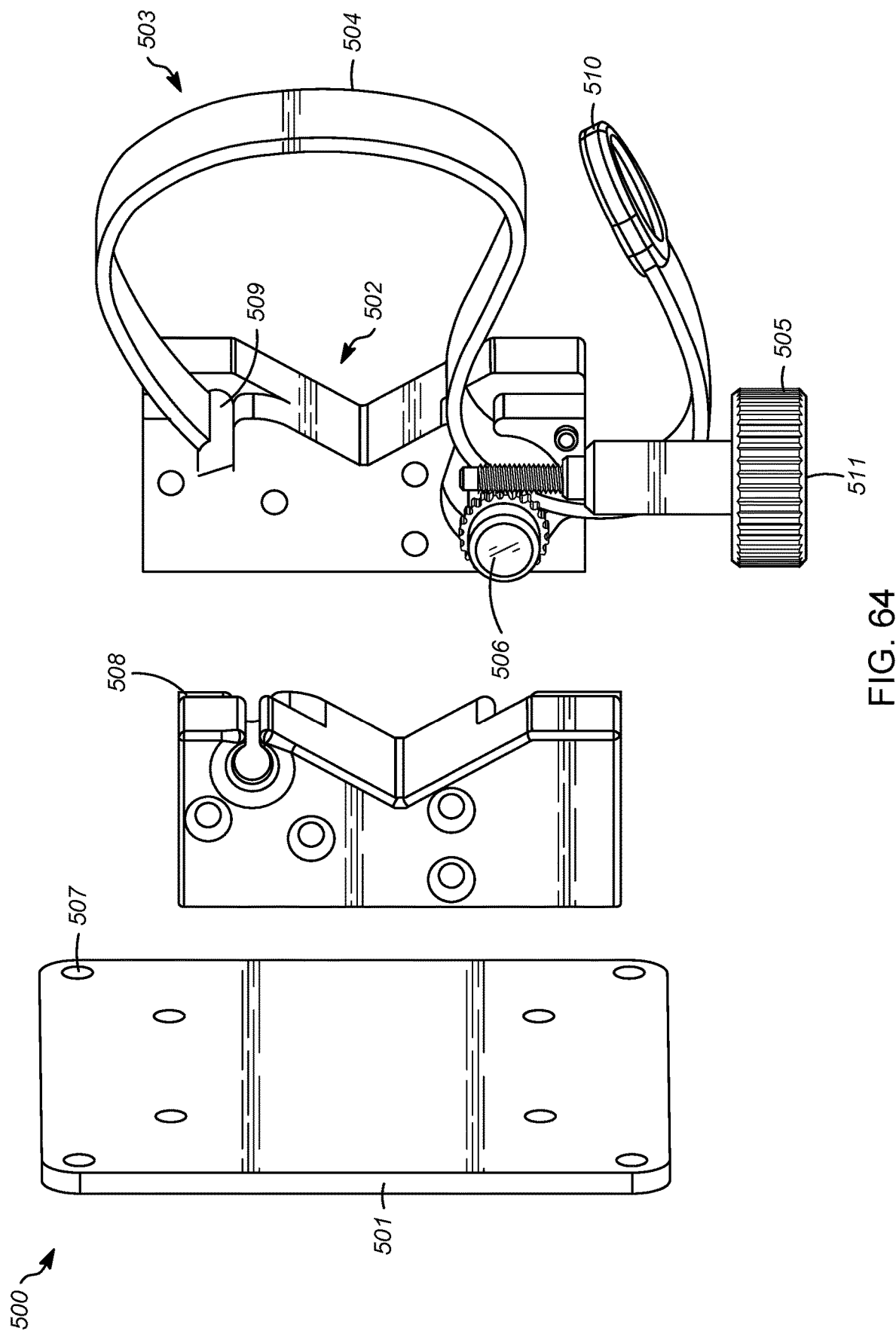
FIG. 64 is an exploded back perspective view of the belt mount including the support plate, the base, the first fastener, and the second fastener.

FIGS. 63 and 64 show a belt mount 500 for detachably securing a device (e.g., monitor, rack, module, etc.) to a support structure (e.g., bed, stretcher, gurney rail, IV pole, ambulance bar, monitor mount, workstation, stand, etc.). The belt mount 500 includes a support plate 501, a base 502, a first fastener 503, and a second fastener 505. The support plate 501 can include any mounting interface such as a VESA mounting interface 507. The base 502 is fixed to one side of the support plate 501 and may be formed as a substrate comprised of a material such as another polymer, metal, etc. An end of the first fastener 503 may be slidably attachable and detachable from a first part of the base 502. The end of the first fastener 503 may comprise a removable pin 509 and the first part of the base 502 may comprise a first recess 508 operable to receive the removable pin 509. The removable pin 509 and the belt member 504 may be formed as a single unit. The first fastener 503 may include a belt member 504 and a tab 510. The belt member 504 may extend through a second part of the base 502. The belt member 504 may be comprised of a flexible material such as a polymer (e.g., epoxy or resin) including polyurethane, neoprene, urethane, etc. and the surface of the belt member 504 may be elastomeric for friction. The belt member 504 may also be reinforced with fibers such as Kevlar fibers, glass fibers, carbon fibers, aramid fibers, basalt fibers, etc. The belt member 504 may also be configured to resist stretching. The tab 510 may be in the form of a ring. The first recess 508 may also provide a cutout which can allow the belt member 504 to lie flush with the surface of the base 502 if the belt mount 500 is mounted to a planar surface such as the side of a GCX arm, for example. A corresponding second recess (not shown) may also be provided on another side of the base 502 than the first recess 508. The second fastener 505 may include a knob 511 attached to a shaft which extends into the base 502, and a drum 506 located inside the base 502. The shaft may include a threaded portion configured to mesh with a toothed portion around the drum 506. A user may wrap the belt member 504 around a support structure, and pull the tab 510 so as to initially tighten the belt member 504 to the support structure. The user may then turn the knob 511 which thus rotates the drum 506 such that the drum 506 fastens the belt member 504 to the support structure. This process may be reversed so as to remove the belt mount 500 from the support structure. In other words, the first fastener 503 is configured to be detachably secured to the base 502, and is configured to fasten and release the belt mount 500 to the support structure by the belt member 504; and the second fastener 505 is configured to be detachably secured to the base 502, and is configured to fasten and release the belt member 504. The removable pin 509 can allow the belt member 504 to be secured around a support structure, then slack in the belt member 504 can be pulled out via the tab 510, and subsequently the belt member 504 can be tightened via the knob 511. Therefore, the belt mount 500 enables a user to quickly and easily secure and remove a device from a support structure.

FIGS. 65-68 show a coupling 600 for detachably securing a device (e.g., monitor, rack, module, etc.) to a mount (e.g., monitor mount, workstation, stand, etc.). The coupling 600 includes a first leaf 601, a second leaf 602, a pin 607, and a handle 603. The first leaf 601 can be fixed to one of the device and the mount and the second leaf 602 can be fixed to the other of the device and the mount. The first leaf 601 can include any mounting interface such as a first VESA mounting interface 606 and the second leaf 602 can include any mounting interface such as a second VESA mounting interface 609. The first leaf 601 defines a first knuckle 604 at a first end thereof and a first protruding edge 610 at a second end thereof. The second leaf 602 defines a second knuckle 605 at a first end thereof and a second protruding edge 608 at a second end thereof. Each of the first and second knuckles 604, 605 has an aperture defined therein. The pin 607 is configured to extend through the first aperture and the second aperture. The first knuckle 604 can include a first portion and a second portion, and the second knuckle 605 can be positioned in between the first portion of the first knuckle 604 and the second portion of the first knuckle 604. Furthermore, the first knuckle 604 and/or the second knuckle 605 can be beveled or filleted so as to optimize contact between the first and second knuckles 604, 605 and enhance rotatability. In other embodiments (not shown), the first and second knuckles 604, 605 may be non-round in cross section. The handle 603 can be attached to an end of the pin 607 outside the first leaf 601 and the second leaf 602. The pin 607 may be spring-loaded (not shown) such that when the first leaf 601 and the second leaf 602 are brought together, the pin 607 retracts and then slides into place upon full alignment. The first leaf 601 and the second leaf 602 can thus be fixed in a locked position at which the first protruding edge 610 and the second protruding edge 608 are engaged. For example, a user can detachably secure the device to the mount by first inserting the first protruding edge 610 into the second protruding edge 608 at any angle. Locating the second protruding edge 608 with the first protruding edge 610 is very easy since there is no inherent starting alignment required because the first protruding edge 610 and the second protruding edge 608 fit together precisely as the first protruding edge 610 and the second protruding edge 608 are moved into position. The first protruding edge 610 and the second protruding edge 608 can therefore provide physical or tactile confirmation of engagement of the first and second leaves 601, 602. As the first protruding edge 610 and the second protruding edge 608 are pressed together and the first and second leaves 601, 602 are rotated so as to be parallel with each other, and the second knuckle 605 fits in between the first portion of the first knuckle 604 and the second portion of the first knuckle 604 until the first and second leaves 601, 602 are fully aligned. In this process, the pin 607 is forced to retract and then slides into place when the first and second leaves 601, 602 are fully mated. Accordingly, the first protruding edge 610 and the second protruding edge 608 are easy to initially mate because it is easy for a user to see the first protruding edge 610 and fit the second protruding edge 608 into the first protruding edge 610, and then simply rotate the first and second leaves 601, 602 into alignment such that mating of the first and second leaves 601, 602 is achieved. Such mating is a very short action compared to a slide, for example, and is much easier to initiate as opposed to blind rotating mating attempts where the user cannot see all of the mating interfaces. Therefore, the coupling 600 enables a user to quickly and easily secure and remove a device from a mount. In other embodiments (not shown), alternative latching features other than a pin may be used to ensure engagement of the first protruding edge 610 and the second protruding edge 608.

FIGS. 69-81 show various exemplary implementations of a system including a rack 250 for detachably securing a module 300. The rack 250 can detachably secure the module 300 in a first position in which a female connector 702 of the rack 250 and a male connector 701 of the module 300 are electrically connected and the module 300 and the rack 250 are mechanically connected. The rack 250 can also detachably secure the module 300 therein in a second position in which the female connector 702 and the male connector 701 are electrically disconnected and the module 300 and the rack 250 are mechanically connected. In other words, the module 300 remains mechanically connected to the rack 250 in both the first position and the second position; i.e., the module 300 can be partially released from the rack 250 and electrically disconnected while still being mechanically retained. In this way, the rack 250 can catch and hold the module 300 in a secondary position such that the module 300 is docked, but power to the module 300 is cut while other connections such as gas and/or pump connections (e.g., EEG, NMT, gas analysis, EKG, $SBO_2$, blood pressure, etc.) are maintained.

The module may include a groove 302 defined in a periphery of the module 300. The groove 302 may allow a user to grasp sides of the module 300 and accommodate a broader range of hand sizes, particularly smaller hand sizes. By being able to grasp the sides of the module 300, the user is not forced to grasp a top and a bottom of the module 300 which can be of substantial length and therefore cumbersome. The module 300 may further include one or more third electrical connectors 305 such as a circular connector for electrical connection with another device outside the rack 250. In the embodiments shown in FIGS. 69-75, the rack 250 includes a first latch 253 adapted to engage with first and second recesses 303, 304 in the module 300. The first and second recesses 303, 304 can be located on a top face of the module 300 at different positions along a longitudinal direction of the module 300. In the first position, the first latch 253 may be engaged in the first recess 303. In the second position, the first latch 253 may be engaged in the second recess 304. The release of the module 300 can be effected by a releaser 251 which may be a push-button mechanism configured to drive a rod 252 against the first latch 253 so as to release the first latch 253 from engagement and allow removal of the module 300 from the rack 250.

In some variations, the rack 250 may include a second latch 254 adjacent to the first latch 253 whereby: (i) the first latch 253 is a spring-loaded latch and the second latch 254 is a lever latch; (ii) in the first position, the first latch 253 is engaged in the first recess 303 and the second latch 254 is disengaged from the first and second recesses 303, 304; and (iii) in the second position, the second latch 254 is engaged in the second recess 304 and the first latch 253 is disengaged from the first and second recesses 303, 304. The rack 250 may further include one or more spring-loaded plungers 255, 256 for biasing the module 300 away from the rack 250 such that the female connector 702 is disconnected from the male connector 701 and there is a clearance between the female connector 702 and the male connector 701. In addition, the one or more spring-loaded plungers 255, 256 may facilitate module removal (e.g., overcoming any friction between the rack and module or overcoming the mating force of the connector). Alternatively, the mechanical retention of the modules can be effected by friction features (not shown) or graduated press or interference fitting (not shown). Such a rack 250 does not require the complexity of a second latching mechanism.

In the embodiments shown in FIGS. 76-81, the module 1300 includes a latch 1306 adapted to engage with a recess 1261 in the rack 1250. The recess 1261 can be located on a top face of a bottom portion of the rack 1250. In the first position, the latch 1306 may be engaged in the recess 1261. In the second position, the latch 1306 may be disengaged from the recess 1261. The release of the module 1300 can be effected by a releaser 1307 which may be a tab configured to depress the latch 1306 so as to release the latch 1306 from engagement and allow removal of the module 1300 from the rack 1250. In the embodiments shown in FIGS. 76-81, the releaser and the first latch may be omitted from the rack 1250 and the rack 1250 may simply include the second latch 1254 (e.g., the lever latch) whereby: (i) in the first position, the second latch 1254 is disengaged from a recess 1304 in the module 1300; and (ii) in the second position, the second latch 1254 is engaged in the recess 1304. In embodiments not shown in FIGS. 76-81, the rack 1250 could include one or more additional recesses located on the top face of the bottom portion of the rack 1250 behind the recess 1261. In embodiments not shown in FIGS. 76-81, the module 1300 could include one or more additional latches behind the latch 1306. The module 1300 further includes one or more third electrical connectors 1305 such as a circular connector for electrical connection with another device outside the rack 1250.

Figure 61:
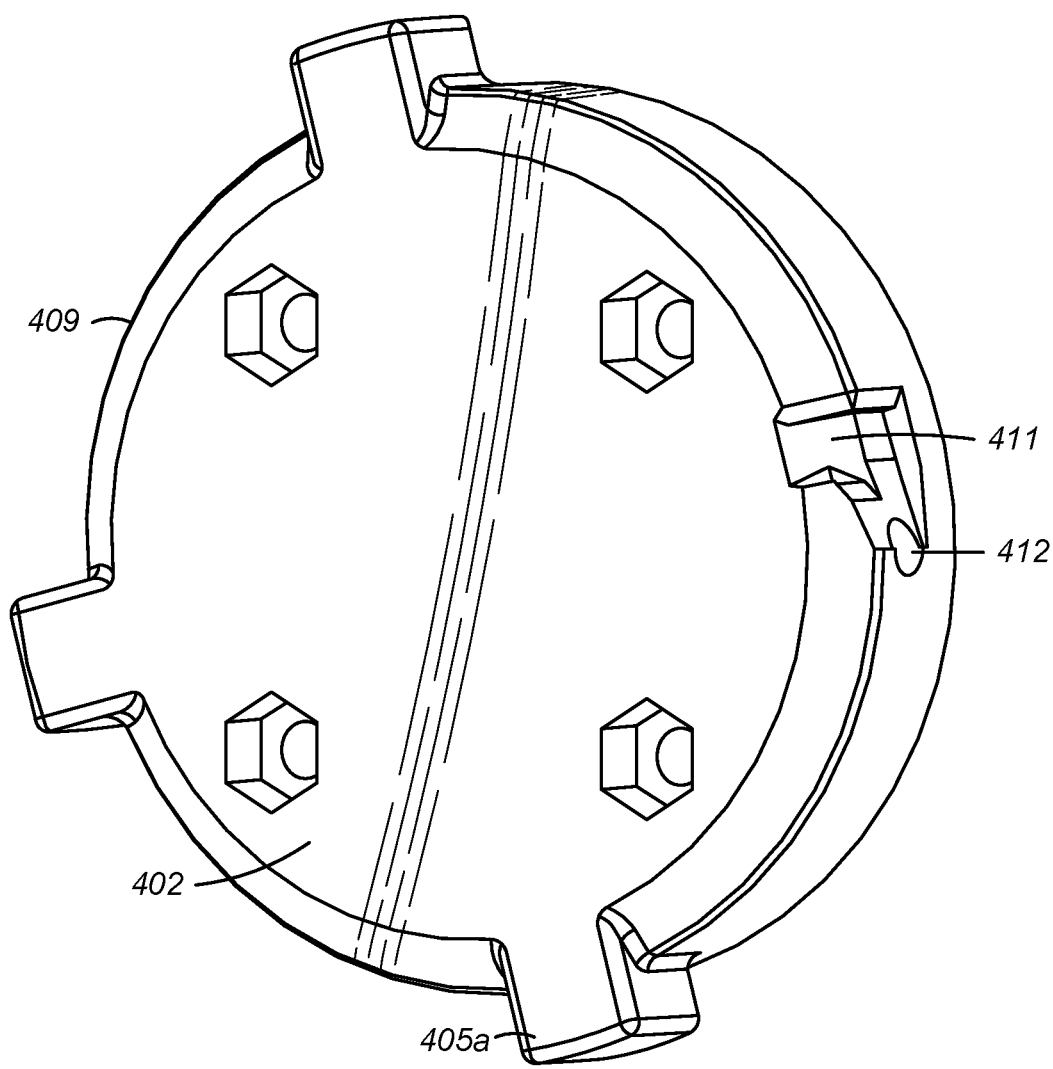
FIG. 61 is a bottom view of the top piece.
Figure 62:
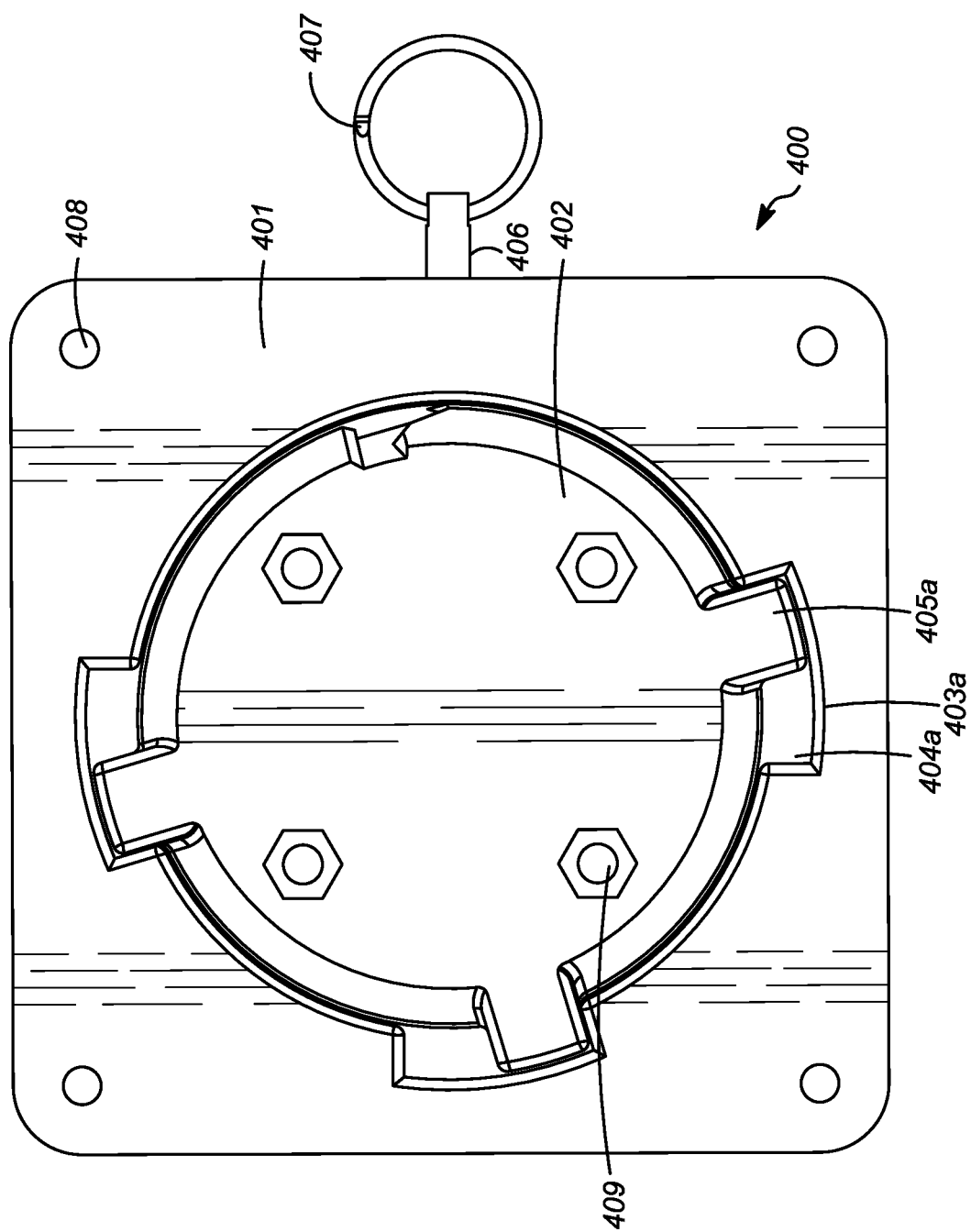
FIG. 62 is a bottom view of the coupling including the base plate, the top piece, and the locking mechanism.

A groove 1302 may be defined in a periphery of the module 1300. The groove 1302 may allow a user to grasp sides of the module 1300 and accommodate a broader range of hand sizes, particularly smaller hand sizes. By being able to grasp the sides of the module 1300, the user is not forced to grasp a top and a bottom of the module 1300 which can be of substantial length and therefore cumbersome. The groove 1302 may extend 360° around the module 300. A channel 1257 may be defined in a back wall of the rack 1250. The channel 1257 may provide a space between the back wall of the rack 1250 and the module 1300 when the module 1300 is detachably secured in the rack 1250. The channel 1257 can vent air from the back of any module 1300 requiring cooling and exhaust the air out of the side of the rack 1250 thereby assisting with thermal mitigation. The rack 1250 may include one or more couplings (see couplings 258 in FIG. 71) defining a bay for receiving the module 1300. The rack can include any number of couplings, for example, in the illustrated embodiment, four couplings 1258 may be provided such that the rack 1250 has four bays. An aperture may be defined in the back wall of the rack 1250. The aperture may receive the female connector 702 such that the female connector 702 protrudes through the back wall of the rack 1250 for connection to the male connector 701. The male connector 701 may be recessed in the module 300. A tab (not shown) such as a pull ring may be included at a front face of the module 1300 so as to facilitate removal of the module 1300 from the rack 1250. The rack 1250 may also include any mounting interface such as a VESA mounting interface. The rack 1250 may further include at least one cable management feature 1262 (as shown in FIG. 61) for preventing tangling or fraying of associated cables connected to the module 1300 and/or the rack 1250. Therefore, the rack 1250 enables a user to store multiples of module 1300 in an additional position in which they are physically or mechanically connected to the rack 1250 but electrically disconnected from the rack 1250. Furthermore, the combination of providing the first latch 1253 or first and second latches 1253, 1254 on the rack 1250 and providing the recessed male connector 701 on the module 1300 creates a hospital environment where the burden of hygienic reprocessing is borne by the rack as opposed to the modules. Typically, the rack is fixed and the modules are mobile or transportable. Consequently, having the rack bear the burden of hygienic reprocessing is advantageous and more convenient because the modules are handled and relocated with greater frequency than the rack.

FIGS. 82-87 show various exemplary implementations of a system including a rack 2250 for detachably securing a module 2300. The rack 2250 can detachably secure the module 2300 in a first position in which a first electrical connector 2251 of the rack 2250 and a second electrical connector 2301 of the module 2300 are electrically connected and the module 2300 and the rack 2250 are mechanically connected. The rack 2250 can also detachably secure the module 2300 therein in a second position in which the first electrical connector 2251 and the second electrical connector 2301 are electrically disconnected and the module 2300 and the rack 2250 are mechanically connected. In other words, the module 2300 remains mechanically connected to the rack 2250 in both the first position and the second position; i.e., the module 2300 can be partially released from the rack 2250 and electrically disconnected while still being mechanically retained. In this way, the rack 2250 can catch and hold the module 2300 in a secondary position such that the module 2300 is docked, but power to the module 2300 is cut while other connections such as gas and/or pump connections (e.g., EEG, NMT, gas analysis, EKG, SBO$_2$, blood pressure, etc.) are maintained. In the embodiments shown in FIGS. 82 & 83, sides of the rack 2250 are closed. In other embodiments not shown, sides of the rack 2250 may be open. The module 2300 may further include one or more third electrical connectors 2304 such as a circular connector for electrical connection with another device outside the rack 2250.

Figure 84:
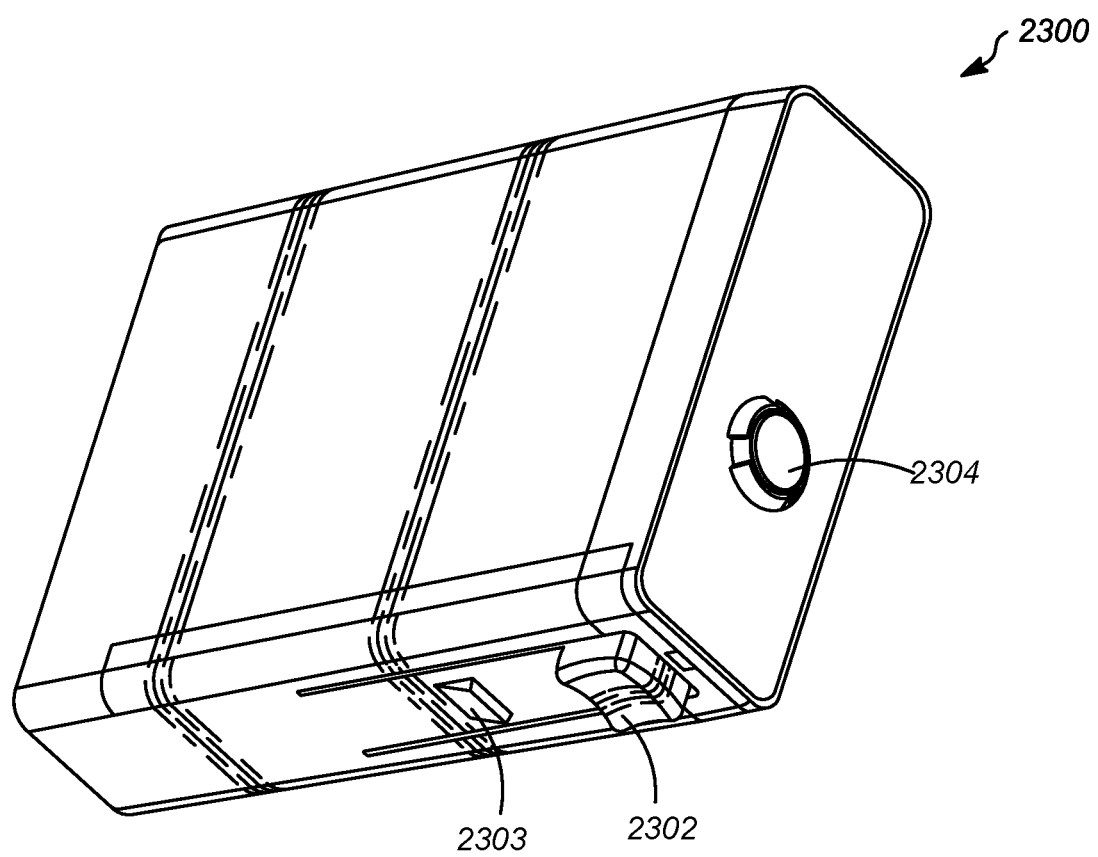
FIG. 84 is a bottom perspective view of the third exemplary implementation of the module.

In the embodiments shown in FIGS. 82-87, the module 2300 includes a latch 2303 adapted to engage with first and second recesses 2252, 2253 in the rack 2250. The first and second recesses 2252, 2253 can be located on an upper surface of a lower portion the rack 2250 at different positions along a depth direction of the rack 2250. In the first position, the latch 2303 may be engaged in the first recess 2252. In the second position, the latch 2303 may be engaged in the second recess 2253. The release of the module 2300 can be effected by a releaser 2302 (as shown in FIG. 84) which may be a tab configured to release the latch 2303 from engagement and allow removal of the module 2300 from the rack 2250.

Figure 85:
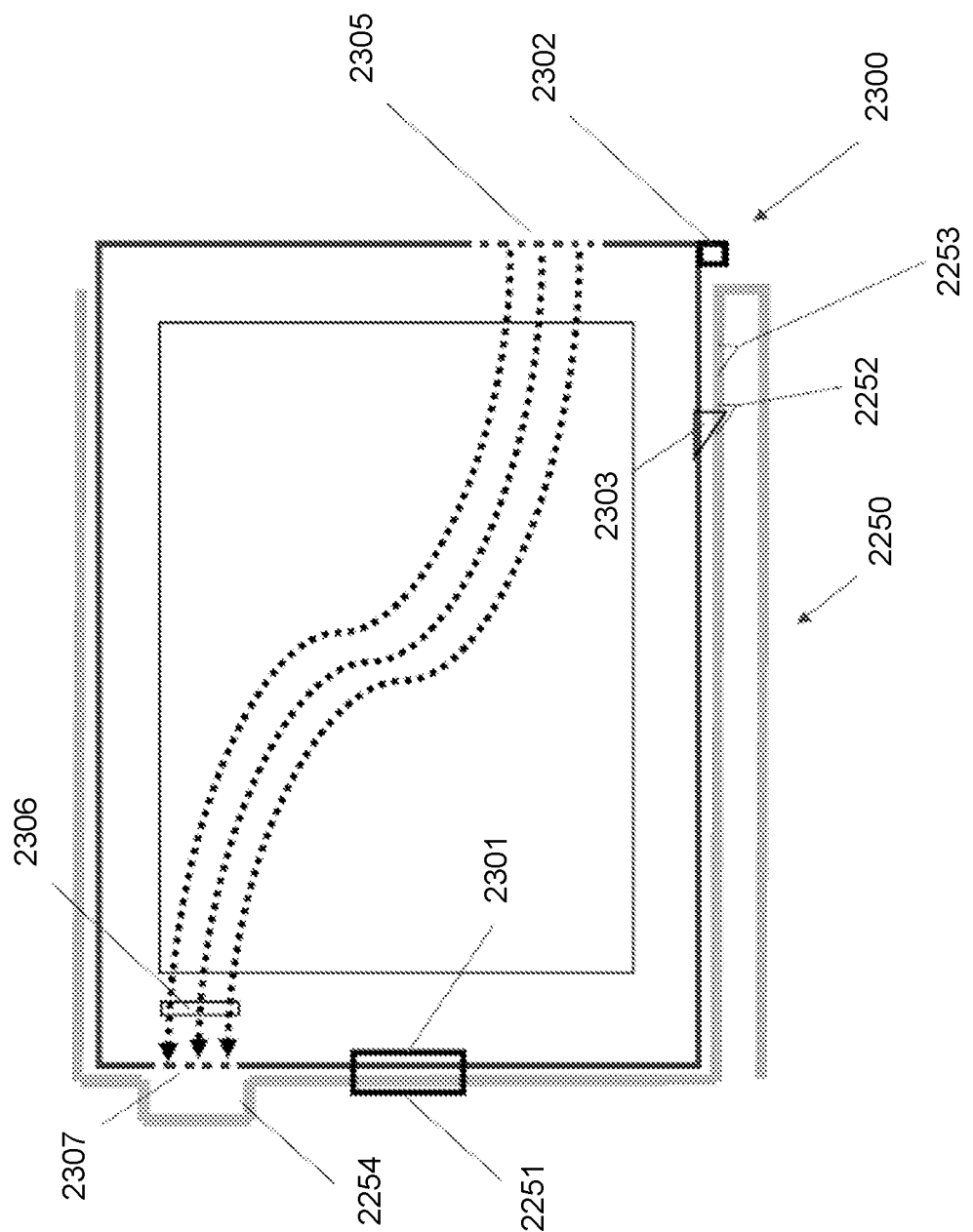
FIG. 85 is a cross-sectional view of the third exemplary implementation of the rack detachably securing the exemplary implementation of the module.
Figure 86:
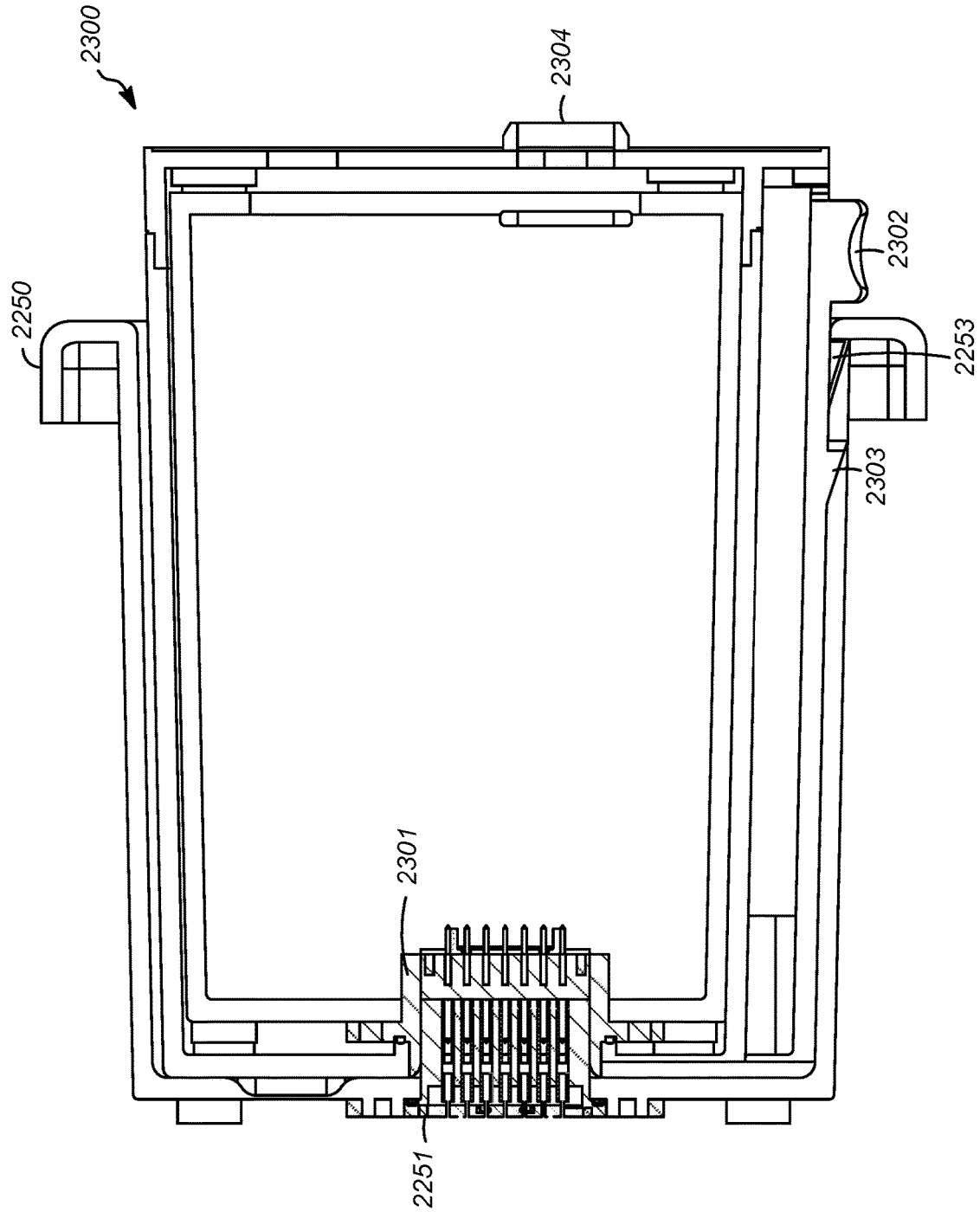
FIG. 86 is another cross-sectional view of the third exemplary implementation of the rack detachably securing the exemplary implementation of the module.
Figure 87:
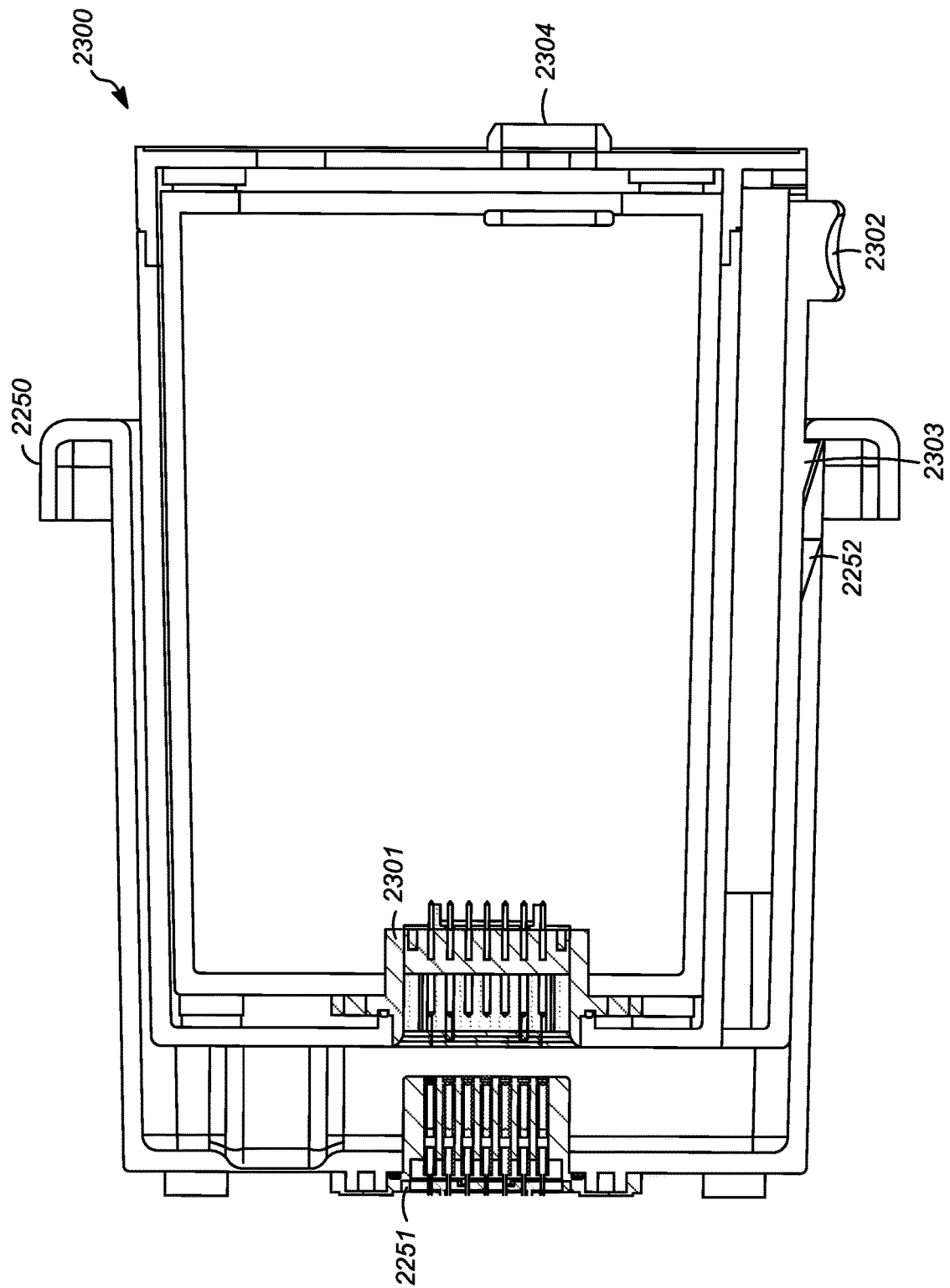
FIG. 87 is a further cross-sectional view of the third exemplary implementation of the rack 2250 detachably securing the exemplary implementation of the module.
Figure 88:
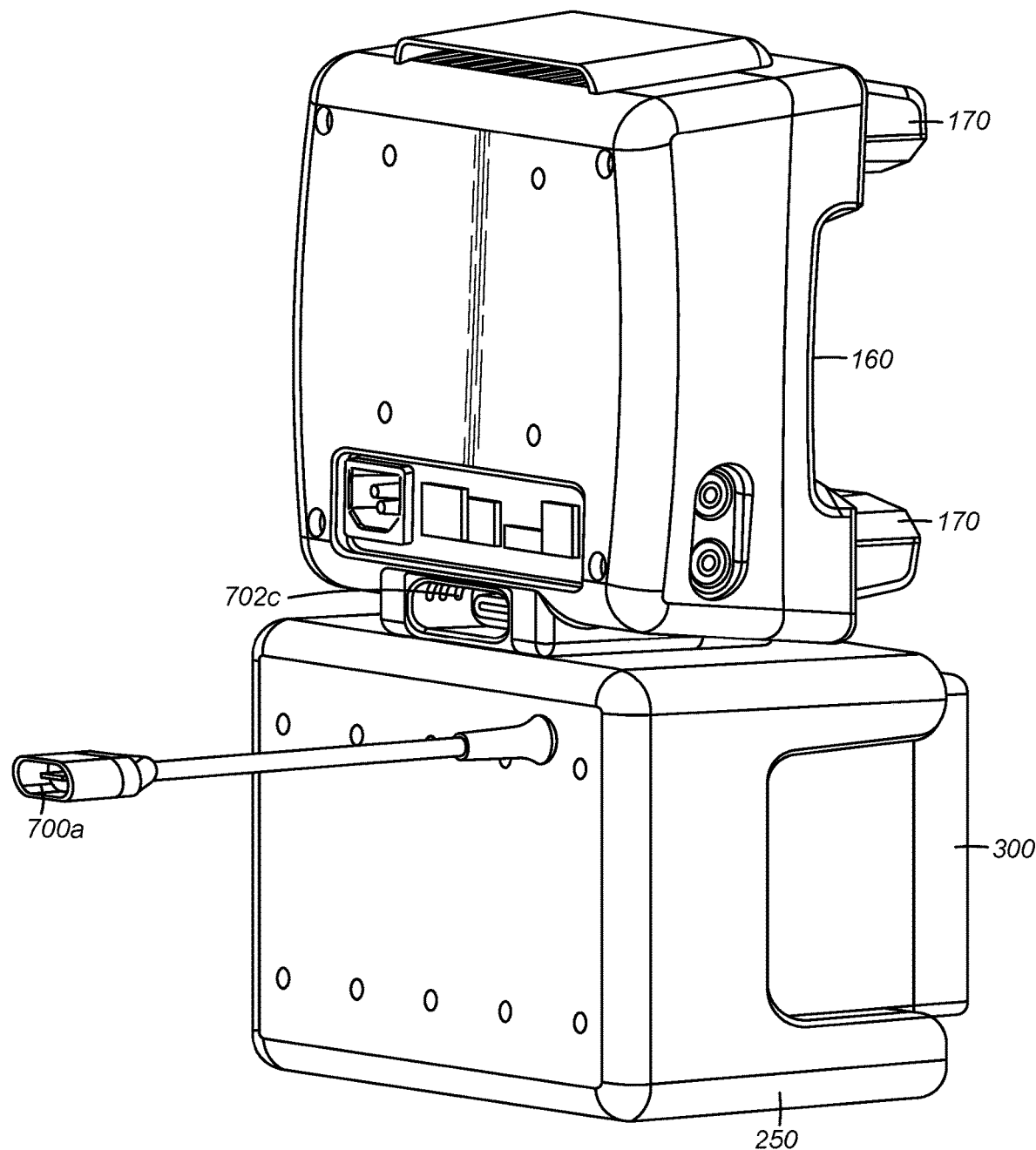
FIG. 88 is a back perspective view of an exemplary system including a monitor mount, a rack, a module, and a first exemplary implementation of a cable.
Figure 89:
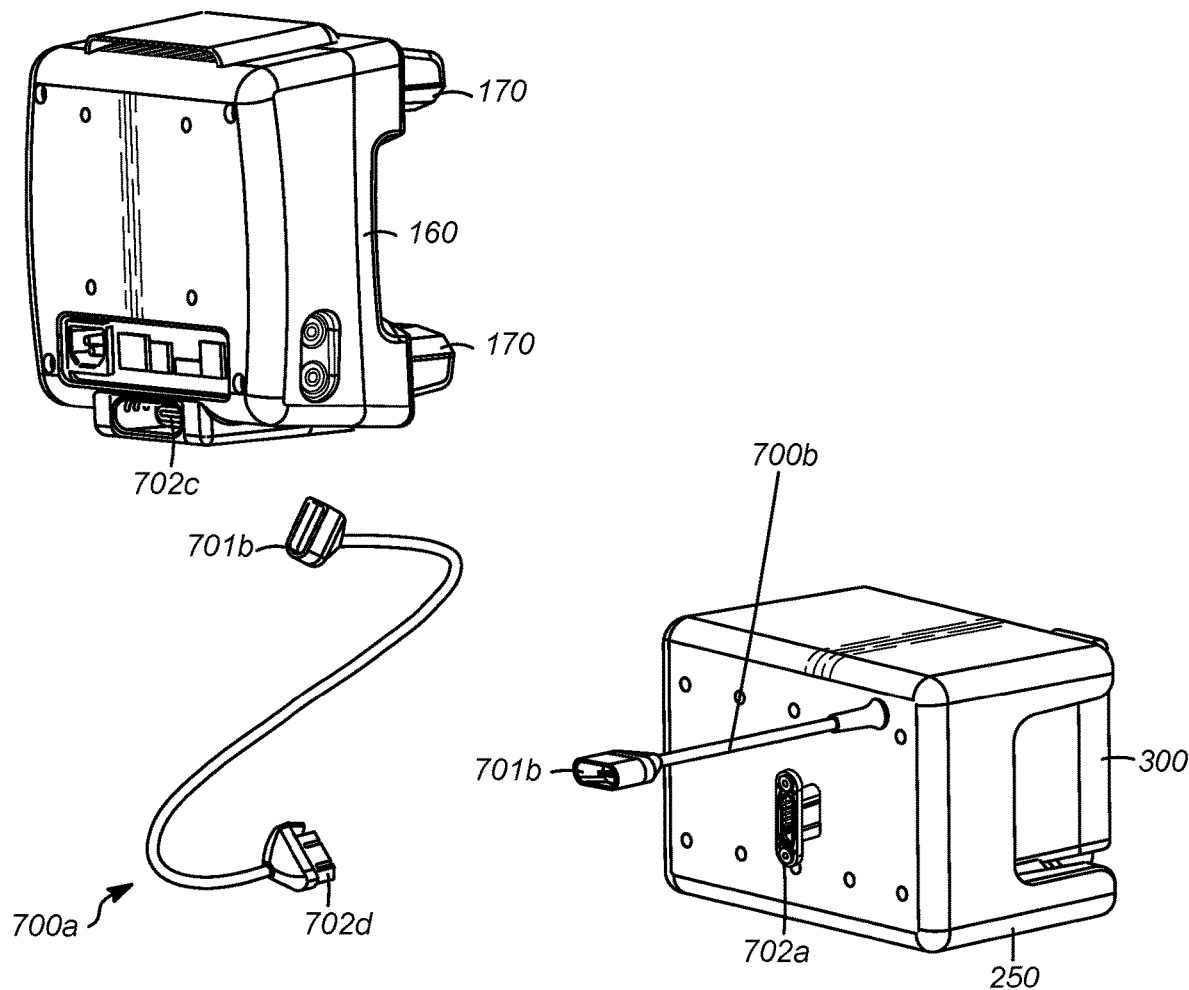
FIG. 89 is an exploded back perspective view of an exemplary system including a monitor mount, a rack, a module, and first and second exemplary implementations of cables.

A channel 2254 may be defined in a back wall of the rack 2250. The channel 2254 may provide a space between the back wall of the rack 2250 and the module 2300 when the module 2300 is detachably secured in the rack 2250. The channel 2254 can vent air from the back of any module 2300 requiring cooling and exhaust the air out of the front of the rack 2250 thereby assisting with thermal mitigation. The channel 2254 may extend across one or more sides of the rack 2250. For example, the channel 2254 may extend across three sides of the rack 2250. As shown in FIG. 85, the module 2300 may further comprise an air inlet 2305 and an air outlet 2307 configured to vent air to the channel 2254 of the rack 2250. Such venting further assists with thermal mitigation by drawing heat away from internal elements of the module 2300 (e.g., a circuit board of the module 2300). In addition, the module 2300 may further comprise at least one fan 2306 for circulating air to the air outlet 2307. Accordingly, active airflow can be provided by the module 2300 to the rack 2250.

The rack 2250 may include one or more guide rails 2255 each defining one side of a bay for receiving the module 2300. The rack can include any number of guide rails 2255, for example, in the illustrated embodiment, three guide rails 2255 may be provided such that the rack 2250 has four bays. A length of each of the guide rails 2255 may be less than a depth of the rack 2250. Such a partial guide rail length improves cleanability of the rack 2250 because there is a continuous flat section close to an opening of the rack 2250 and there are fewer surfaces to be cleaned.

The rack 2250 may include a first electrical connector 2251 which protrudes through an aperture (see aperture 259 in FIG. 71) defined in the back wall of the rack 2250 for connection to a second electrical connector 2301 of the module 2300. The second electrical connector 2301 may be recessed in the module 2300. The rack 2250 may also include any mounting interface such as a VESA mounting interface. Therefore, the rack 2250 enables a user to store modules 2300 in an additional position in which the modules 2300 are physically or mechanically connected to the rack 2250 but electrically disconnected from the rack 2250.

FIGS. 88-101 show various exemplary implementations of cables 700*a*-700*c*, male portions or connectors 701*a*-701*c*, and female portions or connectors 702*a*-702*e*. The male and female portions or connectors 701*a*-701*c*, 702*a*-702*e* can be used to electrically connect any two or more devices (e.g., a monitor mount 160, a rack 250, and/or a module 300). In particular, the male and female portions or connectors 701*a*-701*c*, 702*a*-702*e* enable power sharing and/or data transfer between the two or more devices.

In some variations, the male portions or connectors 701*a*-701*c* and the female portions or connectors 702*a*-702*e* can be configured in any of cable, monitor mount, or rack versions. For example, as shown in FIGS. 69, 73-75, and 78-81, the male connector 701 of the module 300 and the female connector 702 electrically and mechanically connect directly to each other and no cable is integrated with the female connector 702. In contrast, in FIG. 90, the female connector 702*a* is integrated with a cable 700*c*. Thus, connectors 702*a*-702*e* may be integrated with or simply configured to be coupled to a cable.

Figure 90:
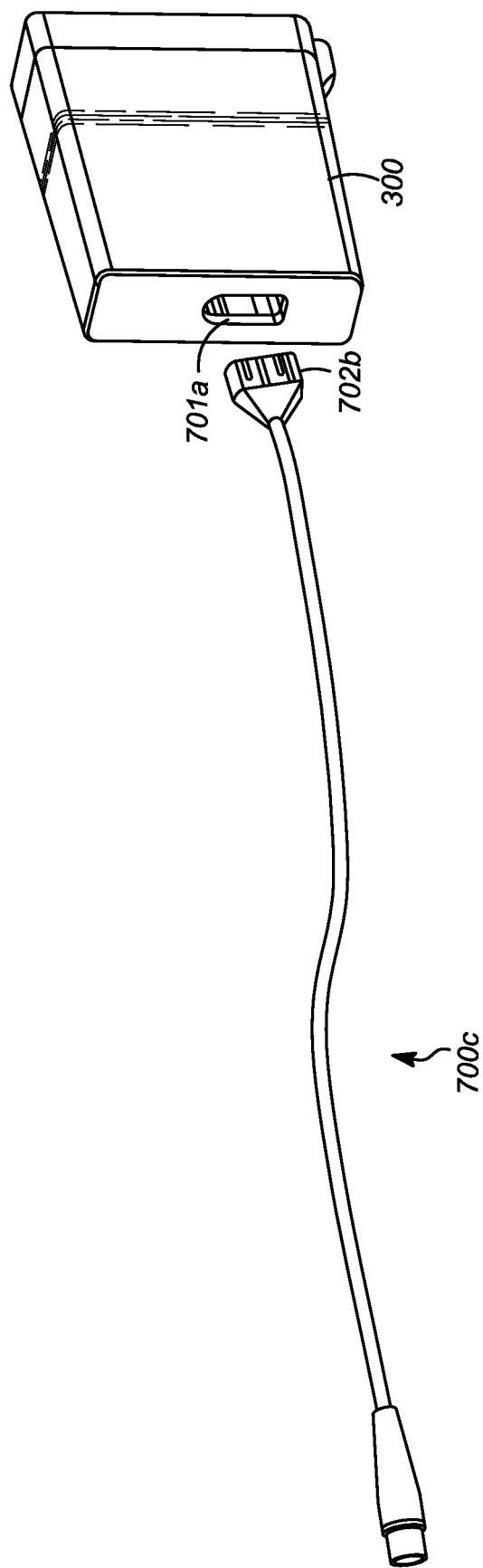
FIG. 90 is an exploded back perspective view of an exemplary system including a module, and a third exemplary implementation of a cable.
Figure 91:
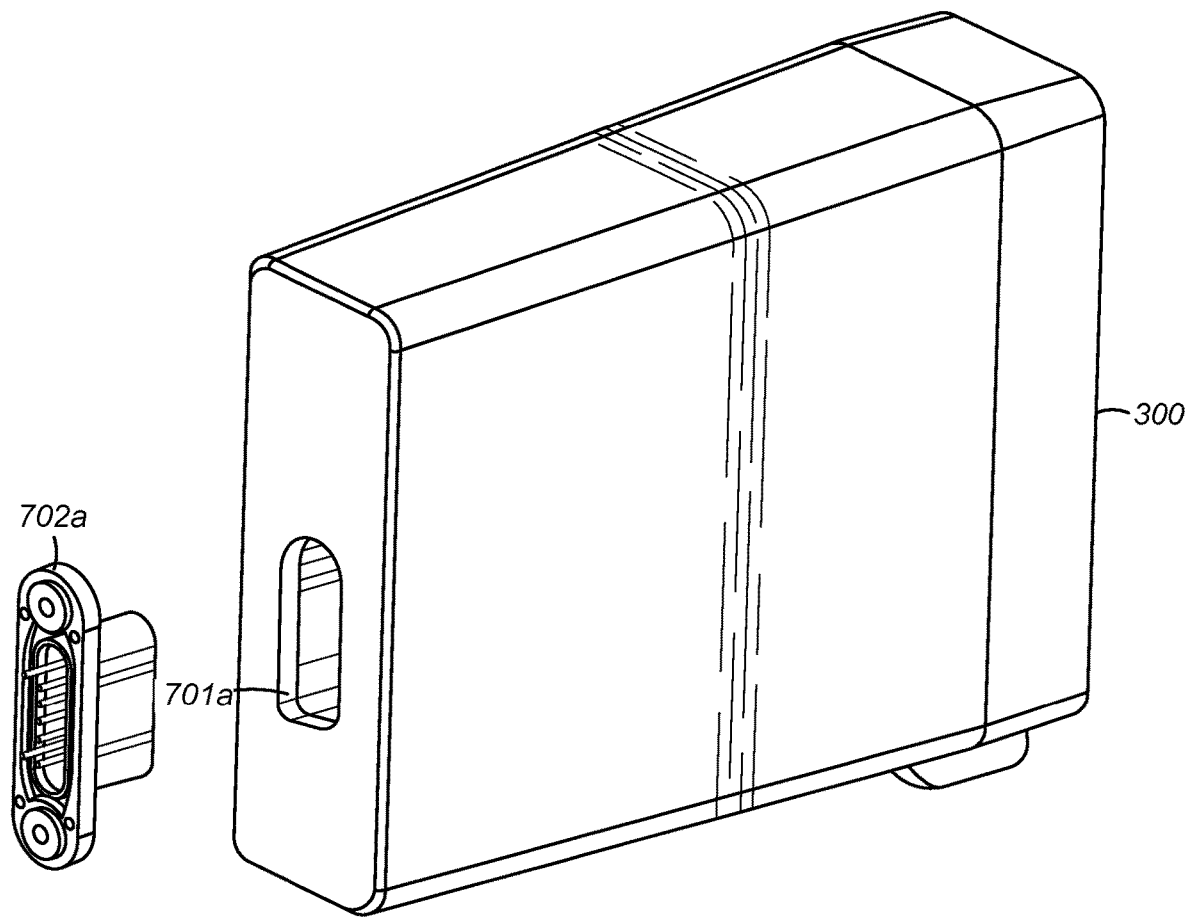
FIG. 91 is an exploded back perspective view of an exemplary system including a module, a male connector and a female connector.

As shown in FIG. 90, for example, a cable 700*c* is integrated with the female connector 702*b*. The cable 700*c* may function as a connection from the module 300 to the monitor mount 160 or a small monitor 120 and/or large monitor 140 by circumventing the rack 250. In other words, the module 300 may be directly connected to the monitor mount 160 or the small monitor 120 and/or large monitor 140 via the cable 700*c*. For example, female portions or connectors 702*a*-702*c* can be connected to male portions or connectors 701*a*-701*c*. The female connector 702*a*-702*e* includes a housing 719 including a pair of longitudinal sides, a planar side connecting first ends of the pair of longitudinal sides of the female connector 702*a*-702*e*, a rounded side connecting second ends of the pair of longitudinal sides of the female connector 702*a*-702*e*, and a front surface including a plurality of sockets 703 located therein, the plurality of sockets 703 being arranged along a line parallel to the pair of longitudinal sides of the female connector 702*a*-702*e*.

The male connector 701a-701c, includes a housing 707 including a recess with a pair of longitudinal sides, a planar side connecting first ends of the pair of longitudinal sides of the male connector 701a-701c, a rounded side connecting second ends of the pair of longitudinal sides of the male connector 701a-701c, and a recessed surface including a plurality of pins 710 extending therefrom, the plurality of pins 710 being arranged along a line parallel to the pair of longitudinal sides of the male connector 701a-701c.

The housing 719 of the female connector 702a-702e is configured to be insertable into the recess of the housing 707 of the male connector 701a-701c such that the plurality of pins 710 of the male connector 701a-701c enter into or are received by the plurality of sockets 703 of the female connector 702a-702e. In some variations, the male connector 701a-701c may include seven pins 710 and the female connector 702a-702e may include seven sockets 703. In some variations, the male connector 701a-701c and the female connector 702a-702e can be connected through a back wall of a rack 250.

The pair of longitudinal sides of the male connector 701a-701c or the pair of longitudinal sides of the female connector 702a-702e may include ribs 704 formed thereon. The ribs 704 may increase friction such that the connector having the ribs 704 cannot be inserted into an incorrect device or interface, thereby forming a unique key arrangement to be matched and engaged with a corresponding male connector and to be rejected by a non-corresponding male connector. For example, the monitor mount 160 may include a female connector 702b having ribs 704. The ribs 704 may increase friction such that a sturdier electrical and mechanical connection is provided. For example, the monitor mount 160 may include a female connector 702b having ribs 704. The cables 700a-700c may also include a female connector 702b having ribs 704.

In some variations, the male connector 701a-701c may include a shield 711 including shield protrusions 708 that provides electromagnetic interference (EMI) protection during signal transfer. The female connector 702a-702e may include shield springs 705 for receiving the shield protrusions 708. The shield springs 705 are arranged within a spring groove that extends from the front portion of the female connector towards the back portion of the female connector. The female connector 702a-702e may also include a shield 718. Accordingly, the male connector 701a-701c and the female connector 702a-702e are configured to engage with each other sufficiently to ensure that the shield protrusions 708 fully compress the shield springs 705. The shield protrusions 708 and the shield grooves that contain the shield springs 705 can be mutually arranged to form a unique key arrangement to be matched and engaged with a corresponding male/female connector and to be rejected by a non-corresponding male/female connector. The shield 711 may be a 360 degree shield and an edge of the 360 degree shield may make contact with the highest point of the shield spring 705. In addition, a minimum engagement required for full shield contact compression may be 4.86 mm.

A gasket 706 may be provided on either of the male connector 701a-701c or the female connector 702a-702e to provide sealing. The gasket 706 may surround the housing 707 of the male connector 701a-701c or the housing 719 of the female connector 702a-702e. The male connector 701a-701c may include holes 709 for fasteners. Similarly, the female connector 702a-702e may also include holes 712 for fasteners. One end of any of the cables 700a-700c may feature a circular connector for electrical connection with a device. A length of any of the cables 700a-700c may be less than 3 meters.

As discussed above, an external shape of one of the male connector 701a-701c and the female connector 702a-702e is asymmetrical such that the one of the male connector 701a-701c and the female connector 702a-702e is configured to be connected to the other of the male connector 701a-701c and the female connector 702a-702e in only one orientation.

Figure 92A:
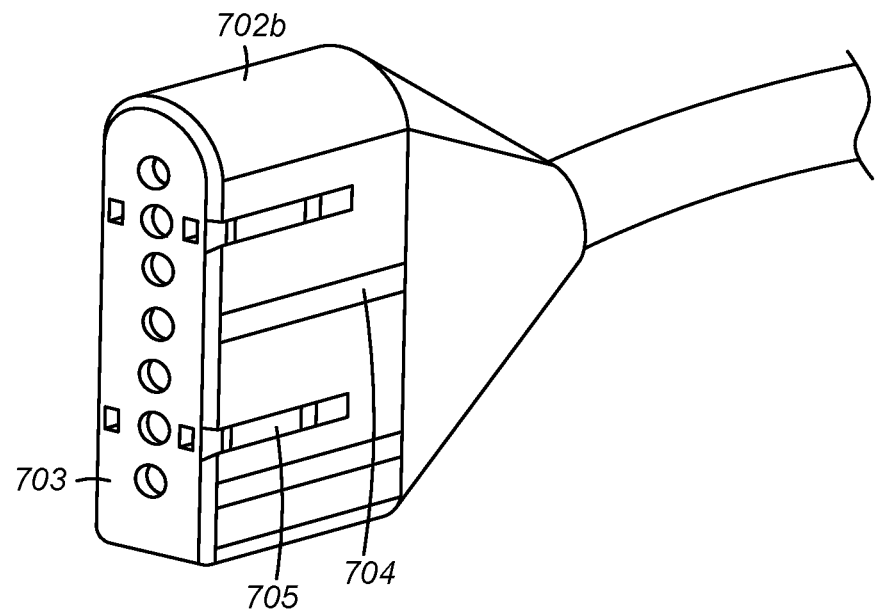
FIG. 92A is a perspective view of a second implementation of a female connector.
Figure 92B:
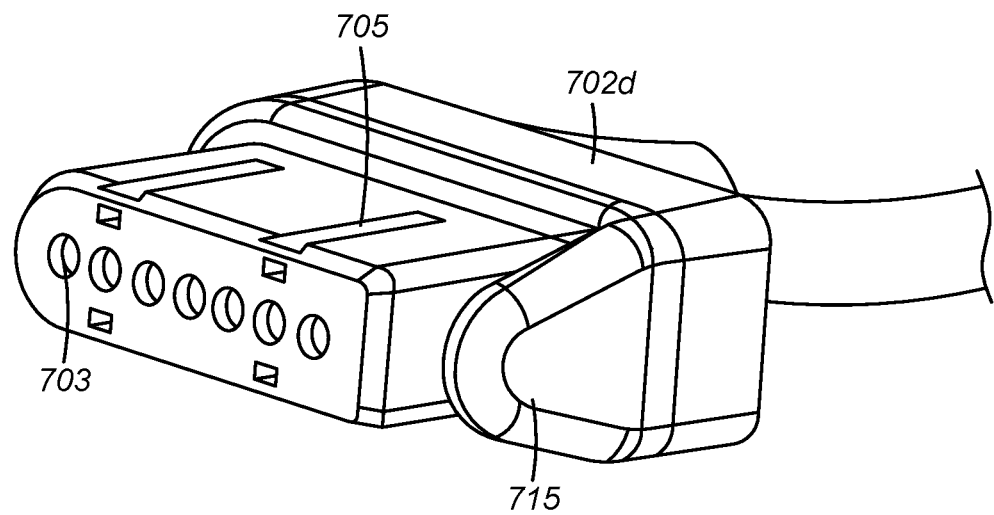
FIG. 92B is a perspective view of a fourth implementation of a female connector.
Figure 92C:
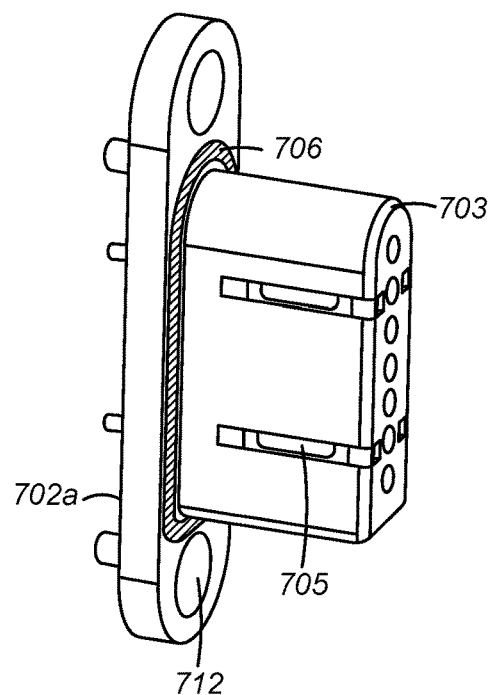
FIG. 92C is a perspective view of a first implementation of a female connector.
Figure 92D:
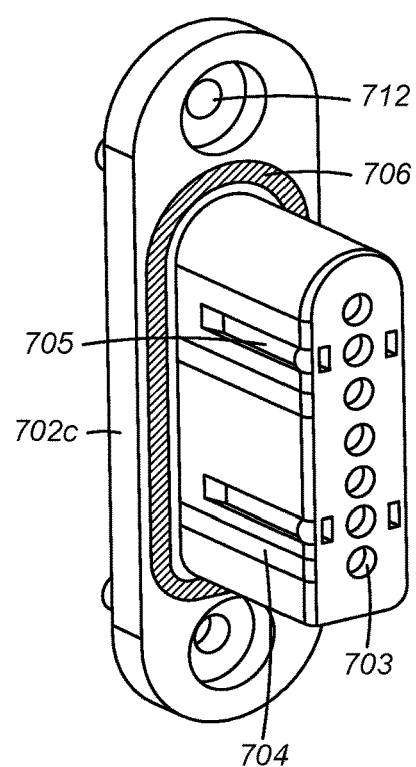
FIG. 92D is a perspective view of a third implementation of a female connector.
Figure 93A:
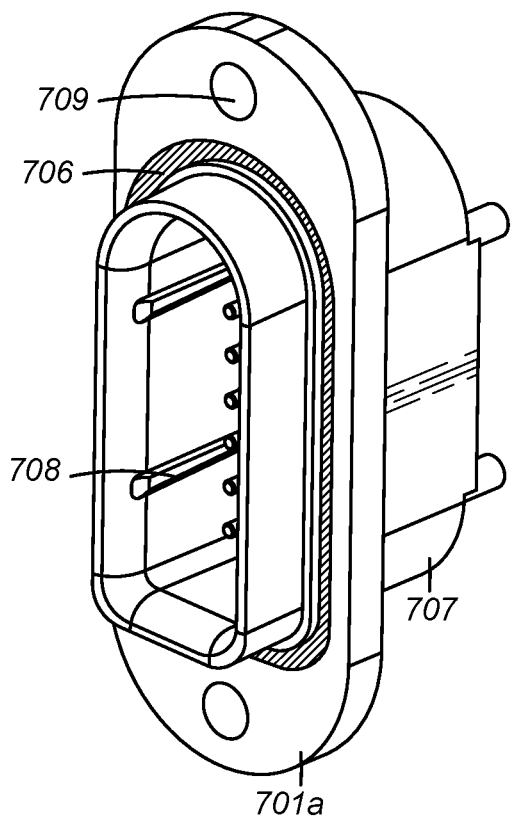
FIG. 93A is a perspective view of a first implementation of a male connector.
Figure 93B:
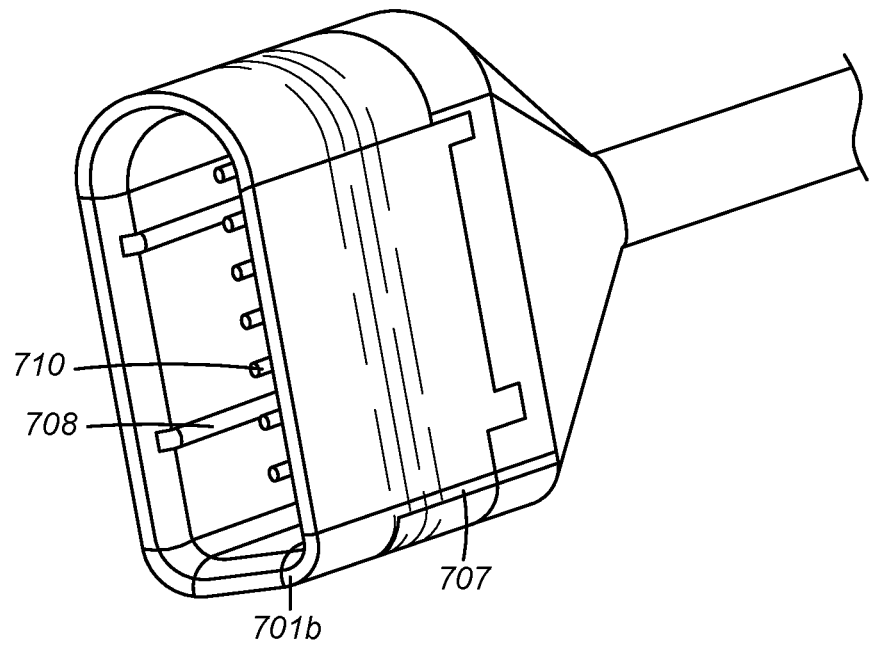
FIG. 93B is a perspective view of a implementations of the male connector.
Figure 94:
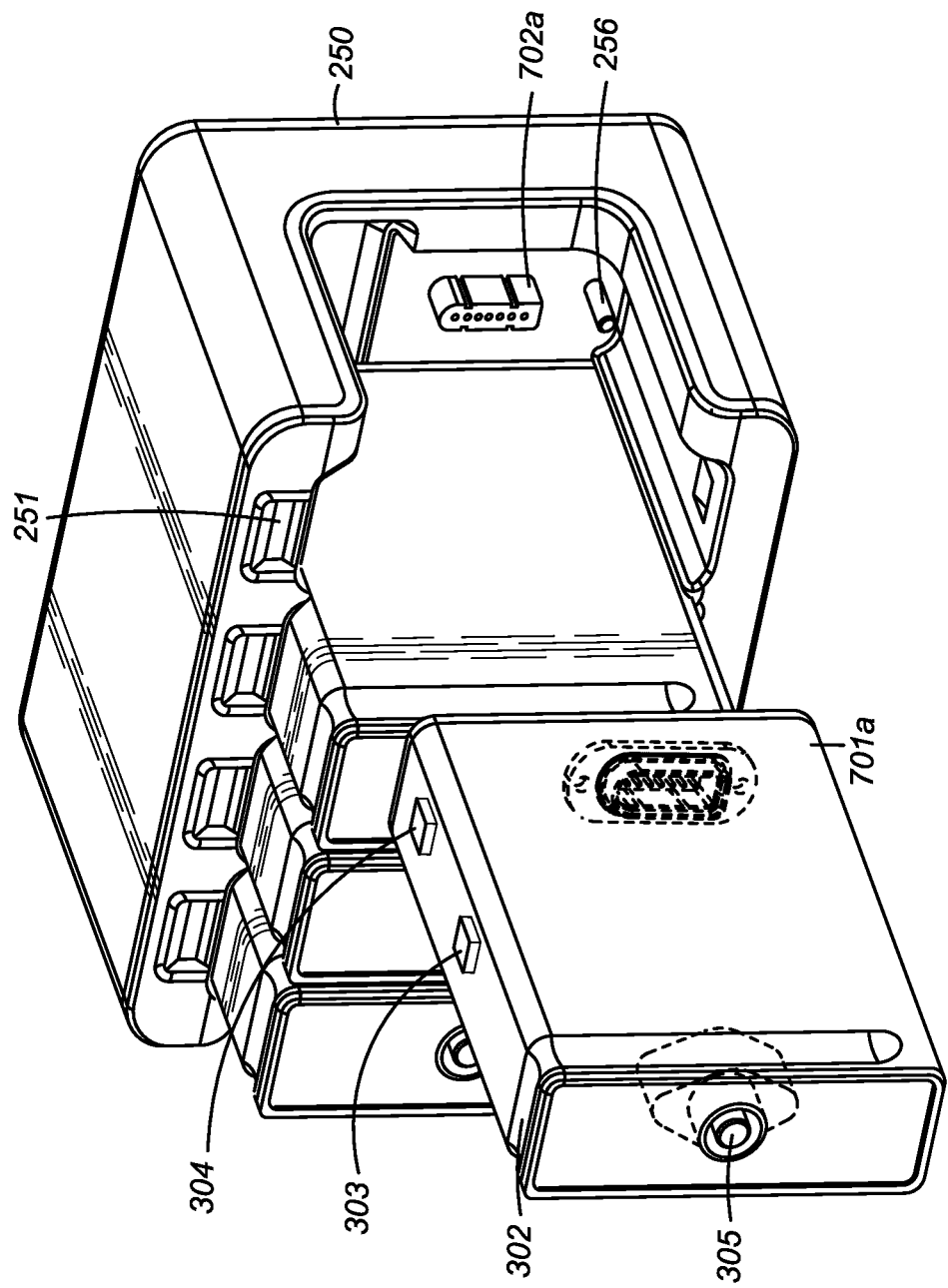
FIG. 94 is an exploded perspective view of an exemplary system including the first exemplary implementation of the rack, and first exemplary implementations of a module 300.
Figure 95B:
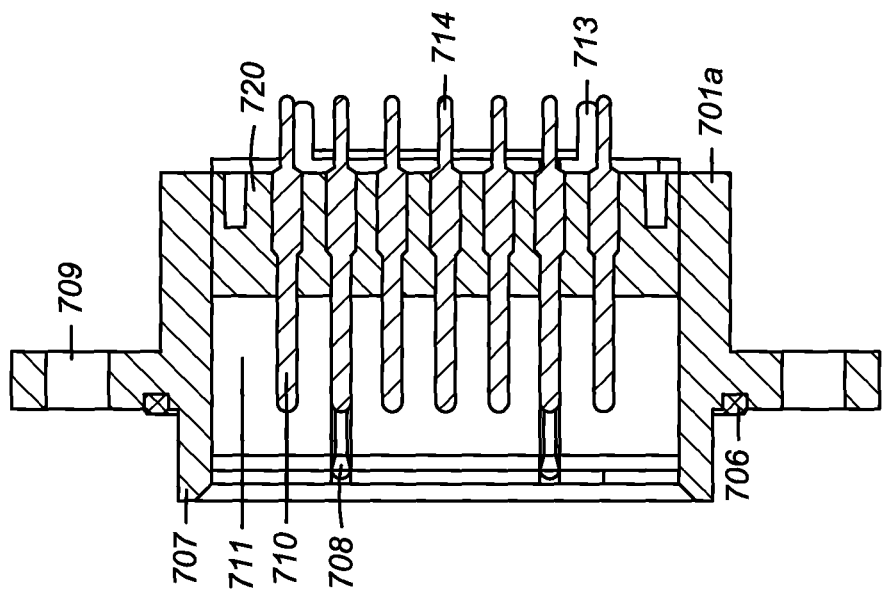
FIG. 95B is a cross-sectional view of the male connector shown in FIG. 95A taken along line 95B-95B and looking in the direction of the arrow.
Figure 95A:
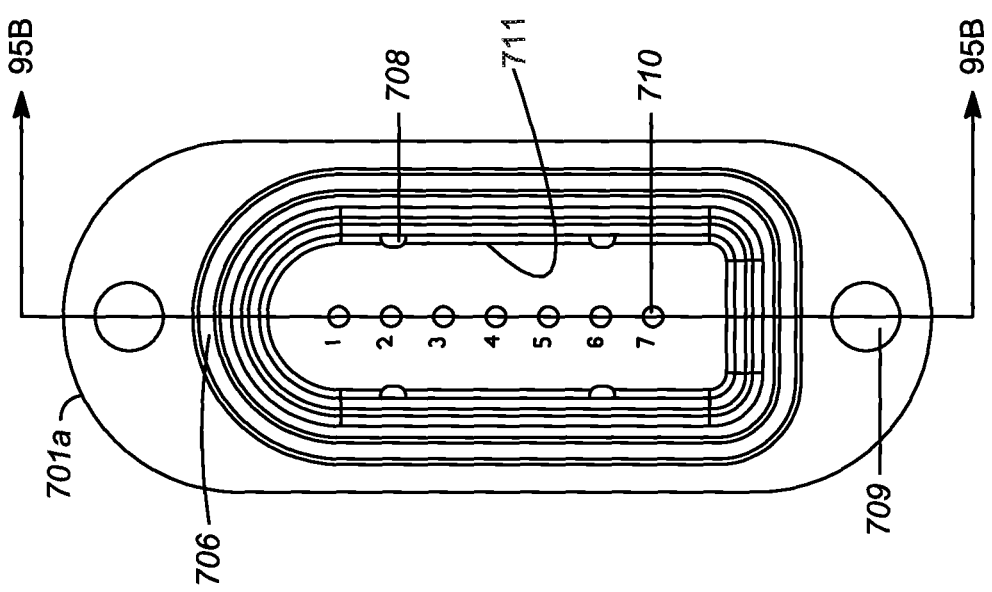
FIG. 95A is a front elevational view of the male connector shown in FIG. 93A.
Figure 95D:
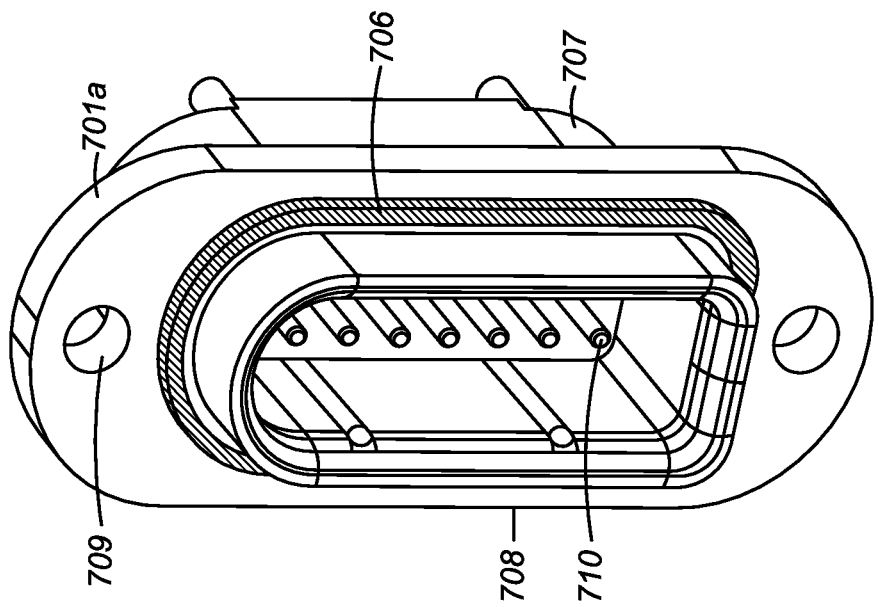
FIG. 95D is a front perspective view of the male connector shown in FIG. 93A.
Figure 95C:
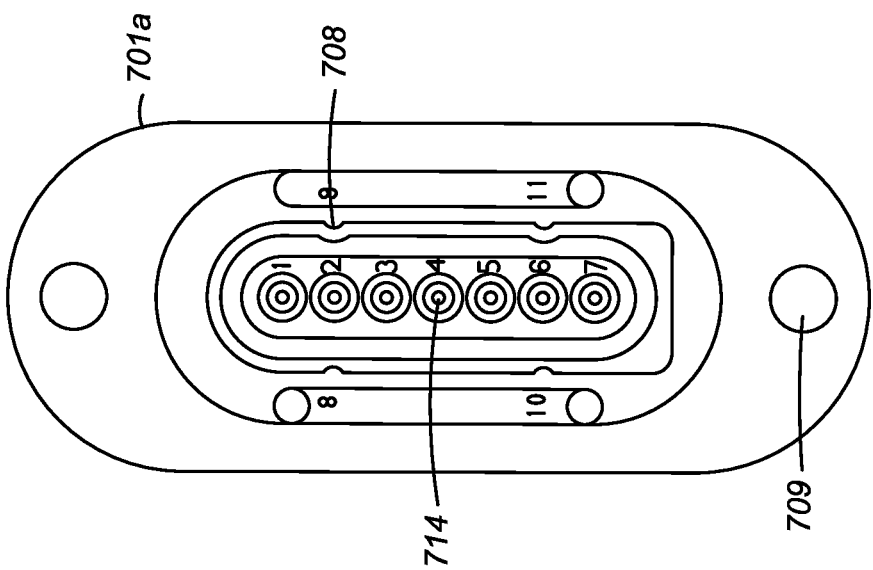
FIG. 95C is a rear elevational view of the male connector shown in FIG. 93A.
Figure 96B:
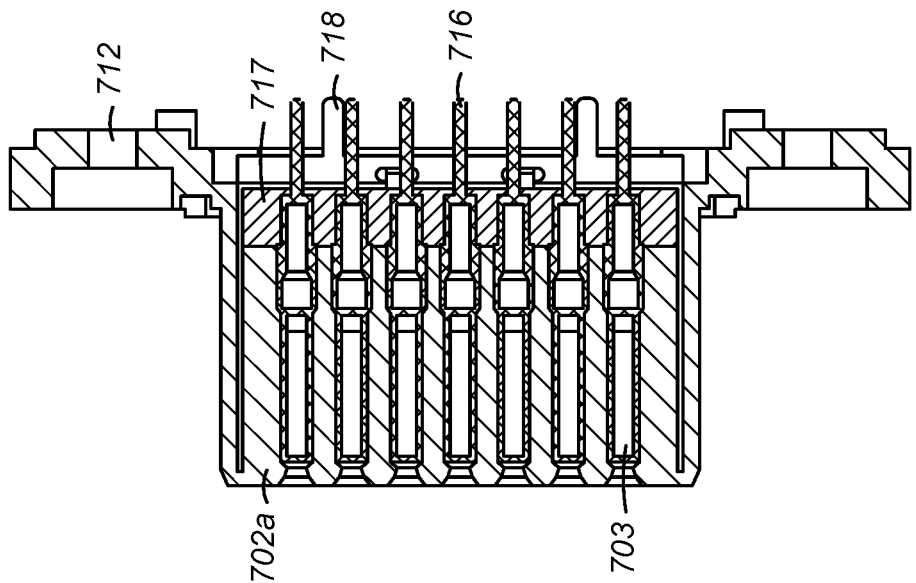
FIG. 96B is a cross-sectional view of the female connector shown in FIG. 96B taken along the line 96B-96B and looking in the direction of the arrow.
Figure 96A:
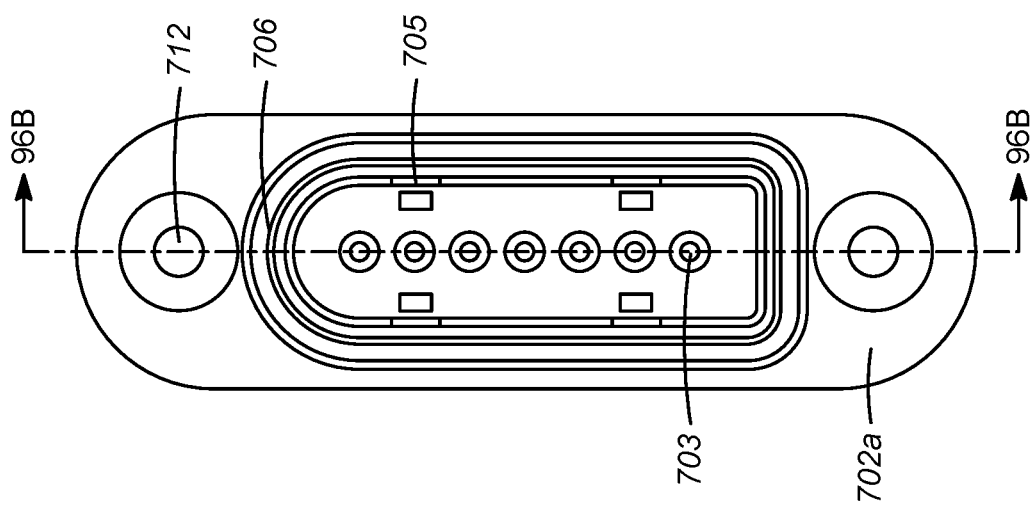
FIG. 96A is a rear elevational view of the female connector shown in FIG. 92C.
Figure 96D:
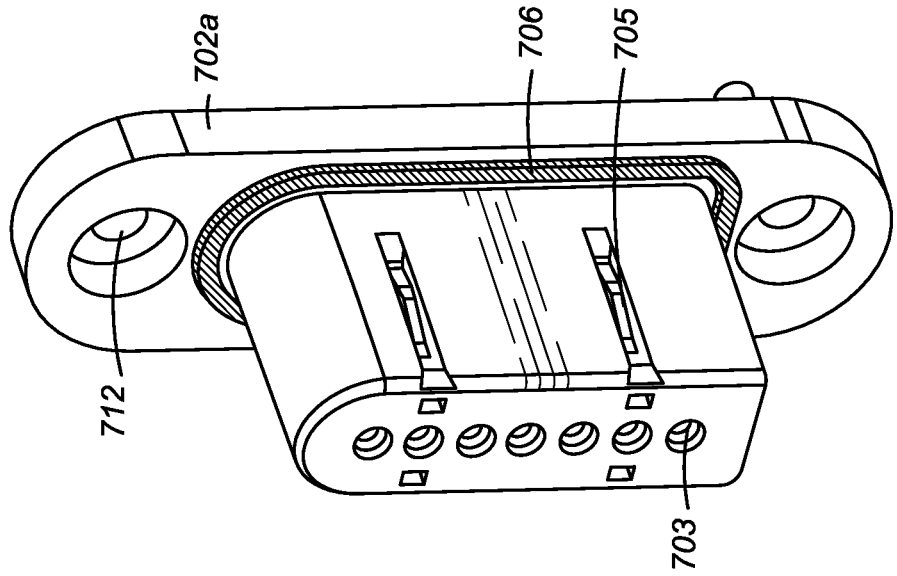
FIG. 96D is a front perspective view of the female connector shown in FIG. 92C.
Figure 96C:
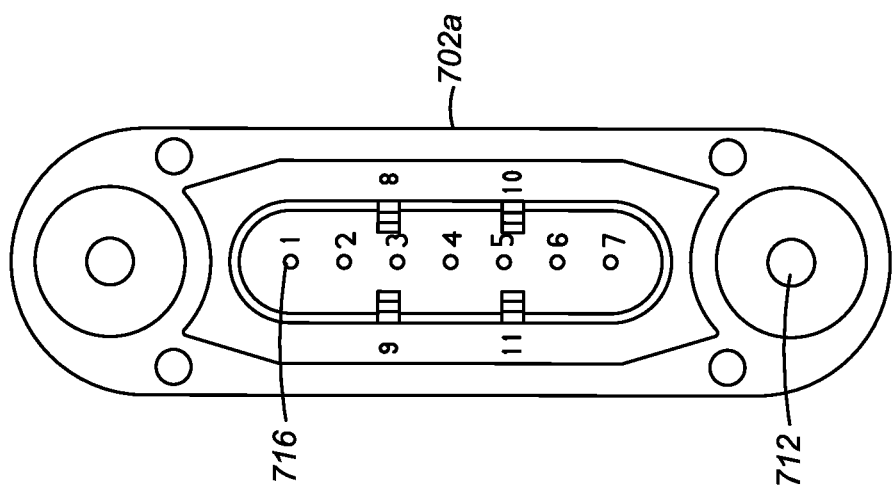
FIG. 96C is a front elevational view of the female connector shown in FIG. 92C.
Figure 97:
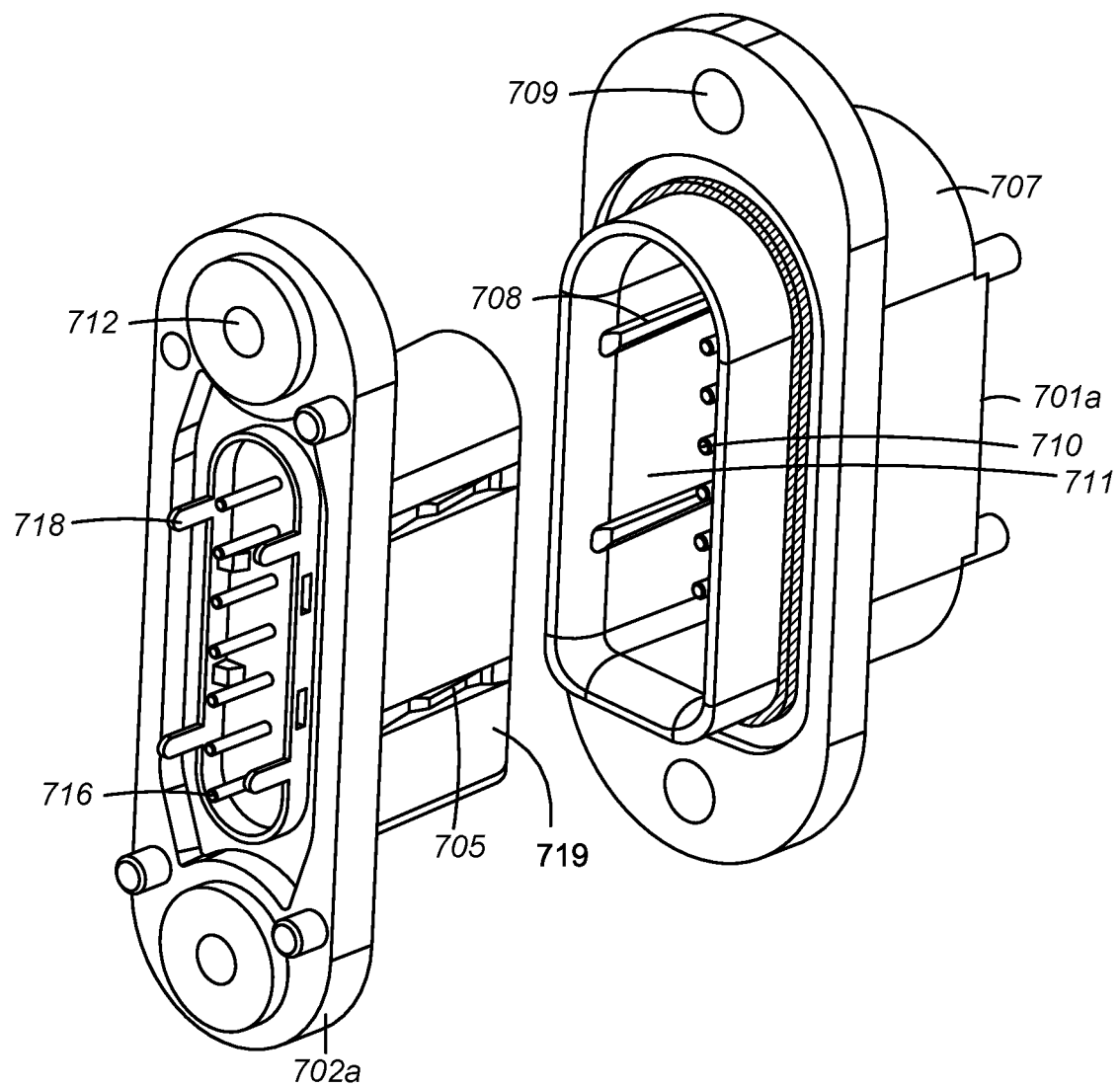
FIG. 97 is an exploded perspective view of the male connector shown in FIG. 93A and the female connector shown in 92C.
Figure 98:
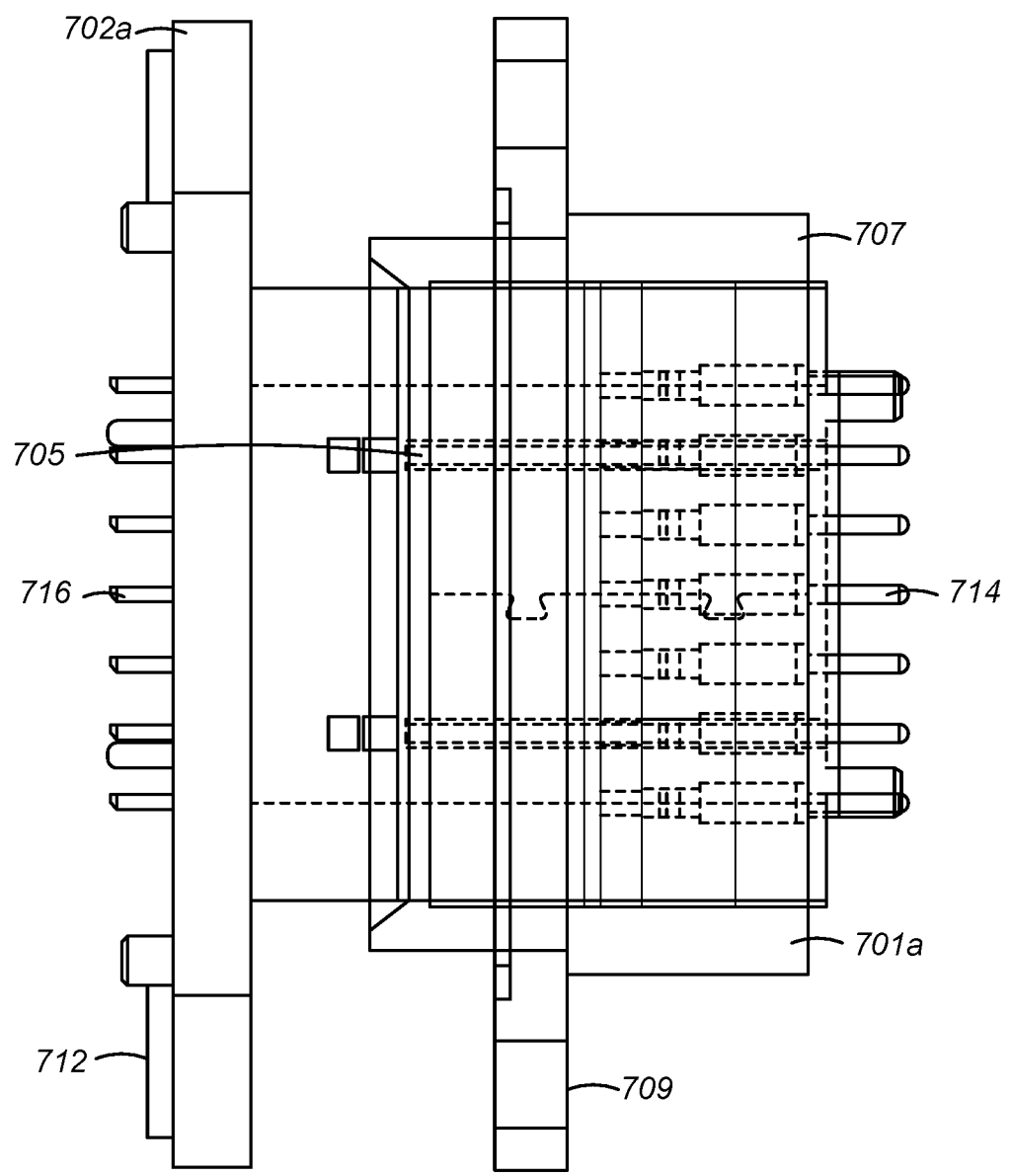
FIG. 98 is a side view of the male and female connectors shown in FIG. 97.

One of the male connector 701a-701c and the female connector 702a-702e may include a shroud 715, shown in FIG. 92B, for ensuring that the connector cannot be inserted into an incorrect device or interface, thereby forming a unique key arrangement to be matched and engaged with a corresponding male connector and to be rejected by a non-corresponding male connector. The shroud 715 may be comprised of an overmolded protrusion which is adjacent to the housing of the connector. For example, the female connector 702a-702e may include the shroud 715 at the planar side of the housing 719. In addition, the male connector 701a-701c or the female connector 702a-702e may include additional features such as a contact holder 720, a socket holder 717, shield tabs 713, etc.

A back face of the male connector 701a-701c may include a harness 714 for further electrical or mechanical connection. Similarly, a back face of the female connector 702a-702e may also include a harness 716 for further electrical or mechanical connection.

Figure 99A:
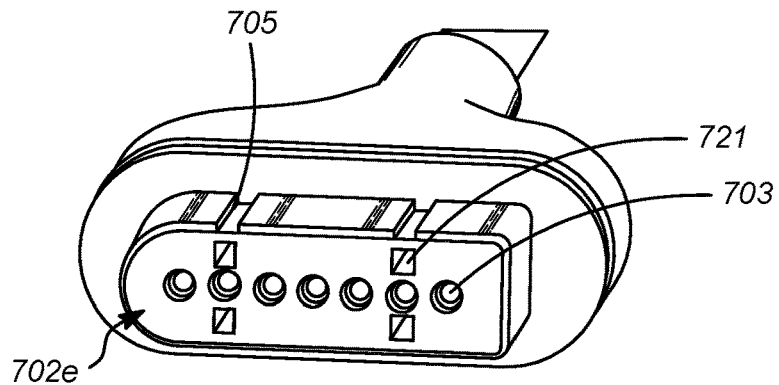
FIG. 99A is a perspective view of a fifth implementation of a female connector.
Figure 99B:
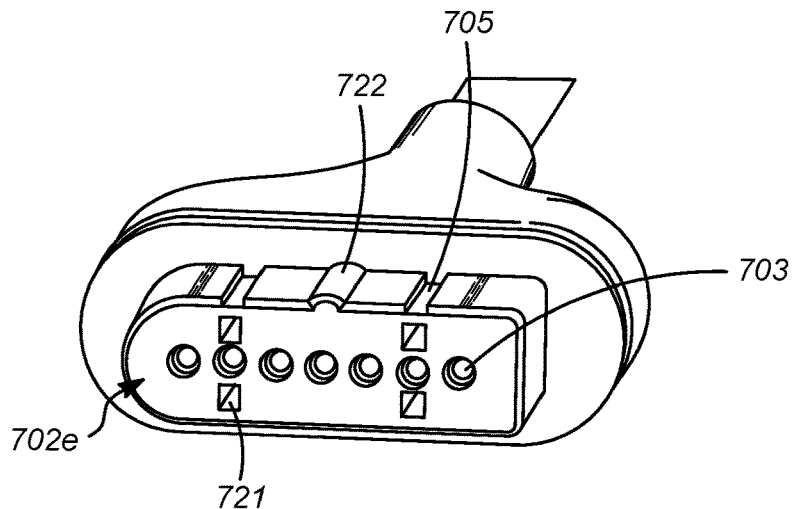
FIG. 99B is a perspective view of the female connector shown in FIG. 99A with an added shield protrusion in a first location.
Figure 99C:
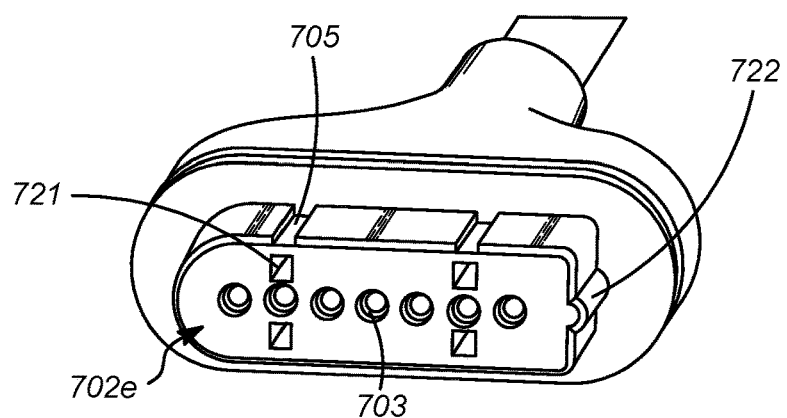
FIG. 99C is a perspective view of the female connector shown in FIG. 99A with an added shield protrusion in a second location.
Figure 99H:
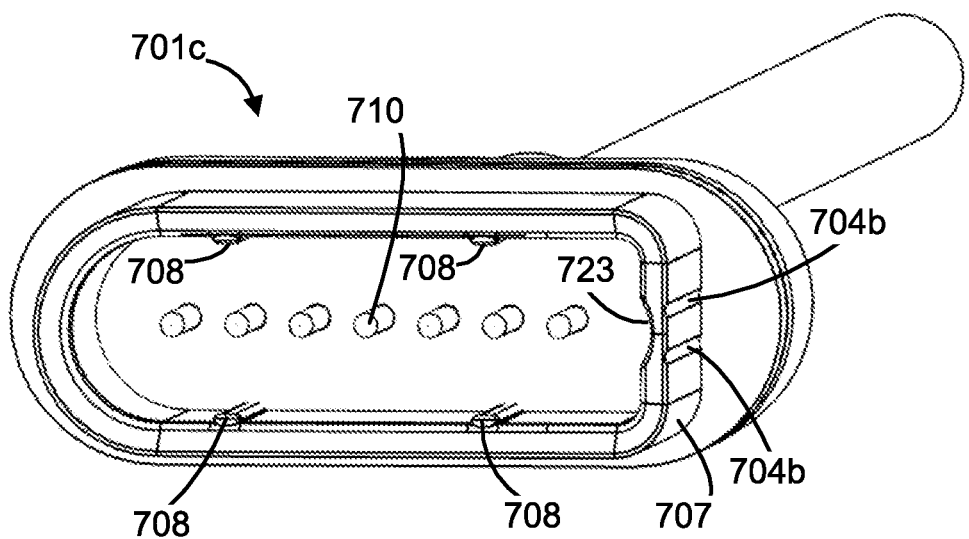
FIG. 99D is a perspective view of the female connector shown in FIG. 99C with a modified shield protrusion.
FIG. 99E is a perspective view of a third implementation of a male connector.
FIG. 99F is a perspective view of the male connector shown in FIG. 99E with an added shield groove in a first location.
FIG. 99G is a perspective view of the male connector shown in FIG. 99E with an added shield groove in a second location.
Figure 99D:
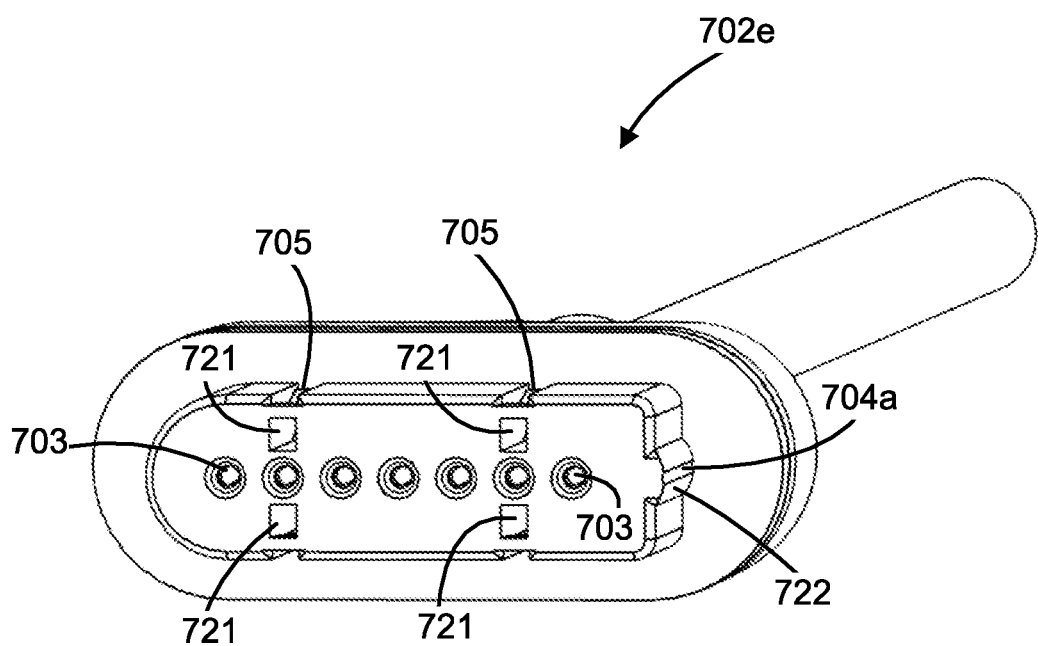
Figure 99E:
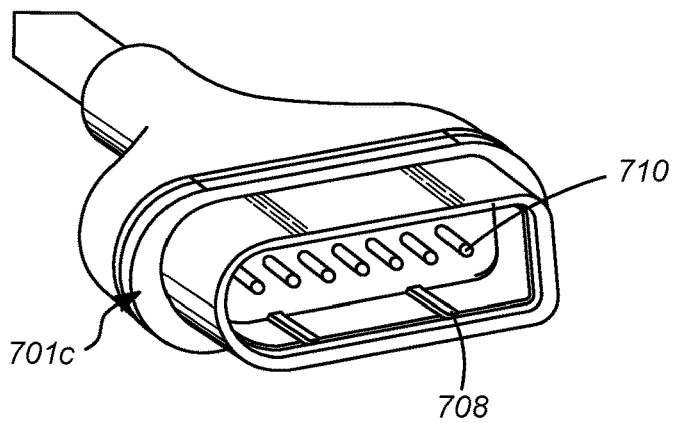

In each of the embodiments shown in FIGS. 99B-99D, the female connector 702e includes at least one shield protrusion 722 formed thereon. The shield protrusion 722 can be formed on one of the longitudinal sides, the rounded side, and/or the planar side of the female connector 702e. In addition, the female connector 702e shown in FIG. 99D includes a shield protrusion 722 with a rib 704a that is arranged as a strip along the shield protrusion 722. The rib 704a serves as a key for matching the female connector 702e with a corresponding male connector 701c, as discussed further below. In one embodiment, the rib 704a may be made of a material such as rubber or other material that increases friction between the female connector and a corresponding male connector.

Figure 99F:
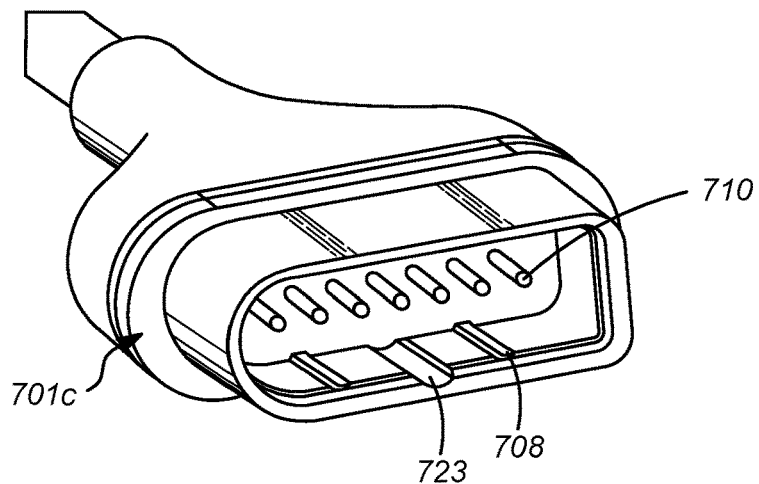
Figure 99G:
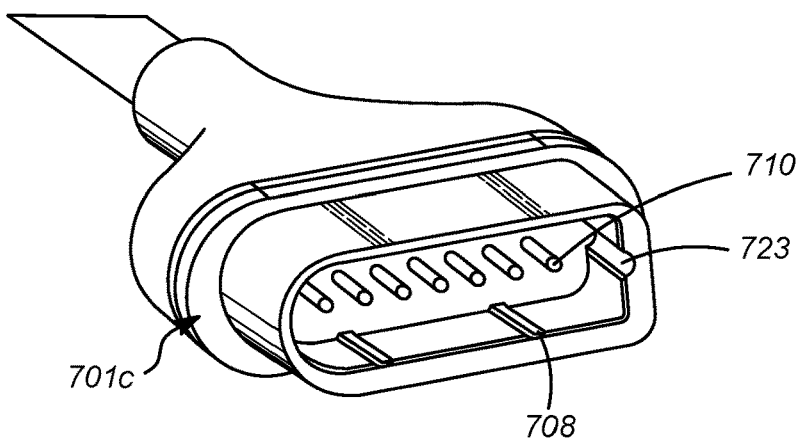

In the embodiments shown in FIGS. 99F-99H, the male connector 701c includes at least one shield groove 723 formed therein. The shield groove 723 can be formed in one of the longitudinal sides, the rounded side, and/or the planar side of the male connector 701c. The shield groove 723 corresponds to and is configured to receive the shield protrusion 722 when the male connector 701c and the female connector 702e are physically connected. The combination of the shield protrusion 722 and the shield groove 723 ensures that the connectors cannot be inserted into incorrect devices or interfaces, thereby forming a unique key arrangement to be matched and engaged with a corresponding male connector and to be rejected by a non-corresponding male connector. It will be further appreciated that structures described herein used to form unique key arrangements may be used in combination to form further unique key arrangements. For example, ribs 704, shield protrusions 708, the shield grooves that contain the shield springs 705, shroud 715, shield protrusion 722, and shield groove 723 may be combined in any and all various ways to form a unique key arrangement.

In addition, the shield groove 723 of the male connector 701c shown in FIG. 99H may further include one or more ribs 704b located on the outside of the housing 707 proximate to the shield groove 723. These ribs 704b serve as keys indicating where the shield groove 723 is on the interior of the housing 707, notifying the user that he or she can only connect the male connector 701c with a corresponding female connector 702e having a shield protrusion 722 in a location that would interface with the shield groove 723 of the male connector 701c. Alternatively, the ribs 704b can be located on an internal surface of the shield groove 723 and arranged to engage with the corresponding shield protrusion 722 such that the rib 704a of the female connector 702e shown in FIG. 99D may be inserted between ribs 704b of the male connector 701c in FIG. 99H, causing the rib 704a to contact and interlock with the ribs 704b.

Any of the female portions or connectors 702a-702e may optionally include apertures 721 adjacent to the sockets 703 for facilitating formation of the sockets 703 and/or facilitating fluid drainage from an interior of the female connector 702a-702e.

Figure 100:
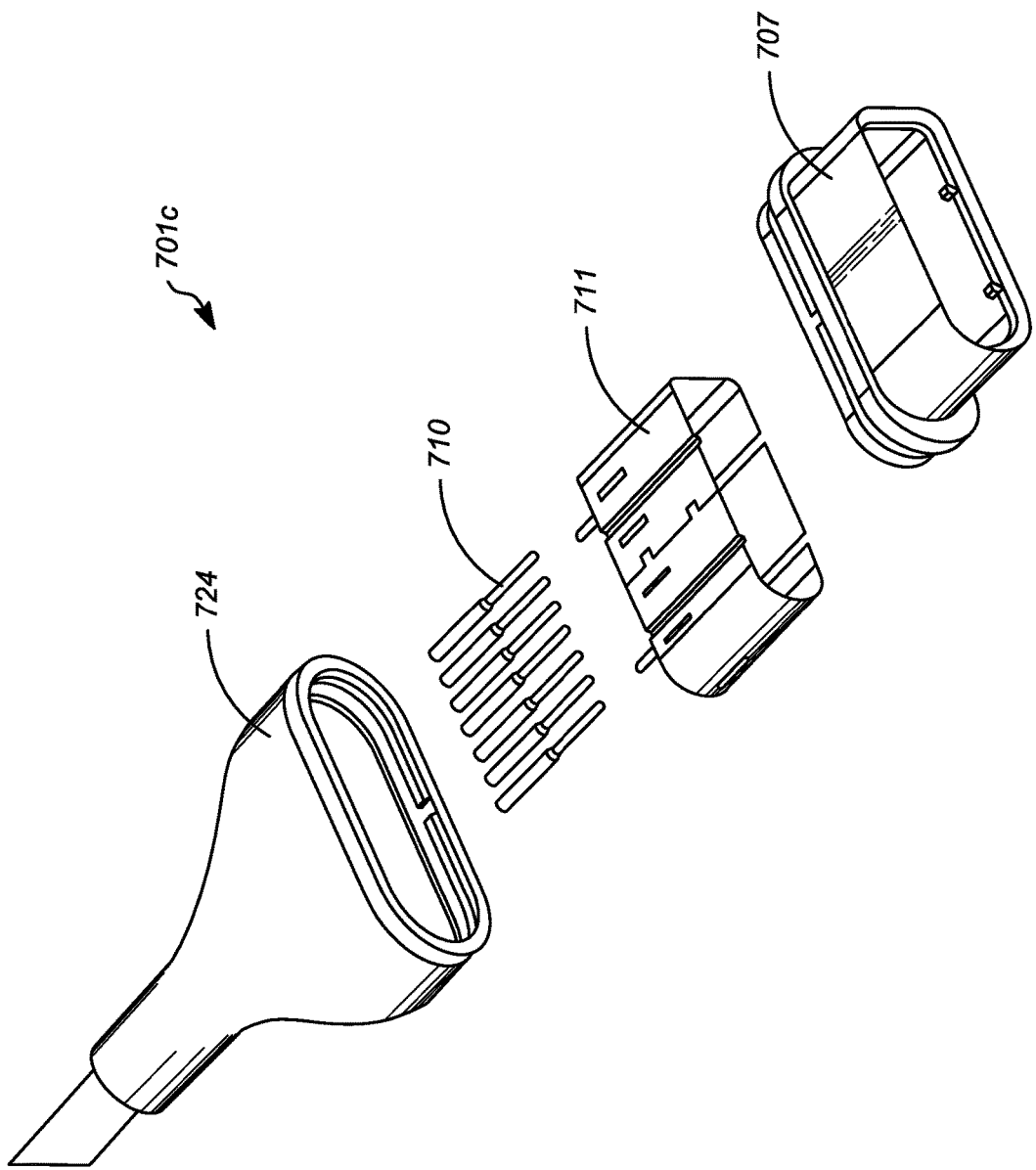
Figure 101:
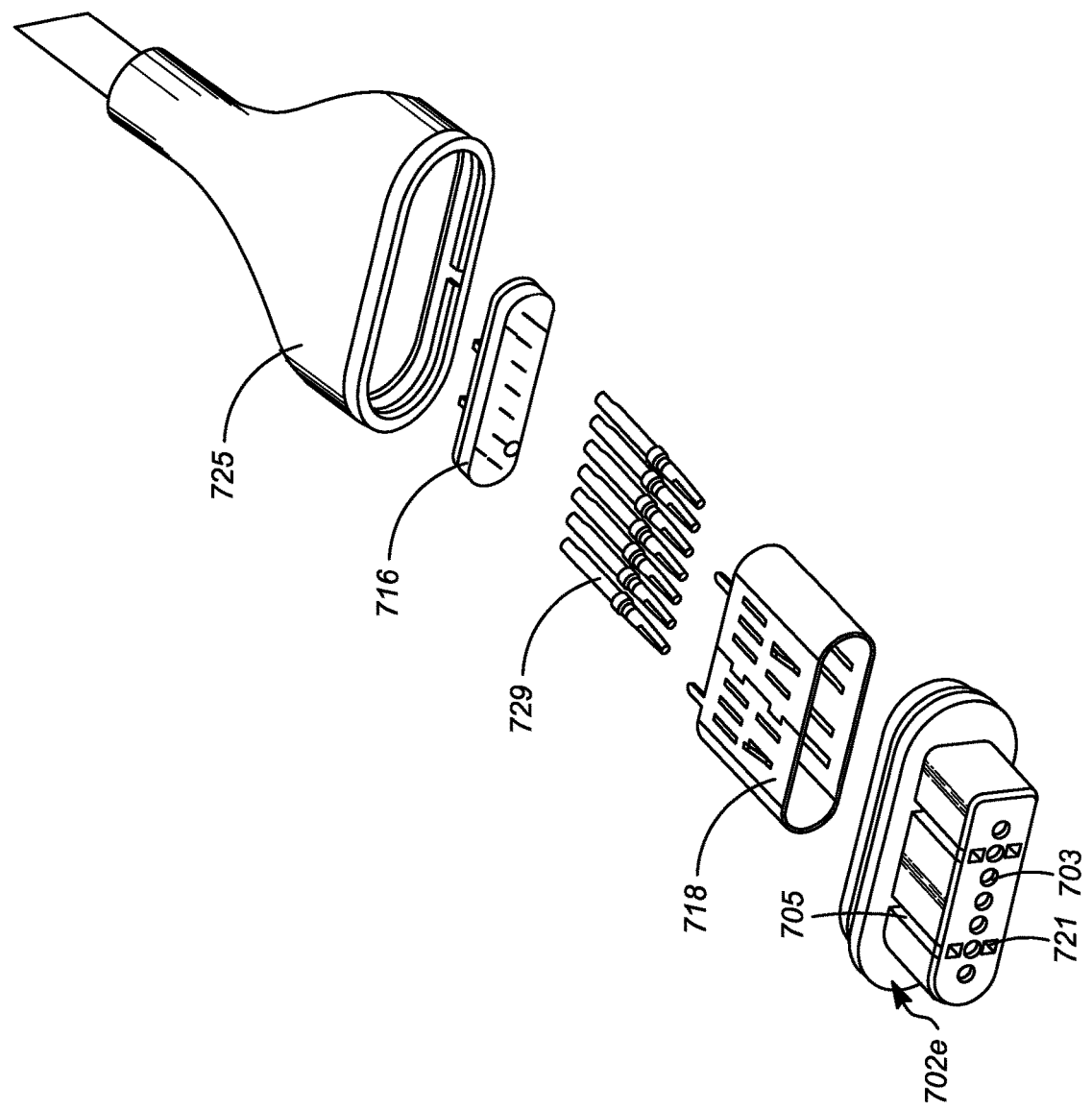

As shown in FIG. 100, the male connector 701c may include a boot 724 to be attached to an end of a cable. Similarly, as shown in FIG. 101, the female connector 702e may include a boot 725 to be attached to an end of a cable. Exemplary construction materials for various elements of the connector can include 10% GF PBT contact pins, and brass with 10 micro inch gold plating over 150 micro inch nickel plate per ASTM B488 Type 1-C. An exemplary color for various elements of the connector can be RAL 7032. The connector or any portion of the connector may be rated to have a 10 mOHM current capacity, an initial mating force may be less than 5N and the connector or any portion of the connector should be able to withstand a minimum of 5000 mate and unmate cycles such that a change in the contact resistance is no greater than 0.50 mOHM. The connector may also be sealed watertight IP54 minimum between contacts and a PCB therein. Therefore, the male and female portions or connectors 701a-701c, 702a-702e have conspicuous keying and external shapes that are asymmetrical and can be felt in low light conditions, are easy to mate with corresponding devices or interfaces, and provide electrical and mechanical connections that can be simply physically or tactually confirmed.

Figure 102:
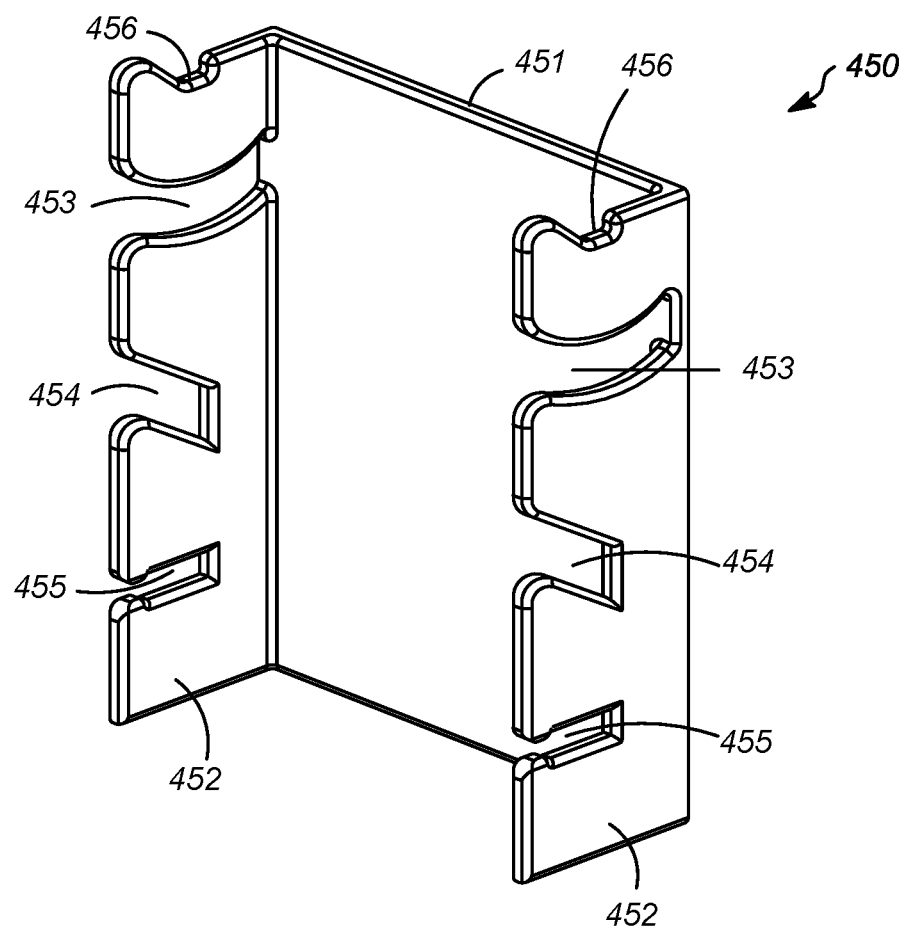

FIG. 102 is a front perspective view of a cable holder 450. As shown in FIG. 102, the cable holder 450 may comprise a back wall 451 and at least one side wall 452. The side wall 452 may extend from one end of the back wall 451. The side wall 452 may include apertures 453-455 defined therein. Each of the apertures 453-455 may be configured to receive a cable 650 therethrough. A first of the apertures 453 may be arcuate. A second of the apertures 454 may be parallelogram-shaped and oblique with respect to the back wall 451. A third of the apertures 455 may be rectangular and perpendicular to the back wall 451. The side wall 452 may further include a notch 456 at one end thereof. In addition, the third of the apertures 455 may have a first end at a distal end of the side wall 452 and a second end adjacent to a proximal end of the side wall 452 and a width of the first end of the third of the apertures 455 may be less than a width of the second end of the third of the apertures 455. In addition, the side wall 452 may be one of two side walls at respective ends of the back wall 451.

Figure 103:
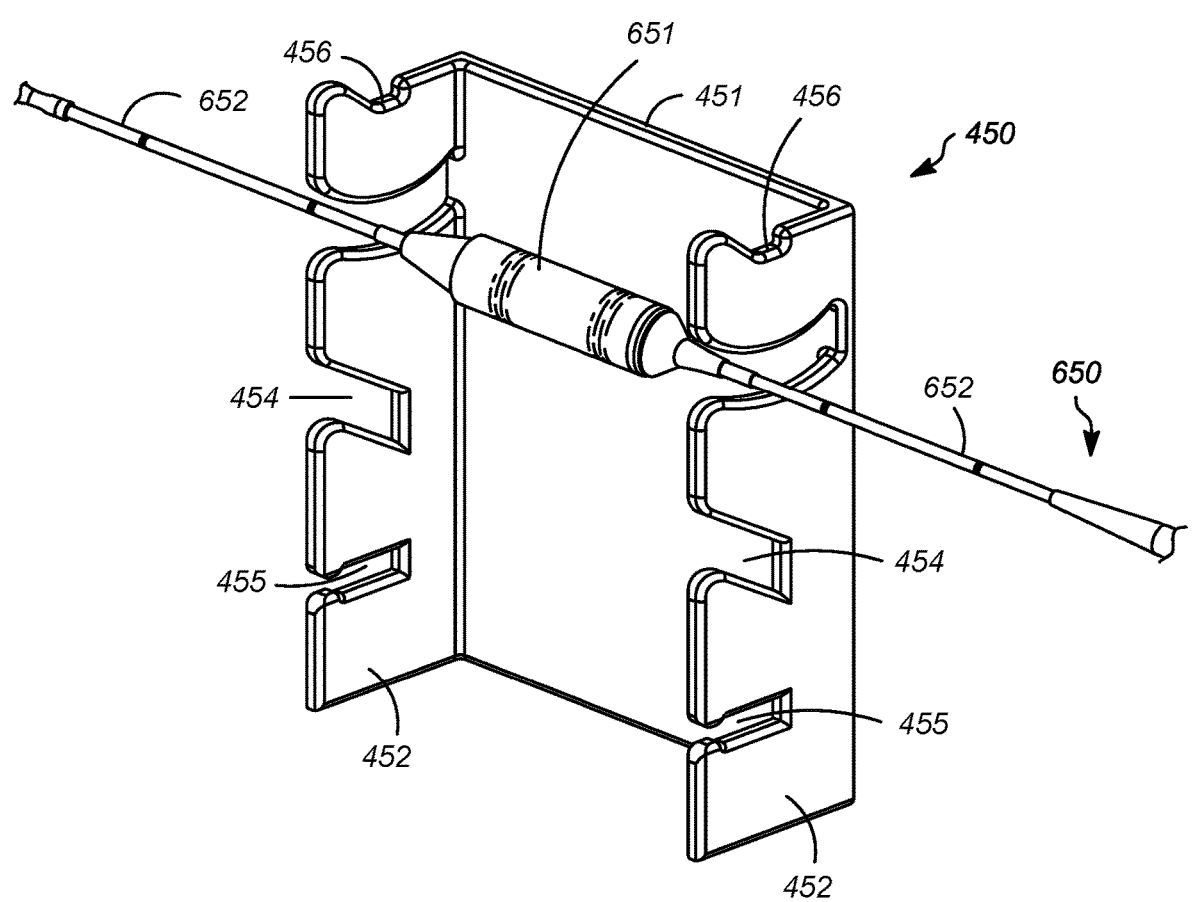

FIG. 103 is a front perspective view of the cable holder 450 detachably securing a cable 650. As shown in FIG. 103, the cable 650 may include a housing portion 651. The housing portion 651 may, for example, be configured to house a translator configured to translate protocols across cable portions 652 on respective sides of the housing portion 651. As shown in FIG. 103, the cable holder 450 may be configured to detachably secure the cable 650 such that the housing portion 651 of the cable 650 rests on a side wall 452 of the cable holder 450.

Figure 104:
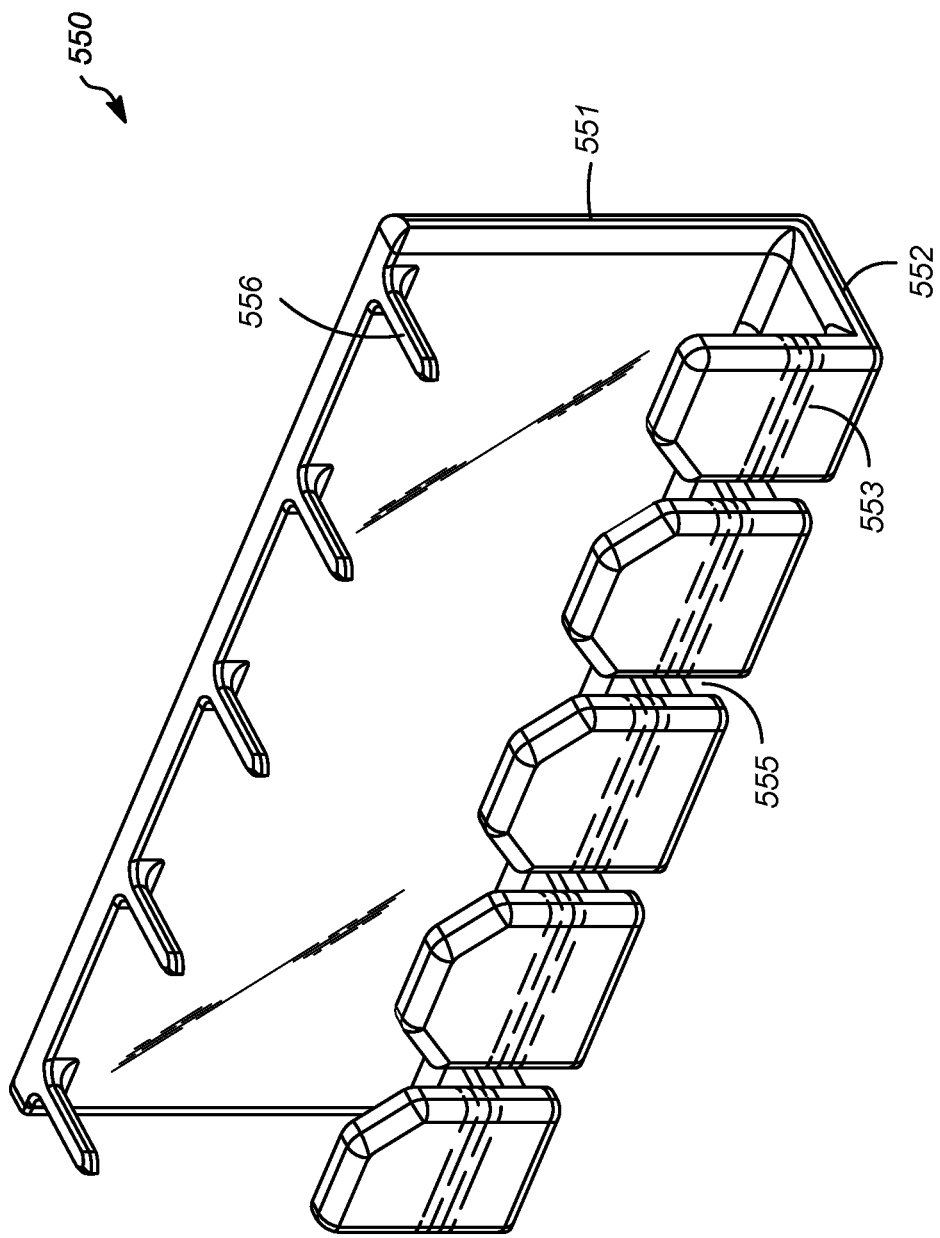
Figure 105:
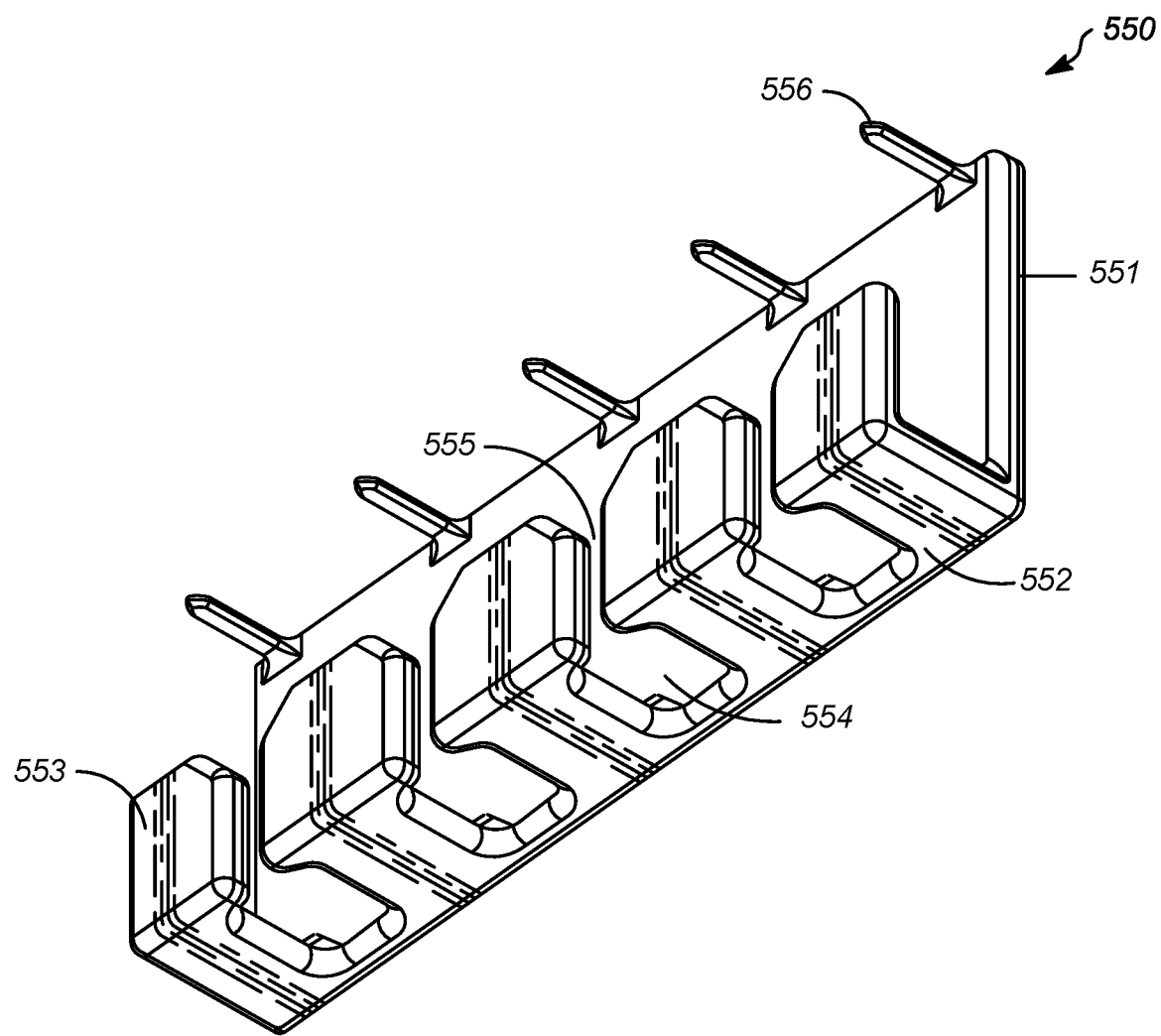

FIG. 104 is a front perspective view of a cable holder 550. FIG. 105 is a bottom perspective view of the cable holder 550. As shown in FIGS. 104 & 105, the cable holder 550 may comprise a back wall 551, a side wall 552, a front wall 553, and projections 556. The side wall 552 may extend from a first end of the back wall 551. The side wall 552 may include apertures 554 defined therein. The front wall 553 may extend from an end of the side wall 552 opposite to the back wall 551. The front wall 553 may include slots 555 defined therein. The projections 556 may extend from a second end of the back wall 551. Each of the apertures 554 and the slots 555 may be configured to receive a cable 650 therethrough such that the cable 650 is positioned between two of the projections 556. As shown in FIG. 105, the apertures 554 may be polygonal. Each of the slots 555 may have a first end at a distal end of the front wall 553 and a second end at a proximal end of the front wall 553. For each of the slots 555, a width of the first end of the slot 555 may be greater than a width of the second end of the slot 555.

Figure 106:
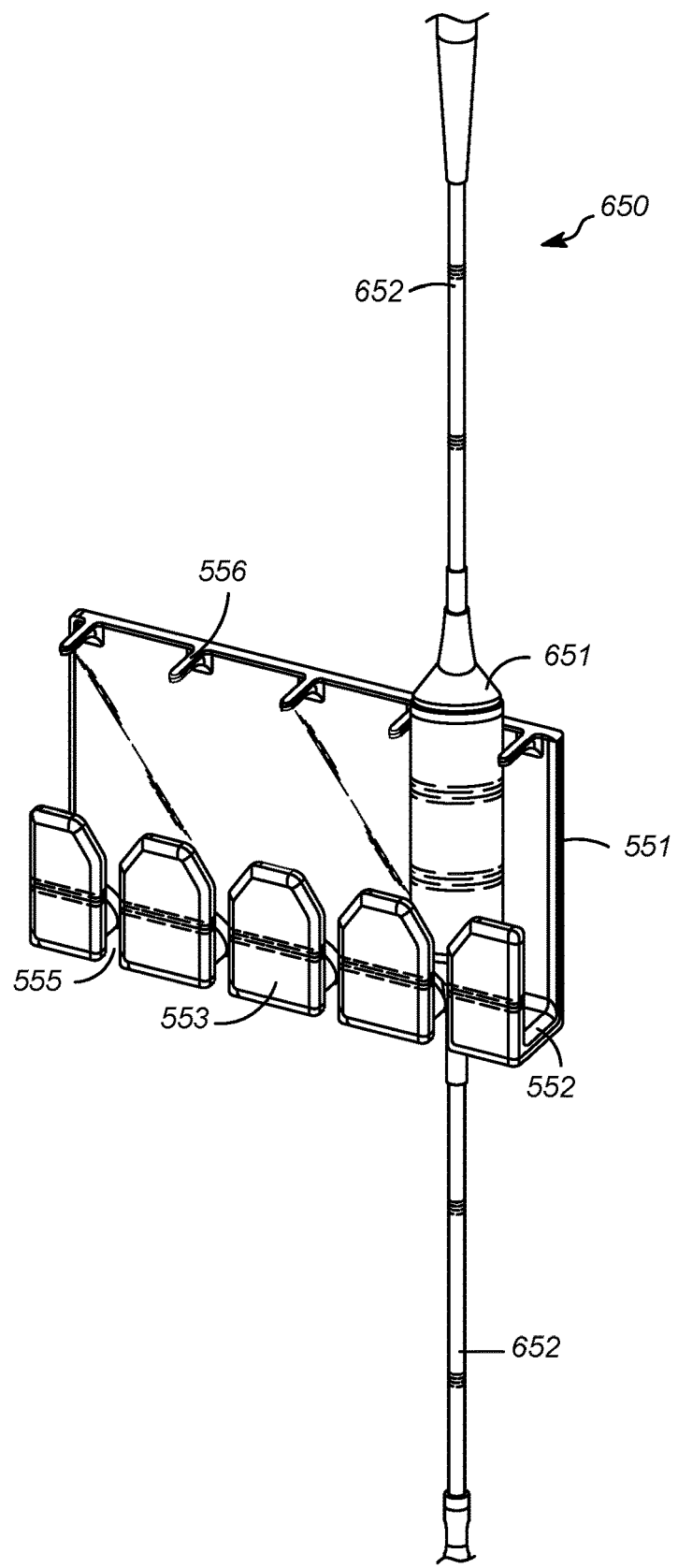

FIG. 106 is a front perspective view of the cable holder 550 detachably securing a cable 650. As shown in FIG. 106, the cable 650 may include a housing portion 651. The housing portion 651 may, for example, be configured to house a translator configured to translate protocols across cable portions 652 on respective sides of the housing portion 651. As shown in FIG. 106, the cable holder 550 may be configured to detachably secure the cable 650 such that the housing portion 651 of the cable 650 rests on a side wall 552 of the cable holder 550. In addition, as shown in FIG. 106, the cable holder 550 may be configured to detachably secure the cable 650 such that the housing portion 651 of the cable 650 is positioned between two of the projections 556 of the cable holder 550.

Although various embodiments have been described above, these are to be regarded as merely examples. Accordingly, those of ordinary skill in the art will recognize that various changes and modifications of the examples described herein can be made without departing from the spirit and scope of the present disclosure. Further, it is noted that the present disclosure may be implemented as any combination of a system, an integrated circuit, and a computer program on a non-transitory computer readable recording medium. The processor and any other parts of the computing system may be implemented as Integrated Circuits (IC), Application-Specific Integrated Circuits (ASIC), or Large Scale Integrated circuits (LSI), system LSI, super LSI, or ultra LSI components which perform a part or all of the functions of the computing system.

Each of the parts of the present disclosure can be implemented using many single-function components, or can be one component integrated using the technologies described above. The circuits may also be implemented as a specifically programmed general purpose processor, CPU, a specialized microprocessor such as Digital Signal Processor that can be directed by program instructions on a memory, a Field Programmable Gate Array (FPGA) that can be programmed after manufacturing, or a reconfigurable processor. Some or all of the functions may be implemented by such a processor while some or all of the functions may be implemented by circuitry in any of the forms discussed above.

The present disclosure may be implemented as a non-transitory computer-readable recording medium having recorded thereon a program embodying methods/algorithms for instructing the processor to perform the methods/algorithms. The non-transitory computer-readable recording medium can be, for example, a CD-ROM, DVD, Blu-ray disc, or an electronic memory device.

Each of the elements of the present disclosure may be configured by implementing dedicated hardware or a software program on a memory controlling a processor to perform the functions of any of the components or combinations thereof. Any of the components may be implemented as a CPU or other processor reading and executing a software program from a recording medium such as a hard disk or a semiconductor memory.

It is also contemplated that the implementation of the components of the present disclosure can be done with any newly arising technology that may replace any of the above implementation technologies.

The system of the present disclosure is a modular system providing a universal and scalable platform including a monitor mount capable of mixed use with monitors having different sizes. Traditionally, each type of patient monitor typically required a dedicated monitor mount, a dedicated controller, and a dedicated user interface. Accordingly, traditional monitors of different sizes are not interoperable and the performance advantages of each type of monitor cannot be combined and leveraged. However, since the system of the present disclosure enables the mounting of two monitors having different sizes, shapes, and functionality on a single monitor mount, the two monitors are interoperable with the same controller and the same user interface, and can be universally docked to the monitor mount.

The dock of the present disclosure is mobile or transportable dock which improves the ability to record and store data and transfer data between monitors and/or modules. The dock of the present disclosure therefore addresses deficiencies of transferring data between monitors and/or modules.

The monitor of the present disclosure features a back portion having a shape for improving grip, hygiene, and the accommodation of differently sized batteries. The monitor of the present disclosure therefore addresses deficiencies of difficulty in gripping, difficulty in cleaning, and limitations on the size and shape of stored batteries.

The coupling of the present disclosure is a quick release coupling which only requires a user to use one hand to fasten and release a device from a mount, only requires the device to be fastened to one side of the mount for stability, allows the device to be fastened to the mount in multiple orientations, and does not require visual confirmation of the orientation of the device and the mount before fastening. The coupling of the present disclosure therefore addresses deficiencies of requiring a user to use two hands to fasten and release the device from the mount, requiring the device to be fastened to two opposite sides of the mount for stability, failing to enable the device to be fastened to the mount in multiple orientations, and requiring the use of specialized tools.

The belt mount of the present disclosure can be both quickly and rigidly secured to mobile or transportable support structures in addition to stationary support structures. The belt mount of the present disclosure therefore addresses deficiencies of difficulty in both quickly and rigidly securing devices to mobile or transportable support structures such as bed or stretcher or gurney rails, IV poles, ambulance bars, etc. in addition to stationary support structures, and failing to enable a device be attached directly to a tubular or rectangular support structure.

The coupling of the present disclosure is a quick release coupling which does not require specialized tools or visual confirmation of the orientation of the device and the mount before fastening. The coupling of the present disclosure therefore addresses deficiencies of requiring a user to visually confirm the orientation of the device and the monitor mount before fastening.

The rack of the present disclosure can store modules in an additional position in which the modules are physically connected to the rack but electrically disconnected from the rack. The coupling of the present disclosure therefore addresses deficiencies of only being able to secure modules in one position inside a rack, and electrically disconnected modules falling or dropping out of the rack due to gravity.

The connector of the present disclosure has conspicuous keying and external shapes that are asymmetrical and can be felt in low light conditions, are easy to mate with corresponding interfaces, and provide electrical and mechanical connections that can be simply physically or tactually confirmed. The connector of the present disclosure therefore addresses deficiencies of inconspicuous keying and difficulty in mating with corresponding interfaces, and requiring painstaking visual confirmation of the orientations of the interfaces in order to ensure a proper connection.

For the avoidance of doubt, the present disclosure includes the subject matter recited in the following numbered "Statements":

Statement 1. A dock comprising:
a case; and
a coupling,
wherein:
the coupling extends from a side of the case;
the coupling is configured to detachably secure a monitor including an electronic visual display;
the coupling is adapted to have the monitor transversely inserted into and removed therefrom from each of a first lateral direction of the case and a second lateral direction of the case; and
the first lateral direction of the case is opposite to the second lateral direction of the case.

Statement 2. A dock comprising:
a case; and
a coupling,
wherein:
the coupling extends from a side of the case;
the coupling is configured to detachably secure a monitor including an electronic visual display; and
the coupling is configured to detachably secure opposite sides of a center of a perimeter of the monitor therebetween such that end portions of the perimeter of the monitor extend beyond opposite ends of the coupling in a direction along a lateral direction of the case when the monitor is secured to the dock.

Statement 3. A dock comprising:
a case; and
a coupling,
wherein:
the coupling extends from a side of the case;
the coupling is configured to detachably secure a monitor including an electronic visual display; and
the dock does not include electrical connections such that the dock is configured to provide only physical support for the monitor.

Statement 4. A dock comprising:
a first case;
a second case including a first electrical connector;
a handle;
a processor;

a communications interface configured to transmit and receive data over a computing network;

an electronic visual display configured to visualize at least a portion of received data and provide a user interface, the electronic visual display including a second electrical connector, wherein:

the electronic visual display is configured to be detachably secured in the second case such that the first electrical connector is connected to the second electrical connector; and the handle extends from a side of the first case or a side of the second case.

Statement 5. A system comprising:

a dock; and a coupling, wherein:

the dock includes a frame, a handle, a first clamp, and a second clamp;

the frame includes a base and a wall portion, the wall portion extending from a top face of the base;

the coupling is configured to be located at a first side of the wall portion;

the coupling is configured to detachably secure a monitor including an electronic visual display;

the dock is configured to detachably secure a module to a second side of the wall portion;

the first clamp is configured to lock the module to the frame; and the second clamp is configured to lock the monitor to the frame.

Statement 6. The dock or system of any of the preceding Statements, further comprising:

a housing portion; and a handle, wherein:

the side of the case is a first side of the case;

the housing portion extends from a second side of the case;

the handle extends from the case;

the coupling is a first coupling;

the housing portion includes a second coupling;

the second coupling is configured to detachably secure a module; and the housing portion is configured to surround at least a portion of the module when the module is secured to the dock.

Statement 7. The dock or system of any of the preceding Statements, further comprising:

a handle;

wherein:

the handle extends from the case;

the coupling is a first coupling;

the dock comprises a second coupling;

the second coupling extends from a second side of the case;

the second coupling is configured to detachably secure a module for acquiring and processing data generated by at least one physiological sensor monitoring a physiological parameter of a patient.

Statement 8. A system comprising the dock of any of the preceding Statements and the monitor.

Statement 9. A system comprising the dock of any of the preceding Statements and the mount.

Statement 10. A system comprising the dock of any of the preceding Statements and the module.

Statement 11. A system comprising the dock of any of the preceding Statements and the support structure.

Statement 12. The dock or system of any of the preceding Statements, wherein the wall portion and the base are formed as a single unit.

Statement 13. The dock or system of any of the preceding Statements, wherein the first clamp is further configured to cover at least a portion of the module when the module is secured to the dock.

Statement 14. The dock or system of any of the preceding Statements, further comprising at least one of a cradle portion, an adapter, an AC/DC converter, an auxiliary power source, a battery, an extra power accessory, a module accessory, a first module, and a second module.

Statement 15. The dock or system of any of the preceding Statements, wherein the dock further comprises an attachment mechanism configured to be detachably secured to a monitor or a rack.

Statement 16. The dock or system of any of the preceding Statements, wherein the dock further comprises a processor.

Statement 17. The dock or system of any of the preceding Statements, wherein the dock further comprises a power source configured to provide power to the monitor.

Statement 18. The dock or system of any of the preceding Statements, wherein the dock further comprises a communications interface configured to transmit and receive data over a computing network.

Statement 19. The dock or system of any of the preceding Statements, wherein the dock further comprises an attachment mechanism configured to be detachably secured to a support structure.

Statement 20. The dock or system of any of the preceding Statements, wherein the support structure is a bed or stretcher or gurney rail, an arm in an acute care system, a cart in an acute care system, an IV pole, an arm at a workstation, a mount, or a bar in an ambulance.

Statement 21. The dock or system of any of the preceding Statements, wherein the first side of the case is adjacent to the second side of the case.

Statement 22. The dock or system of any of the preceding Statements, wherein the first side of the case is opposite to the second side of the case.

Statement 23. The dock or system of any of the preceding Statements, wherein the handle is positioned in between the housing portion and the first coupling.

Statement 24. The dock or system of any of the preceding Statements, wherein the housing portion includes a third coupling configured to detachably secure another housing portion.

Statement 25. The dock or system of any of the preceding Statements, wherein the case and the handle are formed as a single unit.

Statement 26. The dock or system of any of the preceding Statements, wherein:

the handle is a first handle; and the dock further comprises a second handle.

Statement 27. The dock or system of any of the preceding Statements, wherein:

the first handle extends from a first lateral side of the case;

the second handle extends from a second lateral side of the case; and the first lateral side of the case is opposite to the second lateral side of the case.

Statement 28. The dock or system of any of the preceding Statements, wherein the housing portion includes a third coupling configured to detachably secure another housing portion.

Statement 29. The dock or system of any of the preceding Statements, wherein the electronic visual display of the dock is configured to operate with less power than the electronic visual display of the monitor.

Statement 30. The dock or system of any of the preceding Statements, wherein the electronic visual display of the dock is an electronic ink electronic visual display.

Statement 31. The dock or system of any of the preceding Statements, wherein:
the module is one of a plurality of modules;
the second coupling is one of a plurality of second couplings;
each of the modules is configured to be detachably secured to the dock by one of the second couplings; and
the housing portion is configured to surround at least a portion of each of the modules when each of the modules is secured to the dock.

Statement 32. The dock or system of any of the preceding Statements, wherein:
the third coupling includes one of a notch and a groove; and
the second coupling includes another of the notch and the groove which is configured to be detachably secured to the one of the notch and the groove.

Statement 33. The dock or system of any of the preceding Statements, wherein:
the second of the plurality of modules includes a fourth coupling; and
a third of the plurality of modules is configured to be detachably secured to the second of the plurality of modules by the fourth coupling.

Statement 34. The dock or system of any of the preceding Statements, wherein the handle is configured to be detachably secured to the wall portion.

Statement 35. The dock or system of any of the preceding Statements, wherein the handle is rotatable with respect to the frame.

Statement 36. The dock or system of any of the preceding Statements, wherein the base is configured to detachably secure another module to a bottom face thereof, the bottom face being opposite to the top face.

Statement 37. The dock or system of any of the preceding Statements, wherein the module is configured to acquire and process data generated by at least one physiological sensor monitoring a physiological parameter of a patient.

Statement 38. The dock or system of any of the preceding Statements, wherein the dock is mobile or transportable.

Statement 39. The dock or system of any of the preceding Statements, wherein the dock does not include electrical connections and therefore is configured to provide only physical support for the monitor.

Statement 40. A monitor comprising:
an electronic visual display;
a back portion including a first concave surface and a second concave surface; and
a modular handle,
wherein:
the first concave surface is defined in a first longitudinal side of the back portion at a central part of the back portion;
the second concave surface is defined in a second longitudinal side of the back portion at the central part of the back portion;
the first longitudinal side of the back portion is opposite to the second longitudinal side of the back portion;
a distance between the first concave surface and the second concave surface at the central part of the back portion is less than a distance between the first longitudinal side of the back portion and the second longitudinal side of the back portion at any part of the back portion other than the central part of the back portion;
the modular handle is configured to be detachably secured to the electronic visual display in a first orientation of the electronic visual display and a second orientation of the electronic visual display; and the first orientation is different from the second orientation.

Statement 41. A monitor comprising:
an electronic visual display; and
a back portion including a first concave surface and a second concave surface,
wherein:
the first concave surface is defined in a first longitudinal side of the back portion at a central part of the back portion;
the second concave surface is defined in a second longitudinal side of the back portion at the central part of the back portion;
the first longitudinal side of the back portion is opposite to the second longitudinal side of the back portion; and
a distance between the first concave surface and the second concave surface at the central part of the back portion is less than a distance between the first longitudinal side of the back portion and the second longitudinal side of the back portion at any part of the back portion other than the central part of the back portion.

Statement 42. A monitor comprising:
an electronic visual display; and
a modular handle,
wherein:
the modular handle is configured to be detachably secured to the electronic visual display in a first orientation of the electronic visual display and a second orientation of the electronic visual display; and
the first orientation is different from the second orientation.

Statement 43. The monitor of any of the preceding Statements, wherein the first concave surface includes a first recess and the second concave surface includes a second recess, the first recess and the second recess defining a grip portion for holding the monitor.

Statement 44. The monitor of any of the preceding Statements, wherein each of the first recess and the second recess extends in a direction perpendicular to the first concave surface or the second concave surface.

Statement 45. The monitor of any of the preceding Statements, wherein the modular handle is in line with a perimeter of the monitor surrounding the electronic visual display.

Statement 46. The monitor of any of the preceding Statements, wherein the modular handle is at an oblique angle with respect to a perimeter of the monitor surrounding the electronic visual display.

Statement 47. A system comprising:
a monitor;
a monitor mount; and
a coupling including a top piece, a base plate and a locking mechanism,
wherein:
the monitor is configured to be detachably secured to the monitor mount;
the monitor mount is configured to be detachably secured to the coupling;

the base plate includes an opening and an inner surface around the opening, the inner surface including at least one indentation;

the top piece includes an outer surface including at least one projection;

the locking mechanism is configured to move between: (i) a locked position at which a part of the locking mechanism is engaged with the top piece such that the top piece is not rotatable in the opening of the base plate; and (ii) an unlocked position at which the locking mechanism is disengaged from the top piece such that the top piece is rotatable in the opening of the base plate;

the top piece is configured to be inserted into and released from the base plate when: (i) the locking mechanism is in the unlocked position; and (ii) the top piece is in a position at which the at least one projection and the at least one indentation are in alignment; and the top piece is configured to be secured to the base plate when: (i) the locking mechanism is in the locked position; or (ii) the top piece is in any position at which the at least one projection and the at least one indentation are out of alignment.

Statement 48. A system comprising:

a monitor mount; and a coupling including a top piece, a base plate and a locking mechanism, wherein:

the monitor mount is configured to be detachably secured to the coupling;

the base plate includes an opening and an inner surface around the opening, the inner surface including at least one indentation;

the top piece includes an outer surface including at least one projection;

the locking mechanism is configured to move between: (i) a locked position at which a part of the locking mechanism is engaged with the top piece such that the top piece is not rotatable in the opening of the base plate; and (ii) an unlocked position at which the locking mechanism is disengaged from the top piece such that the top piece is rotatable in the opening of the base plate;

the top piece is configured to be inserted into and released from the base plate when: (i) the locking mechanism is in the unlocked position; and (ii) the top piece is in a position at which the at least one projection and the at least one indentation are in alignment; and the top piece is configured to be secured to the base plate when: (i) the locking mechanism is in the locked position; or (ii) the top piece is in any position at which the at least one projection and the at least one indentation are out of alignment.

Statement 49. A coupling comprising:

a top piece;

a base plate; and a locking mechanism, wherein:

the base plate includes an opening and an inner surface around the opening, the inner surface including at least one indentation;

the top piece includes an outer surface including at least one projection;

the locking mechanism is configured to move between: (i) a locked position at which a part of the locking mechanism is engaged with the top piece such that the top piece is not rotatable in the opening of the base plate; and (ii) an unlocked position at which the locking mechanism is disengaged from the top piece such that the top piece is rotatable in the opening of the base plate;

the top piece is configured to be inserted into and released from the base plate when: (i) the locking mechanism is in the unlocked position; and (ii) the top piece is in a position at which the at least one projection and the at least one indentation are in alignment; and the top piece is configured to be secured to the base plate when: (i) the locking mechanism is in the locked position; or (ii) the top piece is in any position at which the at least one projection and the at least one indentation are out of alignment.

Statement 50. The coupling or system of any of the preceding Statements, wherein:

the at least one projection includes three projections spaced apart at intervals from one another; and the at least one indentation includes three indentations spaced apart at intervals from one another that correspond with the intervals between the projections.

Statement 51. The coupling or system of any of the preceding Statements, wherein a first circumferential distance between a first adjacent pair of the indentations is greater than a second circumferential distance between a second adjacent pair of the indentations.

Statement 52. The coupling or system of any of the preceding Statements, wherein the locking mechanism includes a spring and a plunger.

Statement 53. The coupling or system of any of the preceding Statements, wherein an end of the plunger is configured to extend into an aperture of the top piece in the locked position of the locking mechanism.

Statement 54. The coupling or system of any of the preceding Statements, wherein the end of the plunger is configured to be withdrawn from the aperture of the top piece in the unlocked position of the locking mechanism.

Statement 55. The coupling or system of any of the preceding Statements, wherein the at least one projection allows for only 10° of rotation of the top piece.

Statement 56. The coupling or system of any of the preceding Statements, wherein:

the end of the plunger configured to extend into the aperture of the top piece in the locked position is a first end of the plunger; and a ring is attached to a second end of the plunger.

Statement 57. The coupling or system of any of the preceding Statements, wherein:

the top piece includes a track configured to guide and depress the plunger upon rotation of the top piece; and the aperture of the top piece is defined at an end of the track.

Statement 58. The coupling or system of any of the preceding Statements, wherein:

a first portion of the at least one indentation defines a slot;

a second portion of the at least one indentation defines an abutment;

the top piece is configured to be inserted into and released from the base plate when: (i) the locking mechanism is in the unlocked position; and (ii) the top piece is in a position at which the at least one projection and the slot are in alignment; and the top piece is configured to be secured to the base plate when the top piece is in a position at which the at least one projection and the abutment are in alignment.

Statement 59. A system comprising:
a monitor;
a monitor mount; and
a belt mount including a support plate, a base, a first fastener including a belt member, and a second fastener,
wherein:
the monitor is configured to be detachably secured to the monitor mount;
the monitor mount is configured to be detachably secured to the belt mount;
the base is on one side of the support plate;
the first fastener is configured to be detachably secured to the base, and is configured to fasten and release the belt mount to a support structure by the belt member; and
the second fastener is configured to be detachably secured to the base, and is configured to fasten and release the belt member.

Statement 60. A system comprising:
a monitor mount; and
a belt mount including a support plate, a base, a first fastener including a belt member, and a second fastener,
wherein:
the monitor mount is configured to be detachably secured to the belt mount;
the base is on one side of the support plate;
the first fastener is configured to be detachably secured to the base, and is configured to fasten and release the belt mount to a support structure by the belt member; and
the second fastener is configured to be detachably secured to the base, and is configured to fasten and release the belt member.

Statement 61. A belt mount comprising:
a support plate;
a base;
a first fastener including a belt member; and
a second fastener,
wherein:
the base is on one side of the support plate;
the first fastener is configured to be detachably secured to the base, and is configured to fasten and release the belt mount to a support structure by the belt member; and
the second fastener is configured to be detachably secured to the base, and is configured to fasten and release the belt member.

Statement 62. The belt mount or system of any of the preceding Statements, wherein:
the second fastener includes a knob and a drum;
upon rotation of the knob, the knob is configured to rotate the drum; and
the drum is configured to fasten and release the belt member.

Statement 63. The belt mount or system of any of the preceding Statements, wherein:
the first fastener includes a ring; and
upon pulling of the ring, the ring is configured to fasten and release the belt member to the support structure.

Statement 64. The belt mount or system of any of the preceding Statements, wherein:
the base includes a recess; and
an end of the first fastener is configured to be insertable into the recess of the base such that the first fastener is detachably secured to the base.

Statement 65. The belt mount or system of any of the preceding Statements, wherein the base is comprised of a rubber material.

Statement 66. The belt mount or system of any of the preceding Statements, wherein the belt member is comprised of a flexible material.

Statement 67. A system comprising:
a monitor mount;
a rack; and
a coupling including a first leaf, a second leaf and a removable pin,
wherein:
the monitor mount is configured to be detachably secured to one of the first leaf and the second leaf;
the rack is configured to be detachably secured to the other of the first leaf and the second leaf;
the removable pin includes a handle;
a first end of the first leaf defines a first knuckle;
a second end of the first leaf defines a first protruding edge;
a first end of the second leaf defines a second knuckle;
a second end of the second leaf defines a second protruding edge;
the first knuckle includes a first aperture;
the second knuckle includes a second aperture; and
the removable pin is configured to connect the first knuckle and the second knuckle by extending through the first aperture and the second aperture such that the first leaf and the second leaf are configured to rotate around the removable pin between: (i) a locked position at which the first protruding edge and the second protruding edge are engaged; and (ii) an unlocked position at which the first protruding edge and the second protruding edge are disengaged.

Statement 68. A coupling comprising:
a first leaf;
a second leaf; and
a removable pin,
wherein:
the removable pin includes a handle;
a first end of the first leaf defines a first knuckle;
a second end of the first leaf defines a first protruding edge;
a first end of the second leaf defines a second knuckle;
a second end of the second leaf defines a second protruding edge;
the first knuckle includes a first aperture;
the second knuckle includes a second aperture; and
the removable pin is configured to connect the first knuckle and the second knuckle by extending through the first aperture and the second aperture such that the first leaf and the second leaf are configured to rotate around the removable pin between: (i) a locked position at which the first protruding edge and the second protruding edge are engaged; and (ii) an unlocked position at which the first protruding edge and the second protruding edge are disengaged.

Statement 69. The coupling or system of any of the preceding Statements, further comprising a monitor configured to be detachably secured to the monitor mount.

Statement 70. The coupling or system of any of the preceding Statements, further comprising a module configured to be detachably secured to the rack.

Statement 71. The coupling or system of any of the preceding Statements, wherein:
the first knuckle includes a first portion and a second portion; and
the second knuckle is configured to be positioned in between the first portion of the first knuckle and the second portion of the first knuckle.

Statement 72. The coupling or system of any of the preceding Statements, wherein at least one of the first knuckle and the second knuckle is beveled.

Statement 73. The coupling or system of any of the preceding Statements, wherein at least one of the first knuckle and the second knuckle is filleted.

Statement 74. A system comprising:
a rack; and
a module,
wherein:
the rack includes a first electrical connector;
the module includes a second electrical connector;
the rack is configured to detachably secure the module therein in a first position in which the first electrical connector and the second electrical connector are electrically connected; and
the rack is configured to detachably secure the module therein in a second position in which the first electrical connector and the second electrical connector are electrically disconnected.

Statement 75. A rack comprising:
an electrical connector,
wherein:
the rack is configured to detachably secure a module therein in a first position in which the electrical connector of the rack and an electrical connector of the module are electrically connected; and
the rack is configured to detachably secure the module therein in a second position in which the electrical connector of the rack and the electrical connector of the module are electrically disconnected.

Statement 76. A system comprising:
a rack; and
a module,
wherein:
the rack includes a first electrical connector, a releaser and a latch;
the module includes a second electrical connector and a recess;
the releaser is configured to release the latch from engagement;
the rack is configured to detachably secure the module therein in a first position in which: (i) the first electrical connector and the second electrical connector are electrically connected, and (ii) the latch is engaged in the recess; and
the rack is configured to detachably secure the module therein in a second position in which: (i) the first electrical connector and the second electrical connector are electrically disconnected.

Statement 77. A rack comprising:
an electrical connector;
a releaser; and
a latch,
wherein:
the releaser is configured to release the latch from engagement;
the rack is configured to detachably secure a module therein in a first position in which: (i) the electrical connector of the rack and an electrical connector of the module are electrically connected, and (ii) the latch is engaged in a recess of the module; and
the rack is configured to detachably secure the module therein in a second position in which: (i) the electrical connector of the rack and the electrical connector of the module are electrically disconnected.

Statement 78. A system comprising:
a rack; and
a module,
wherein:
the rack includes a first electrical connector, a releaser and a plurality of latches; the module includes a second electrical connector and a plurality of recesses; the releaser is configured to release the latches from engagement;
the rack is configured to detachably secure the module therein in a first position in which: (i) the first electrical connector and the second electrical connector are electrically connected, and (ii) each of the latches is engaged in a respective one of the recesses; and the rack is configured to detachably secure the module therein in a second position in which: (i) the first electrical connector and the second electrical connector are electrically disconnected, (ii) one of the latches is engaged in one of the recesses, and (iii) one of the latches is disengaged in any of the recesses.

Statement 79. A rack comprising:
an electrical connector;
a releaser; and
a plurality of latches,
wherein:
the releaser is configured to release the latches from engagement;
the rack is configured to detachably secure a module therein in a first position in which: (i) the electrical connector of the rack and an electrical connector of the module are electrically connected, and (ii) each of the latches is engaged in a respective one of recesses of the module; and
the rack is configured to detachably secure the module therein in a second position in which: (i) the electrical connector of the rack and the electrical connector of the module are electrically disconnected, (ii) one of the latches is engaged in one of the recesses, and (iii) one of the latches is disengaged in any of the recesses.

Statement 80. A system comprising:
a rack; and
a module,
wherein:
the rack includes a first electrical connector and a recess;
the module includes a second electrical connector and a tab and a latch;
the tab is configured to release the latch from engagement;
the rack is configured to detachably secure the module therein in a first position in which: (i) the first electrical connector and the second electrical connector are electrically connected, and (ii) the latch is engaged in the recess; and
the rack is configured to detachably secure the module therein in a second position in which: (i) the first electrical connector and the second electrical connector are electrically disconnected, and (ii) the latch is disengaged from the recess.

Statement 81. A module comprising:
an electrical connector;
a tab; and
a latch,
wherein:
the tab is configured to release the latch from engagement;
the module is configured to be detachably secured in a rack in a first position in which: (i) an electrical connector of the rack and the electrical connector of the module are electrically connected, and (ii) the latch is engaged in the recess; and the module is configured to be detachably secured in the rack in a second position in which: (i) the electrical connector of the rack and the electrical connector of the module are electrically disconnected, and (ii) the latch is disengaged in from the recess.

Statement 82. The rack, module or system of any of the preceding Statements, wherein the latch is spring-loaded.

Statement 83. The rack, module or system of any of the preceding Statements, wherein the releaser is a button configured to drive the latch from engagement.

Statement 84. The rack, module or system of any of the preceding Statements, further comprising a rod positioned adjacent to the releaser, wherein the releaser is configured to drive the rod against the latch so as to release the latch from engagement.

Statement 85. The rack, module or system of any of the preceding Statements, wherein the rack includes a spring-loaded plunger for biasing the module away from the rack such that the electrical connector of the rack is disconnected from the electrical connector of the module.

Statement 86. The system of any of the preceding Statements, wherein a groove configured to facilitate grasping is defined in a periphery of the module.

Statement 87. The rack, module or system of any of the preceding Statements, wherein a channel configured to vent air is defined in a back wall of the rack such that the channel provides a space between the back wall of the rack and the module when the module is detachably secured in the rack.

Statement 88. The rack, module or system of any of the preceding Statements, wherein an aperture configured to receive the electrical connector of the rack is define in a back wall of the rack such that the electrical connector of the rack protrudes through the back wall of the rack.

Statement 89. The rack, module or system of any of the preceding Statements, wherein the latch is spring-loaded.

Statement 90. The rack, module or system of any of the preceding Statements, wherein the releaser is a button configured to drive the latch from engagement.

Statement 91. The rack, module or system of any of the preceding Statements, further comprising a rod positioned adjacent to the releaser, wherein the releaser is configured to drive the rod against the latch so as to release the latch from engagement.

Statement 92. The rack, module or system of any of the preceding Statements, wherein the rack includes a spring-loaded plunger for biasing the module away from the rack such that the electrical connector of the rack is disconnected from the electrical connector of the module.

Statement 93. The system of any of the preceding Statements, wherein a groove configured to facilitate grasping is defined in a periphery of the module.

Statement 94. The rack, module or system of any of the preceding Statements, wherein a channel configured to vent air is defined in a back wall of the rack such that the channel provides a space between the back wall of the rack and the module when the module is detachably secured in the rack.

Statement 95. The rack, module or system of any of the preceding Statements, wherein an aperture configured to receive the electrical connector of the rack is define in a back wall of the rack such that the electrical connector of the rack protrudes through the back wall of the rack.

Statement 96. The rack, module or system of any of the preceding Statements, wherein the module further comprises a recess, the rack further comprises a latch, and the latch of the rack is configured to engage with the recess of the module.

Statement 97. The rack, module or system of any of the preceding Statements, wherein the rack further comprises at least one cable management feature.

Statement 98. A system comprising:
a monitor mount;
a rack;
a module; and
a module connector cable,
wherein:
the module is configured to be electrically connected to the monitor mount by the module connector cable;
the module is configured to be detachably secured to the rack;
the module includes a male portion;
one of the rack and the module connector cable includes a female portion;
the female portion includes a housing including a pair of longitudinal sides, a planar side connecting first ends of the pair of longitudinal sides of the female portion, a rounded side connecting second ends of the pair of longitudinal sides of the female portion, and a front surface including a plurality of sockets located therein, the plurality of sockets being arranged along a line parallel to the pair of longitudinal sides of the female portion;
the male portion includes a housing including a recess with a pair of longitudinal sides, a planar side connecting first ends of the pair of longitudinal sides of the male portion, a rounded side connecting second ends of the pair of longitudinal sides of the male portion, and a recessed surface including a plurality of pins extending therefrom, the plurality of pins being arranged along a line parallel to the pair of longitudinal sides of the male portion; and
the housing of the female portion is configured to be insertable into the recess of the housing of the male portion such that the plurality of pins of the male portion enter into the plurality of sockets of the female portion.

Statement 99. A system comprising:
a monitor mount;
a rack;
a module; and
a module connector cable,
wherein:
the module is configured to be electrically connected to the monitor mount by the module connector cable;
the module is configured to be detachably secured to the rack;
the monitor mount includes a female portion;
the module connector cable includes a male portion;
the female portion includes a housing including a pair of longitudinal sides including a ribs formed thereon, a planar side connecting first ends of the pair of longitudinal sides of the female portion, a rounded side connecting second ends of the pair of longitudinal sides of the female portion, and a front surface including a plurality of sockets located therein, the plurality of sockets being arranged along a line parallel to the pair of longitudinal sides of the female portion;
the male portion includes a housing including a recess with a pair of longitudinal sides, a planar side connecting first ends of the pair of longitudinal sides of the male portion, a rounded side connecting second ends of the pair of longitudinal sides of the male portion, and a recessed surface including a plurality of pins extending therefrom, the plurality of pins being arranged along a line parallel to the pair of longitudinal sides of the male portion; and the housing of the female portion is configured to be insertable into the recess of the housing of the male portion such that the plurality of pins of the male portion enter into the plurality of sockets of the female portion.

Statement 100. A monitor mount comprising:

a coupling configured to detachably secure a monitor to the monitor mount; and a release mechanism configured to disengage the coupling so as to release the monitor from the monitor mount, wherein:

the release mechanism includes an actuator, a cam and a slider;

the cam is attached to the actuator;

the cam is configured to be rotated by the actuator and is configured to cause the slider to slide;

the slider is linked to the coupling; and the slider is configured to disengage the coupling upon sliding.

Statement 101. The monitor mount or system of any of the preceding Statements, further comprising:

a mounting plate attached to a back surface of the monitor mount; and a clip configured to detachably secure the monitor mount to a support structure, wherein the clip is attached to the mounting plate by a hinge such that the mounting plate is rotatable with respect to the clip.

Statement 102. A monitor comprising:

an electronic visual display;

a back portion; and a coupling, wherein:

the coupling of the monitor is configured to detachably secure another monitor;

the back portion of the monitor is configured to be detachably secured to a monitor mount by a coupling of the monitor mount which is also configured to detachably secure a back portion of the other monitor; and the monitor is configured to surround at least a portion of an electronic visual display of the other monitor when the other monitor is detachably secured to the monitor.

Statement 103. A system comprising:

the monitor mount of any of the preceding Statements; and the monitor of any of the preceding Statements.

Statement 104. A system comprising:

the monitor mount of any of the preceding Statements;

the monitor of any of the preceding Statements; and the other monitor.

Statement 105. The monitor mount of any of the preceding Statements, wherein the monitor mount further comprises a support portion configured to suspend a hook portion of the monitor therefrom.

Statement 106. The monitor of any of the preceding Statements, wherein the monitor further comprises a hook portion configured to be suspended from a support portion of the monitor mount.

Statement 107. The system of any of the preceding Statements, wherein:

the monitor mount further comprises a support portion;

the monitor further comprises a hook portion; and the support portion of the monitor mount is configured to suspend the hook portion of the monitor therefrom.

Statement 108. A monitor comprising:

an electronic visual display; and a back surface, wherein:

the back surface of the monitor is continuous;

the back surface of the monitor does not include couplings or electrical connections.

Statement 109. The monitor mount or system of any of the preceding Statements, wherein the actuator is a lever.

Statement 110. The monitor mount or system of any of the preceding Statements, wherein:

the lever is a first lever;

the cam is a first cam;

the monitor mount further includes a second lever corresponding to the first lever and a second cam corresponding to the first cam;

the second cam is configured to be rotated by the second lever; and the slider is configured to slide based on rotation of at least one of the first cam and the second cam.

Statement 111. The monitor mount or system of any of the preceding Statements, wherein the actuator is a button.

Statement 112. The monitor mount or system of any of the preceding Statements, wherein:

the coupling of the monitor mount includes a latch; and the slider is configured to disengage the latch upon sliding.

Statement 113. The monitor mount or system of any of the preceding Statements, wherein:

the coupling of the monitor mount includes a latch and a pin;

the coupling of the monitor mount is attached to the release mechanism of the monitor mount by a hinge;

the slider is configured to displace the pin such that the latch rotates outwardly via the hinge so as to release the monitor from the monitor mount.

Statement 114. The monitor mount or system of any of the preceding Statements, wherein the monitor mount further comprises a power bus configured to power the monitor when the monitor is secured to the monitor mount.

Statement 115. The system of any of the preceding Statements, wherein:

the power bus is a first power bus;

the monitor further comprises a second power bus; and the second power bus is configured to power the monitor when the monitor is secured to the monitor mount.

Statement 116. The system of any of the preceding Statements, wherein the monitor is operable solely via the second power bus.

Statement 117. The system of any of the preceding Statements, wherein the monitor is operable via either of the first power bus or the second power bus.

Statement 118. The monitor or system of any of the preceding Statements, wherein the monitor further comprises a self-contained power source configured to allow the monitor to be operated independently of the monitor mount.

Statement 119. The monitor or system of any of the preceding Statements, wherein the monitor further comprises a sensor interface configured to receive data generated by a physiological sensor monitoring a physiological parameter of a patient.

Statement 120. The monitor or system of any of the preceding Statements, wherein the physiological sensor comprises a wired connection to the sensor interface.

Statement 121. The monitor or system of any of the preceding Statements, wherein the physiological sensor comprises a wireless connection to the sensor interface.

Statement 122. The system of any of the preceding Statements, wherein:
the monitor mount further comprises a first communications interface coupled to a computing network; and
the monitor comprises a second communications interface configured to transmit and receive data over the computing network via the first communications interface when the monitor is secured to the monitor mount.

Statement 123. The monitor or system of any of the preceding Statements, wherein the monitor further is configured to visualize at least a portion of received data thereon.

Statement 124. The monitor or system of any of the preceding Statements, wherein the monitor is configured to be detachably secured to and removed from a front face of the monitor mount.

Statement 125. The system of any of the preceding Statements, wherein a connector of the monitor is electrically connected to a connector of the monitor mount.

Statement 126. The monitor mount or system of any of the preceding Statements, wherein the monitor mount is configured to receive interchangeable first and second top portions for accommodating monitors of different types.

Statement 127. The monitor mount or system of any of the preceding Statements, wherein the monitors of different types include monitors of different sizes.

Statement 128. The monitor mount or system of any of the preceding Statements, wherein the monitor mount includes a cutout on a back surface thereof configured to permit a flow of fluid.

Statement 129. The monitor mount or system of any of the preceding Statements, wherein the monitor mount does not include electrical connections and therefore is configured to provide only physical support for the monitor.

Statement 130. The monitor or system of any of the preceding Statements, wherein the monitor includes a latch configured to grip the coupling of the monitor mount.

Statement 131. The monitor mount or system of any of the preceding Statements, wherein the clip defines a hook including a base plate on a first side of the clip and a back plate on a second side of the clip.

Statement 132. The monitor mount or system of any of the preceding Statements, wherein the base plate includes a notch configured to receive a vertical member of the support structure.

Statement 133. The monitor mount or system of any of the preceding Statements, wherein at least one of the base plate and the back plate includes an opening defined therein.

Statement 134. A monitor comprising:
a case configured to hold an electronic visual display; and
a cover,
wherein:
the cover is configured to be detachably secured to the case in a first orientation of the case and a second orientation of the case; and
the first orientation of the case is different from the second orientation of the case.

Statement 135. The monitor of any of the preceding Statements, wherein the cover is configured to be detachably secured to a back portion of the case.

Statement 136. The monitor of any of the preceding Statements, wherein the cover is configured to surround the back portion of the case.

Statement 137. The monitor of any of the preceding Statements, wherein the cover includes a handle.

Statement 138. The monitor of any of the preceding Statements, wherein the handle extends from a side portion of the cover.

Statement 139. The monitor of any of the preceding Statements, wherein the handle is in line with a perimeter of the cover.

Statement 140. The monitor of any of the preceding Statements, wherein the handle is at an oblique angle with respect to a perimeter of the cover.

Statement 141. The monitor of any of the preceding Statements, wherein the handle is one of two handles extending from respective side portions of the cover.

Statement 142. The monitor of any of the preceding Statements, wherein the cover is symmetrical with respect to a longitudinal center axis of the monitor.

Statement 143. The monitor of any of the preceding Statements, wherein an interface between the cover and the case is symmetrical with respect to a longitudinal center axis of the monitor and a lateral center axis of the monitor.

Statement 144. The monitor of any of the preceding Statements, wherein the cover includes a first recess and a second recess, the first recess and the second recess together defining a mount portion configured to physically interface with a monitor mount.

Statement 145. The monitor of any of the preceding Statements, wherein:
the first recess is defined in a top portion of the cover; and
the second recess is defined in a bottom portion of the cover.

Statement 146. The monitor of any of the preceding Statements, wherein the cover includes an opening defined in at least one of a side portion of the cover and a back portion of the cover.

Statement 147. The monitor of any of the preceding Statements, further comprising at least one fastener configured to detachably secure the cover to the case.

Statement 148. The monitor of any of the preceding Statements, wherein the at least one fastener is a screw.

Statement 149. The monitor of any of the preceding Statements, wherein the cover is comprised of plastic.

Statement 150. The monitor of any of the preceding Statements, wherein the case is comprised of plastic.

Statement 151. The monitor of any of the preceding Statements, wherein the case and the cover are formed as a single unit.

Statement 152. A system comprising:
a rack; and
a module,
wherein:
the rack includes a first electrical connector;
the module includes a second electrical connector;
the rack is configured to detachably secure the module therein in a first position in which the first electrical connector and the second electrical connector are electrically connected; and
the rack is configured to detachably secure the module therein in a second position in which the first electrical connector and the second electrical connector are electrically disconnected.

Statement 153. A rack comprising:
an electrical connector,
wherein:
the rack is configured to detachably secure a module therein in a first position in which the electrical connector of the rack and an electrical connector of the module are electrically connected; and the rack is configured to detachably secure the module therein in a second position in which the electrical connector of the rack and the electrical connector of the module are electrically disconnected.

Statement 154. A system comprising:
a rack; and
a module,
wherein:
the rack includes a first electrical connector, a first recess and a second recess;
the module includes a second electrical connector, a releaser and a latch;
the releaser is configured to release the latch from engagement;
the rack is configured to detachably secure the module therein in a first position in which: (i) the first electrical connector and the second electrical connector are electrically connected, and (ii) the latch is engaged in the first recess; and
the rack is configured to detachably secure the module therein in a second position in which: (i) the first electrical connector and the second electrical connector are electrically disconnected, and (ii) the latch is engaged in the second recess.

Statement 155. A rack comprising:
an electrical connector;
a first recess; and
a second recess,
wherein:
the rack is configured to detachably secure a module therein in a first position in which: (i) the electrical connector of the rack and an electrical connector of the module are electrically connected, and (ii) the latch is engaged in the first recess; and
the rack is configured to detachably secure the module therein in a second position in which: (i) the electrical connector of the rack and the electrical connector of the module are electrically disconnected, and (ii) the latch is engaged in the second recess.

Statement 156. A module comprising:
an electrical connector;
a releaser; and
a latch,
wherein:
the releaser is configured to release the latch from engagement;
the module is configured to be detachably secured in a rack in a first position in which: (i) an electrical connector of the rack and the electrical connector of the module are electrically connected, and (ii) the latch is engaged in a first recess of the rack; and
the module is configured to be detachably secured in the rack in a second position in which: (i) the electrical connector of the rack and the electrical connector of the module are electrically disconnected, and (ii) the latch is engaged in a second recess of the rack.

Statement 157. The module or system of any of the preceding Statements, wherein the releaser is a tab.

Statement 158. The rack or system of any of the preceding Statements, wherein the first recess and the second recess are defined in an upper surface of a lower portion of the rack.

Statement 159. The rack or system of any of the preceding Statements, wherein the rack further comprises a guide rail for positioning the module.

Statement 160. The rack or system of any of the preceding Statements, wherein the guide rail is on: (i) an upper surface of a lower portion of the rack, or (ii) a lower surface of an upper portion of the rack.

Statement 161. The rack or system of any of the preceding Statements, wherein:
the rack further comprises guide rails for positioning the module;
a first of the guide rails is on an upper surface of a lower portion of the rack; and
a second of the guide rails is on a lower surface of an upper portion of the rack.

Statement 162. The rack or system of any of the preceding Statements, wherein a length of the guide rail is less than a depth of the rack.

Statement 163. The rack or system of any of the preceding Statements, wherein a channel configured to vent air is defined in a back wall of the rack such that the channel is configured to provide a space between the back wall of the rack and the module when the module is secured in the rack.

Statement 164. The rack or system of any of the preceding Statements, wherein the channel extends across three sides of the rack.

Statement 165. The module or system of any of the preceding Statements, wherein the module further comprises:
an air inlet; and
an air outlet,
wherein the air outlet is configured to vent the air to the channel.

Statement 166. The module or system of any of the preceding Statements, wherein the module further comprises at least one fan configured to circulate the air to the air outlet.

Statement 167. The rack or system of any of the preceding Statements, wherein an aperture configured to receive the electrical connector of the rack is defined in a back wall of the rack such that the electrical connector of the rack protrudes through the back wall of the rack.

Statement 168. A cable holder, comprising:
a back wall; and
a side wall,
wherein:
the side wall extends from one end of the back wall;
the side wall includes apertures defined therein;
each of the apertures is configured to receive a cable therethrough;
a first of the apertures is arcuate;
a second of the apertures is parallelogram-shaped and is oblique with respect to the back wall; and
a third of the apertures is rectangular and is perpendicular to the back wall.

Statement 169. The cable holder of Statement 168, wherein the side wall further includes a notch at one end thereof.

Statement 170. The cable holder of any of the preceding Statements, wherein:
the third of the apertures has a first end at a distal end of the side wall and a second end adjacent to a proximal end of the side wall;
a width of the first end of the third of the apertures is less than a width of the second end of the third of the apertures.

Statement 171. The cable holder of any of the preceding Statements, wherein:
the side wall is a first side wall and the one end of the back wall is a first end of the back wall;

the cable holder further comprises a second side wall extending from a second end of the back wall; and
the second side wall corresponds to the first side wall.

Statement 172. A cable holder, comprising:
a back wall;
a side wall;
a front wall; and
projections,
wherein:
the side wall extends from a first end of the back wall;
the side wall includes apertures defined therein;
the front wall extends from an end of the side wall opposite to the back wall;
the front wall includes slots defined therein;
the projections extend from a second end of the back wall; and
each of the apertures and the slots is configured to receive a cable therethrough such that the cable is positioned between two of the projections.

Statement 173. The cable holder of Statement 172, wherein the apertures are polygonal.

Statement 174. The cable holder of any of the preceding Statements, wherein:
each of the slots has a first end at a distal end of the front wall and a second end at a proximal end of the front wall; and
for each of the slots, a width of the first end of the slot is greater than a width of the second end of the slot.

Statement 175. A system comprising:
the cable holder of any of the preceding Statements; and
the cable which includes a housing portion,
wherein the cable holder is configured to detachably secure the cable such that the housing portion of the cable rests on the side wall of the cable holder.

Statement 176. The system of any of the preceding Statements, wherein the cable holder is configured to detachably secure the cable such that the housing portion of the cable is positioned between the two of the projections of the cable holder.

Statement 177. The system of any of the preceding Statements, wherein the housing portion is configured to house a translator configured to translate protocols across cable portions on respective sides of the housing portion.

Statement 178. The monitor or system of any of the preceding Statements, wherein the monitor is a patient monitor configured to monitor and display information about a patient.

Statement 179. The module or system of any of the preceding Statements, wherein the module is a patient monitoring module configured to acquire and process data generated by at least one physiological sensor configured to monitor a physiological parameter of a patient.

The invention claimed is:

1. A female connector, comprising:
a housing comprising:
    a front portion;
    a back portion;
    a pair of longitudinal sides that extend from the front portion to the back portion, the pair of longitudinal sides including a first longitudinal side and a second longitudinal side;
    a planar side that extends from the front portion to the back portion, the planar side connecting first ends of the pair of longitudinal sides;
    a rounded side that extends from the front portion to the back portion, the rounded side connecting second ends of the pair of longitudinal sides, the second ends being arranged opposite to the first ends;
    a front surface defined at the front portion by the pair of longitudinal sides, the planar side, and the rounded side;
    a plurality of sockets formed at the front surface such that the plurality of sockets extend from the front surface into the housing, wherein the plurality of sockets are arranged along a line parallel to the pair of longitudinal sides and each of the plurality of sockets is configured to receive one of a plurality of pins;
    at least one spring groove formed in at least one of the first longitudinal side or the second longitudinal side, wherein the at least one spring groove extends from the front portion towards the back portion; and
    at least one shield spring, each formed in a corresponding one of the at least one spring groove, wherein each of the at least one shield spring is configured to be compressed by a corresponding protrusion structure that is received within the corresponding one of the at least one spring groove.

2. The female connector of claim 1, wherein the at least one spring groove is formed at the front surface and extends from the front surface towards the back portion.

3. The female connector of claim 1, wherein the housing further comprises:
an aperture formed in the front surface between one of the plurality of sockets and one of the at least one spring groove.

4. The female connector of claim 1, wherein the at least one shield spring provides electromagnetic interference (EMI) protection during signal transfer.

5. The female connector of claim 1, wherein the housing further comprises:
at least one shield protrusion formed on at least one of the first longitudinal side, the second longitudinal side, the planar side, or the rounded side, wherein each of the at least one shield protrusion extends from the front portion towards the back portion.

6. The female connector of claim 1, wherein the housing further comprises:
a first aperture formed in the front surface between one of the plurality of sockets and the first longitudinal side; and
a second aperture formed in the front surface between the one of the plurality of sockets and the second longitudinal side.

7. The female connector of claim 1, wherein the housing further comprises:
an interior portion between the front portion and the back portion;
an aperture formed in the front surface between one of the plurality of sockets and the first longitudinal side, wherein the aperture is configured to expel fluid from the interior portion to an exterior of the housing.

8. The female connector of claim 1, wherein
the at least one spring groove forms a unique key arrangement configured to be received by a corresponding male connector and to be rejected by a non-corresponding male connector.

9. The female connector of claim 8, wherein the housing further comprises:
at least one shield protrusion formed on at least one of the first longitudinal side, the second longitudinal side, the planar side, or the rounded side, wherein each of the at least one shield protrusion extends from the front portion towards the back portion, wherein the at least one spring groove and the at least one shield protrusion form the unique key arrangement configured to be received by the corresponding male connector and to be rejected by the non-corresponding male connector.

10. The female connector of claim 8, wherein the housing further comprises:
at least one shield groove formed on at least one of the first longitudinal side, the second longitudinal side, the planar side, or the rounded side, wherein each of the at least one shield groove extends from the front portion towards the back portion,
wherein the at least one spring groove and the at least one shield groove form the unique key arrangement configured to be received by the corresponding male connector and to be rejected by the non-corresponding male connector.

11. The female connector of claim 8, further comprising:
a shield coupled to the back portion of the housing and electrically coupled to the at least one shield spring, wherein the shield is configured to provide electromagnetic interference (EMI) protection during signal transfer.

12. The female connector of claim 8, further comprising:
a shroud comprised of an overmolded protrusion formed at the planar side.

13. A male connector, comprising:
a housing comprising:
a front portion;
a back portion;
a pair of longitudinal sides that extend from the front portion to the back portion, the pair of longitudinal sides including a first longitudinal side and a second longitudinal side;
a planar side that extends from the front portion to the back portion, the planar side connecting first ends of the pair of longitudinal sides;
a rounded side that extends from the front portion to the back portion, the rounded side connecting second ends of the pair of longitudinal sides, the second ends being arranged opposite to the first ends;
a recess defined by the pair of longitudinal sides, the planar side, and the rounded side, wherein the recess extends from the front portion to the back portion;
a plurality of pins that extend from the back portion towards the front portion, wherein the plurality of pins are arranged along a line parallel to the pair of longitudinal sides and each of a plurality of sockets is configured to receive one of the plurality of pins; and,
at least one electromagnetic interference (EMI) shield protrusion that extends from the back portion towards the front portion, wherein the at least one EMI shield protrusion is configured to provide EMI protection during signal transfer.

14. The male connector of claim 13, wherein each of the at least one EMI shield protrusion is configured to be received by a corresponding groove of a corresponding female connector.

15. The male connector of claim 13, further comprising:
a shield coupled to the back portion of the housing and electrically coupled to the at least one EMI shield protrusion, wherein the shield is configured to provide the EMI protection during the signal transfer.

16. The male connector of claim 13, wherein the housing further comprises:
at least one shield protrusion formed, inside the recess, on at least one of the first longitudinal side, the second longitudinal side, the planar side, or the rounded side, wherein each of the at least one shield protrusion extends from the front portion towards the back portion.

17. The male connector of claim 13, wherein the housing further comprises:
at least one shield groove formed, inside the recess, on at least one of the first longitudinal side, the second longitudinal side, the planar side, or the rounded side, wherein each of the at least one shield groove extends from the front portion towards the back portion.

18. The male connector of claim 13
wherein the housing further comprises at least one shield protrusion formed, inside the recess, on at least one of the first longitudinal side, the second longitudinal side, the planar side, or the rounded side, wherein each of the at least one shield protrusion extends from the front portion towards the back portion;
wherein the at least one EMI shield protrusion and the at least one shield protrusion form a unique key arrangement configured to be received by a corresponding female connector and to be rejected by a non-corresponding female connector.

19. The male connector of claim 13, further comprising:
wherein the housing further comprises at least one shield groove formed, inside the recess, on at least one of the first longitudinal side, the second longitudinal side, the planar side, or the rounded side, wherein each of the at least one shield protrusion extends from the front portion towards the back portion,
wherein the at least one EMI shield protrusion and the at least one shield groove form a unique key arrangement configured to be received by a corresponding female connector and to be rejected by a non-corresponding female connector.

20. A connector system, comprising:
a male connecter comprising a male housing defining a recess and a plurality of pins arranged within the recess; and
a female connector comprising a female housing configured to be insertable into the recess of the male housing;
wherein the female housing comprises:
a female front portion;
a female back portion;
a female pair of longitudinal sides that extend from the female front portion to the female back portion, the female pair of longitudinal sides including a first female longitudinal side and a second female longitudinal side;
a female planar side that extends from the female front portion to the female back portion, the female planar side connecting first ends of the female pair of longitudinal sides;
a female rounded side that extends from the female front portion to the female back portion, the female rounded side connecting second ends of the female pair of longitudinal sides, the second ends being arranged opposite to the first ends;
a front surface defined at the female front portion by the female pair of longitudinal sides, the female planar side, and the female rounded side; and
a plurality of sockets formed at the front surface such that the plurality of sockets extend from the front surface into the female housing, wherein the plurality of sockets are arranged along a line parallel to the pair of longitudinal sides and each of the plurality of sockets is configured to receive one of the plurality of pins;

wherein the female housing further comprises:

at least one spring groove formed in at least one of the first female longitudinal side or the second female longitudinal side, wherein the at least one spring groove extends from the female front portion towards the female back portion; and at least one shield spring, each formed in a corresponding one of the at least one spring groove, wherein each of the at least one shield spring is configured to be compressed by an EMI shield protrusion of the at least one EMI shield protrusion that is received within the corresponding one of the at least one spring groove, and wherein the male housing comprises:

a male front portion;

a male back portion;

a male pair of longitudinal sides that extend from the male front portion to the male back portion, the male pair of longitudinal sides including a first male longitudinal side and a second male longitudinal side;

a male planar side that extends from the male front portion to the male back portion, the male planar side connecting first ends of the male pair of longitudinal sides;

a male rounded side that extends from the male front portion to the male back portion, the male rounded side connecting second ends of the male pair of longitudinal sides, the second ends being arranged opposite to the first ends; and the recess defined by the male pair of longitudinal sides, the male planar side, and the male rounded side, wherein the recess extends from the male front portion to the male back portion; and, wherein the male connector further comprises at least one electromagnetic interference (EMI) shield protrusion that extends from the male back portion towards the male front portion, wherein the at least one EMI shield protrusion is configured to provide EMI protection during signal transfer.

* * * * *